(12) United States Patent
Fukushima et al.

(10) Patent No.: US 11,687,000 B2
(45) Date of Patent: Jun. 27, 2023

(54) SULFONIUM COMPOUND, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Masahiro Fukushima, Joetsu (JP); Masaki Ohashi, Joetsu (JP); Kazuhiro Katayama, Joetsu (JP); Yuki Kera, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 371 days.

(21) Appl. No.: 16/839,402

(22) Filed: Apr. 3, 2020

(65) Prior Publication Data

US 2020/0319550 A1    Oct. 8, 2020

(30) Foreign Application Priority Data

Apr. 5, 2019 (JP) .............................. JP2019-072757

(51) Int. Cl.
| | | |
|---|---|---|
| G03F 7/039 | (2006.01) | |
| G03F 7/004 | (2006.01) | |
| C07D 319/06 | (2006.01) | |
| G03F 7/038 | (2006.01) | |
| G03F 7/20 | (2006.01) | |
| C07D 317/18 | (2006.01) | |
| G03F 7/32 | (2006.01) | |
| G03F 7/11 | (2006.01) | |
| C07D 321/06 | (2006.01) | |

(52) U.S. Cl.
CPC ......... G03F 7/0045 (2013.01); C07D 317/18 (2013.01); C07D 319/06 (2013.01); C07D 321/06 (2013.01); G03F 7/0382 (2013.01); G03F 7/0392 (2013.01); G03F 7/11 (2013.01); G03F 7/2004 (2013.01); G03F 7/2006 (2013.01); G03F 7/2037 (2013.01); G03F 7/2041 (2013.01); G03F 7/322 (2013.01)

(58) Field of Classification Search
CPC .... G03F 7/0045; G03F 7/0392; G03F 7/0382; G03F 7/2004
See application file for complete search history.

(56) References Cited

U.S. PATENT DOCUMENTS

| | | |
|---|---|---|
| 5,786,131 A | 7/1998 | Allen et al. |
| 8,227,183 B2 | 7/2012 | Tsubaki et al. |
| 8,951,718 B2 | 2/2015 | Tsubaki et al. |
| 9,291,904 B2 | 3/2016 | Tsubaki et al. |
| 9,348,220 B2 | 5/2016 | Aqad et al. |
| 9,465,298 B2 | 10/2016 | Tsubaki et al. |
| 2015/0140489 A1 | 5/2015 | Robinson et al. |
| 2017/0008982 A1 | 1/2017 | Hasegawa et al. |
| 2018/0059543 A1 | 3/2018 | Mitsui et al. |
| 2020/0048191 A1 | 2/2020 | Suga et al. |
| 2020/0379345 A1* | 12/2020 | Fukushima ........... G03F 7/0046 |

FOREIGN PATENT DOCUMENTS

| | | |
|---|---|---|
| JP | 8-15865 A | 1/1996 |
| JP | 2007-145797 A | 6/2007 |
| JP | 2008-281974 A | 11/2008 |
| JP | 2008-281975 A | 11/2008 |
| JP | 4554665 B2 | 9/2010 |
| JP | 5061484 B2 | 10/2012 |
| JP | 2013-8020 A | 1/2013 |
| JP | 5317181 B2 | 10/2013 |
| JP | 2014-102334 A | 6/2014 |
| JP | 2015-060034 A | 3/2015 |
| JP | 2015-63472 A | 4/2015 |
| JP | 5723802 B2 | 5/2015 |
| JP | 5865725 B2 | 2/2016 |
| JP | 2016-147879 A | 8/2016 |
| JP | 6130109 B2 | 5/2017 |
| JP | 6155013 B2 | 6/2017 |
| JP | 2018-43977 A | 3/2018 |
| TW | 201821402 A | 6/2018 |
| TW | I637939 B | 10/2018 |

OTHER PUBLICATIONS

Office Action dated Feb. 19, 2021, issued in counterpart TW Application No. 109110957 (9 pages).

(Continued)

*Primary Examiner* — Daborah Chacko-Davis
(74) *Attorney, Agent, or Firm* — WHDA, LLP

(57) ABSTRACT

A novel sulfonium compound of formula (A) and a chemically amplified resist composition comprising the same as a PAG are provided. When processed by photolithography using KrF or ArF excimer laser, EB or EUV, the resist composition has a high sensitivity and reduced acid diffusion and is improved in lithography properties.

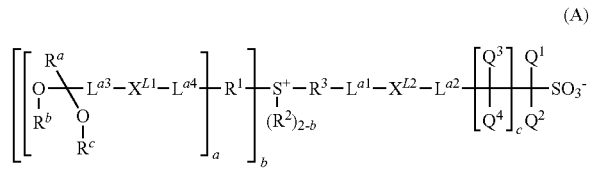

(A)

20 Claims, 4 Drawing Sheets

(56) References Cited

OTHER PUBLICATIONS

Office Action dated Jul. 7, 2021, issued in counterpart KR Application No. 10-2020-0041166, with English Translation. (14 pages).
Dammel et al., "193 nm Immersion Lithography—Taking the Plunge", Journal of Photopolymer Science and Technology, 2004, vol. 17, No. 4, pp. 587-601, cited in Specification, (18 pages).
Lawson et al., "Single Molecule Chemically Amplified Resists Based On Ionic and Non-ionic PAGs", Proc. of SPIE, 2008, vol. 6923, 69230K, pp. 1-10. (10 pages).
Office Action dated Feb. 17, 2022, issued in KR application No. 10-2020-0063173 (counterpart to U.S. Appl. No. 16/858,092, with English Translation. (10 pages).
Non-Final Office Action dated Mar. 31, 2022, issued in U.S. Appl. No. 16/858,092. (10 pages).

* cited by examiner

SULFONIUM COMPOUND, CHEMICALLY AMPLIFIED RESIST COMPOSITION, AND PATTERNING PROCESS

CROSS-REFERENCE TO RELATED APPLICATION

This non-provisional application claims priority under 35 U.S.C. § 119(a) on Patent Application No. 2019-072757 filed in Japan on Apr. 5, 2019, the entire contents of which are hereby incorporated by reference.

TECHNICAL FIELD

This invention relates to a sulfonium compound, a chemically amplified resist composition, and a patterning process.

BACKGROUND ART

While a number of recent efforts are being made to achieve a finer pattern rule in the drive for higher integration and operating speeds in LSIs, DUV and EUV lithography processes are thought to hold particular promise as the next generation in microfabrication technology. In particular, photolithography using an ArF excimer laser is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (wavelength 157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study. As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 describes the prior art PAGs capable of generating α,α-difluoroalkanesulfonic acid, such as di(4-tert-butylphenyl) iodonium 1,1-difluoro-2-(1-naphthyl)ethanesulfonate and PAGs capable of generating α,α,β,β-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety or ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a bulky substituent or polar group into PAG is effective for suppressing acid diffusion. Patent Document 4 discloses a PAG capable of generating 2-acyloxy-1,1,3,3,3-pentafluoropropane-1-sulfonic acid which is fully soluble and stable in resist solvents and allows for a wide span of molecular design. In particular, a PAG having a bulky substituent incorporated therein or capable of generating 2-(1-adamantyloxy)-1,1,3,3,3-pentafluoropropane-1-sulfonic acid is characterized by slow acid diffusion. Patent Documents 5 to 7 describe PAGs having fused ring lactone, sultone or thiolactone incorporated as the polar group. Although some improvement in performance is observed due to the acid diffusion suppressing effect of the polar group incorporated, they are still insufficient in precise control of acid diffusion. Their lithography performance is unsatisfactory when evaluated totally in terms of MEF, pattern profile and sensitivity.

Patent Documents 8 to 14 describe PAGs of betaine structure possessing cation and anion moieties in a common molecule. After exposure, an acid is generated, and the cation moiety is decomposed at the same time. Since the generated acid which is attached to the anion moiety is not substantially reduced in molecular weight, acid diffusion is controlled. However, the PAGs themselves are little soluble in the resist solvent and developer, raising such problems as precipitation during shelf storage and defect formation after development. Although these PAGs are effective for improving performance to some extent, they are still insufficient in sensitivity and precise control of acid diffusion. There is the desire to have a PAG capable of meeting a high sensitivity, low acid diffusion, and solvent solubility.

CITATION LIST

Patent Document 1: JP-A 2008-281974
Patent Document 2: JP-A 2008-281975
Patent Document 3: JP 4554665
Patent Document 4: JP-A 2007-145797
Patent Document 5: JP 5061484
Patent Document 6: JP-A 2016-147879
Patent Document 7: JP-A 2015-063472
Patent Document 8: JP 5317181
Patent Document 9: JP 5723802
Patent Document 10: JP 5865725
Patent Document 11: JP 6130109
Patent Document 12: JP 6155013
Patent Document 13: JP-A 2013-008020
Patent Document 14: JP-A 2018-043977
Non-Patent Document 1: Journal of Photopolymer Science and Technology, Vol. 17, No. 4, p 587 (2004)

DISCLOSURE OF INVENTION

While it is recently demanded to form resist patterns at a high resolution, a resist composition using a conventional PAG fails to fully suppress acid diffusion. As a result, lithography performance factors such as contrast, MEF and LWR are degraded.

An object of the invention is to provide a novel sulfonium compound and a chemically amplified resist composition comprising the same as a photoacid generator, the resist composition, when processed by photolithography using high-energy radiation such as KrF or ArF excimer laser, EB or EUV as the energy source, exhibiting a high sensitivity and reduced acid diffusion and being improved in EL, MEF, and LWR; and a pattern forming process using the resist composition.

The inventors have found that a chemically amplified resist composition comprising a sulfonium compound of specific structure as a photoacid generator has a high sensitivity, is reduced in acid diffusion, improved in many lithography performance factors including EL, MEF, and LWR, and thus best suited for precise micropatterning.

In one aspect, the invention provides a sulfonium compound having the formula (A).

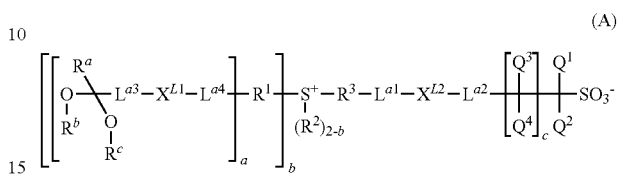

Herein $Q^1$ and $Q^2$ are each independently fluorine or a $C_1$-$C_6$ fluoroalkyl group. $Q^3$ and $Q^4$ are each independently hydrogen, fluorine or a $C_1$-$C_6$ fluoroalkyl group, a is an integer of 1 to 4, b is 1 or 2, and c is an integer of 0 to 3. $L^{a1}$ to $L^{a4}$ are each independently a single bond, ether bond, ester bond, sulfonic acid ester bond, carbonate bond or carbamate bond. $X^{L1}$ and $X^{L2}$ are each independently a single bond or a $C_2$-$C_{40}$ divalent hydrocarbon group which may contain a heteroatom. $R^a$ is hydrogen or a $C_1$-$C_{20}$ monovalent hydrocarbon group which may contain a heteroatom. $R^b$ and $R^c$ are each independently a $C_2$-$C_{40}$ monovalent hydrocarbon group which may contain a heteroatom, $R^b$ and $R^c$ may bond together to form a ring with the oxygen atoms to which they are attached and the intervening carbon atom. $R^1$ is a $C_1$-$C_{50}$ (a+1)-valent hydrocarbon group which may contain a heteroatom. $R^2$ is a $C_1$-$C_{50}$ monovalent hydrocarbon group which may contain a heteroatom. $R^3$ is a $C_1$-$C_{50}$ divalent hydrocarbon group which may contain a heteroatom. In the case of b=1, $R^1$ and $R^2$, or $R^2$ and $R^3$ may bond together to form a ring with the sulfur atom to which they are attached. In the case of b=2, $R^1$ and $R^3$, or two $R^1$ may bond together to form a ring with the sulfur atom to which they are attached.

Preferably the sulfonium compound has the formula (A-1).

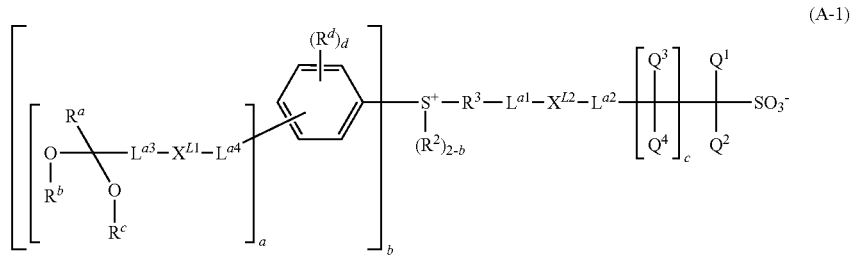

Herein $Q^1$ to $Q^4$, $L^{a1}$ to $L^{a4}$, $X^{L1}$, $X^{L2}$, $R^a$, $R^b$, $R^c$, $R^2$, $R^3$, a, b and c are as defined above, $R^d$ is a $C_1$-$C_{20}$ monovalent hydrocarbon group which may contain a heteroatom, d is an integer of 0 to 4, the sum a+d is 1 to 5, in the case of d≥2, each $R^d$ may be the same or different, and two $R^d$ may bond together to form a ring with the atoms to which they are attached.

More preferably the sulfonium compound has the formula (A-2).

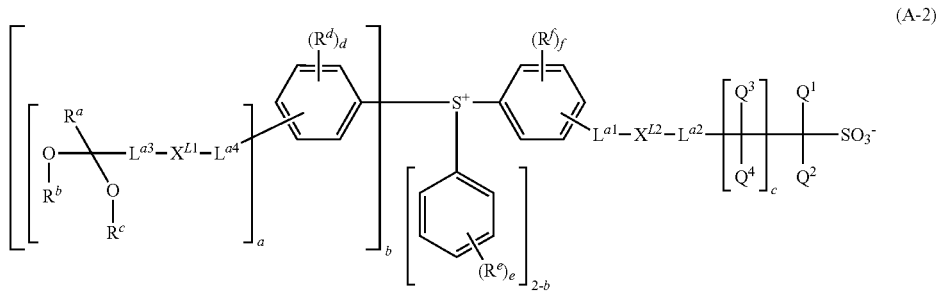

Herein $Q^1$ to $Q^4$, $L^{a1}$ to $L^{a4}$, $X^{L1}$, $X^{L2}$, $R^a$ to $R^d$, a, b, c and d are as defined above, $R^e$ and $R^f$ are each independently a $C_1$-$C_{20}$ monovalent hydrocarbon group which may contain a heteroatom, e is an integer of 0 to 5, f is an integer of 0 to 4, in the case of e≥2, each $R^e$ may be the same or different, and two $R^e$ may bond together to form a ring with the atoms to which they are attached, and in the case of f≥2, each $R^f$ may be the same or different, and two $R^f$ may bond together to form a ring with the atoms to which they are attached.

Even more preferably the sulfonium compound has the formula (A-3).

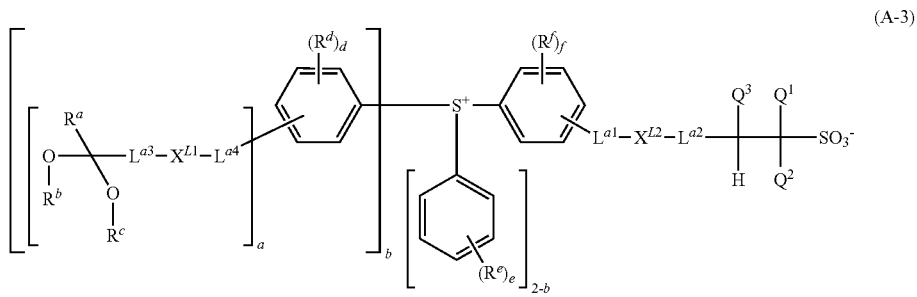

Herein $Q^1$ to $Q^3$, $L^{a1}$ to $L^{a4}$, $X^{L1}$, $X^{L2}$, $R^a$ to $R^f$, a, b, d, e and f are as defined above.

Also provided is a photoacid generator comprising the sulfonium compound defined above.

In another aspect, the invention provides a chemically amplified resist composition comprising the photoacid generator defined above and a base resin comprising recurring units having the formula (a1) or (a2).

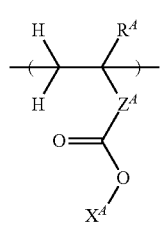

(a1)

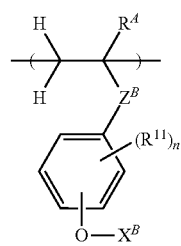

(a2)

Herein $R^A$ is each independently hydrogen, fluorine, methyl or trifluoromethyl, $Z^A$ is a single bond, phenylene, naphthylene or (backbone)-C(=O)—O—$Z^{A1}$—, $Z^{A1}$ is a $C_1$-$C_{10}$ alkanediyl group which may contain a hydroxyl moiety, ether bond, ester bond or lactone ring, or phenylene or naphthylene, $Z^B$ is a single bond or (backbone)-C(=O)—O—, $X^A$ and $X^B$ are each independently an acid labile group, $R^{11}$ is a $C_1$-$C_{20}$ monovalent hydrocarbon group which may contain a heteroatom, and n is an integer of 0 to 4.

In a preferred embodiment, the base resin further comprises recurring units having the formula (b1) or (b2).

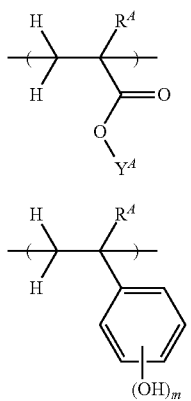

(b1)

(b2)

Herein $R^A$ is each independently hydrogen, fluorine, methyl or trifluoromethyl, $Y^A$ is hydrogen or a polar group containing at least one structure selected from the group consisting of hydroxyl, cyano, carbonyl, carboxyl, ether bond, ester bond, sulfonic acid ester bond, carbonate bond, lactone ring, sultone ring and carboxylic anhydride, and m is 1 or 2.

In a preferred embodiment, the base resin further comprises recurring units of at least one type selected from recurring units having the formulae (c1) to (c3).

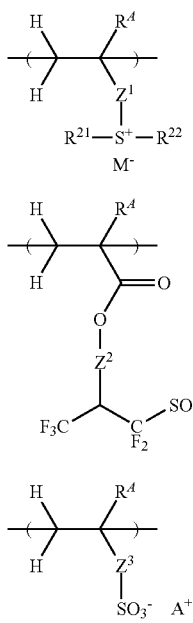

(c1)

(c2)

(c3)

Herein $R^A$ is each independently hydrogen, fluorine, methyl or trifluoromethyl. $Z^1$ is a single bond, phenylene, —O—$Z^{11}$—, —C(=O)—O—$Z^{11}$— or —C(=O)—NH—$Z^{11}$—, wherein $Z^{11}$ is a $C_1$-$C_{20}$ alkanediyl group, $C_2$-$C_{20}$ alkenediyl group or phenylene group, which may contain a carbonyl moiety, ester bond, ether bond or hydroxyl moiety. $Z^2$ is a single bond or —$Z^{21}$—C(=O)—O—, wherein $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$— or —C(=O)—NH—$Z^{31}$—, wherein $Z^{31}$ is a $C_1$-$C_6$ alkanediyl group, $C_2$-$C_6$ alkenediyl group or phenylene group, which may contain a carbonyl moiety, ester bond, ether bond or hydroxyl moiety. $R^{21}$ and $R^{22}$ are each independently a $C_1$-$C_{20}$ monovalent hydrocarbon group which may contain a heteroatom, $R^{21}$ and $R^{22}$ may bond together to form a ring with the sulfur atom to which they are attached. $M^-$ is a non-nucleophilic counter ion. $A^+$ is an ammonium, sulfonium or iodonium cation.

The resist composition may further comprise an organic solvent.

The resist composition may further comprise a photoacid generator other than the photoacid generator defined above.

Preferably, the other photoacid generator has the formula (1) or (2).

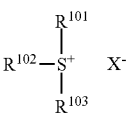

(1)

Herein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the following formulae (1A) to (1D):

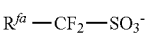

(1A)

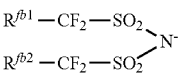

(1B)

(1C)

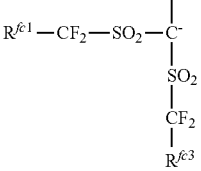

(1D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom, $$R^{201}-S^+-R^{203}-L^A-\underset{\underset{X^d}{|}}{\overset{\overset{X^c}{|}}{C}}-\underset{\underset{X^b}{|}}{\overset{\overset{X^a}{|}}{C}}-SO_3^- \quad (2)$$

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^a$, $X^b$, $X^c$ and $X^d$ are each independently hydrogen, fluorine or trifluoromethyl, at least one of $X^a$, $X^b$, $X^c$ and $X^d$ being fluorine or trifluoromethyl.

The resist composition may further comprise a compound having the formula (3) or (4).

$$R^{q1}-SO_3^-Mq^+ \quad (3)$$

$$R^{q2}-CO_2^-Mq^+ \quad (4)$$

Herein $R^{q1}$ is hydrogen or a $C_1$-$C_{40}$ monovalent hydrocarbon group which may contain a heteroatom, exclusive of the group wherein hydrogen bonded to the carbon atom at α-position relative to the sulfo group is substituted by fluorine or fluoroalkyl, $R^{q2}$ is hydrogen or a $C_1$-$C_{40}$ monovalent hydrocarbon group which may contain a heteroatom, and $Mq^+$ is an onium cation.

The resist composition may further comprise an amine compound.

The resist composition may further comprise a surfactant which is insoluble or substantially insoluble in water and soluble in alkaline developer, and/or a surfactant which is insoluble or substantially insoluble in water and alkaline developer.

In a further aspect, the invention provides a pattern forming process comprising the steps of applying the chemically amplified resist composition defined above to form a resist film on a substrate, exposing a selected region of the resist film to KrF excimer laser, ArF excimer laser, EB or EUV, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

The organic solvent is typically selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens.

In a preferred embodiment, a protective film is formed on the resist film prior to the exposure step, and immersion lithography is carried out while the liquid is held between the protective film and the projection lens.

Advantageous Effects of Invention

The inventive sulfonium compound is useful as a PAG in a chemically amplified resist composition. When the chemically amplified resist composition comprising the inventive sulfonium compound is processed by photolithography, a resist pattern with improved EL, MEF, and LWR is formed, because the extent of acid diffusion is significantly controlled.

DESCRIPTION OF EMBODIMENTS

Figure 1:
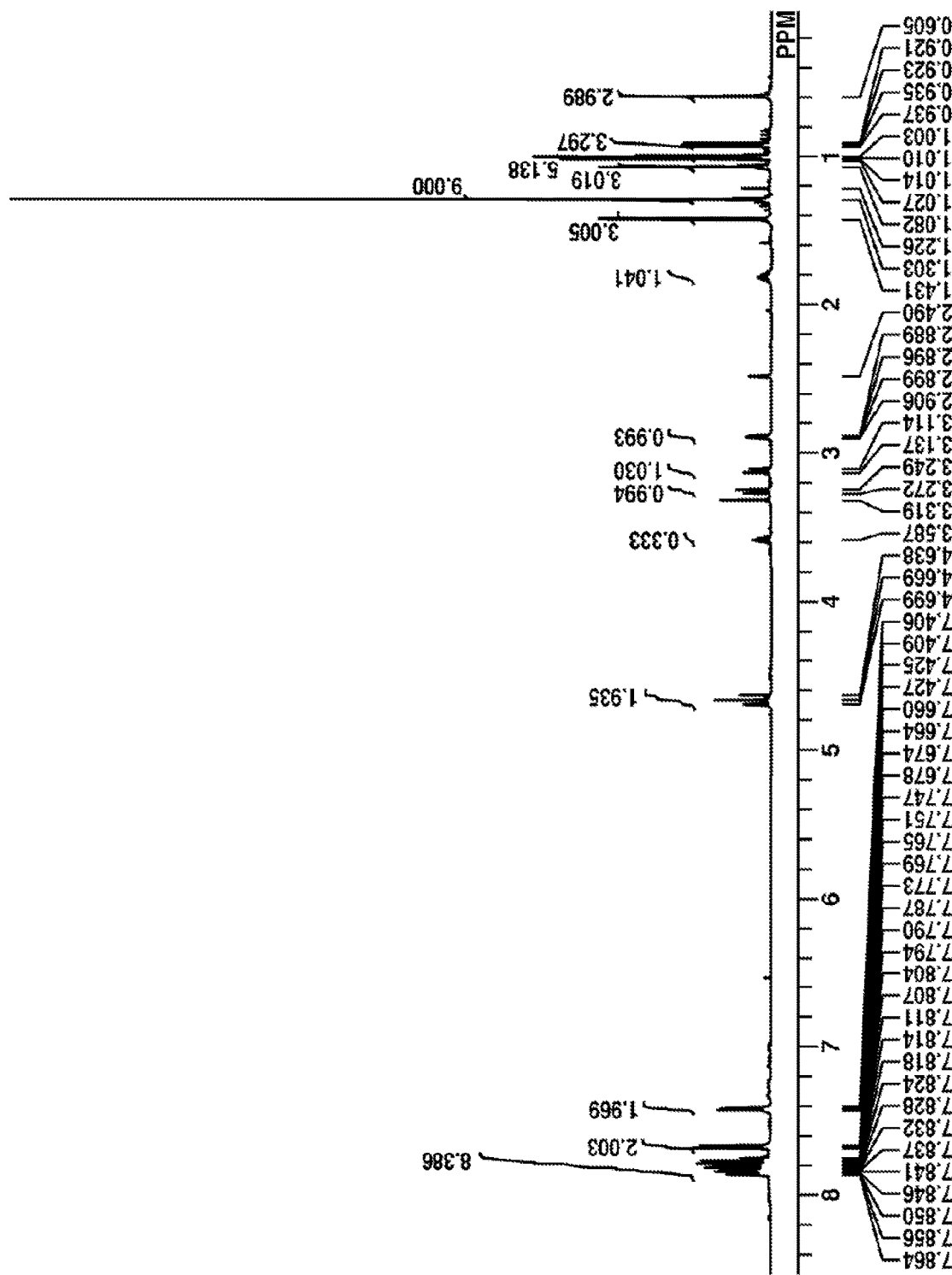
FIG. 1 is a diagram showing the $^1$H-NMR spectrum of PAG-1 in Example 1-1-6.

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac for acetyl, and the broken line designates a valence bond.

The abbreviations and acronyms have the following meaning.

EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
EL: exposure latitude
LWR: line width roughness
MEF: mask error factor
CDU: critical dimension uniformity
DOF: depth of focus Sulfonium Compound The invention provides a sulfonium compound having the formula (A).

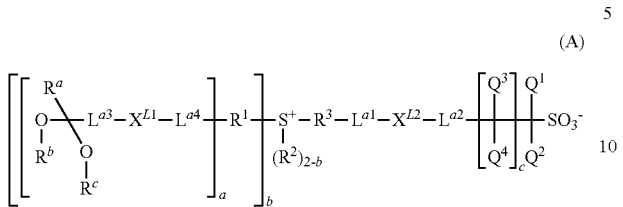
(A)

In formula (A), $Q^1$ and $Q^2$ are each independently fluorine or a $C_1$-$C_6$ fluoroalkyl group. $Q^3$ and $Q^4$ are each independently hydrogen, fluorine or a $C_1$-$C_6$ fluoroalkyl group.

In formula (A), a is an integer of 1 to 4, preferably 1; b is 1 or 2; c is an integer of 0 to 3, preferably 1.

In formula (A), $L^{a1}$ to $L^{a4}$ are each independently a single bond, ether bond, ester bond, sulfonic acid ester bond, carbonate bond or carbamate bond. Preferably, $L^{a1}$ is a single bond, ether bond or ester bond, more preferably a single bond; $L^{a2}$ is a single bond, ether bond or ester bond, more preferably an ether bond; $L^{a3}$ is a single bond, ether bond or ester bond, more preferably a single bond; and $L^{a4}$ is a single bond, ether bond or ester bond, more preferably a single bond.

In formula (A), $X^{L1}$ and $X^{L2}$ are each independently a single bond or a $C_2$-$C_{40}$ divalent hydrocarbon group which may contain a heteroatom. The divalent hydrocarbon group may be straight, branched or cyclic and examples thereof include alkanediyl groups and divalent saturated cyclic hydrocarbon groups. Typical of the heteroatom are oxygen, nitrogen and sulfur. Preferably $X^{L1}$ and $X^{L2}$ each are a single bond.

Preferred examples of the $C_2$-$C_{40}$ divalent hydrocarbon group represented by $X^{L1}$ and $X^{L2}$ are shown below. In the following formulae, * at one end designates a bond to $L^{a1}$ or $L^{a2}$, and $L^{a3}$ or $L^{a4}$.

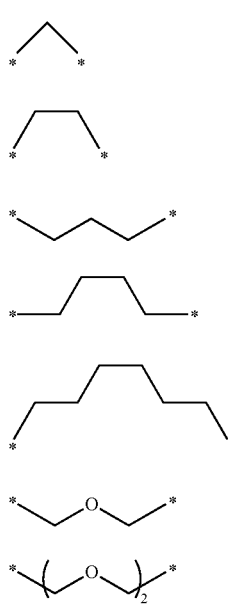

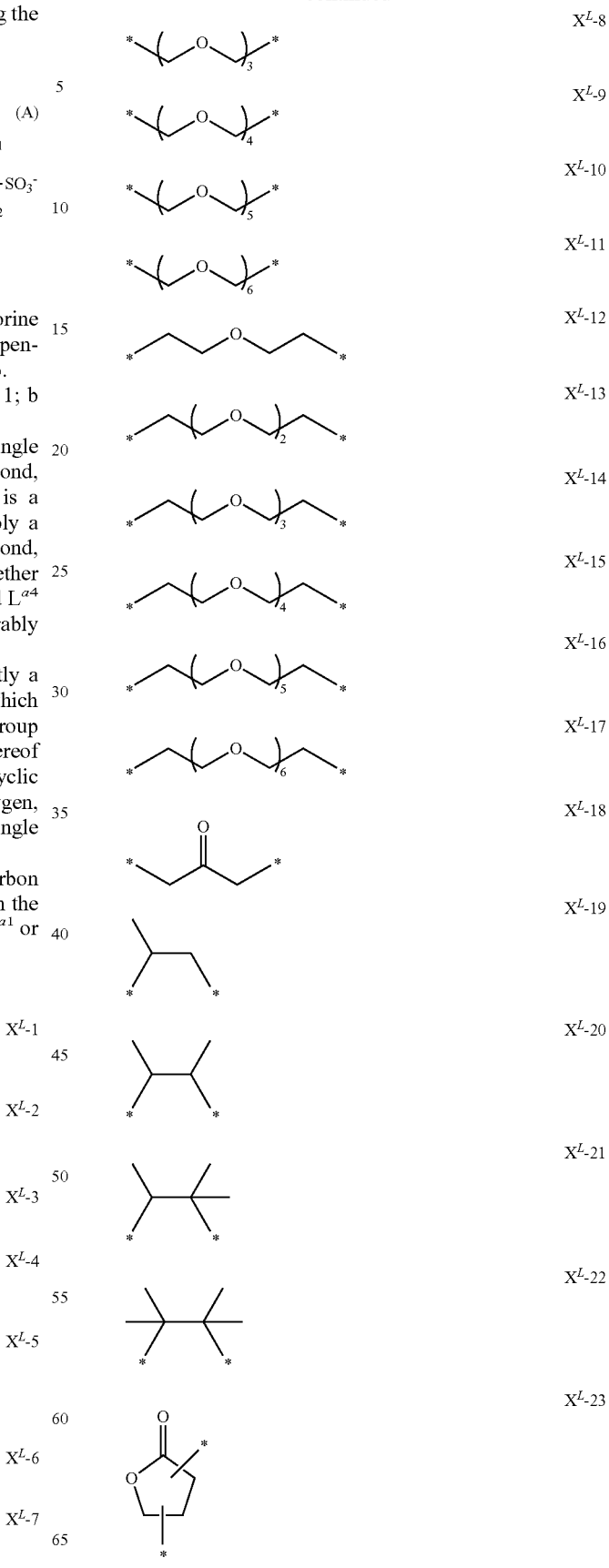

-continued
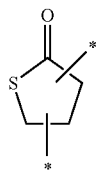 X$^L$-24
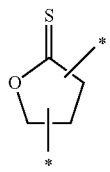 X$^L$-25
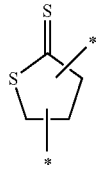 X$^L$-26
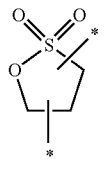 X$^L$-27
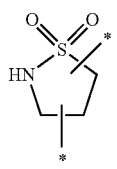 X$^L$-28
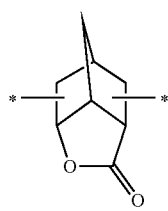 X$^L$-29
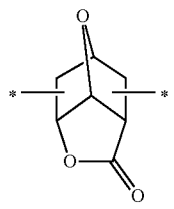 X$^L$-30
 X$^L$-31
-continued
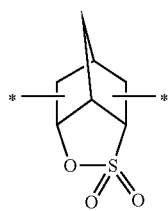 X$^L$-32
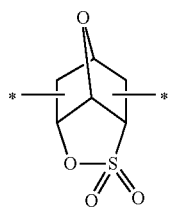 X$^L$-33
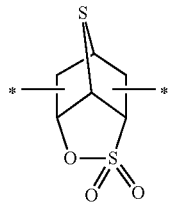 X$^L$-34
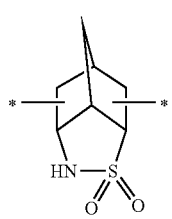 X$^L$-35
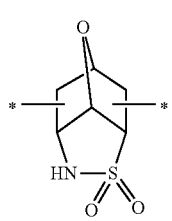 X$^L$-36
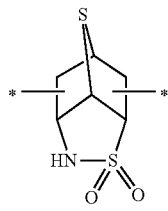 X$^L$-37
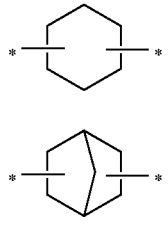 X$^L$-38
X$^L$-39

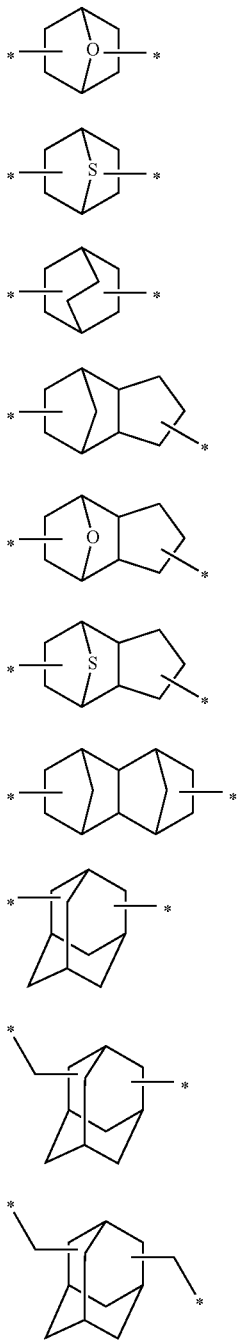

X$^L$-40

X$^L$-41

X$^L$-42

X$^L$-43

X$^L$-44

X$^L$-45

X$^L$-46

X$^L$-47

X$^L$-48

X$^L$-49

Of these, structures X$^L$-1 to X$^L$-22 and X$^L$-47 to X$^L$-49 are preferred, with structures X$^L$-1 to X$^L$-17 being more preferred.

In formula (A), R$^a$ is hydrogen or a C$_1$-C$_{20}$ monovalent hydrocarbon group which may contain a heteroatom. The monovalent hydrocarbon group may be straight, branched or cyclic. Examples include alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and aryl groups such as phenyl, naphthyl and anthracenyl. In the monovalent hydrocarbon group, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, carbamate bond, amide bond, imide bond, lactone ring, sultone ring, thiolactone ring, lactam ring, sultam ring, carboxylic anhydride (—C(═O)—O—C(═O)—), or haloalkyl moiety. Inter alia, R$^a$ is preferably hydrogen, C$_1$-C$_6$ alkyl or C$_6$-C$_{10}$ aryl, more preferably hydrogen or methyl, most preferably methyl.

In formula (A), R$^b$ and R$^c$ are each independently a C$_2$-C$_{40}$ monovalent hydrocarbon group which may contain a heteroatom, R$^b$ and R$^c$ may bond together to form a ring with the oxygen atoms to which they are attached and the intervening carbon atom. The monovalent hydrocarbon group may be straight, branched or cyclic and examples thereof are as exemplified above for R$^a$. When some hydrogen in the monovalent hydrocarbon group is substituted by halogen, fluorine substitution is preferred.

Where R$^b$ and R$^c$ do not bond together to form a ring structure, each forms an acyclic acetal structure with the adjacent oxygen atom. Where R$^b$ and R$^c$ bond together to form a ring, they form a cyclic acetal structure with the adjacent oxygen atoms. Of these cases, the formation of a cyclic acetal structure is preferred in view of the stability of acetal structure. Of the cyclic acetal structures, 5-, 6- and 7-membered ring acetal structures are more preferred.

Examples of the acyclic or cyclic acetal structure are shown below, but not limited thereto. Herein R$^a$ is as defined above, and the broken line designates a valence bond to L$^{a3}$.

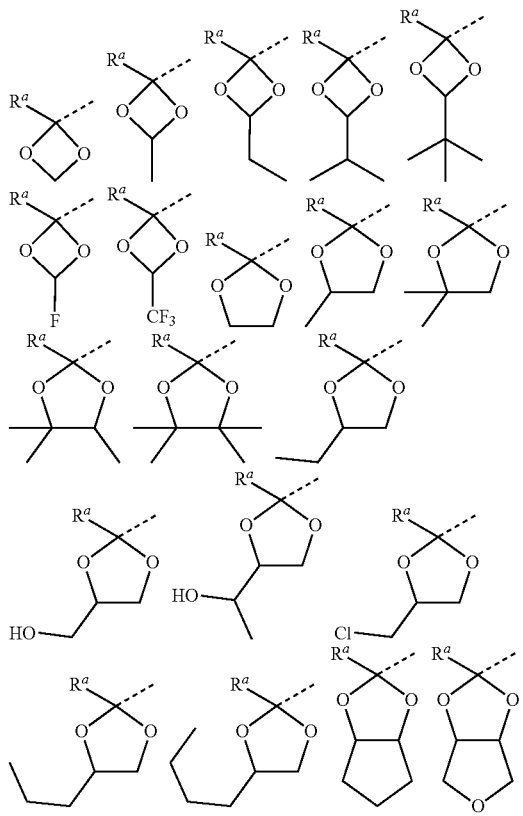

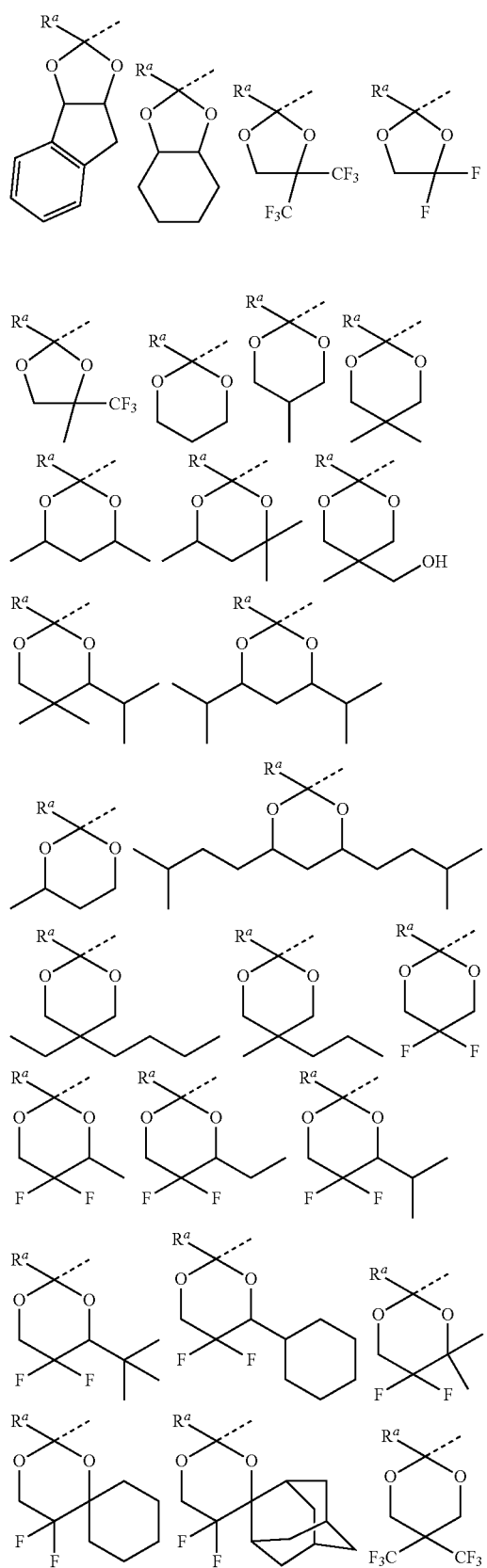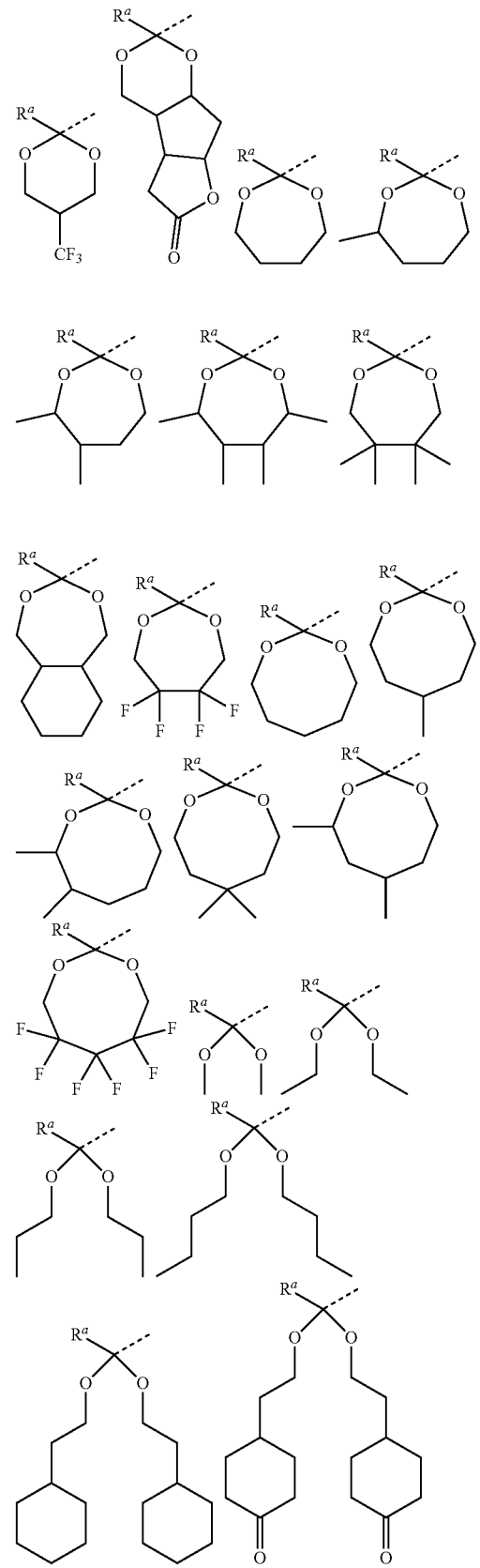

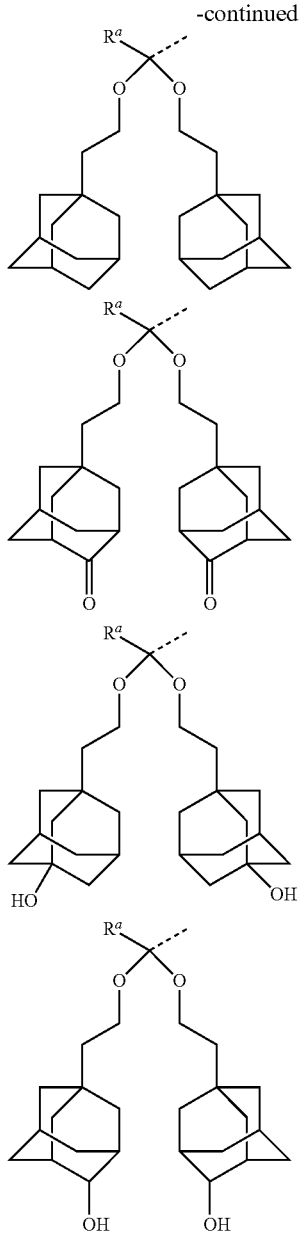
In formula (A), $R^1$ is a $C_1$-$C_{50}$ (a+1)-valent hydrocarbon group which may contain a heteroatom, preferably of $C_1$-$C_{20}$.
The hydrocarbon group $R^1$ may be straight, branched or cyclic, and aliphatic or aromatic. Exemplary, non-limiting structures are shown below. In the formulae, the broken line designates a valence bond to $S^+$ or $L^{a4}$.
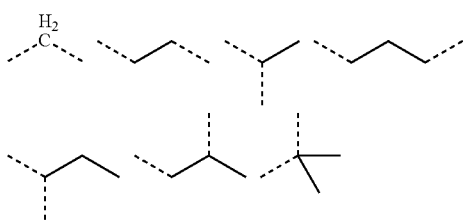
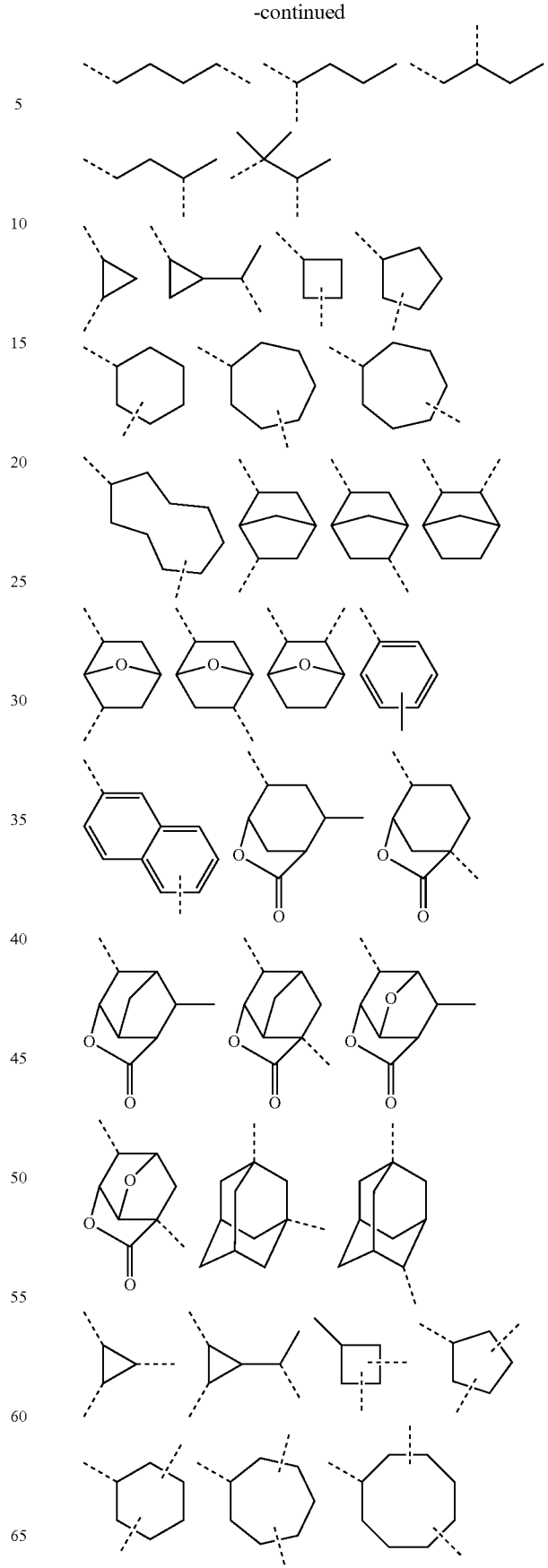

-continued

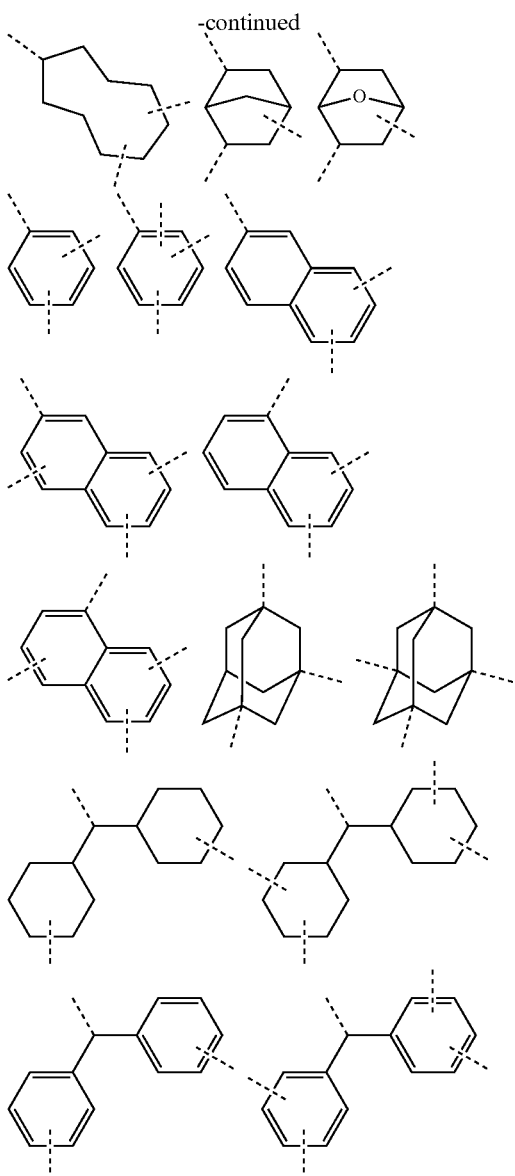

R[1] is preferably an aromatic hydrocarbon group, more preferably a group derived from benzene or naphthalene, most preferably a group derived from benzene.

In formula (A), R[2] is a $C_1$-$C_{50}$ monovalent hydrocarbon group which may contain a heteroatom, preferably of $C_1$-$C_{20}$. The monovalent hydrocarbon group maybe straight, branched or cyclic. Examples thereof include monovalent aliphatic hydrocarbon groups such as alkyl and alkenyl groups and monovalent aromatic hydrocarbon groups such as aryl and aralkyl groups.

Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl and cyclohexenyl.

Suitable aryl groups include phenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; naphthyl; alkylnaphthyl groups such as methylnaphthyl and ethylnaphthyl; and dialkylnaphthyl groups such as dimethylnaphthyl and diethylnaphthyl. Suitable aralkyl groups include benzyl, 1-phenylethyl and 2-phenylethyl.

In these hydrocarbon groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride, or haloalkyl moiety.

Examples of the heteroatom-containing monovalent aliphatic hydrocarbon group include oxo-containing alkyl groups such as 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Examples of the heteroatom-containing monovalent aromatic hydrocarbon group include heteroaryl groups such as thienyl; hydroxyphenyl groups such as 4-hydroxyphenyl; fluorinated phenyl groups such as fluorophenyl and difluorophenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkoxynaphthyl groups such as methoxynaphthyl, ethoxynaphthyl, n-propoxynaphthyl, and n-butoxynaphthyl; dialkoxynaphthyl groups such as dimethoxynaphthyl and diethoxynaphthyl; and aryloxoalkyl groups such as 2-phenyl-2-oxoethyl, 2-(1-naphthyl)-2-oxoethyl, and 2-(2-naphthyl)-2-oxoethyl.

Of these, R[2] is preferably a monovalent aromatic hydrocarbon group which may contain a heteroatom, more preferably an aryl group which may contain a heteroatom, and even more preferably phenyl, alkylphenyl or fluorinated phenyl.

In formula (A), R[3] is a $C_1$-$C_{50}$ divalent hydrocarbon group which may contain a heteroatom, preferably of $C_1$-$C_{20}$. The divalent hydrocarbon group maybe straight, branched or cyclic. Examples thereof include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; divalent saturated cyclic hydrocarbon groups such as cyclopentanediyl, cyclohexanediyl, norbornanediyl, and adamantanediyl; and divalent aromatic hydrocarbon groups such as phenylene and naphthylene. Also included are the foregoing groups in which some hydrogen is substituted by an alkyl group such as methyl, ethyl, propyl, n-butyl or tert-butyl, or in which some hydrogen is substituted by a moiety containing a heteroatom such as oxygen, sulfur, nitrogen or halogen, so that the group may contain a hydroxyl, cyano, carbonyl, ether bond, ester bond, sulfonic acid ester bond, carbonate bond, lactone ring, sultone ring, carboxylic anhydride or haloalkyl moiety. Of these, R[3] is preferably a divalent aromatic hydrocarbon group, more preferably phenylene or a phenylene group substituted with an alkyl moiety or heteroatom-containing moiety.

In formula (A), any two of R[1], R[2] and R[3] may bond together to form a ring with the sulfur atom to which they are attached. Examples of the sulfonium cation moiety in this embodiment include the following.

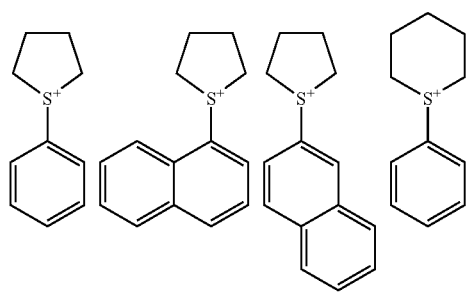
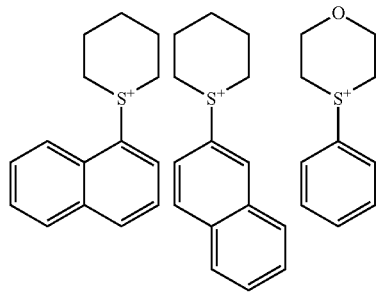
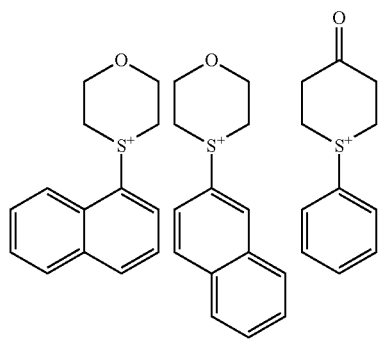
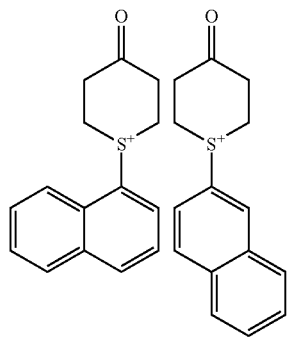
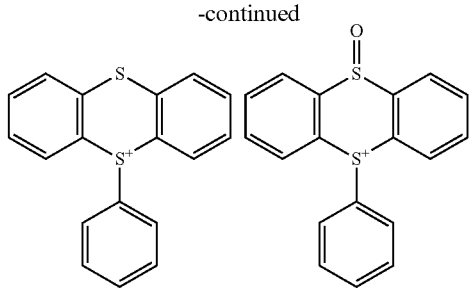
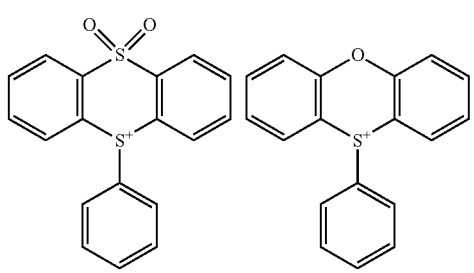
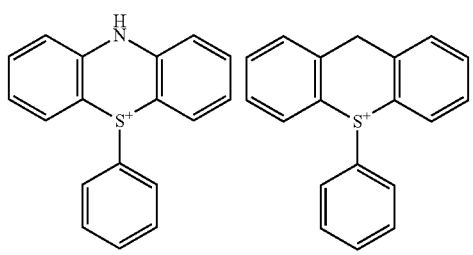
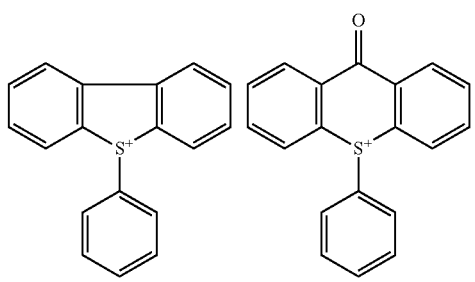
Of the sulfonium compounds having formula (A), those compounds having the formula (A-1) are preferred.
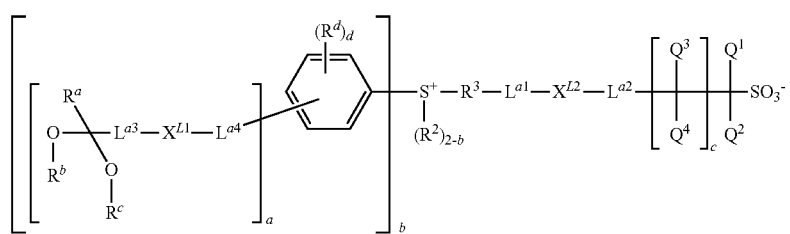

Herein $Q^1$ to $Q^4$, $L^{a1}$ to $L^{a4}$, $X^{L1}$, $X^{L2}$, $R^a$, $R^b$, $R^c$, $R^2$, $R^3$, a, b and c are as defined above. $R^d$ is a $C_1$-$C_{20}$ monovalent hydrocarbon group which may contain a heteroatom, d is an integer of 0 to 4, and the sum a+d is 1 to 5. In the case of d≥2, each $R^d$ may be the same or different, and two $R^d$ may bond together to form a ring with the atoms to which they are attached.

Of the sulfonium compounds having formula (A-1), those compounds having the formula (A-2) are more preferred.

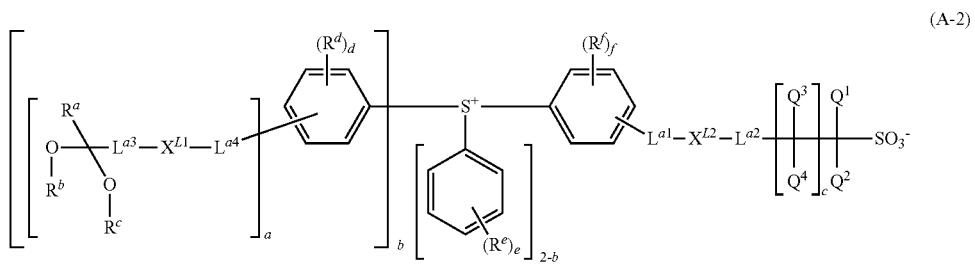

(A-2)

Herein $Q^1$ to $Q^4$, $L^{a1}$ to $L^{a4}$, $X^{L1}$, $X^{L2}$, $R^a$ to $R^d$, a, b, c and d are as defined above. $R^e$ and $R^f$ are each independently a $C_1$-$C_{20}$ monovalent hydrocarbon group which may contain a heteroatom, e is an integer of 0 to 5, and f is an integer of 0 to 4. In the case of e≥2, each $R^e$ may be the same or different, and two $R^e$ may bond together to form a ring with the atoms to which they are attached. In the case of f≥2, each $R^f$ may be the same or different, and two $R^f$ may bond together to form a ring with the atoms to which they are attached.

Of the sulfonium compounds having formula (A-2), those compounds having the formula (A-3) are preferred.

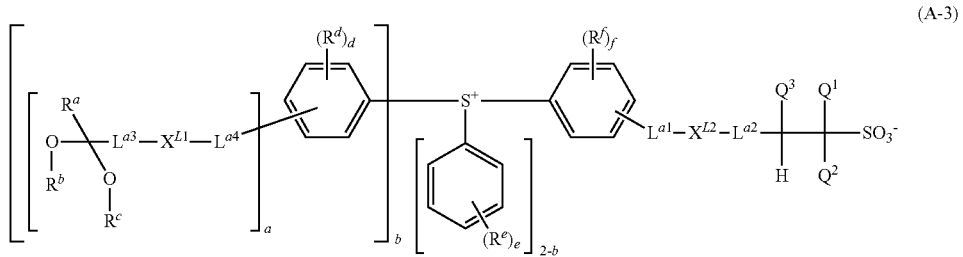

(A-3)

Herein $Q^1$ to $Q^3$, $L^{a1}$ to $L^{a4}$, $X^{L1}$, $X^{L2}$, $R^a$ to $R^f$, a, b, d, e and f are as defined above.

Examples of the sulfonium compound having formula (A) are shown below, but not limited thereto. Herein $Q^3$ is as defined above.

-continued

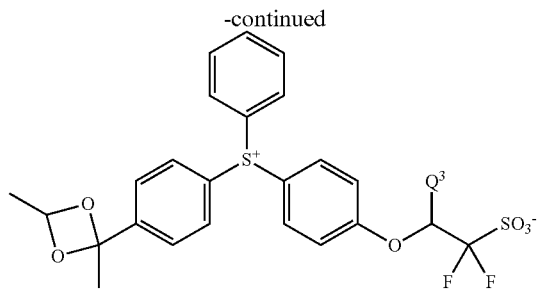

-continued

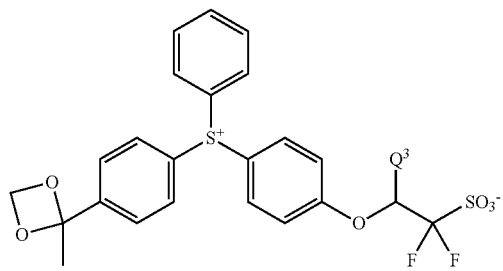

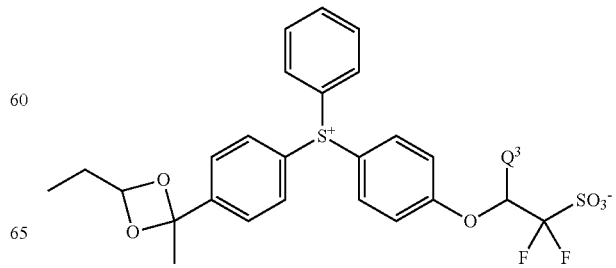

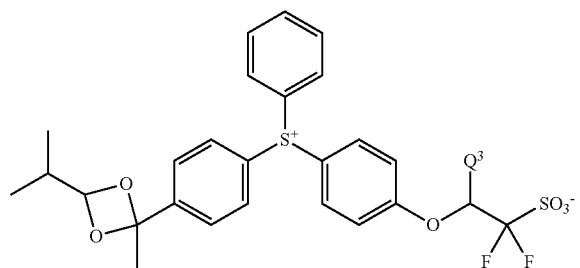
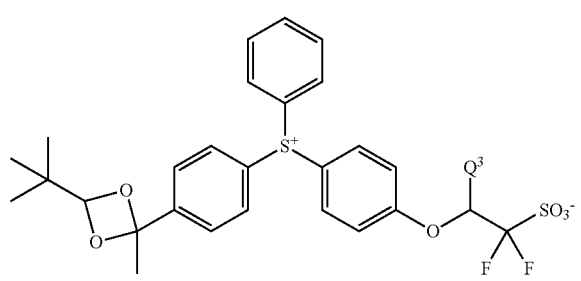
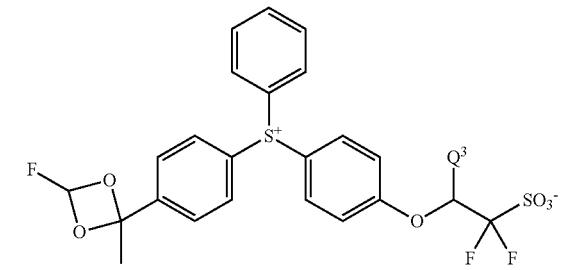
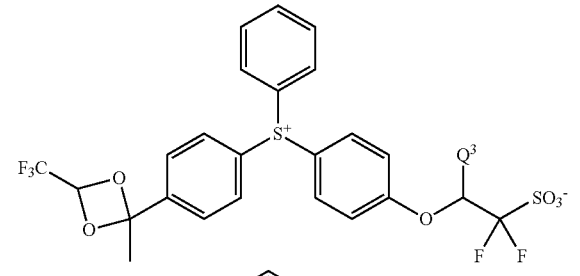
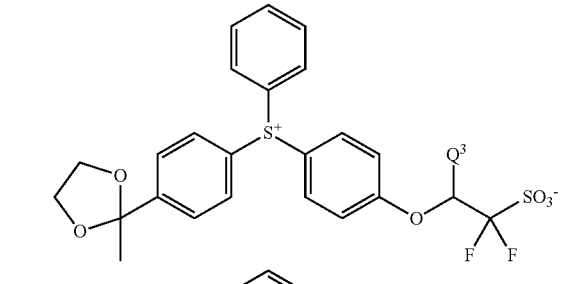
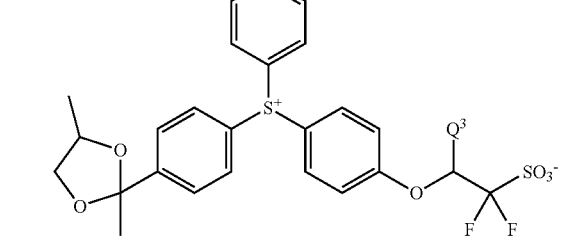
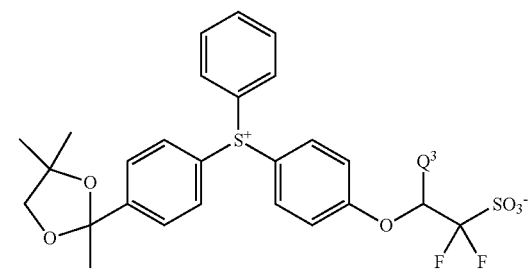
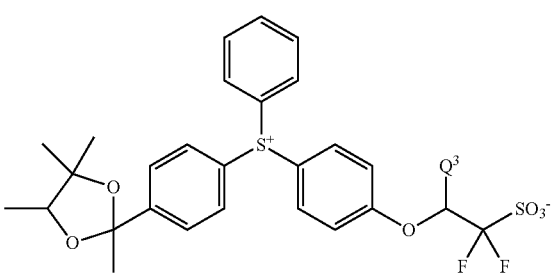
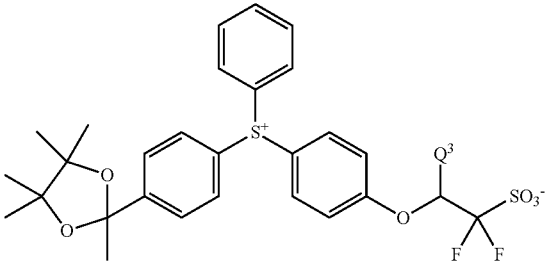
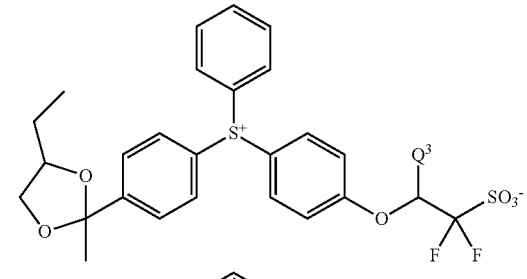
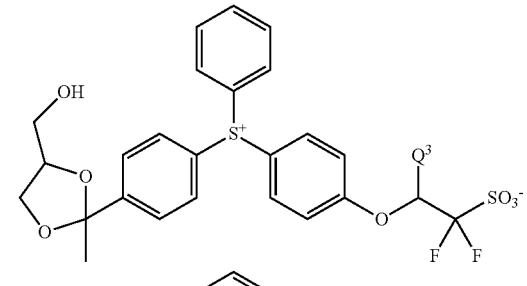
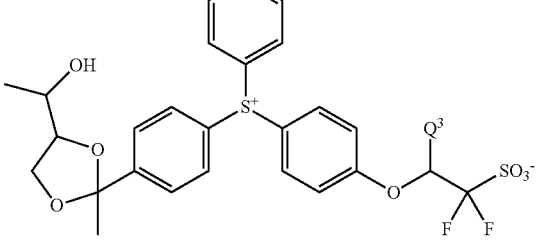

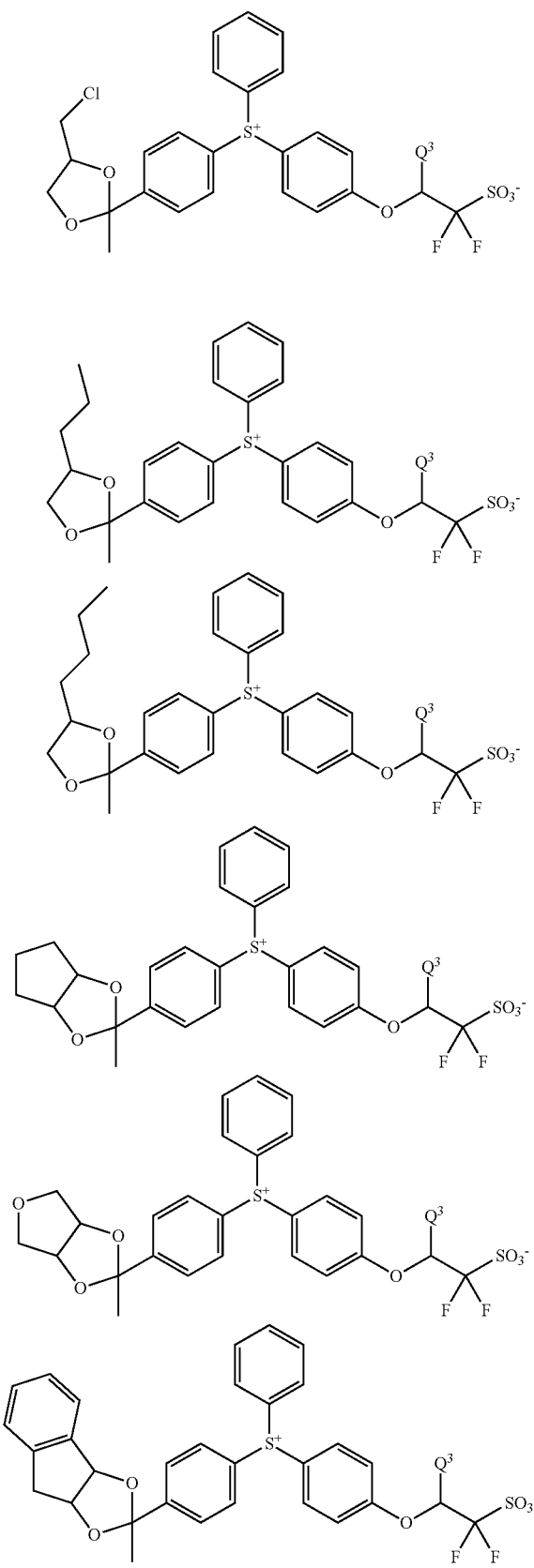
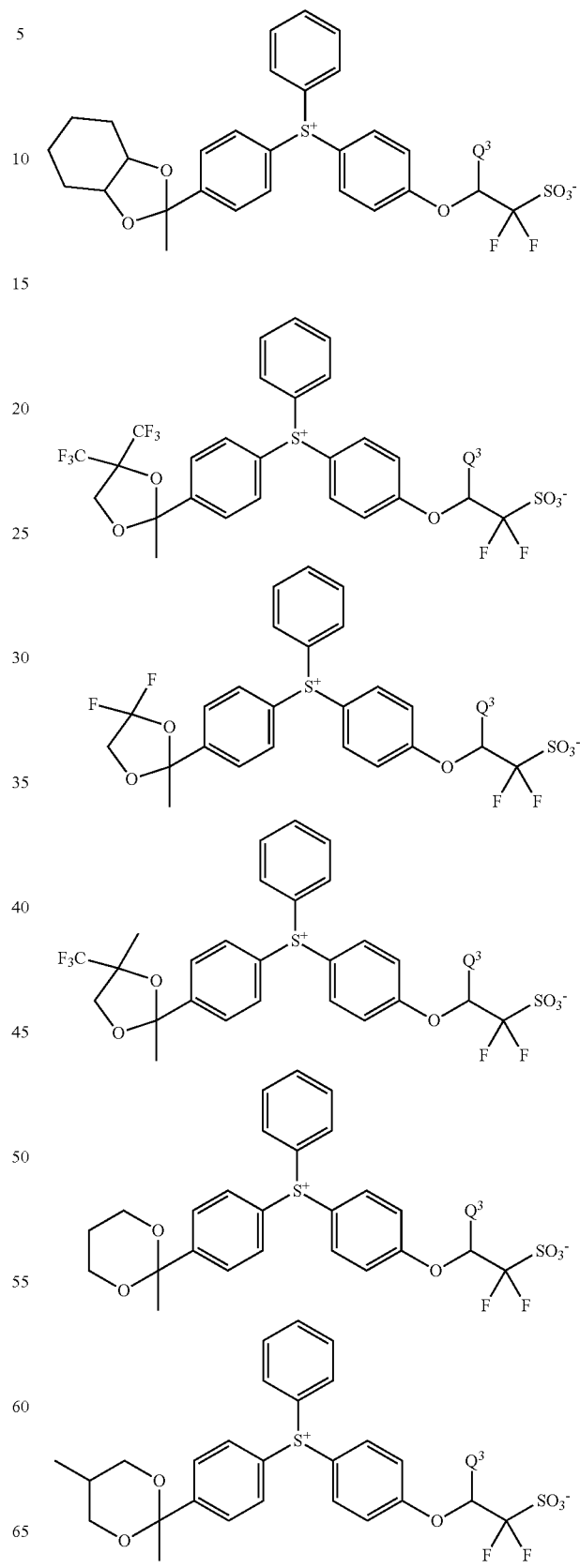

31
-continued
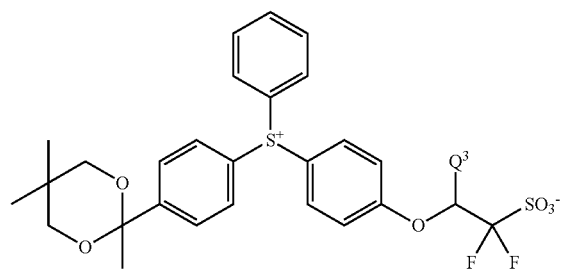
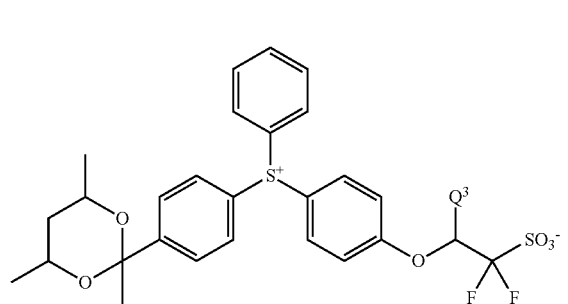
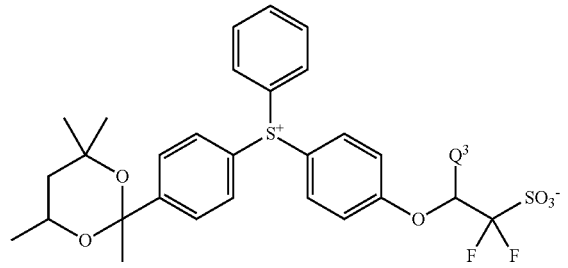
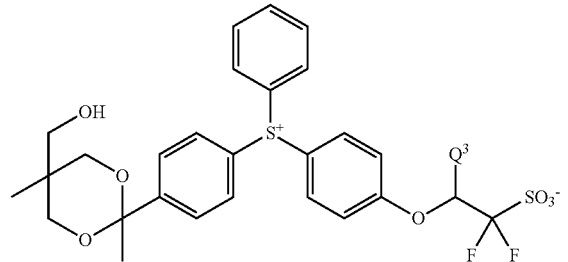
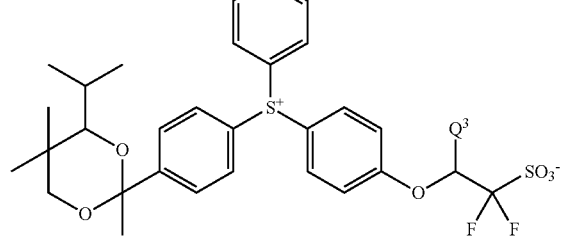
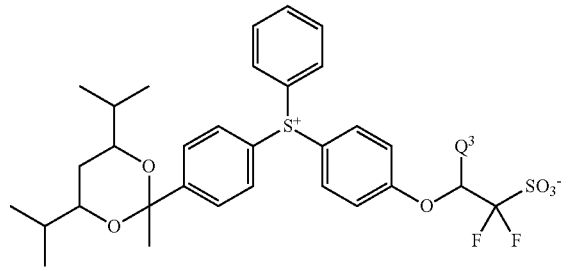
32
-continued
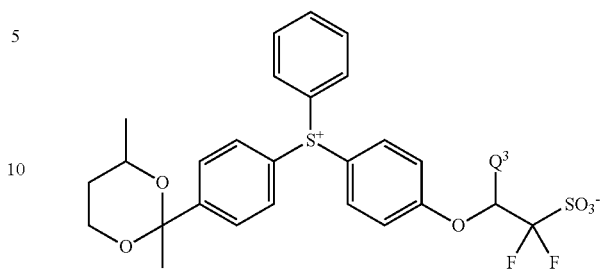
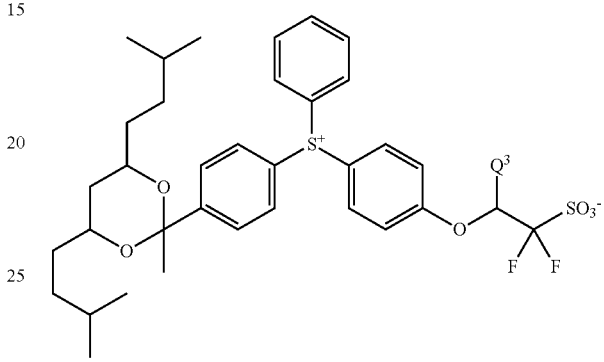
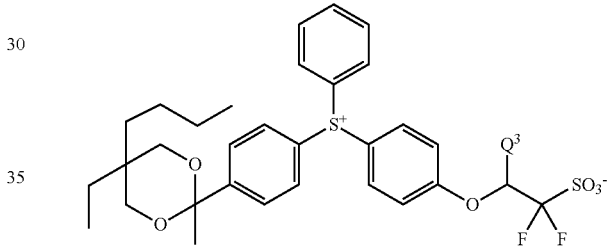
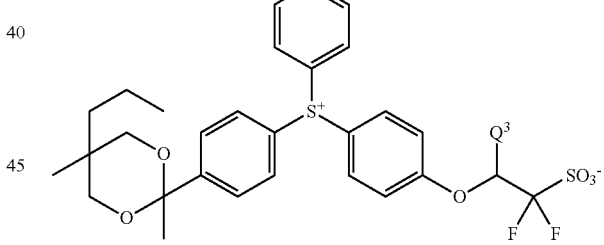
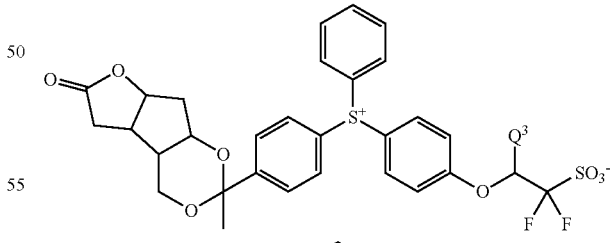
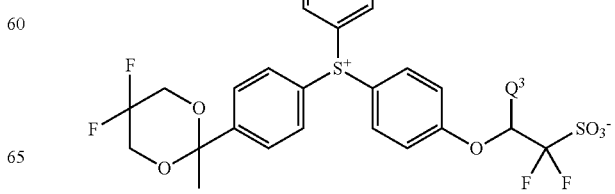

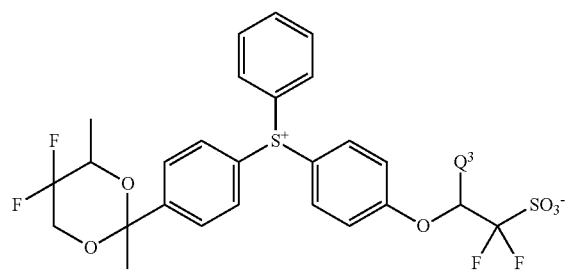
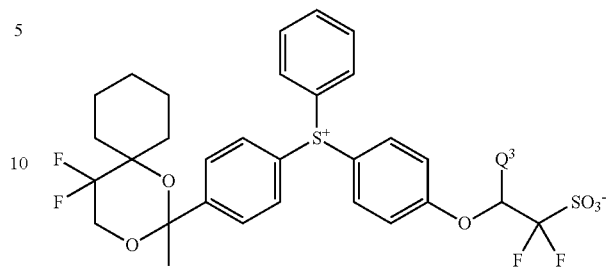
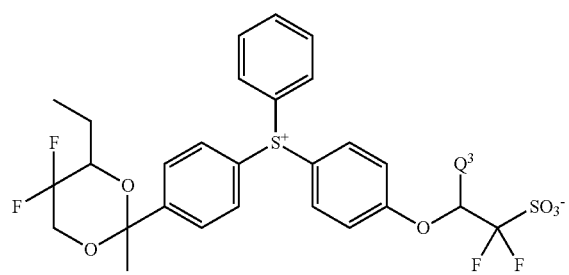
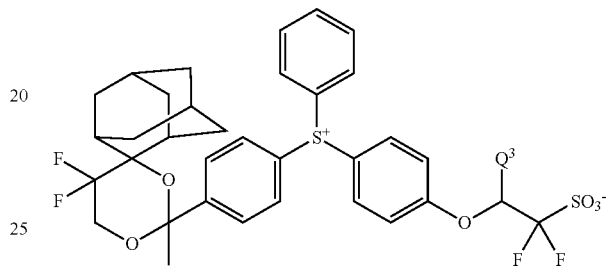
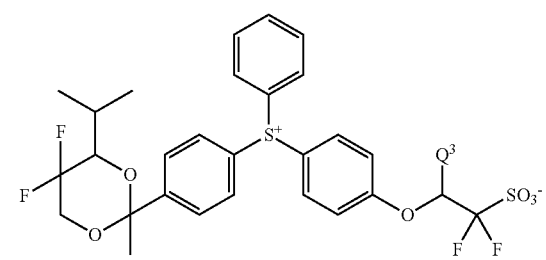
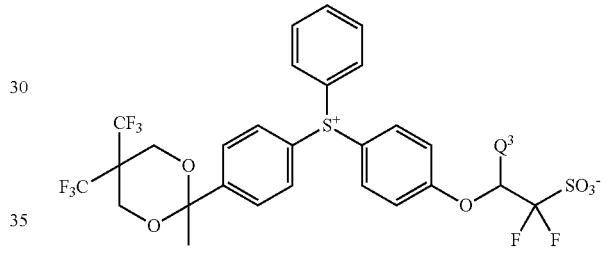
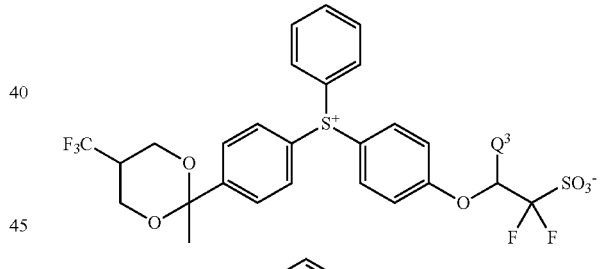
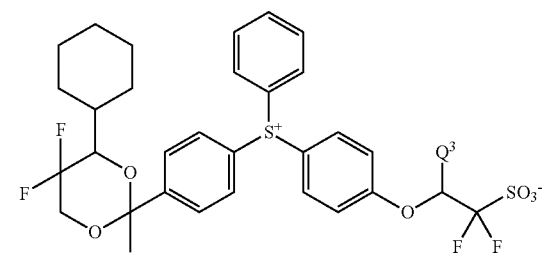
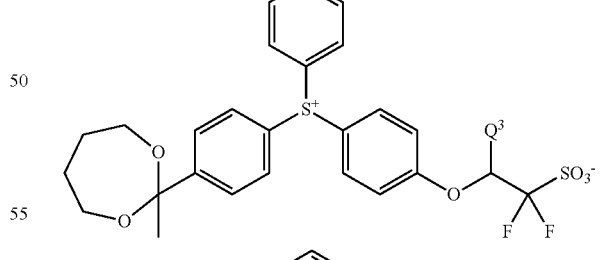
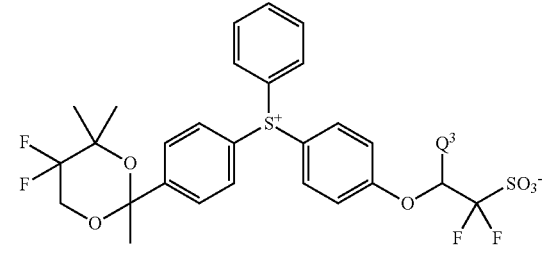
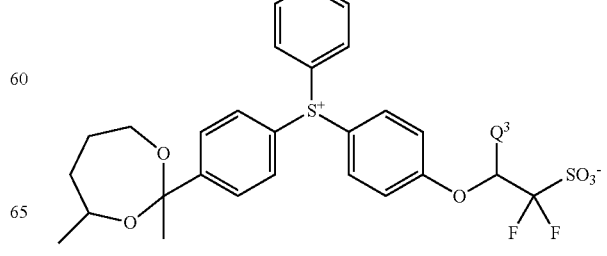

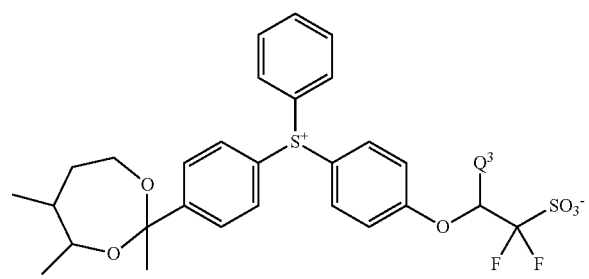
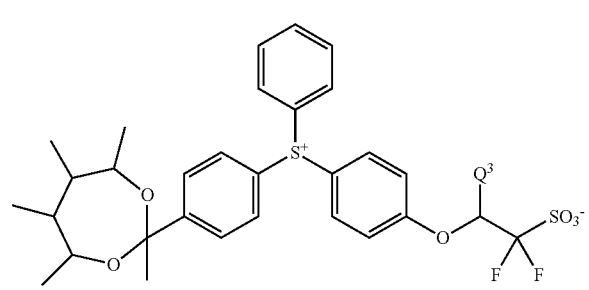
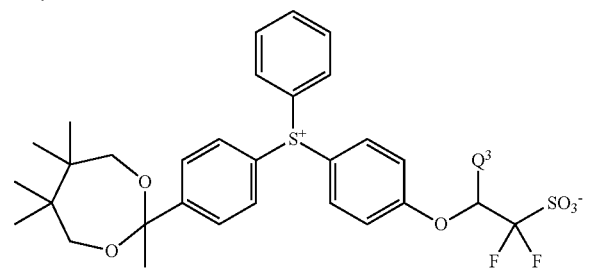
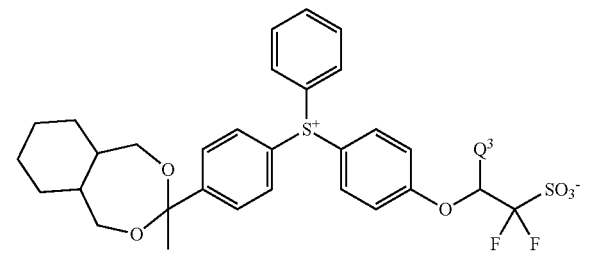
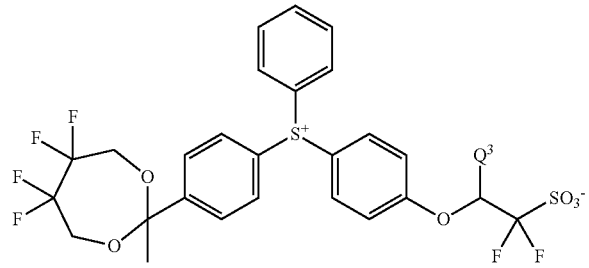
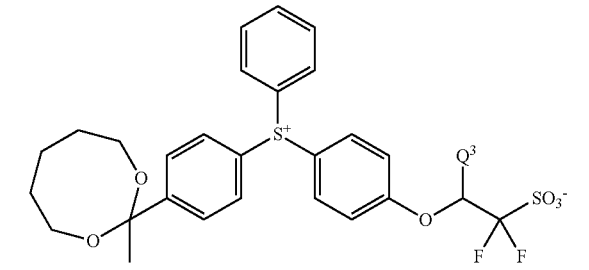
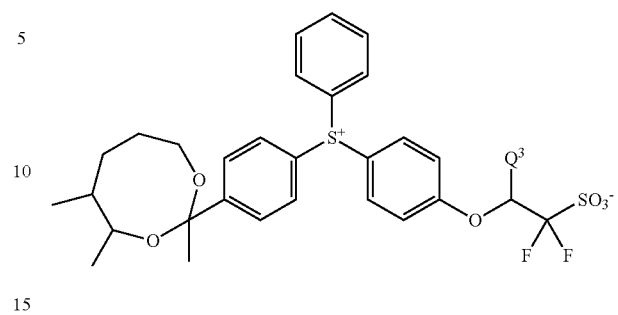
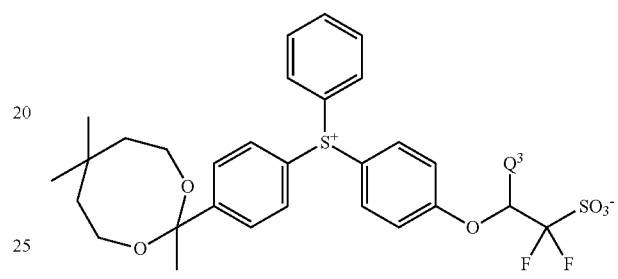
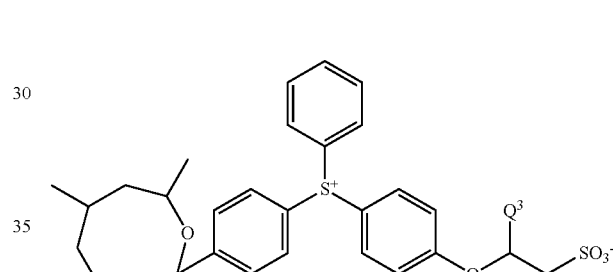
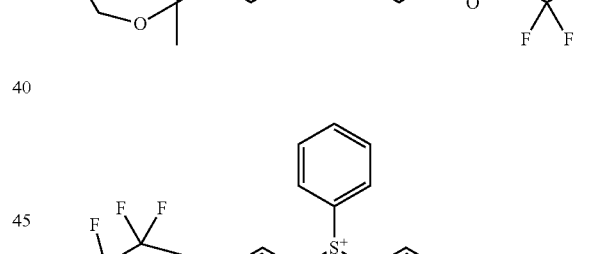
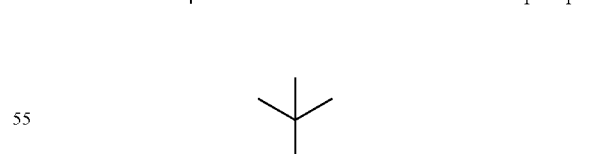

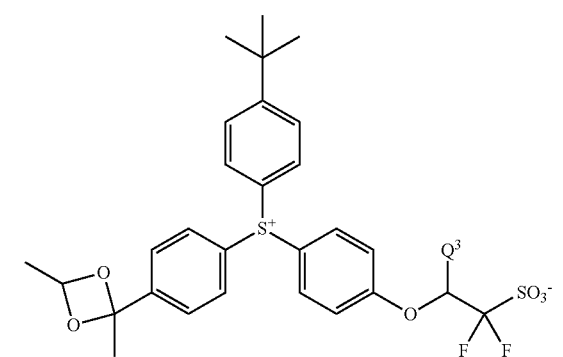
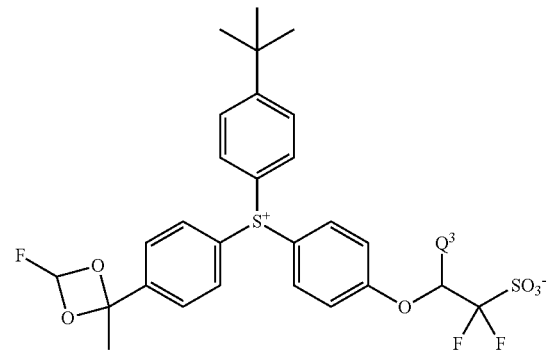
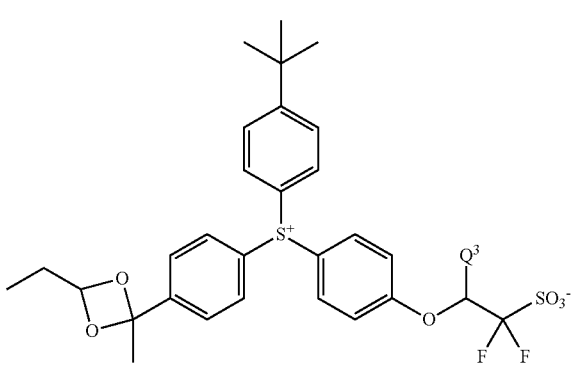
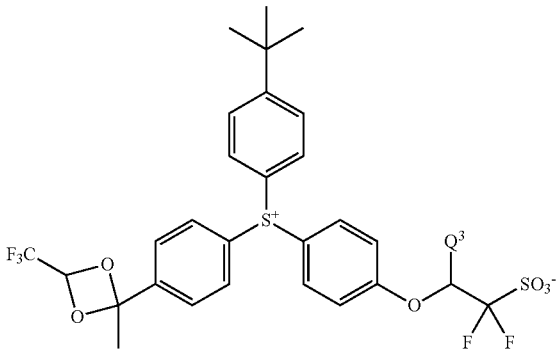
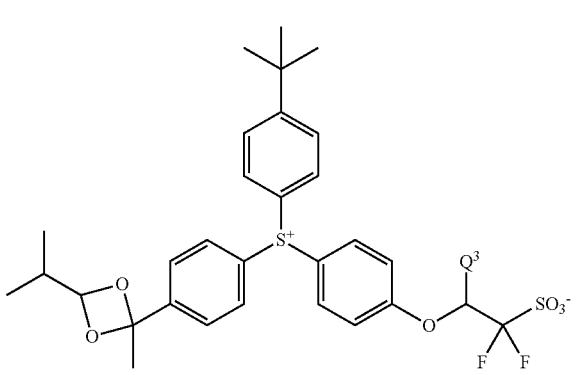
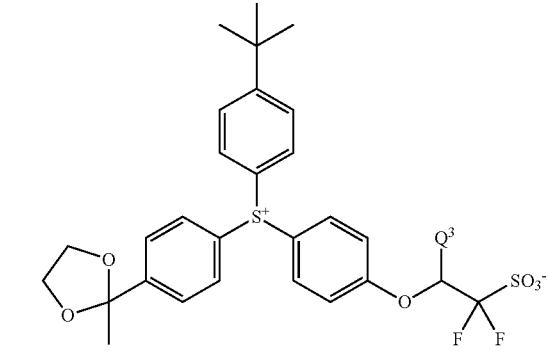
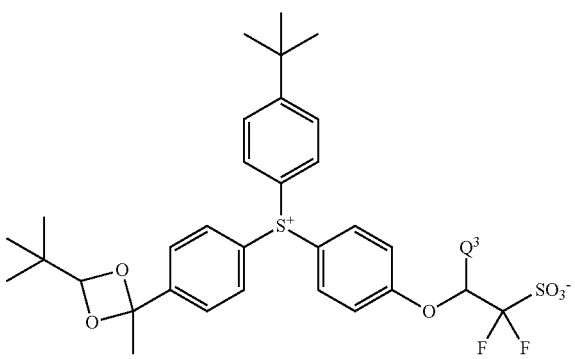
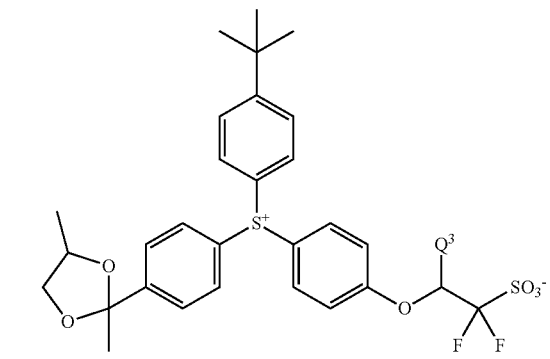

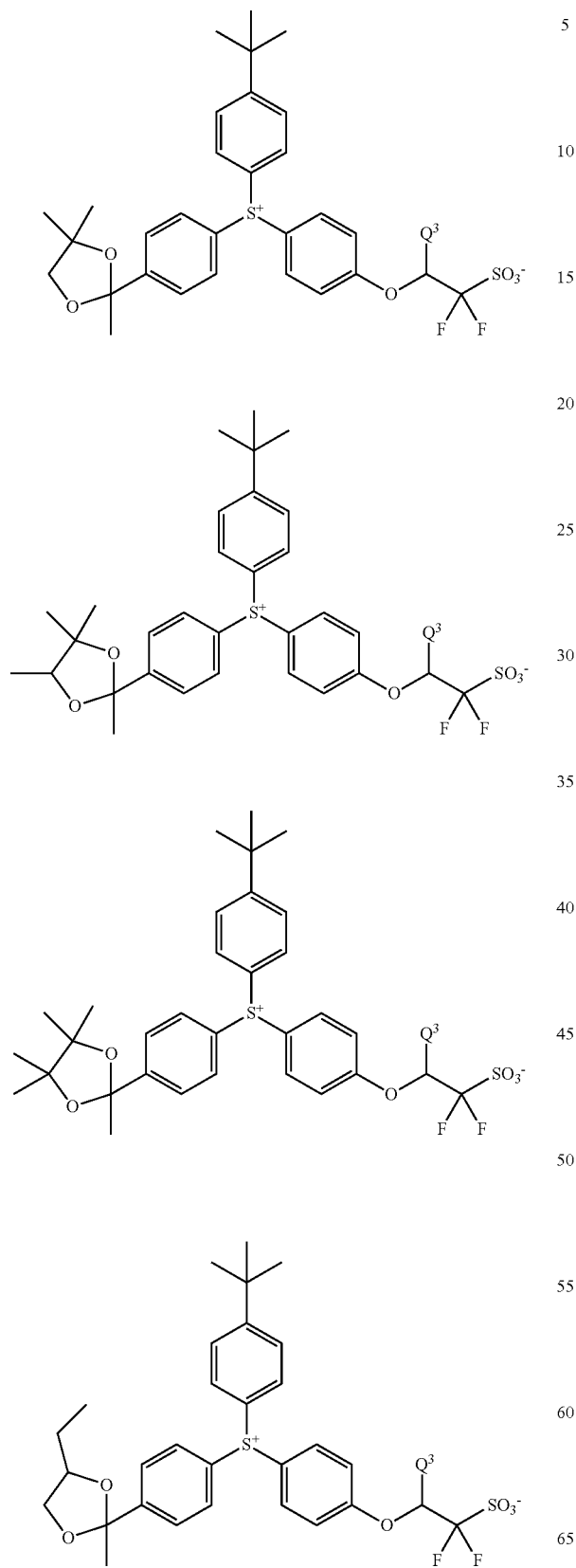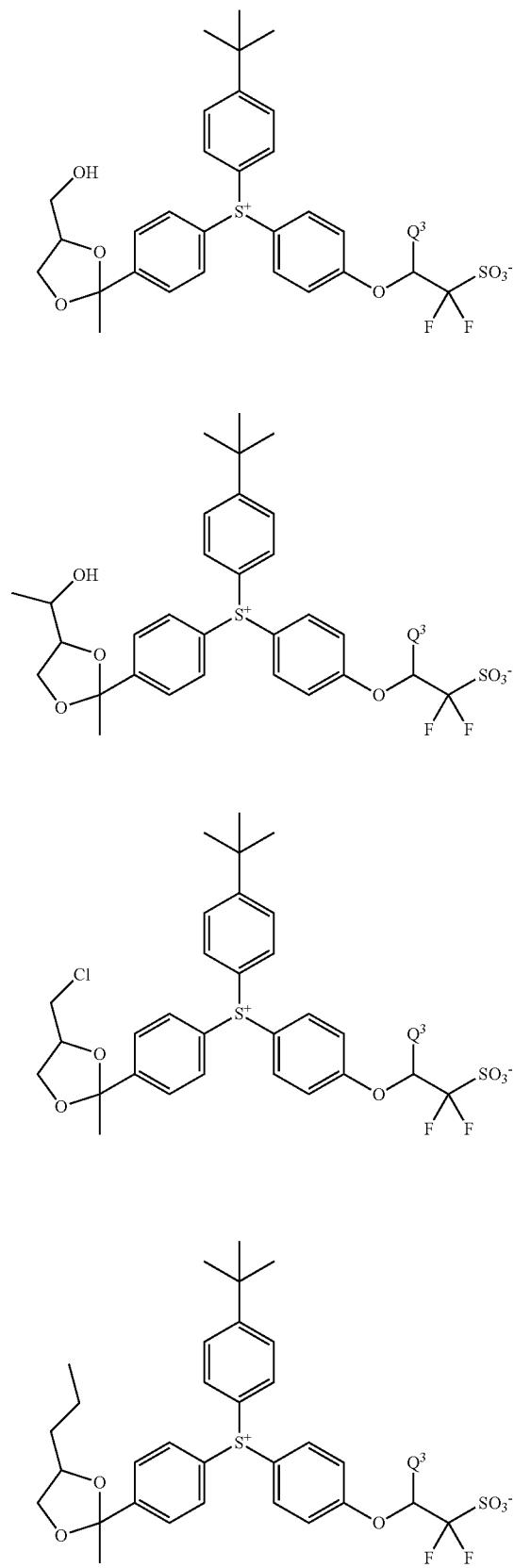

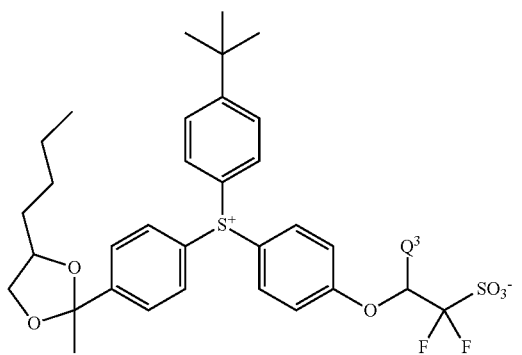
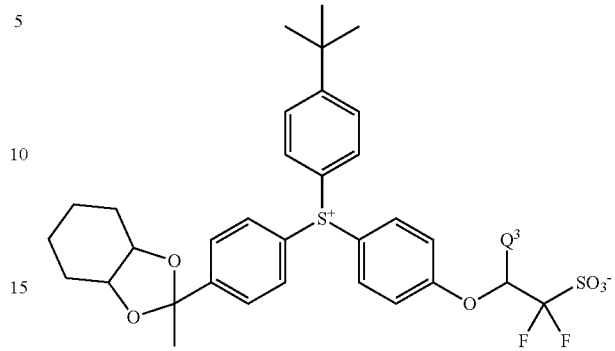
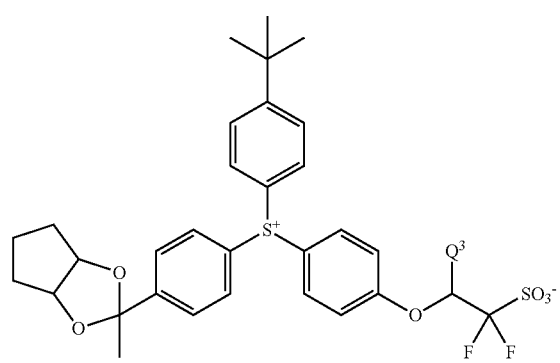
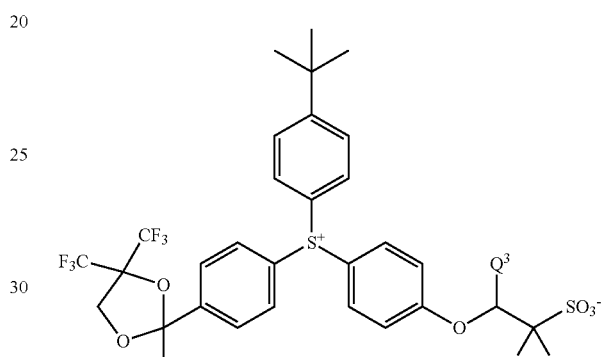
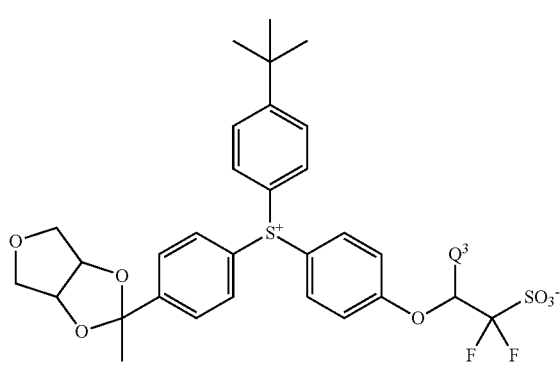
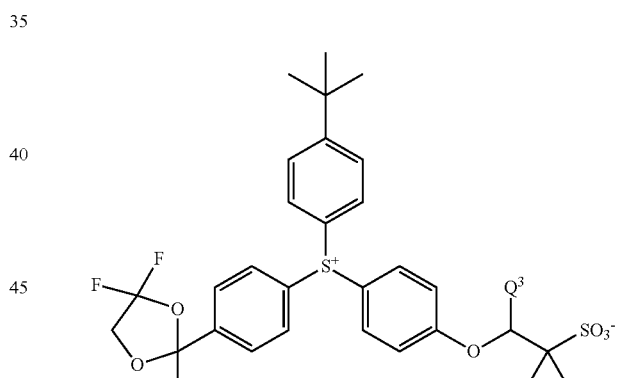
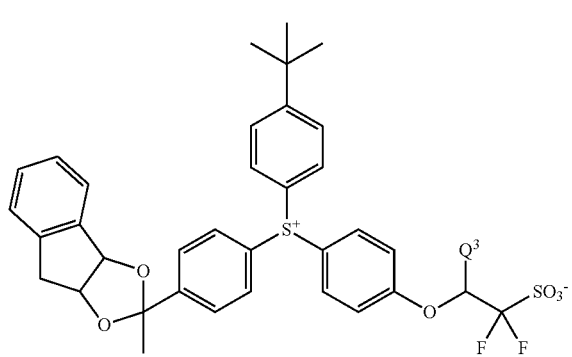
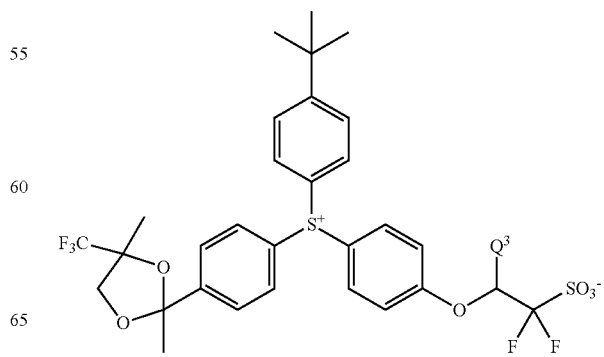

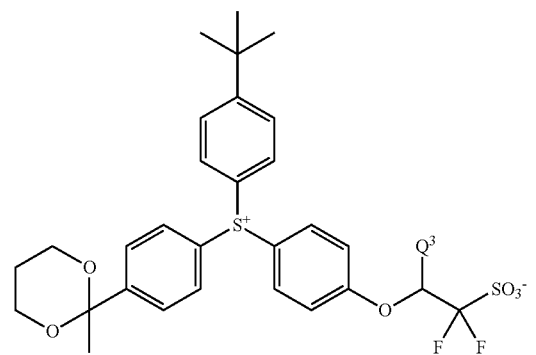
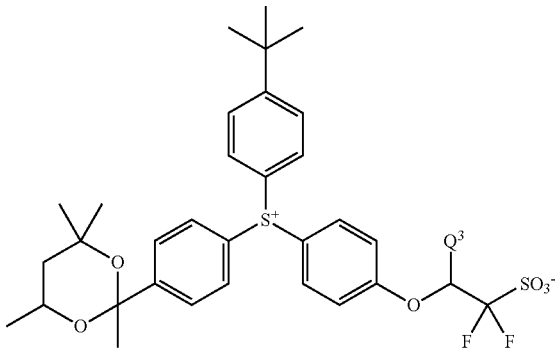
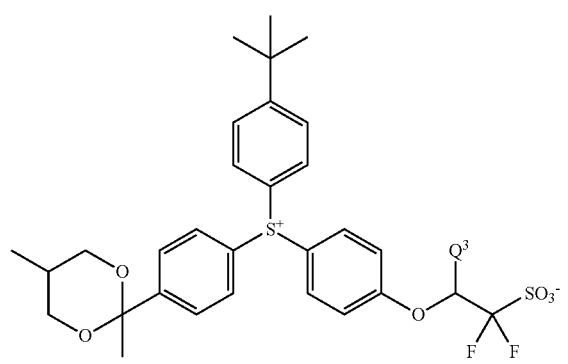
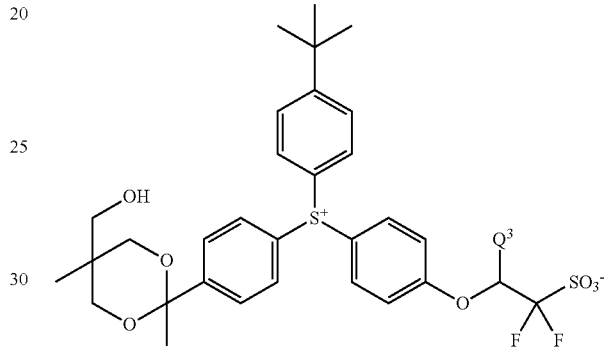
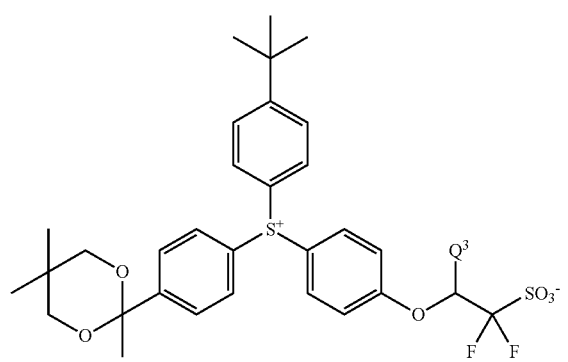
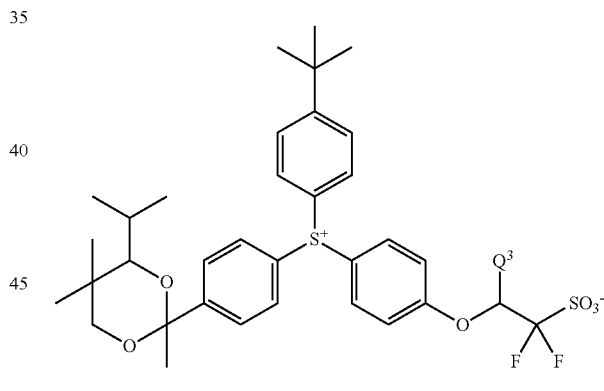
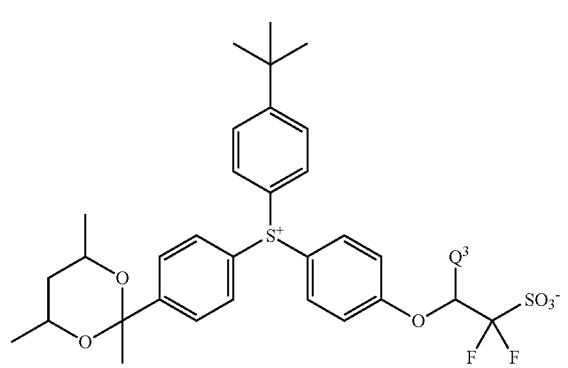
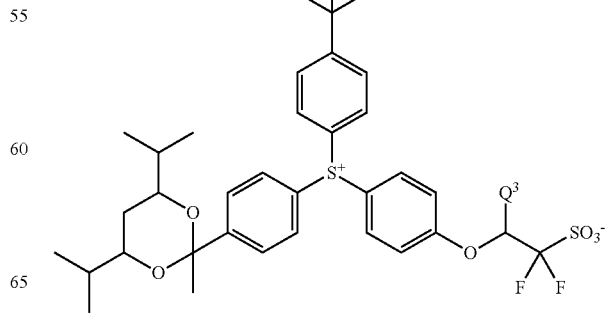

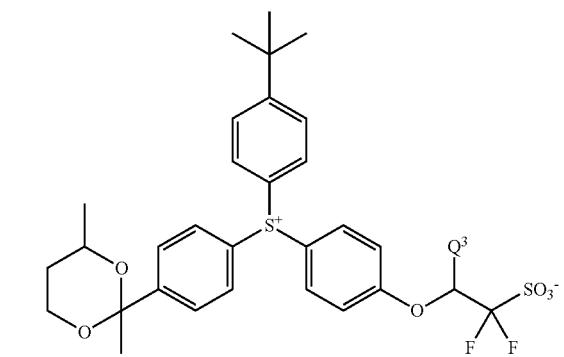
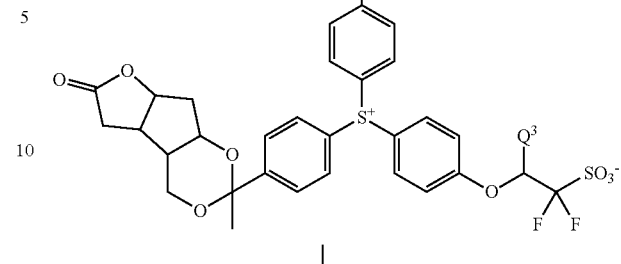
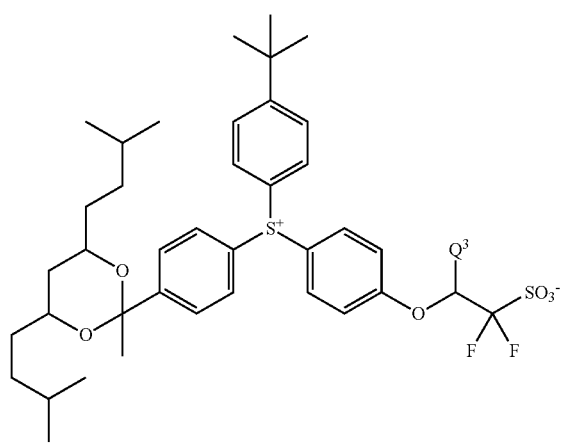
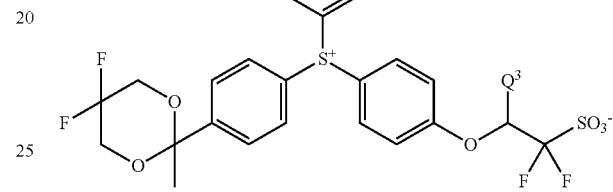
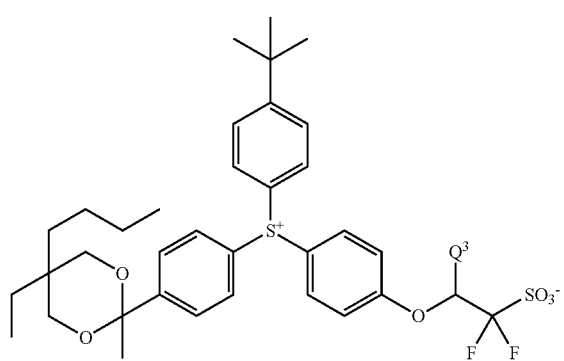
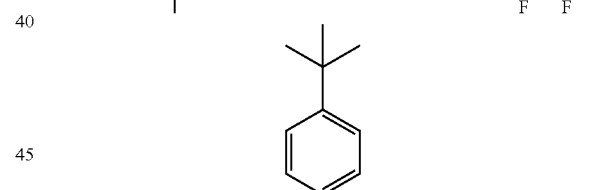
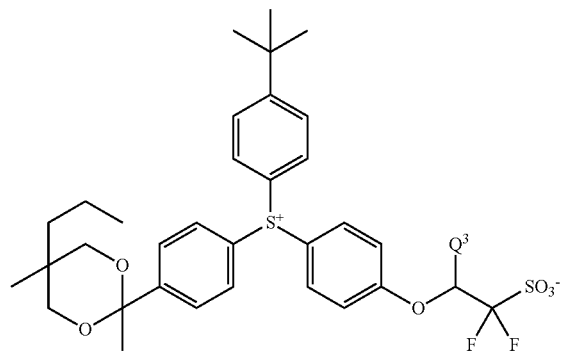
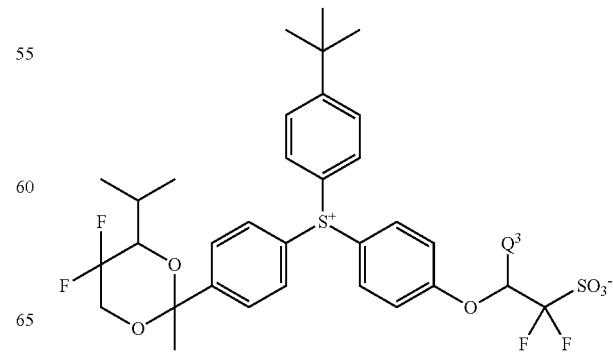

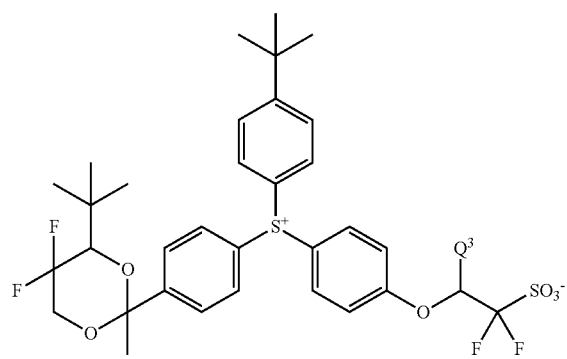
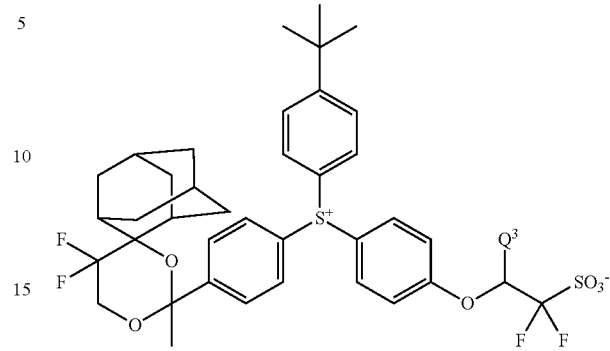
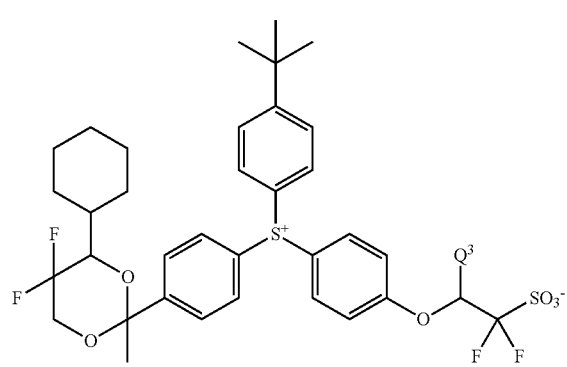
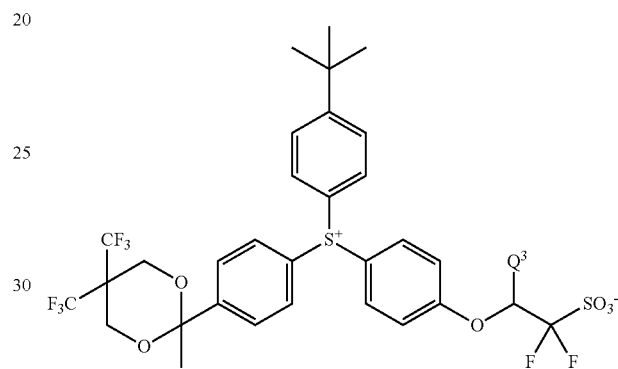
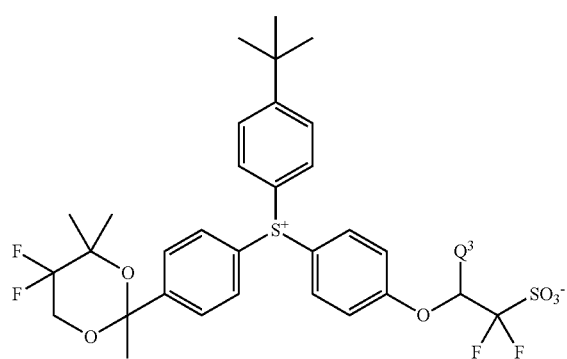
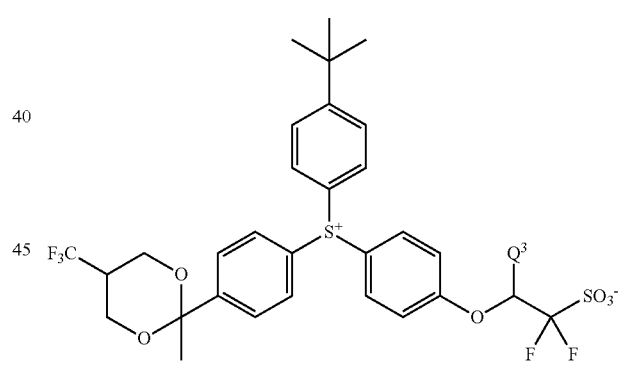
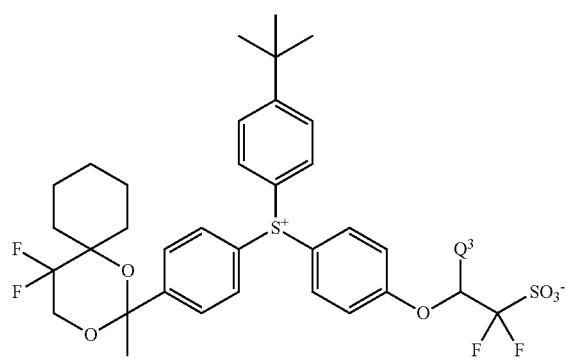
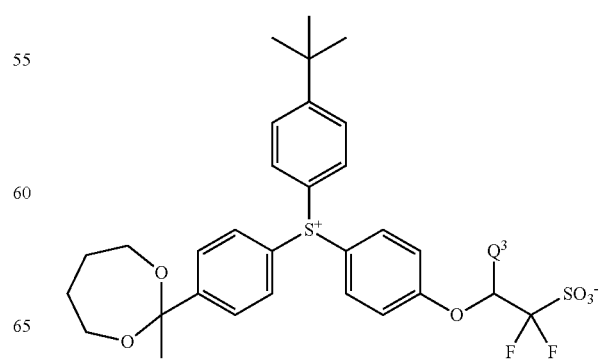

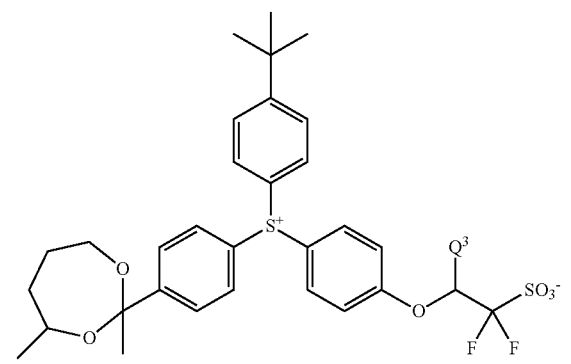
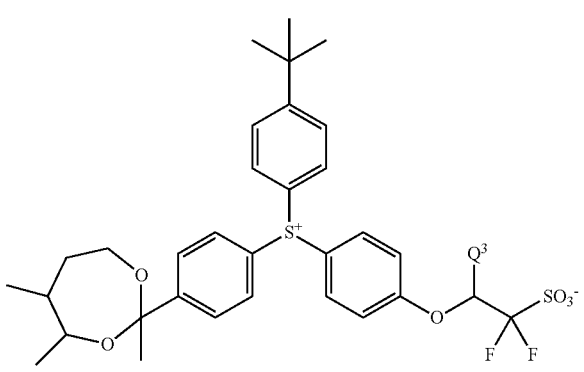
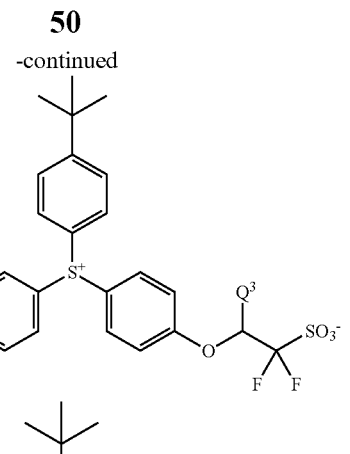
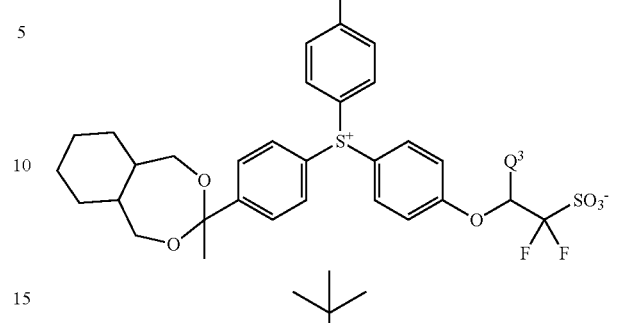
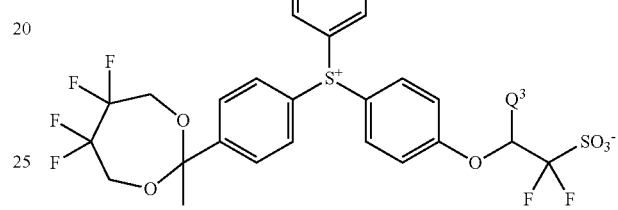
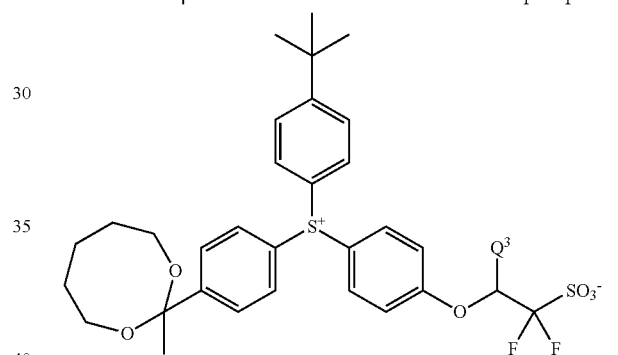
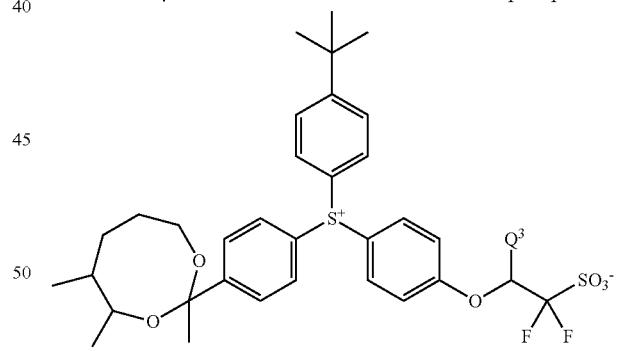
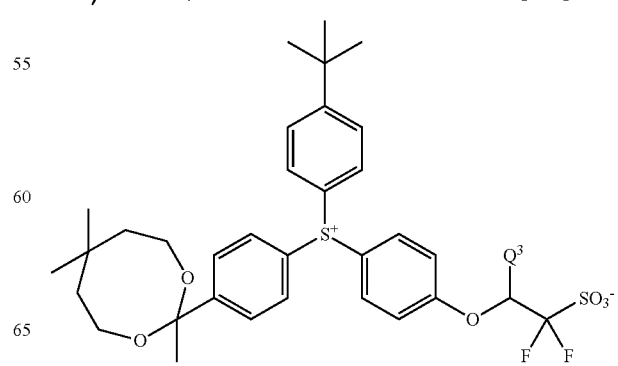

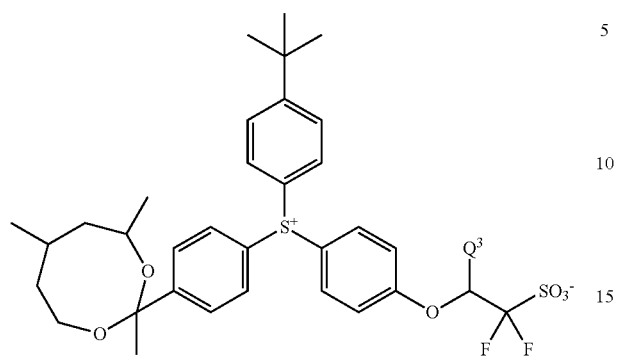
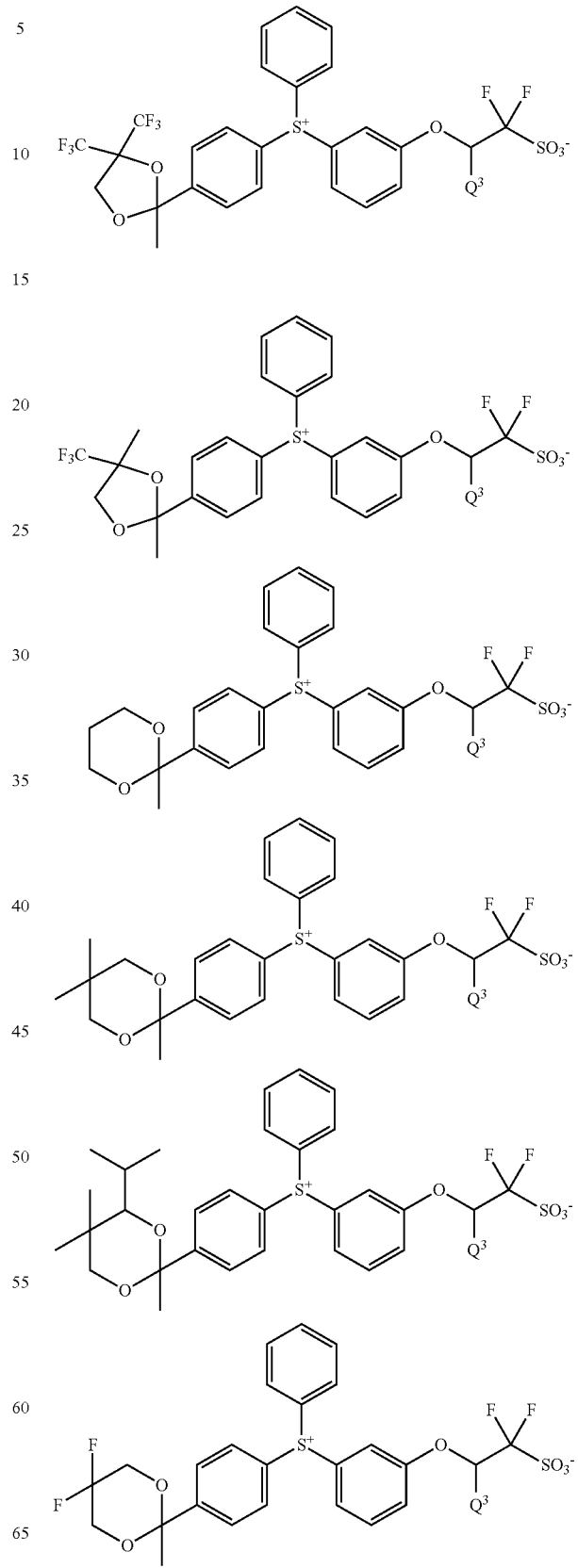

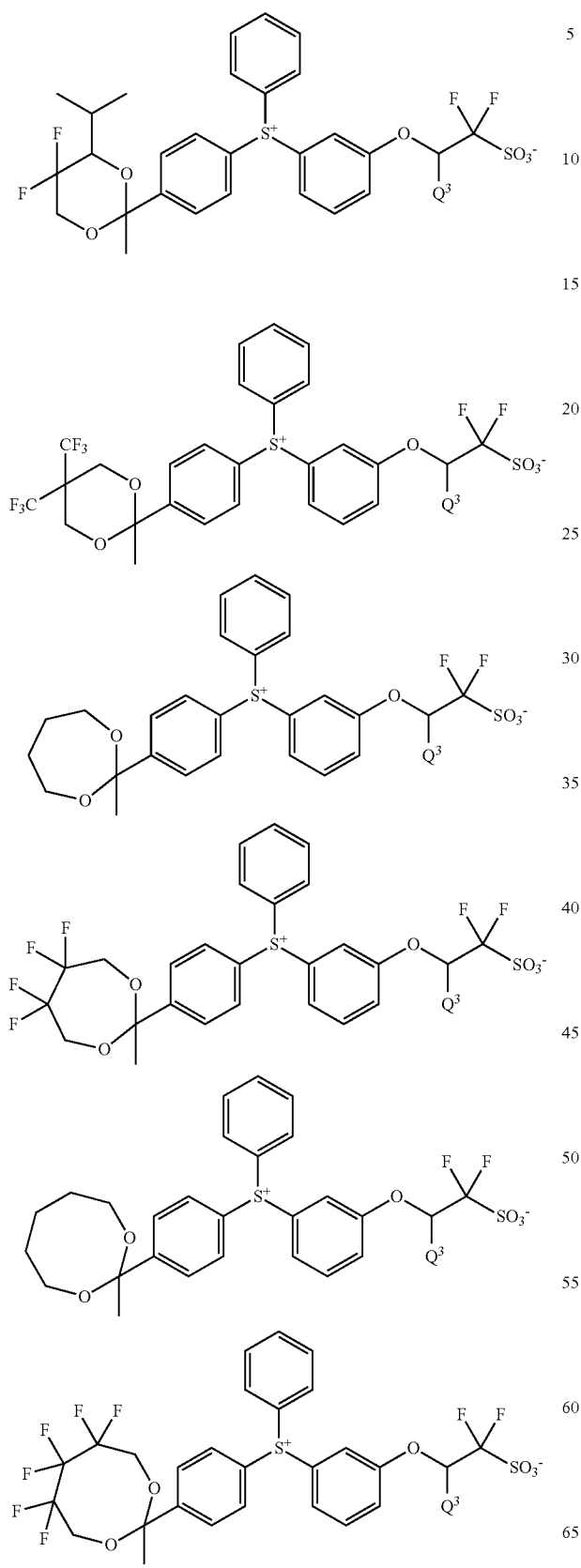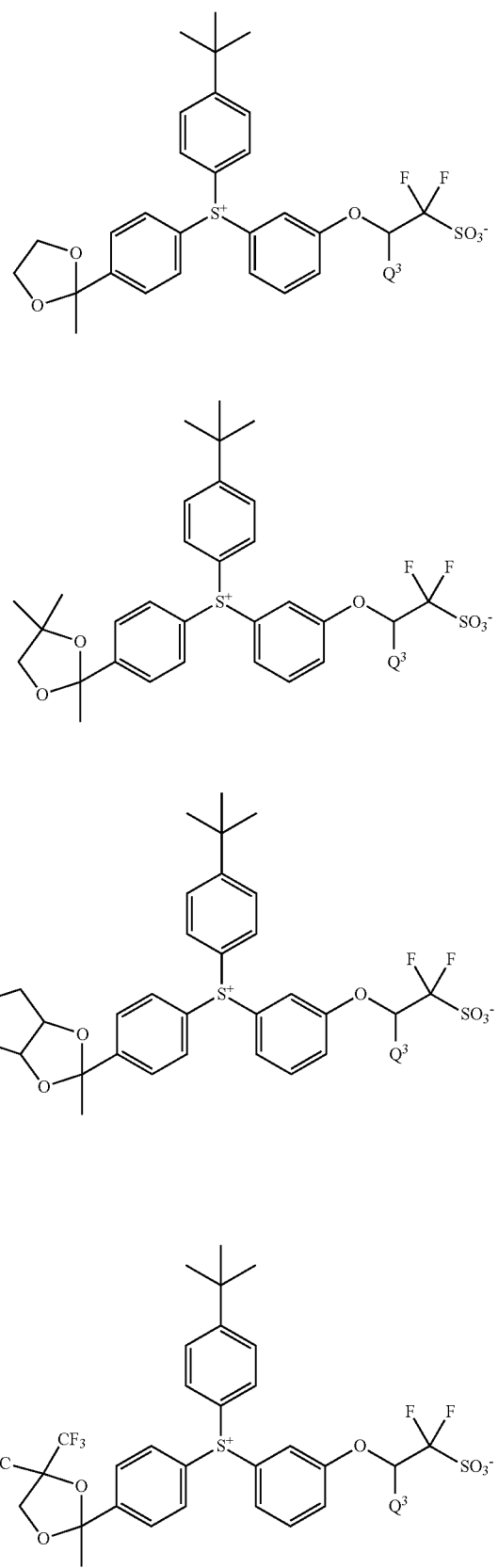

55
-continued
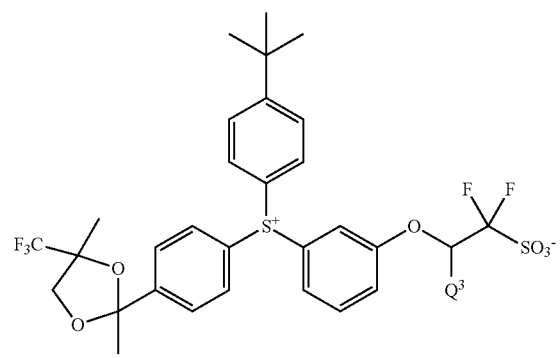
56
-continued
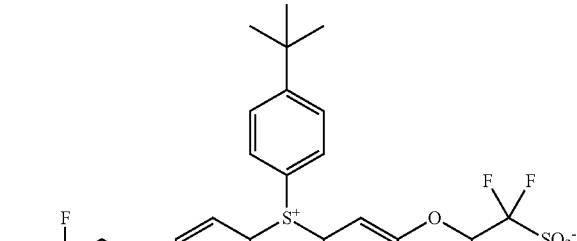
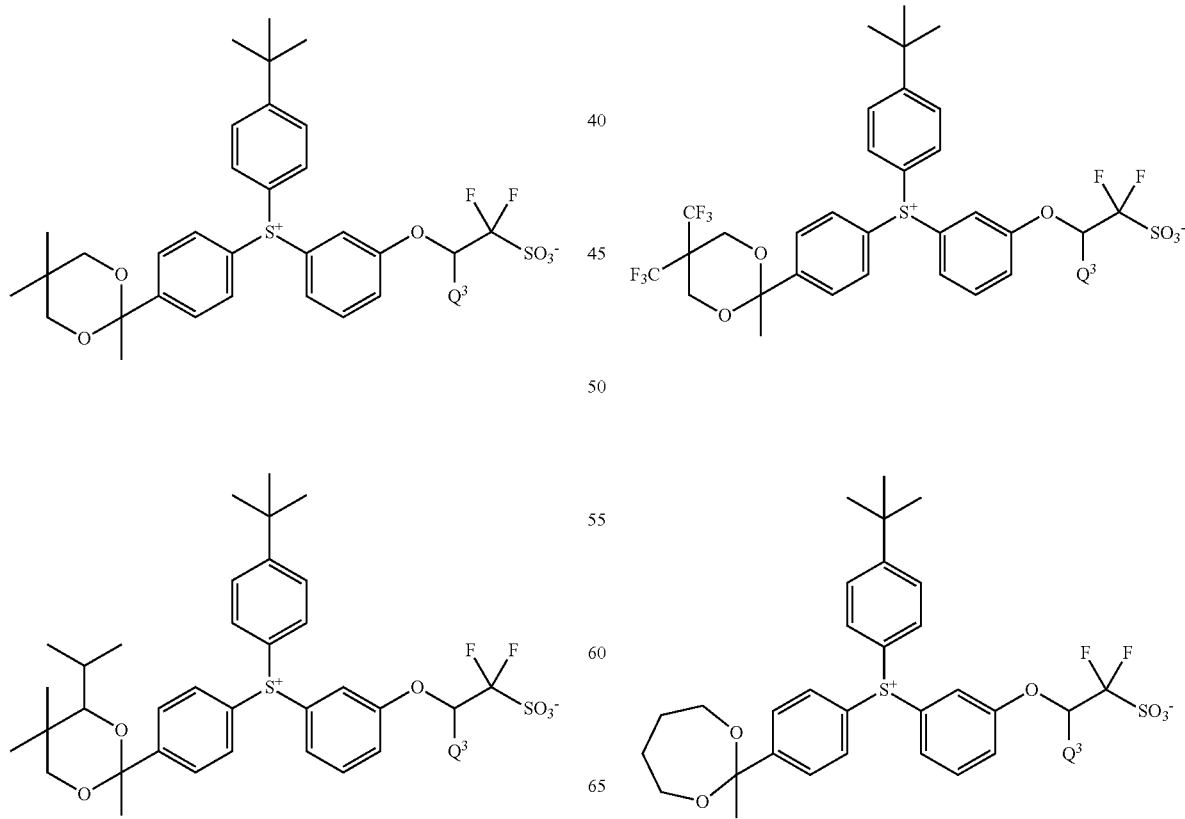

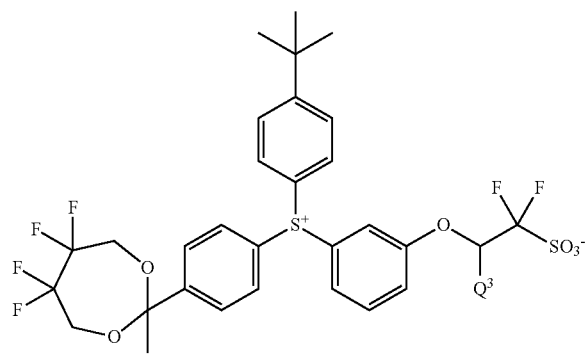
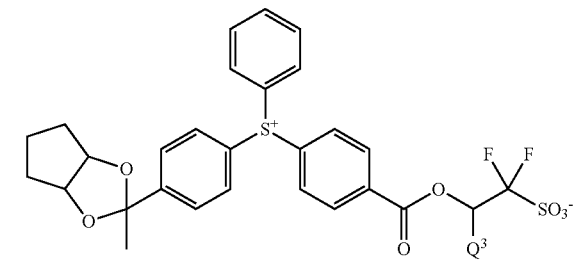
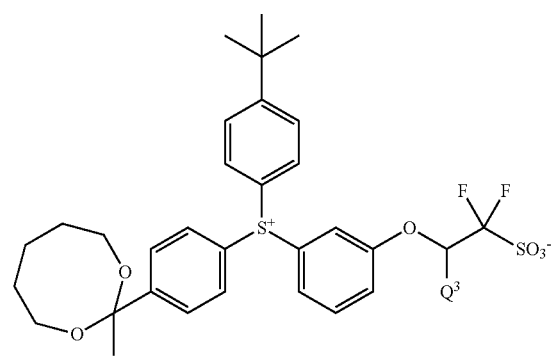
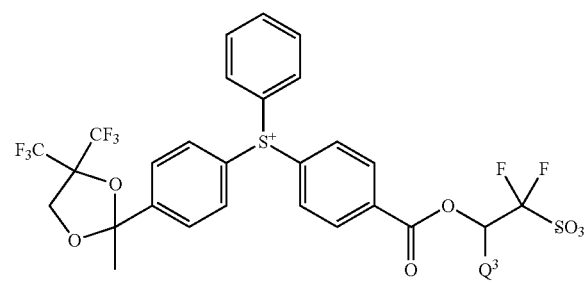
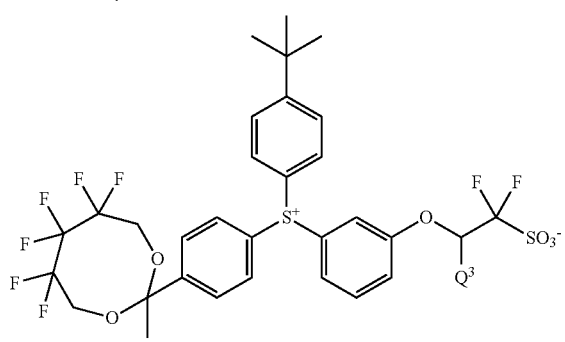
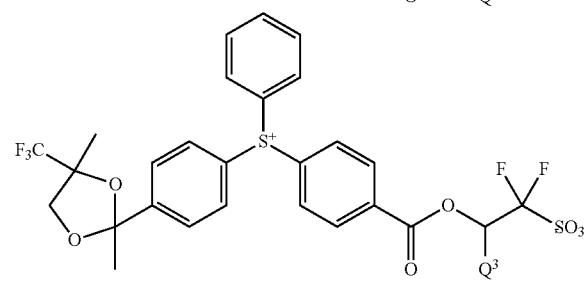
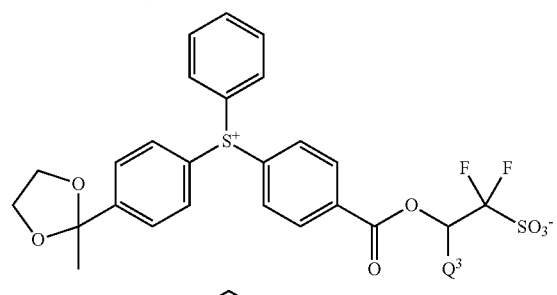
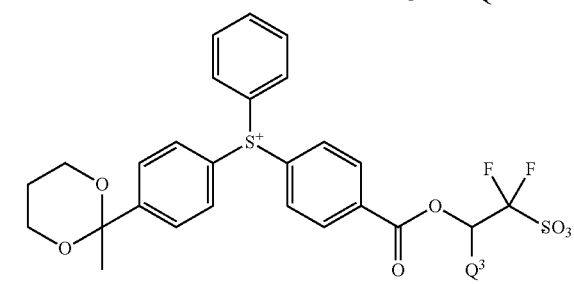
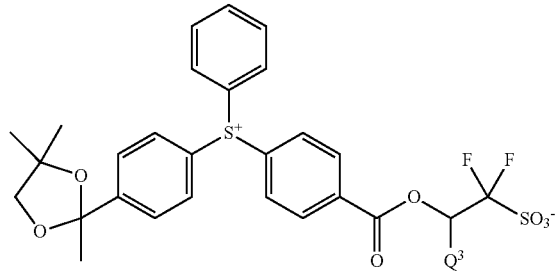
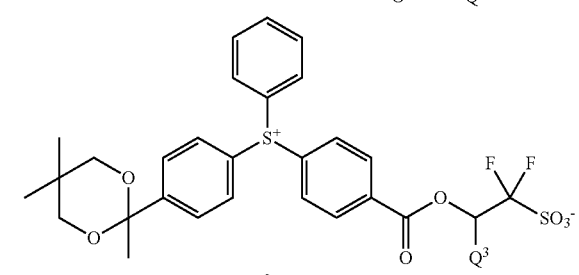

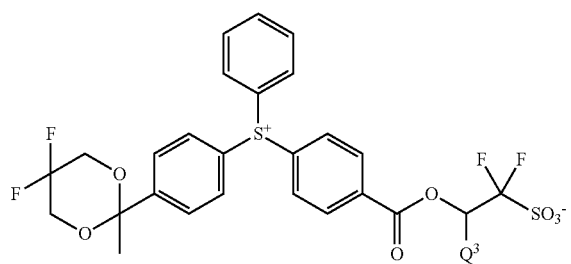
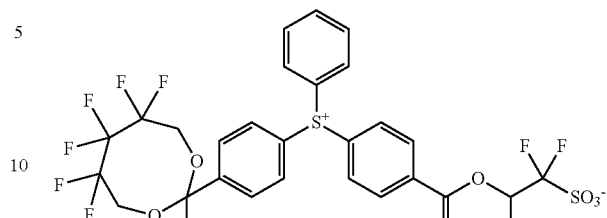
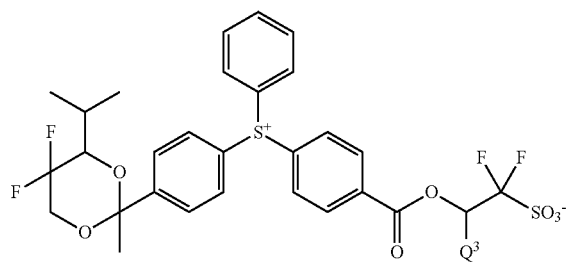
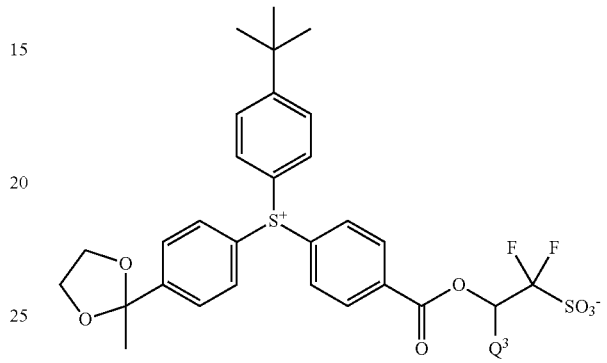
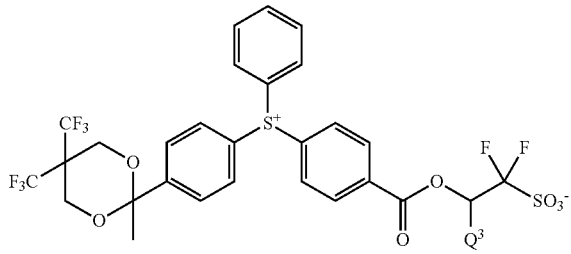
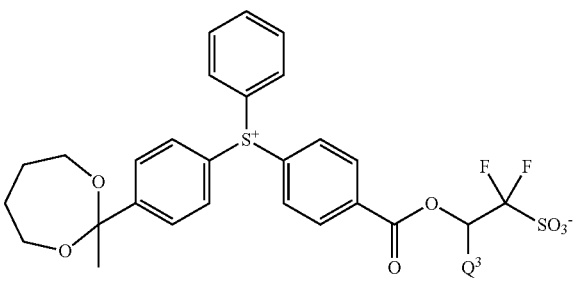
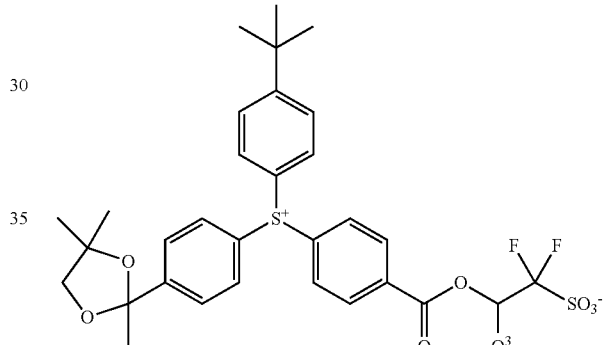
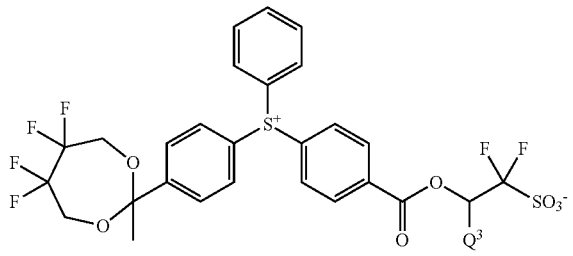
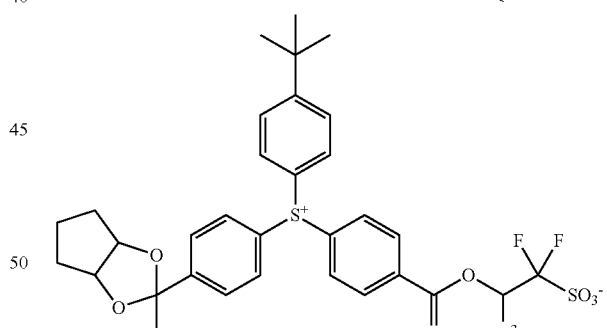
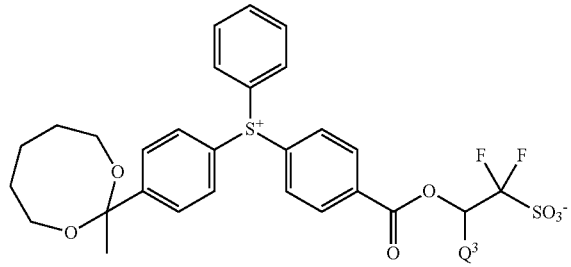
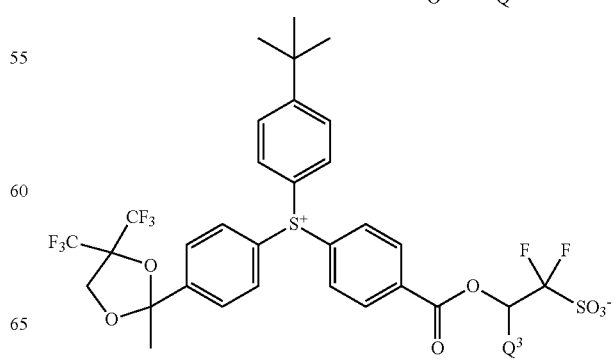

61
-continued
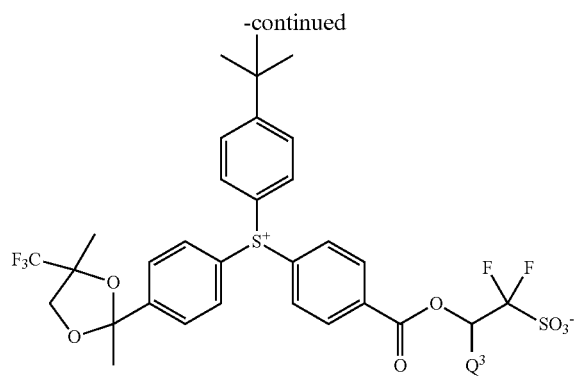
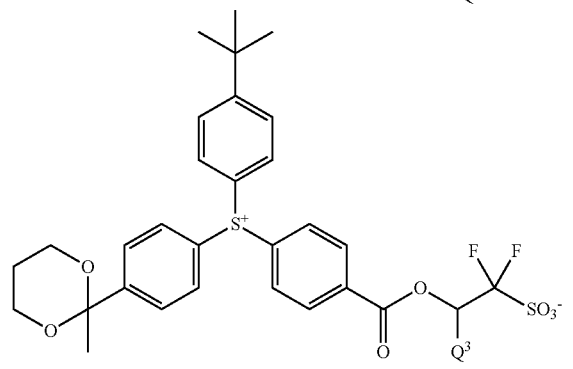
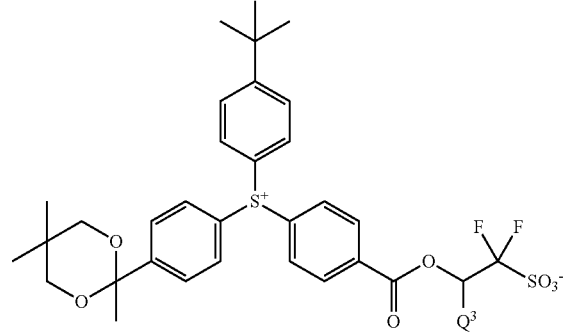
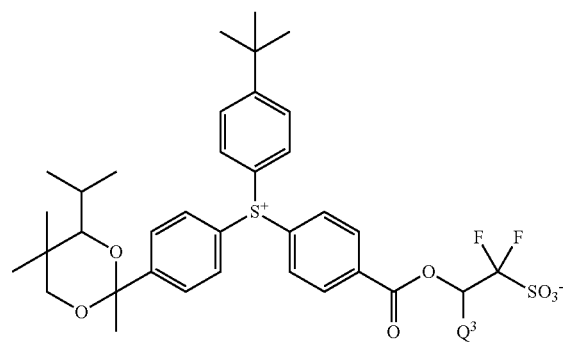
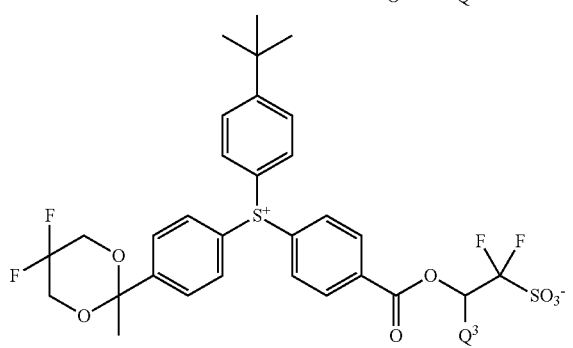
62
-continued
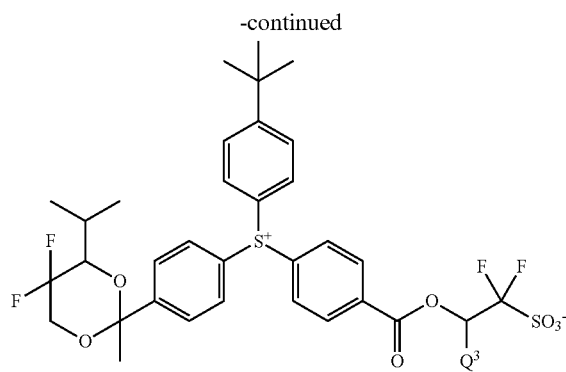
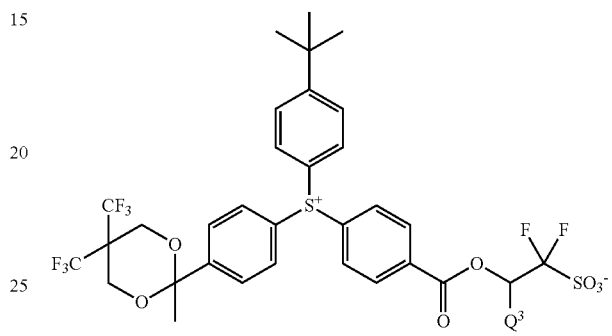
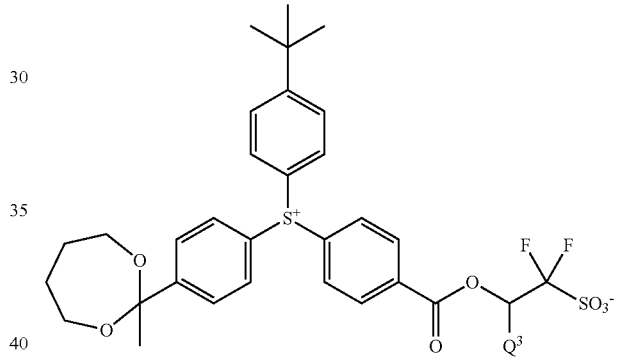
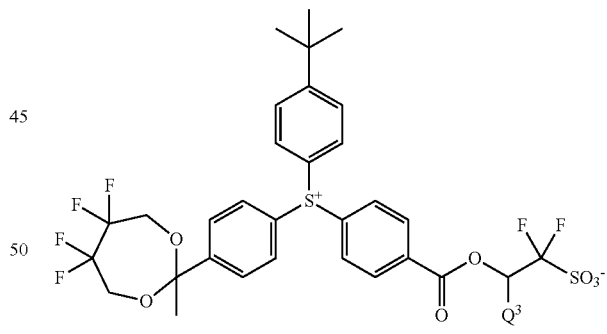
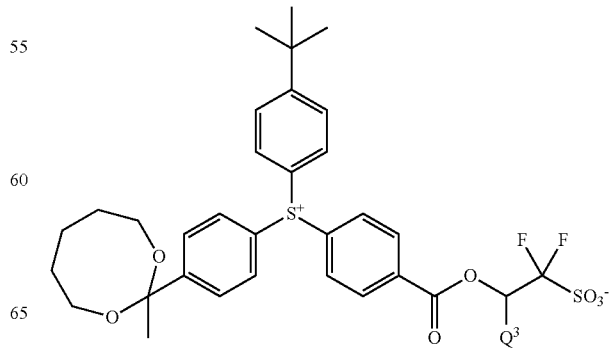

-continued
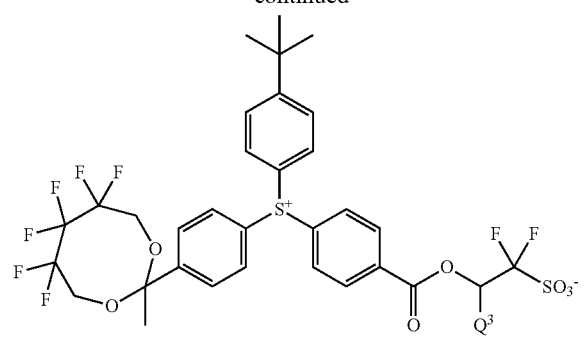
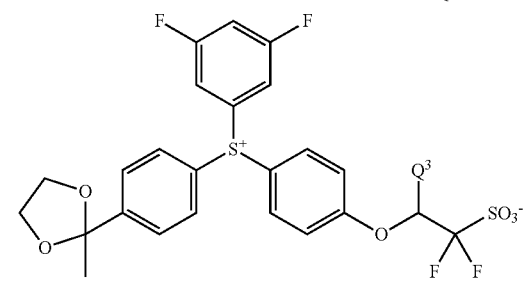
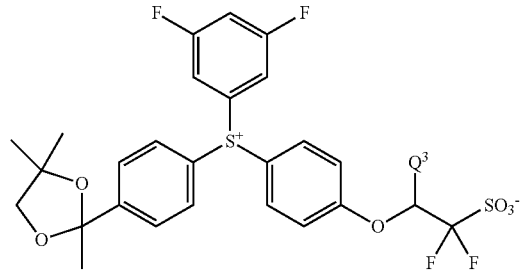
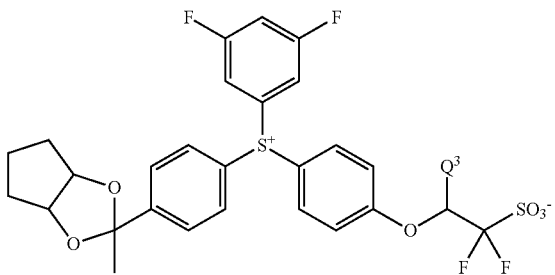
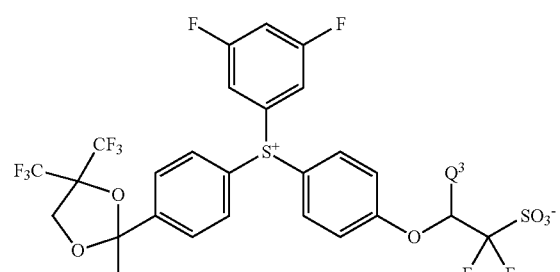
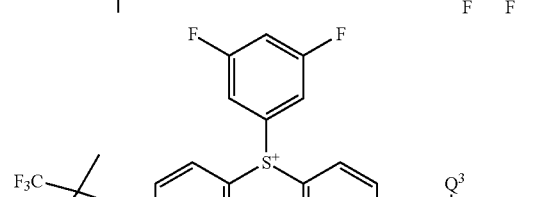
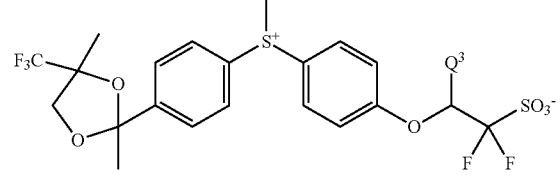
-continued
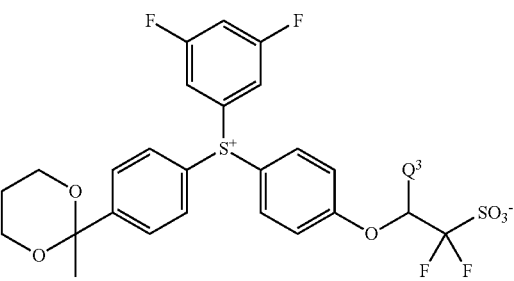
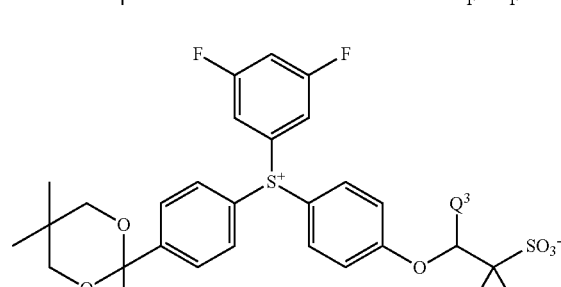
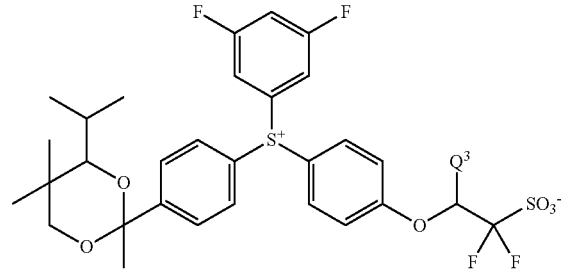
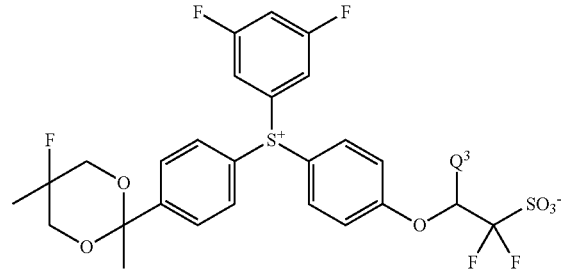
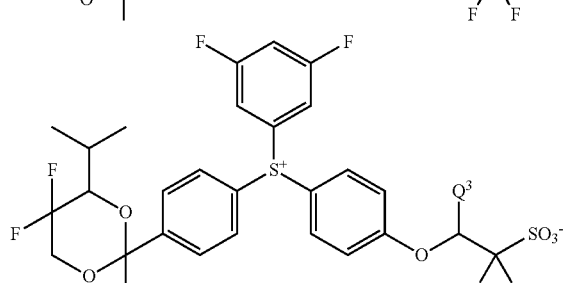

-continued
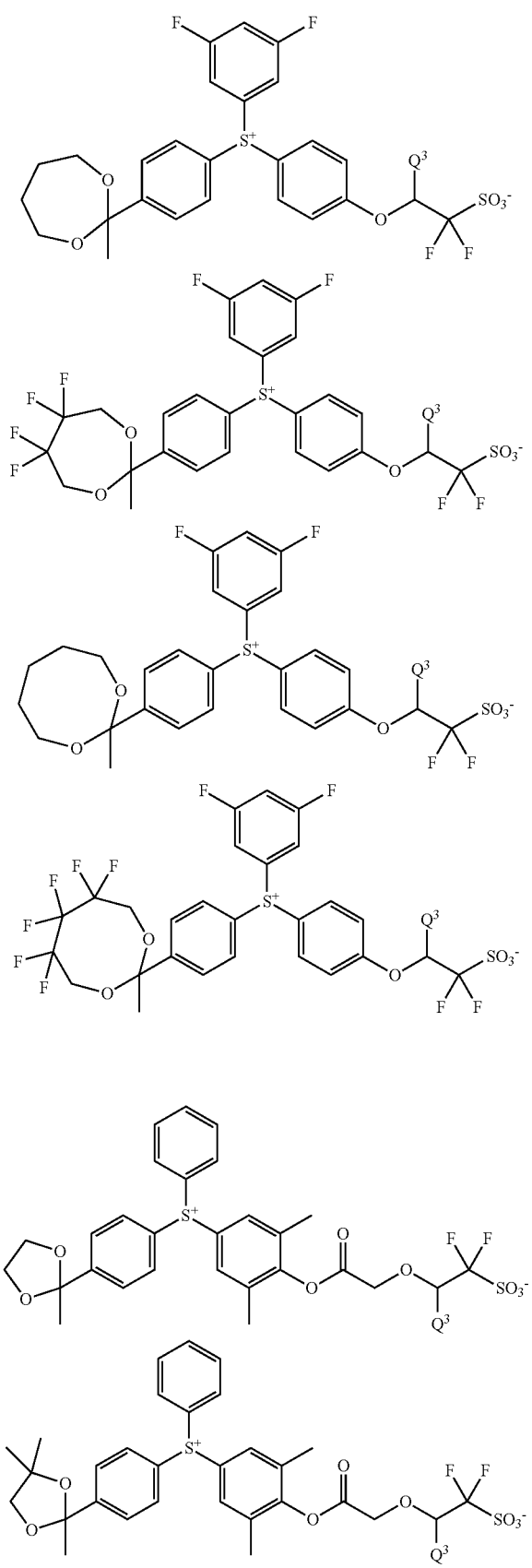
-continued
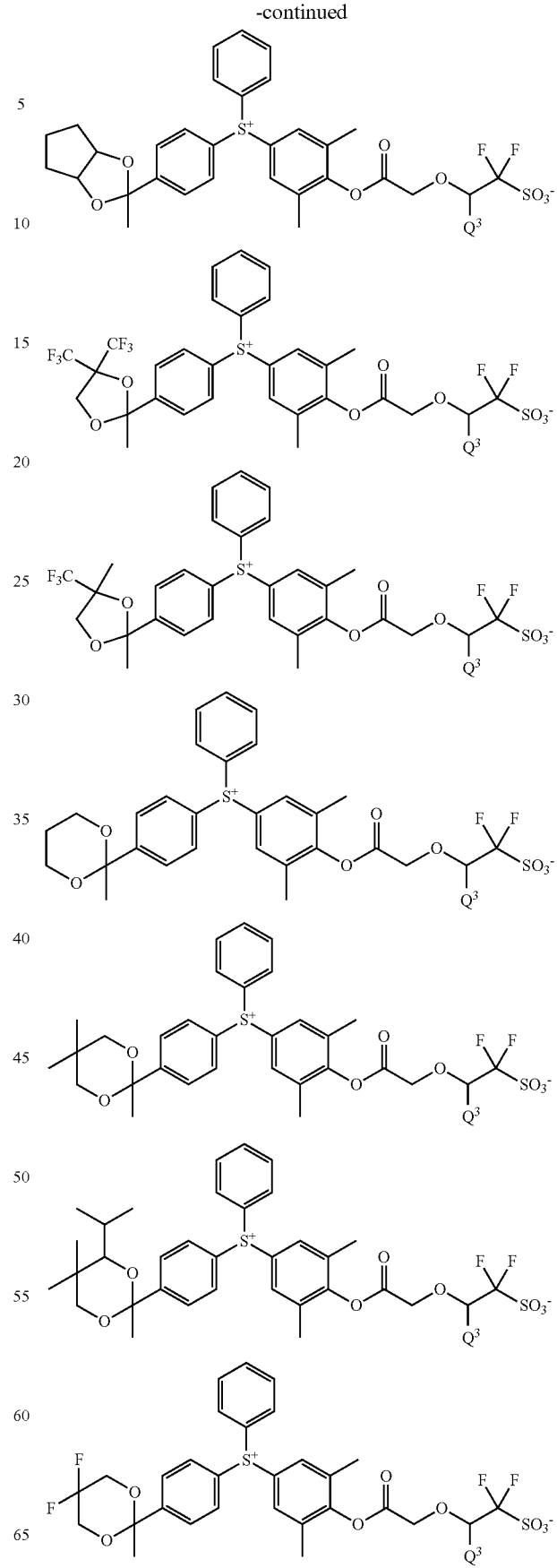

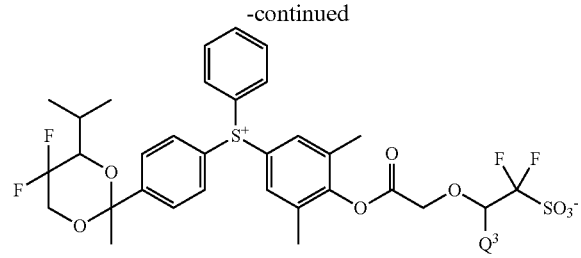
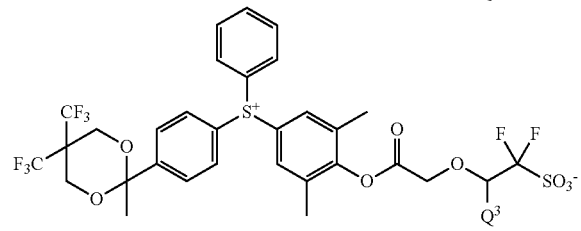
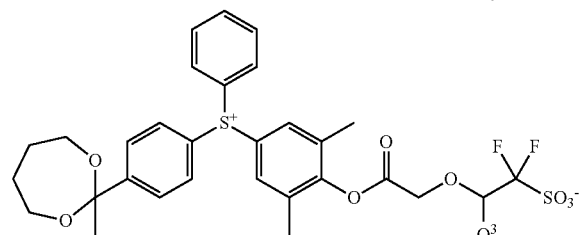
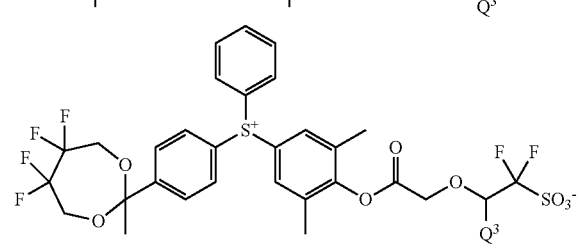
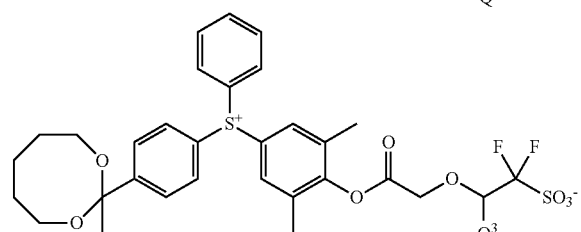
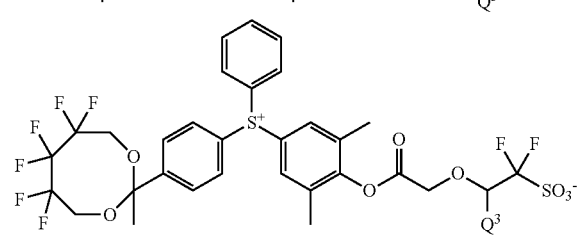
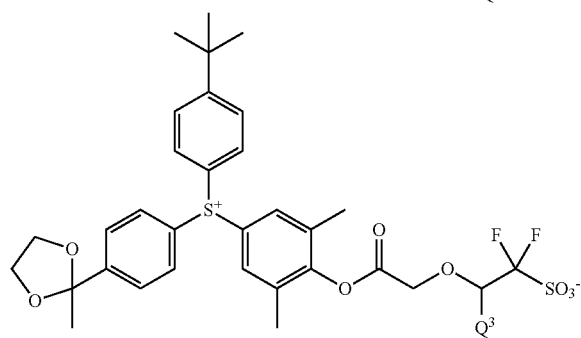
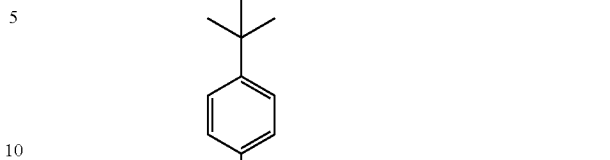
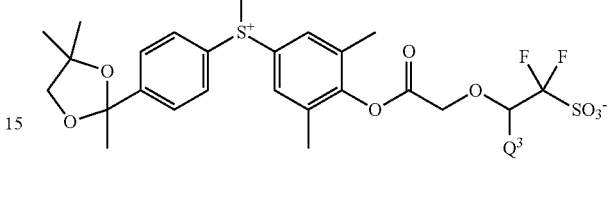
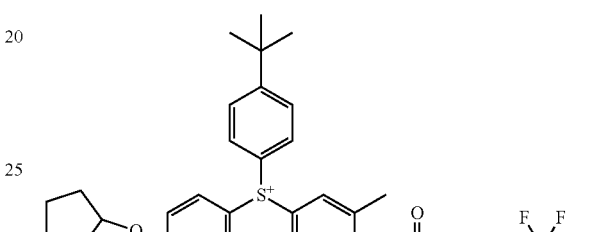
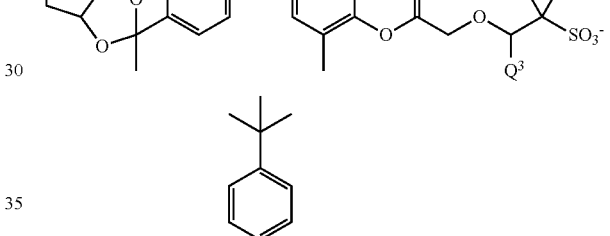
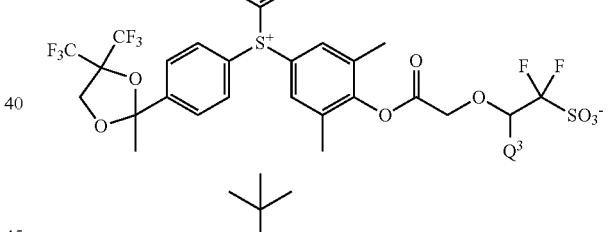
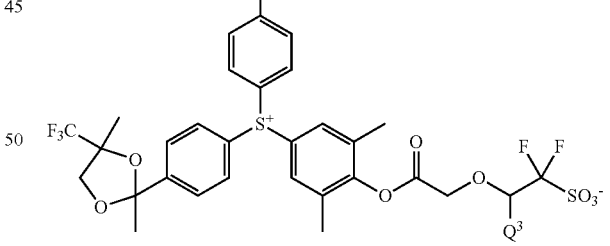
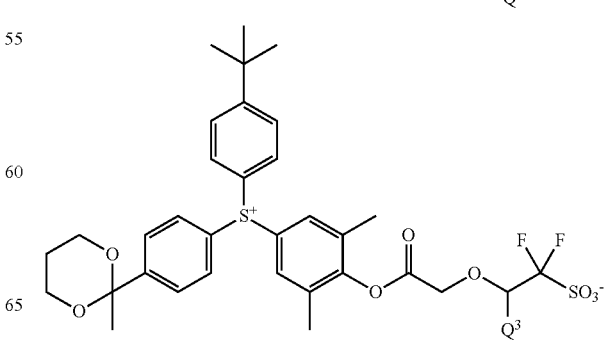

69
-continued
70
-continued
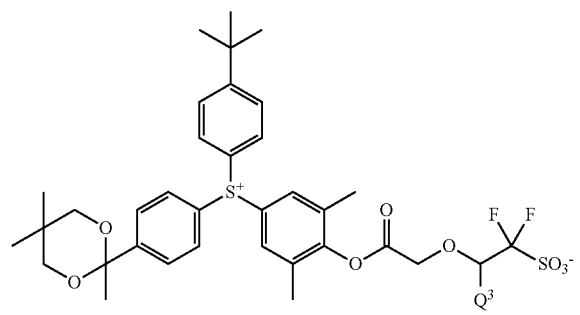
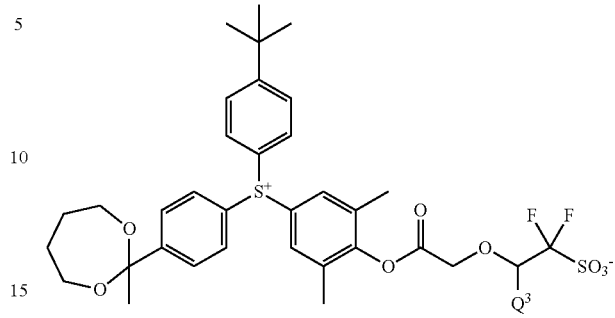
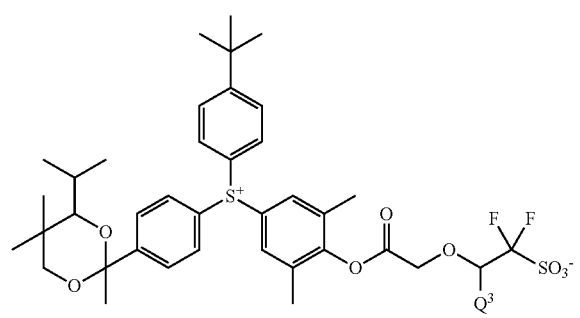
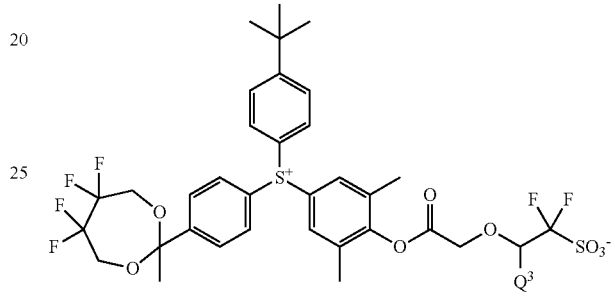
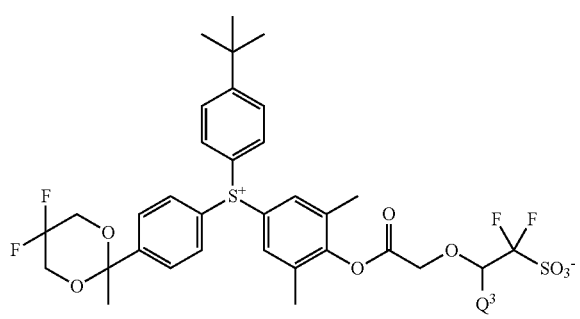
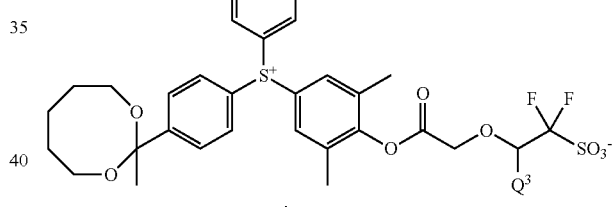
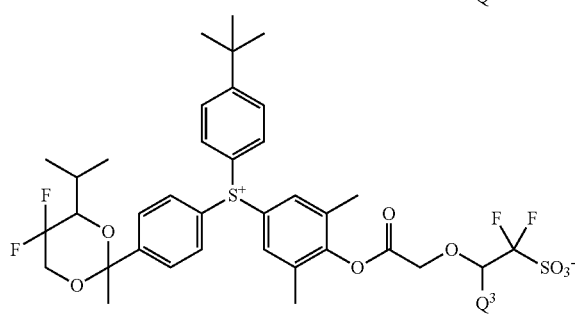
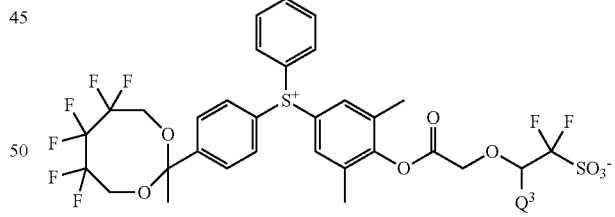
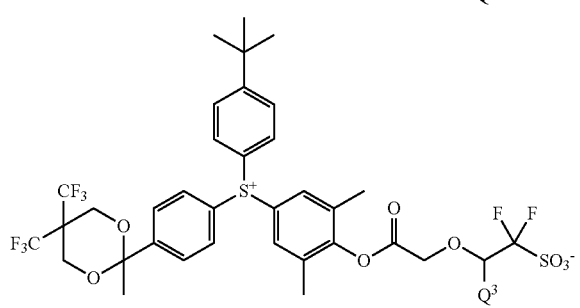
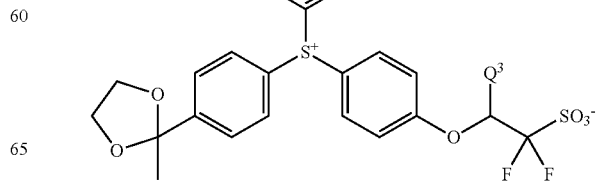

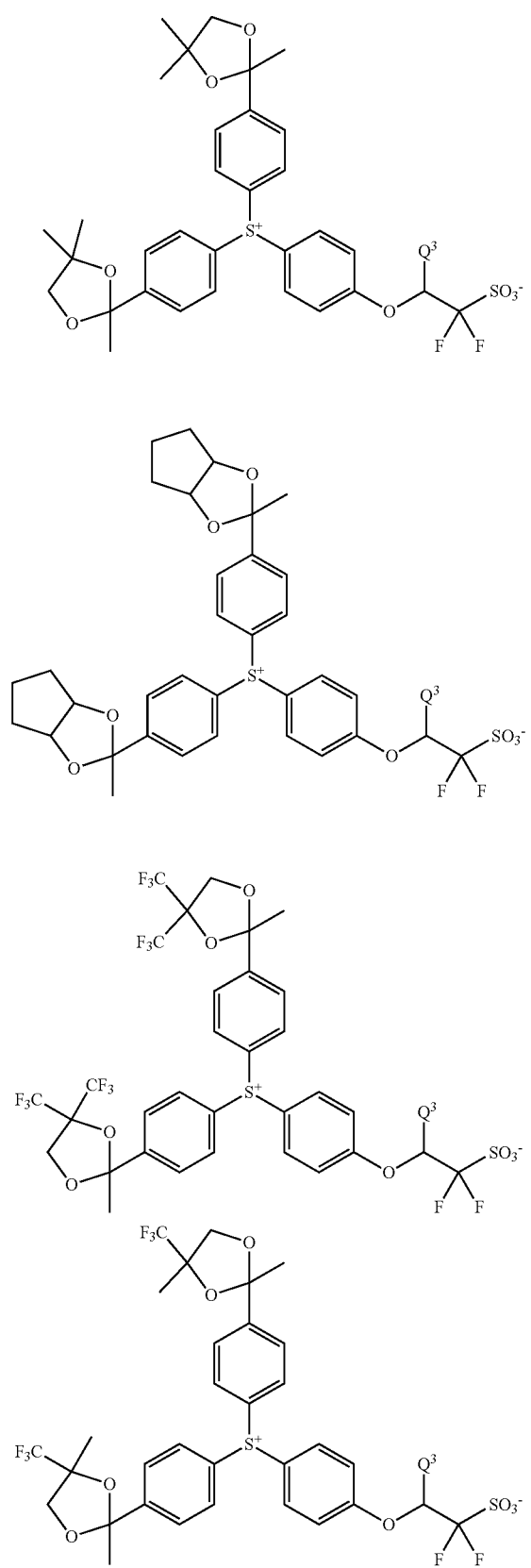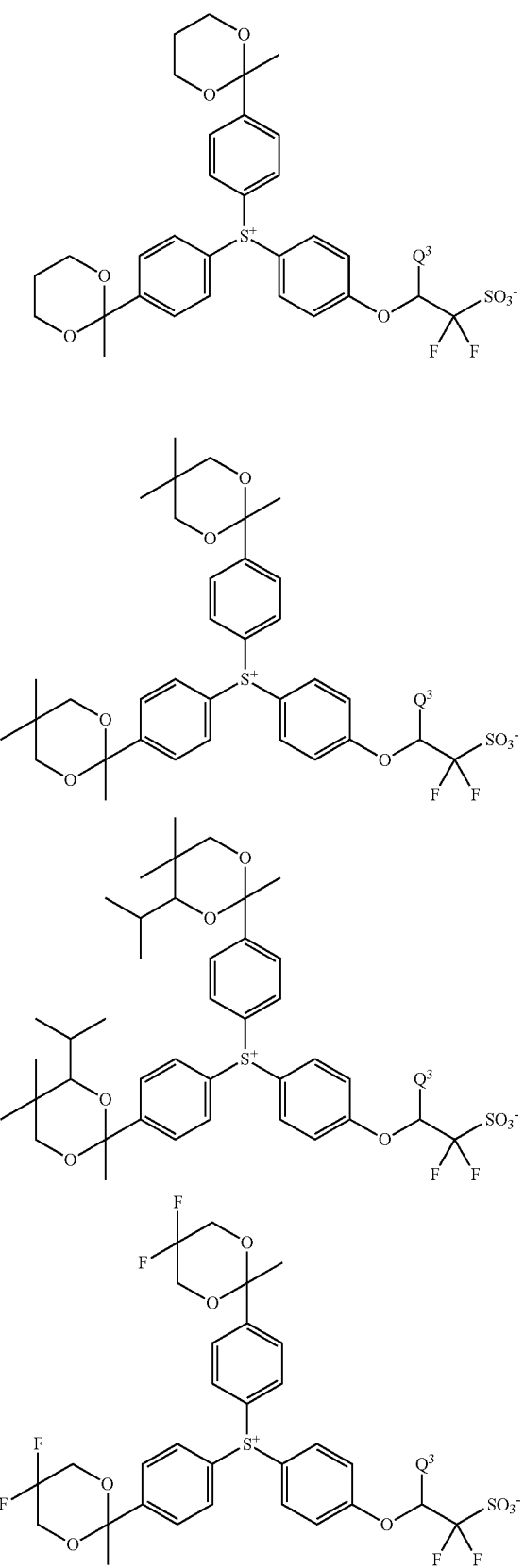

73
-continued
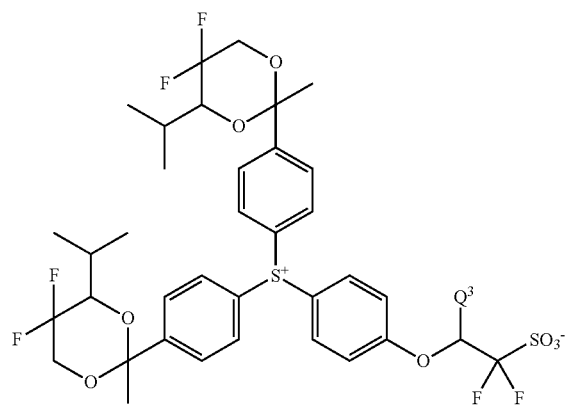
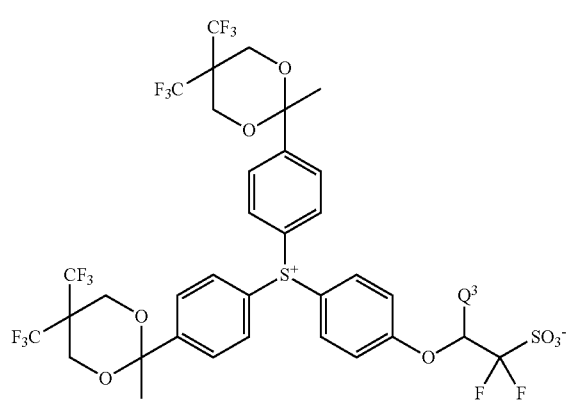
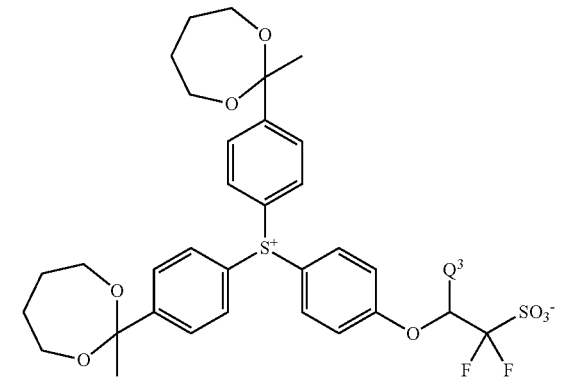
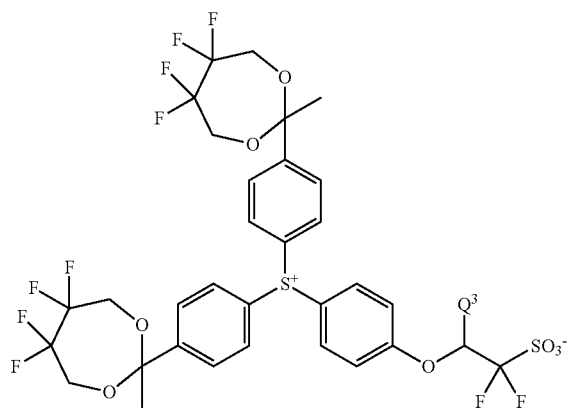
74
-continued
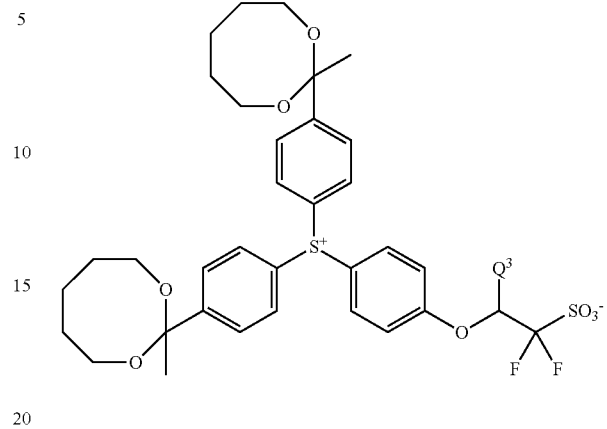
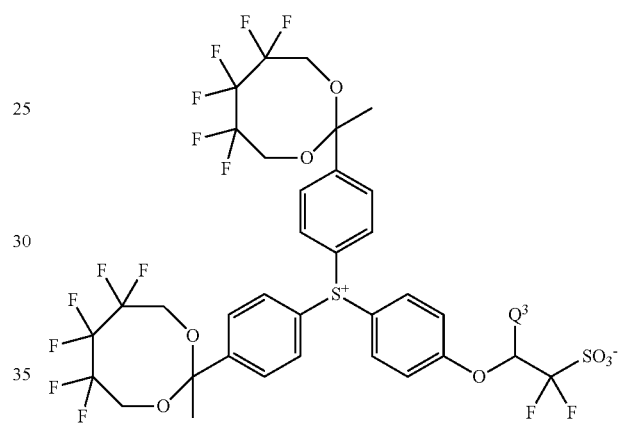
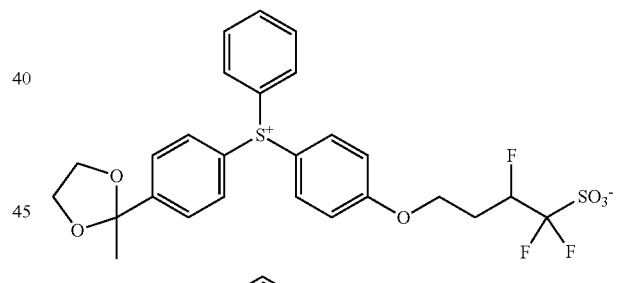
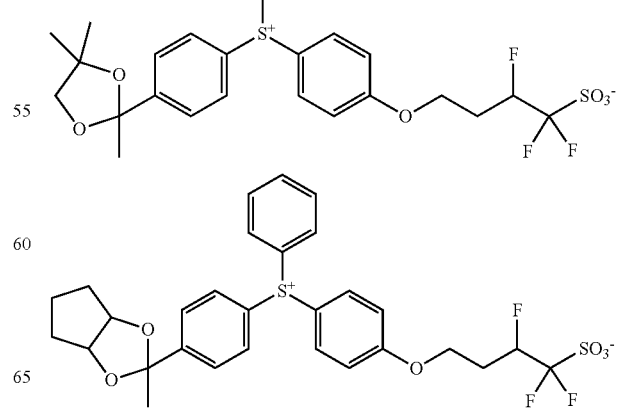

75
-continued
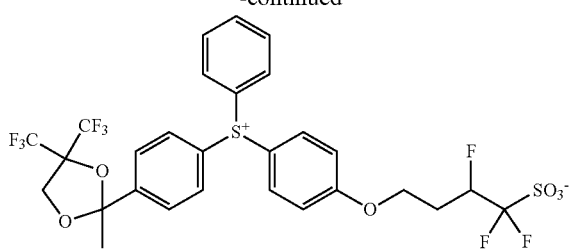
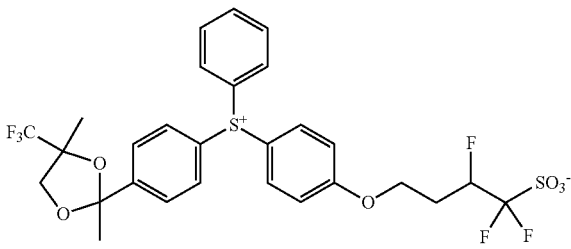
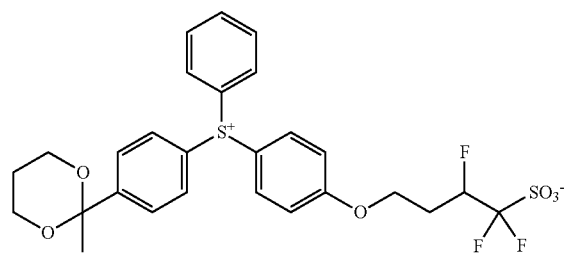
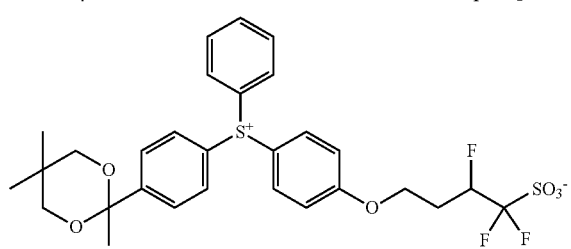
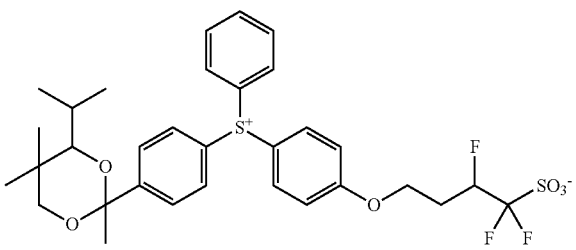
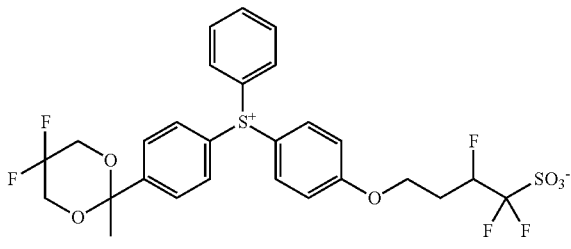
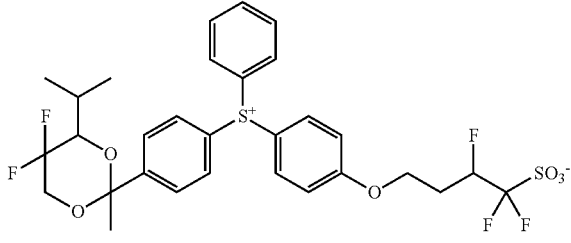
76
-continued
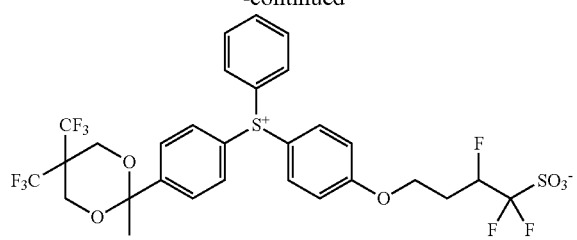
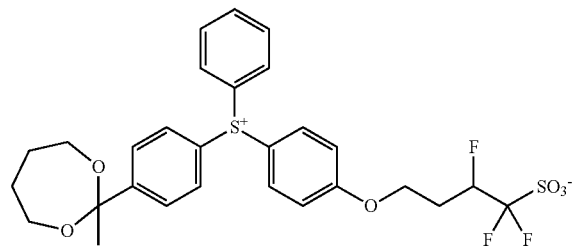
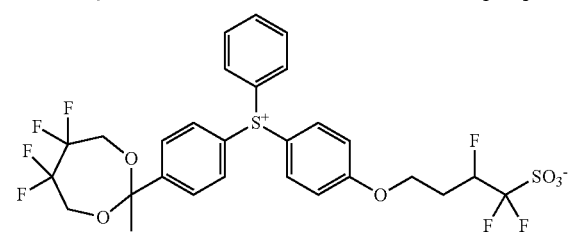
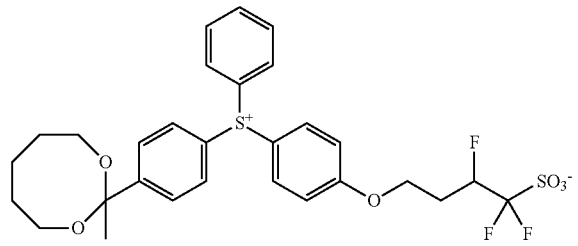
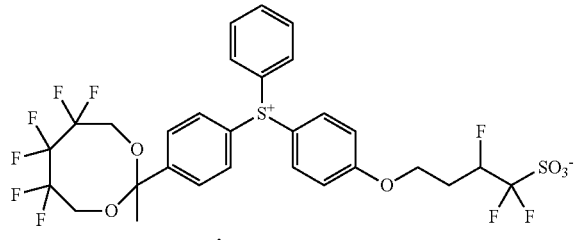
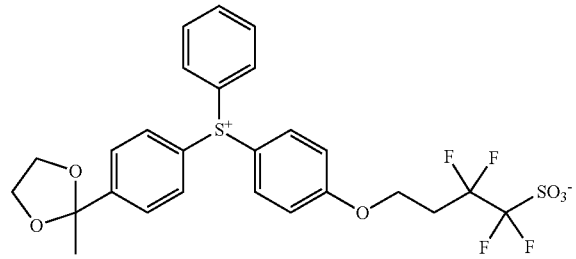
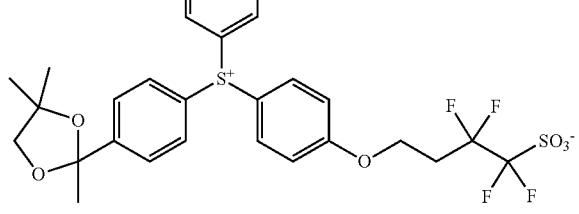

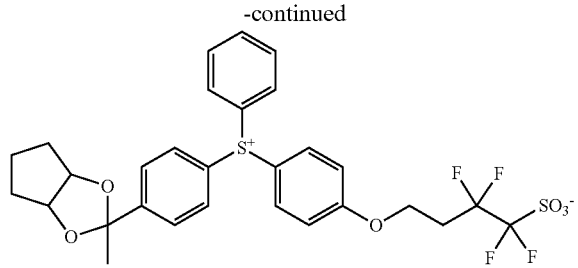
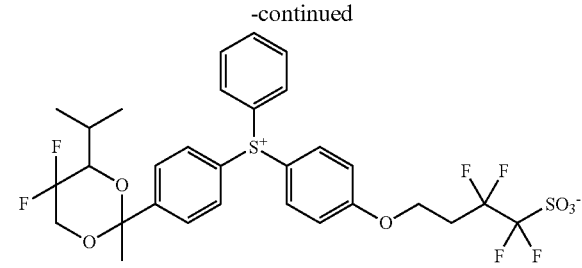
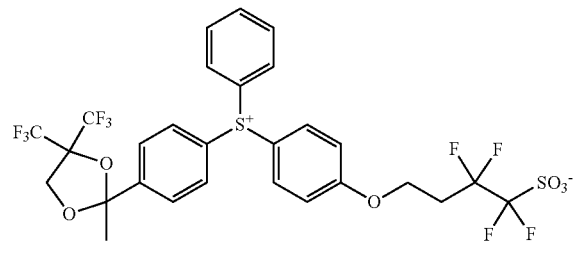
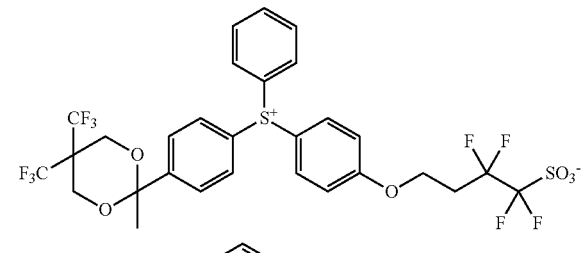
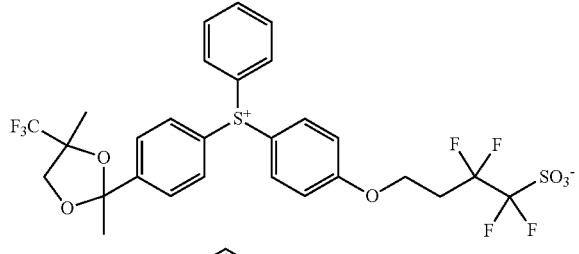
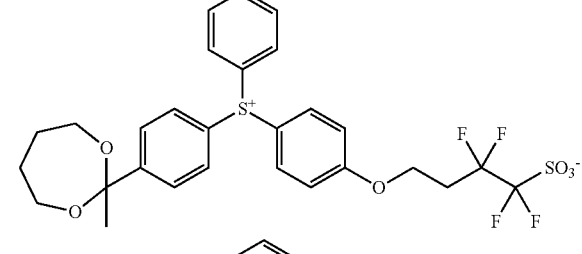
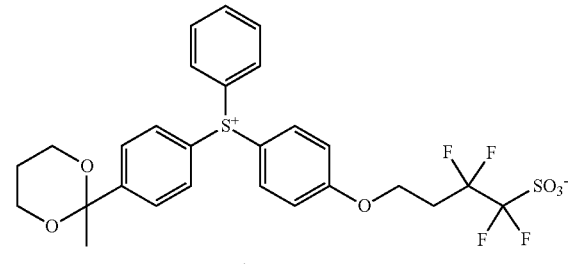
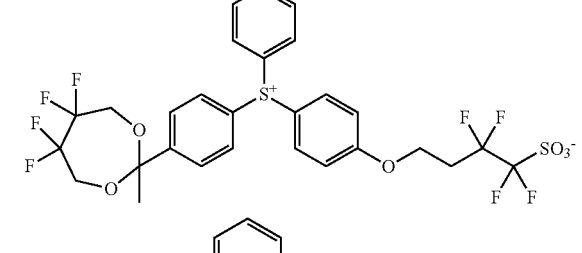
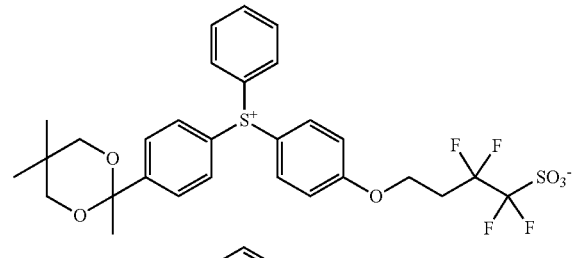
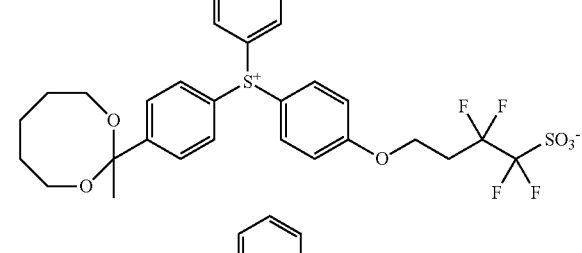
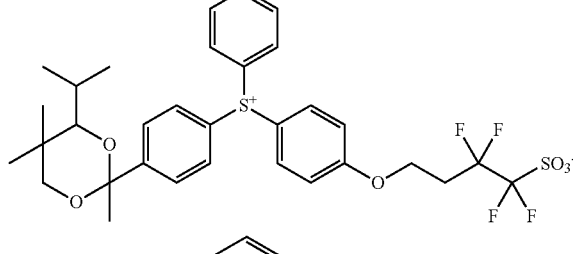
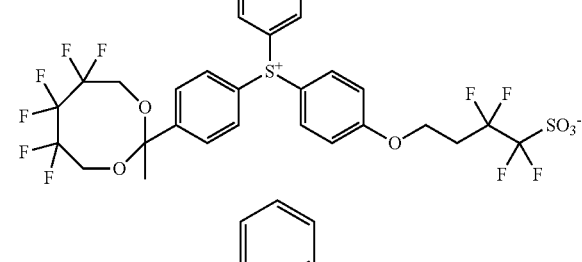
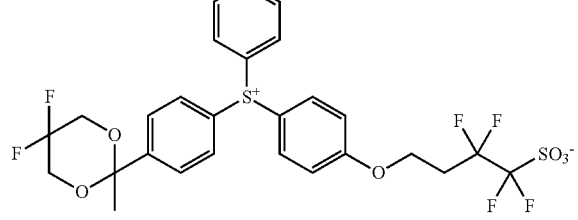
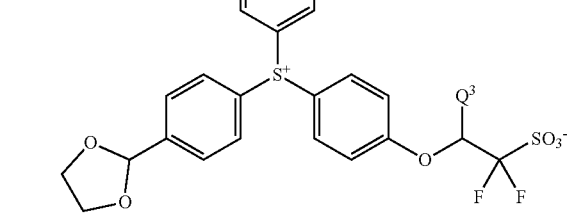

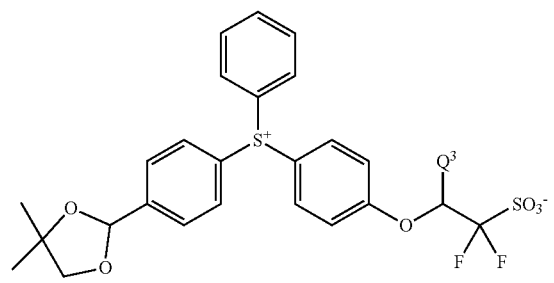
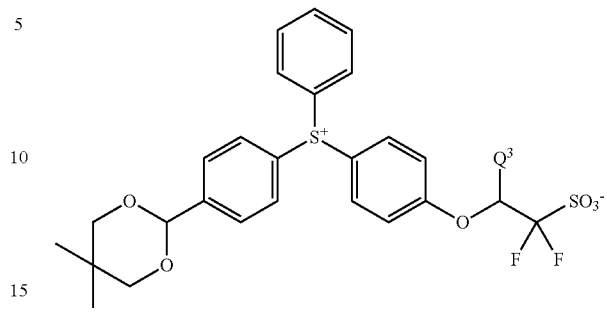
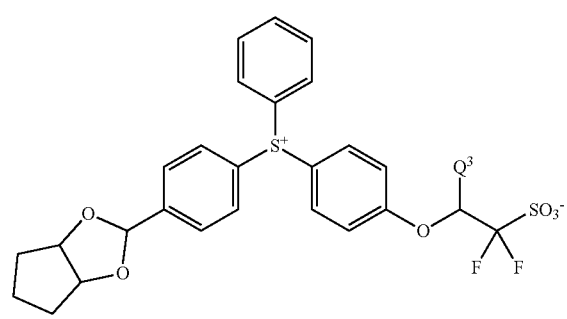
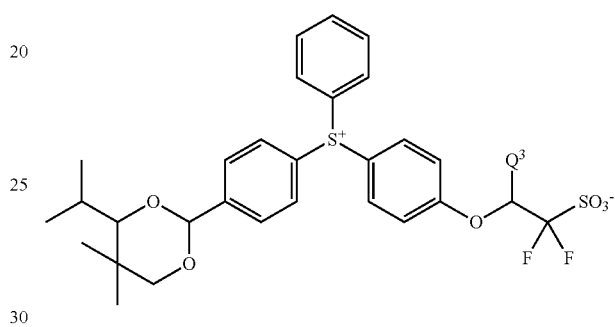
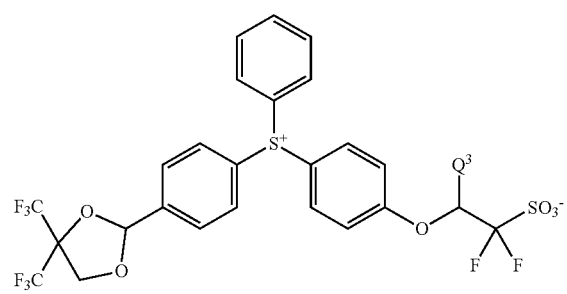
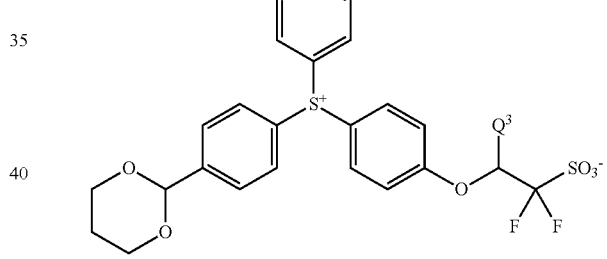
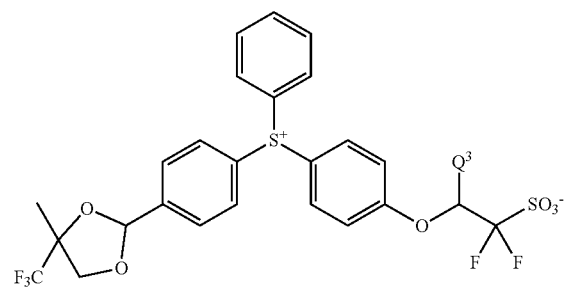
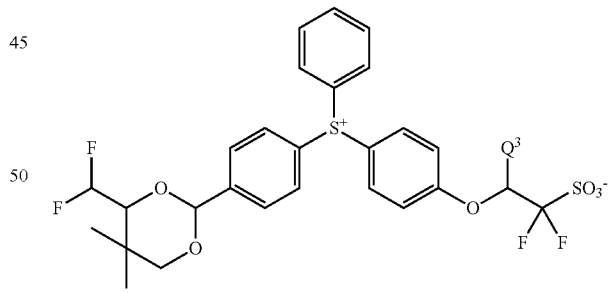
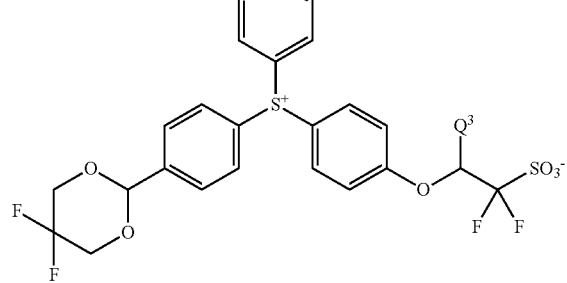
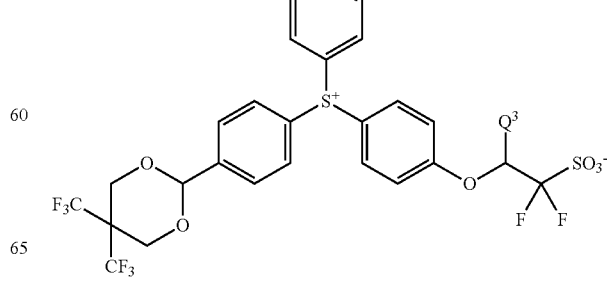

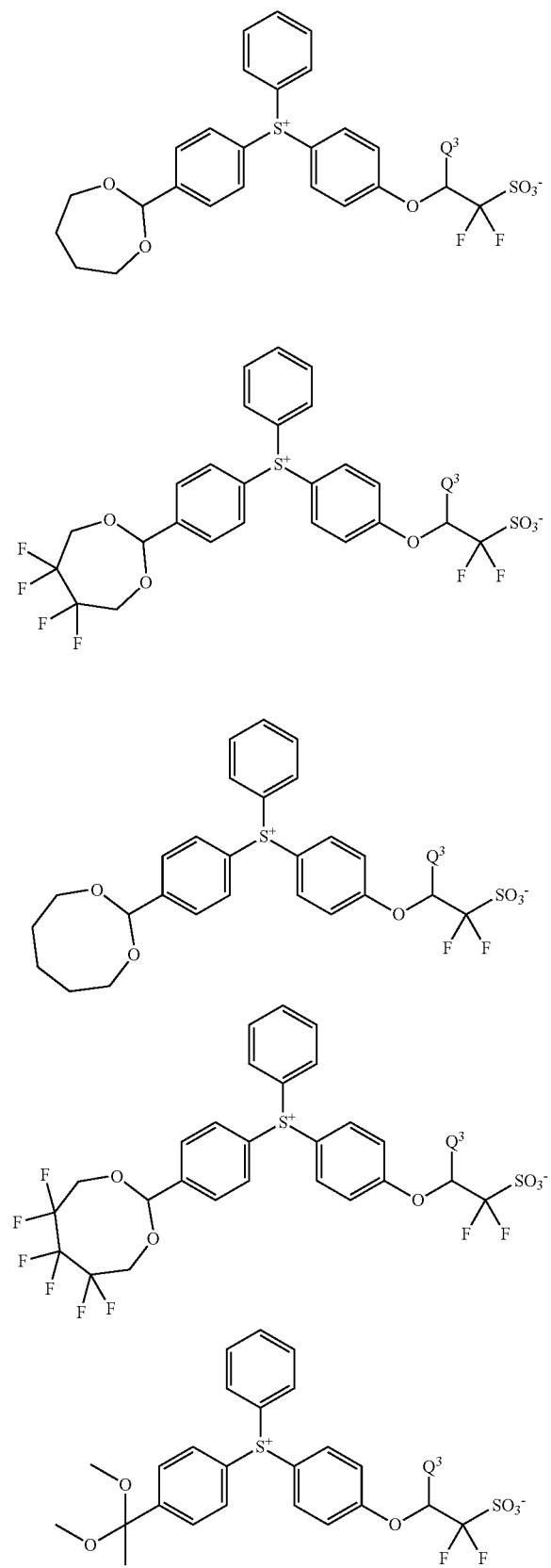
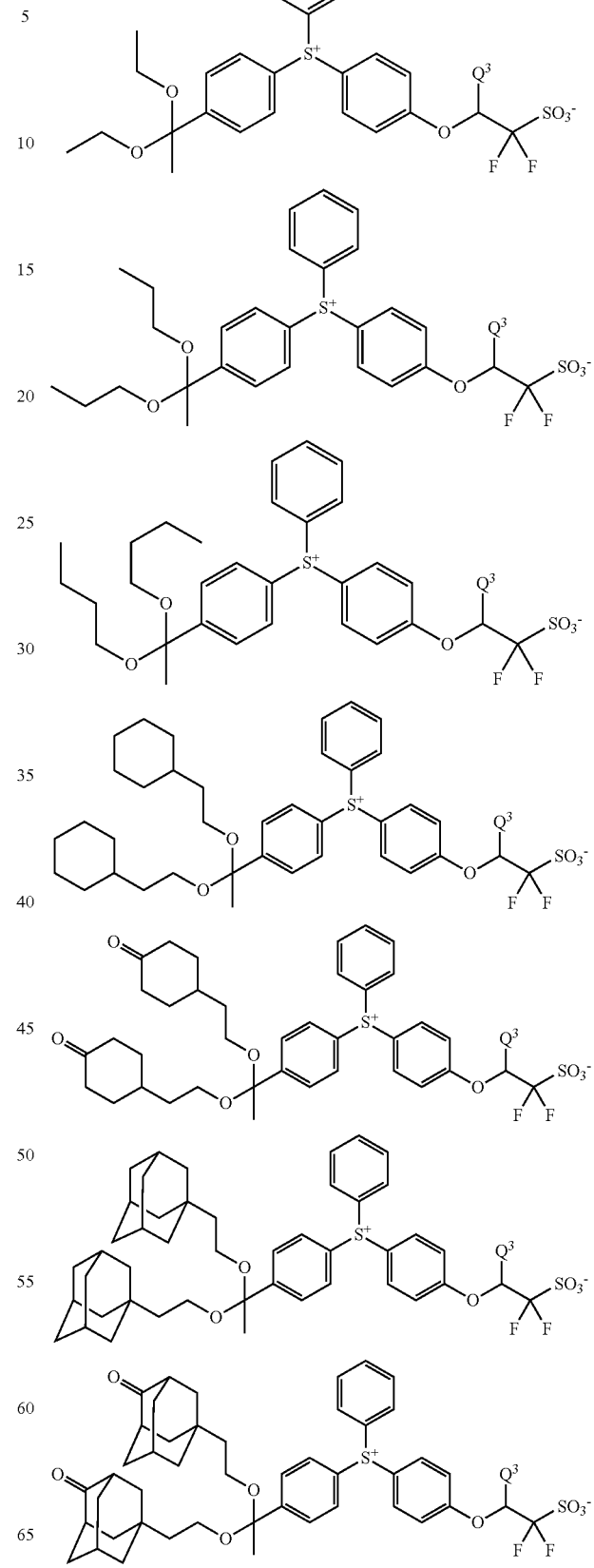

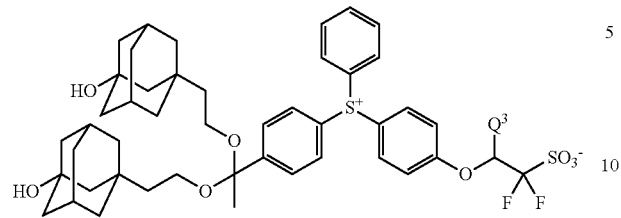
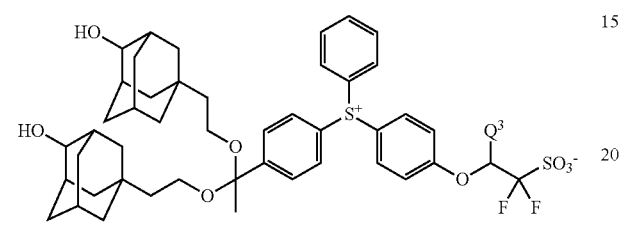
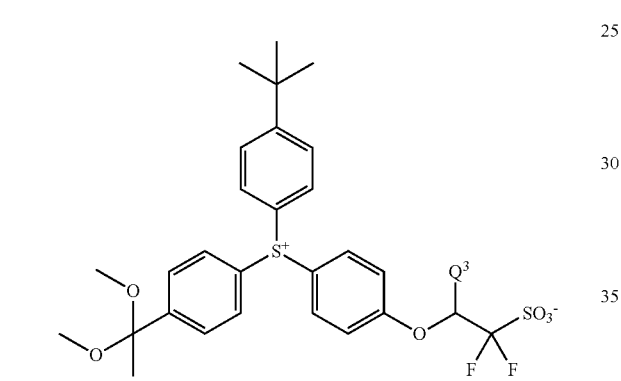
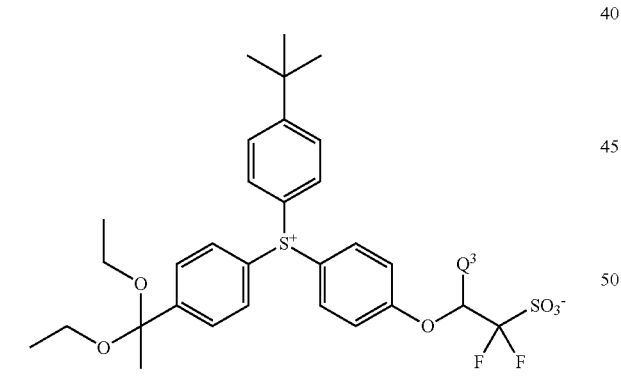
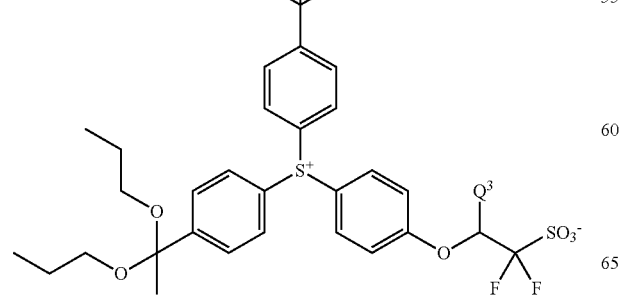
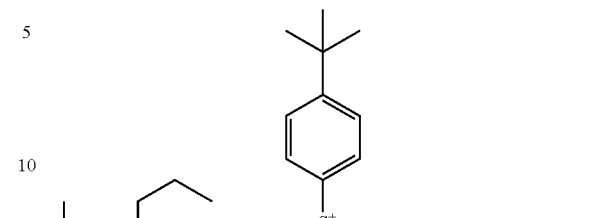
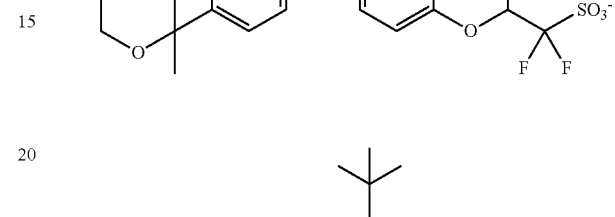
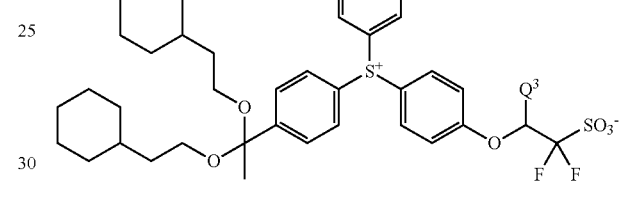
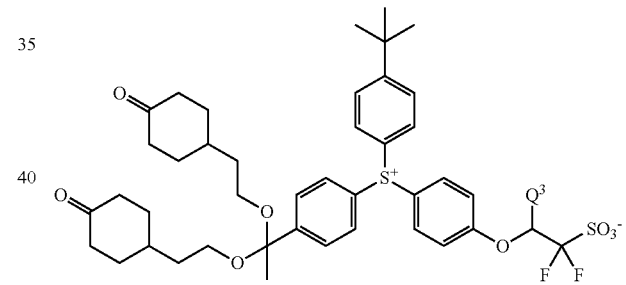
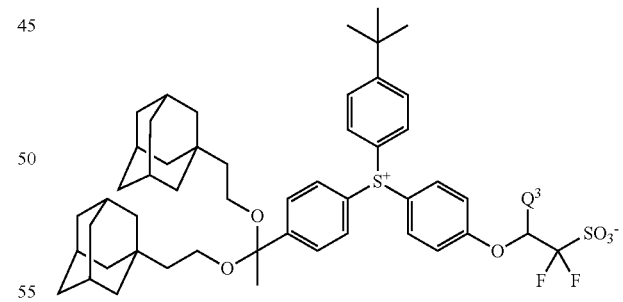
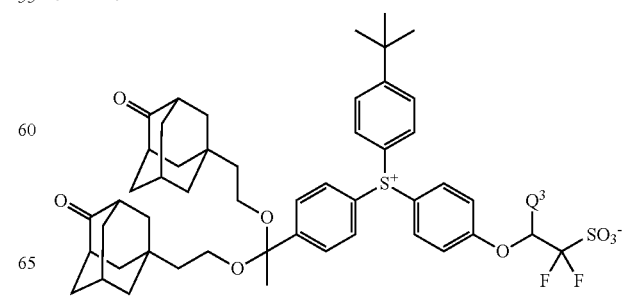

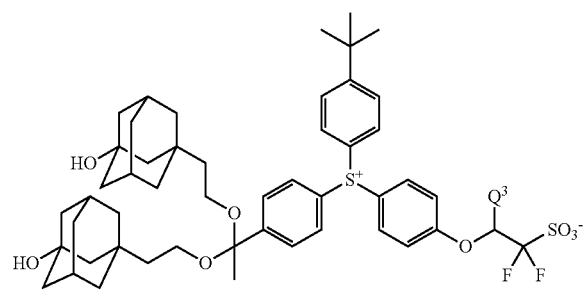
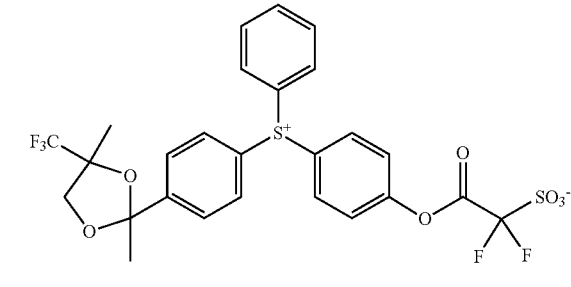
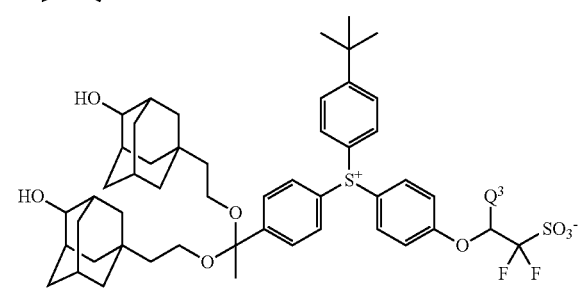
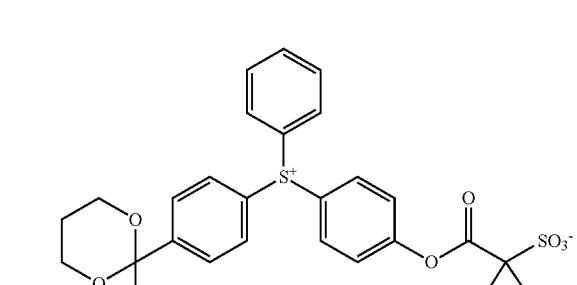
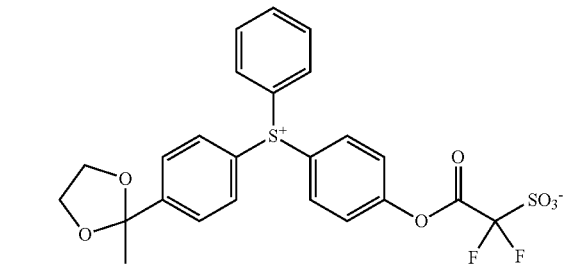
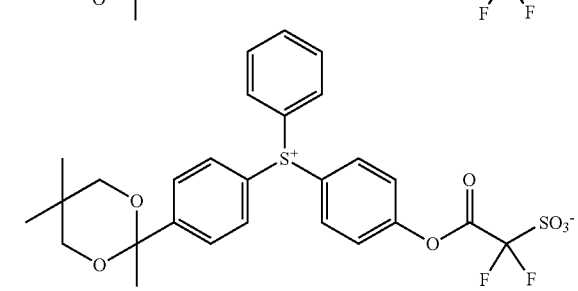
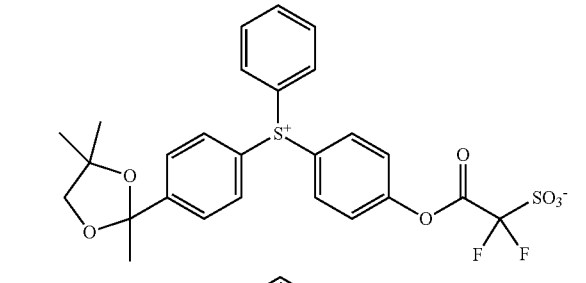
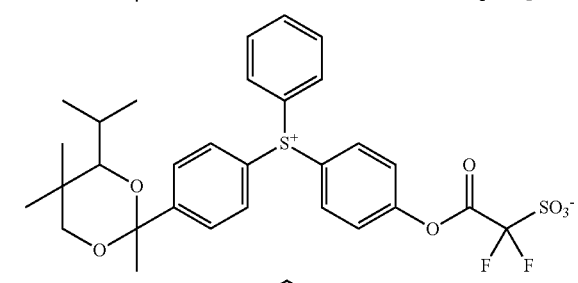
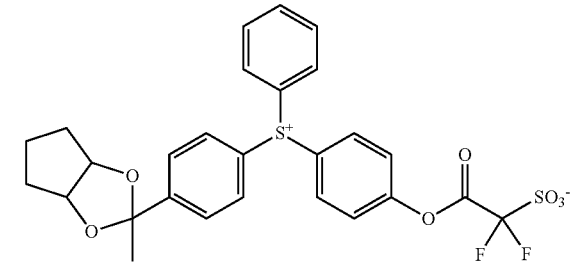
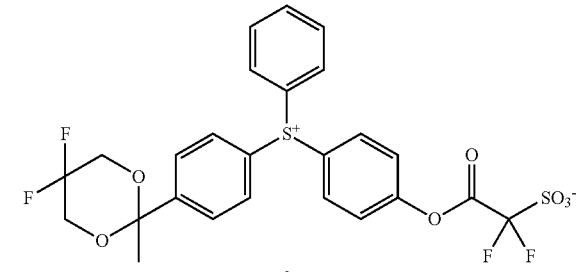
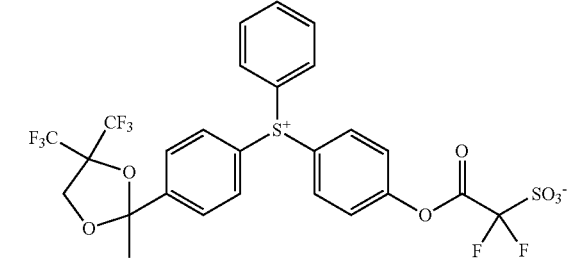
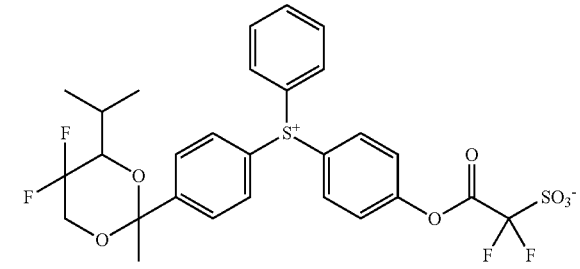

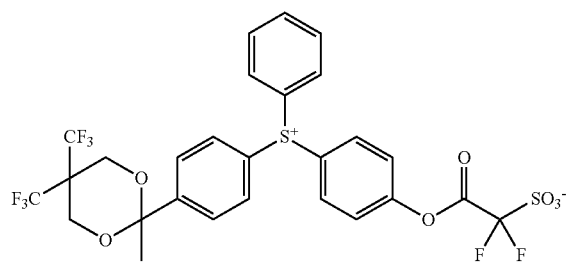
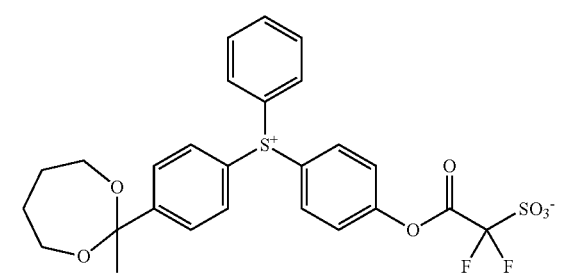
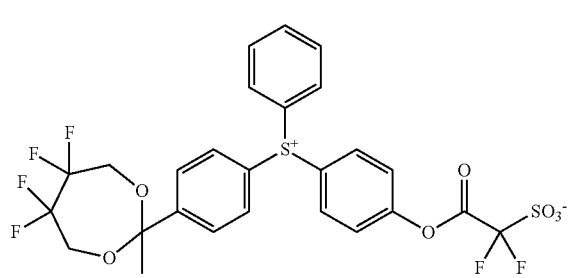
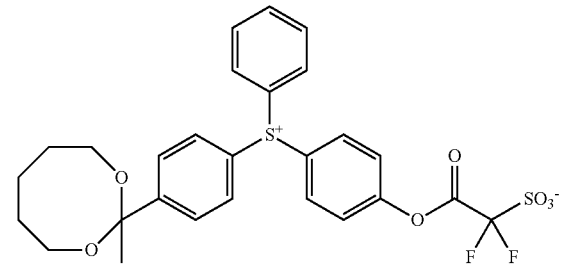
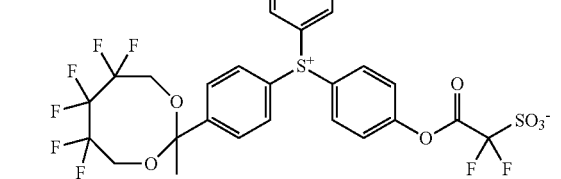
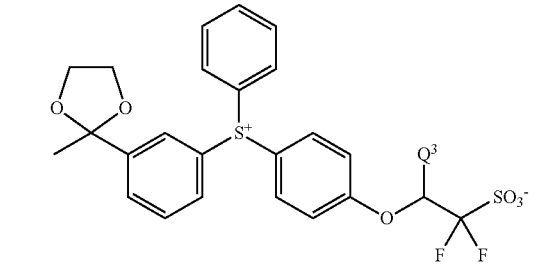
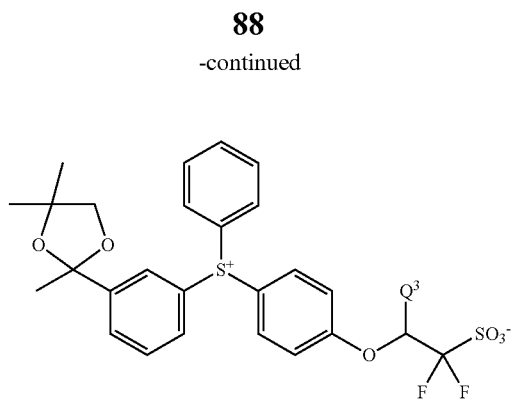
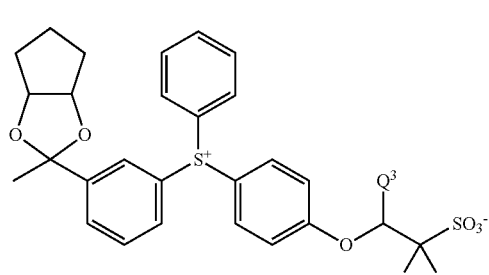
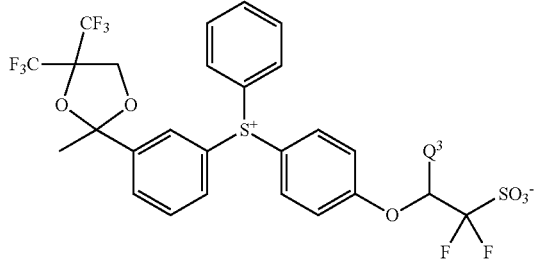
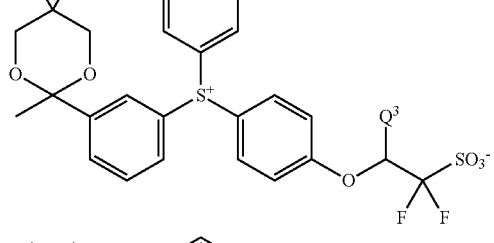
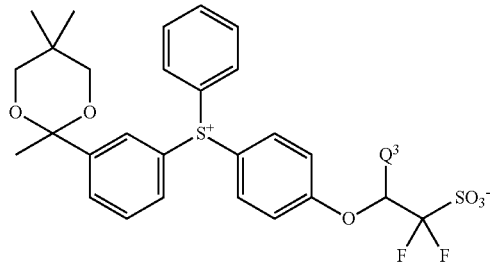

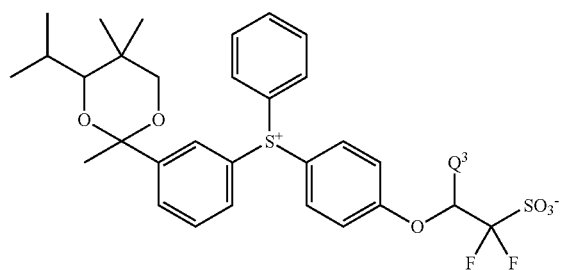
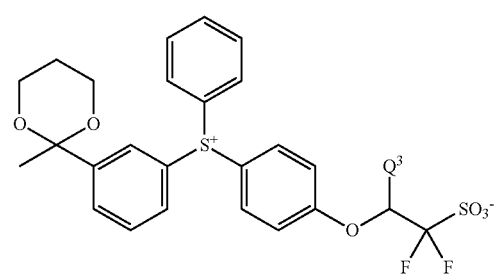
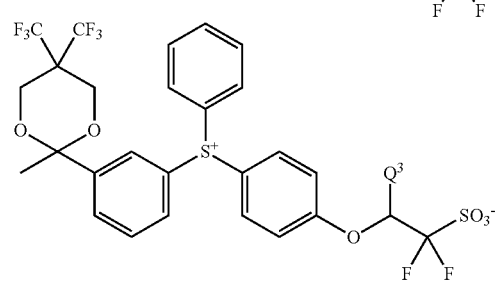
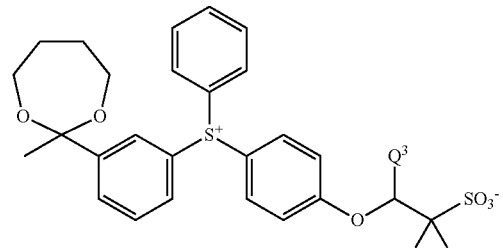
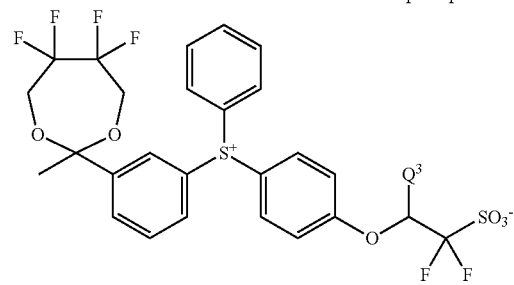
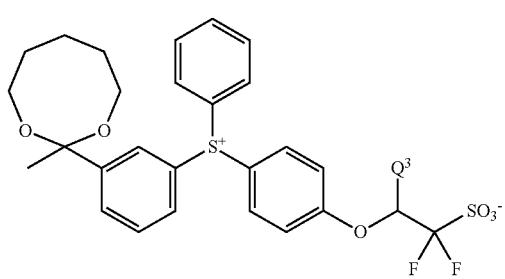
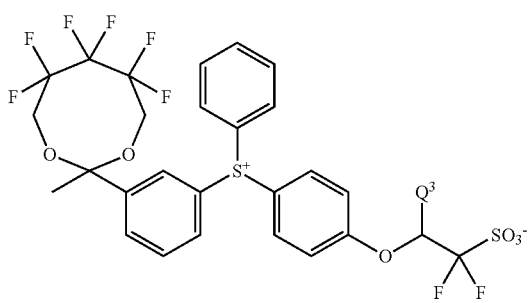
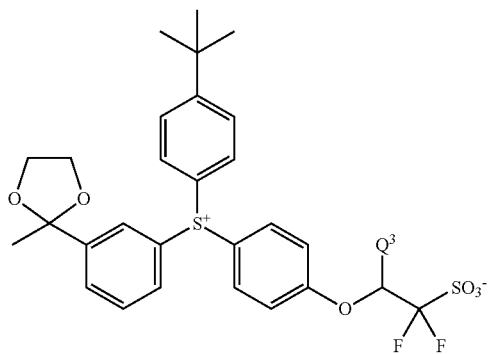
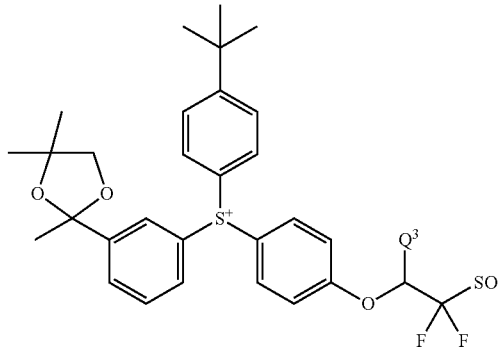
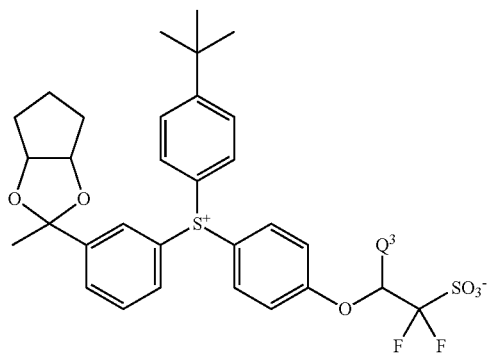

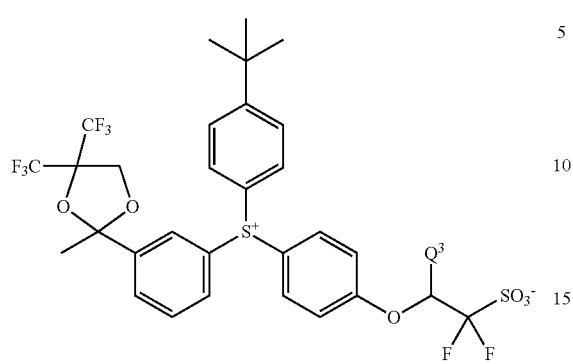
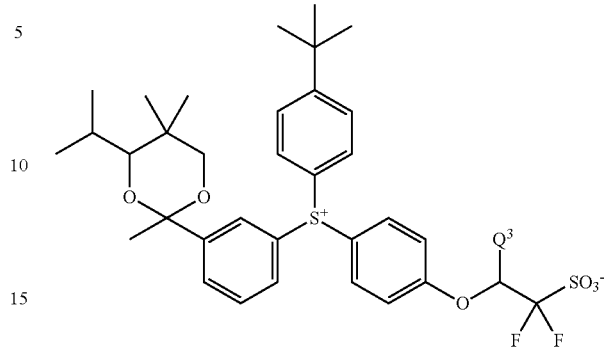
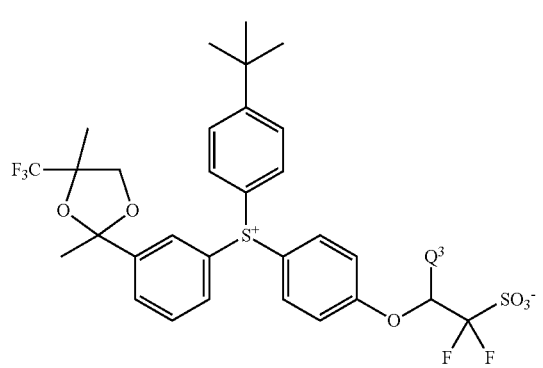
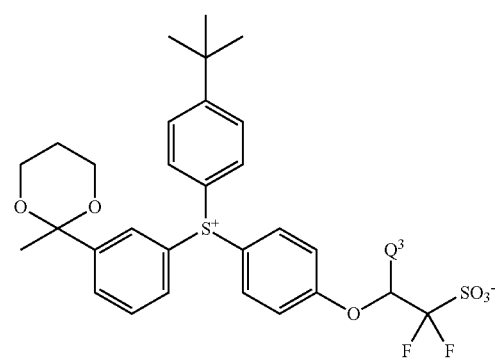
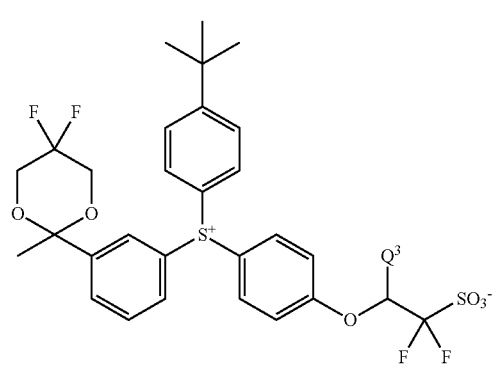
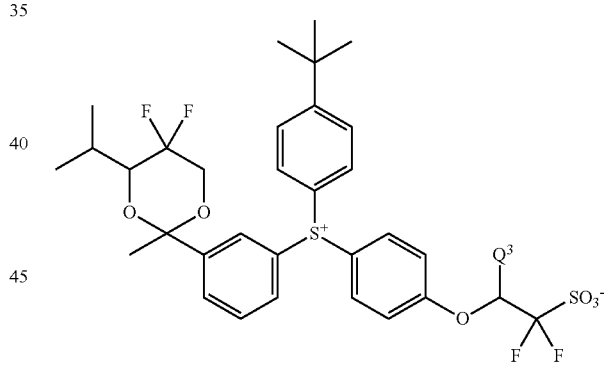
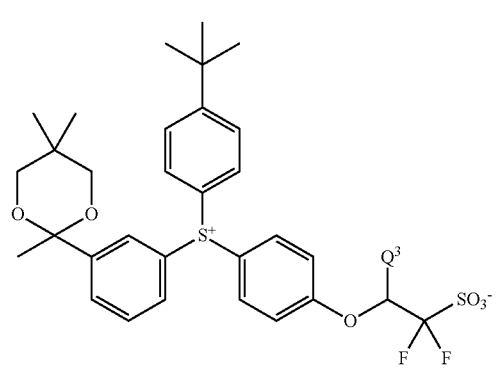
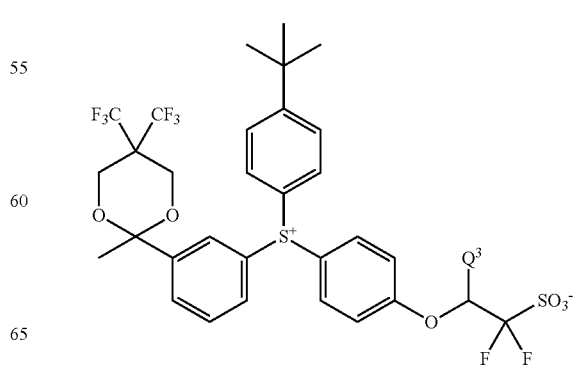

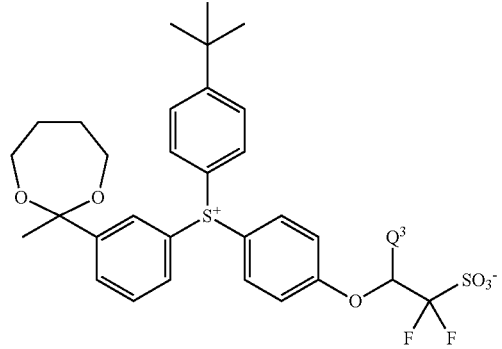
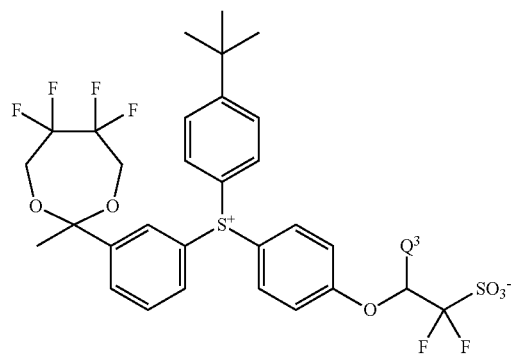
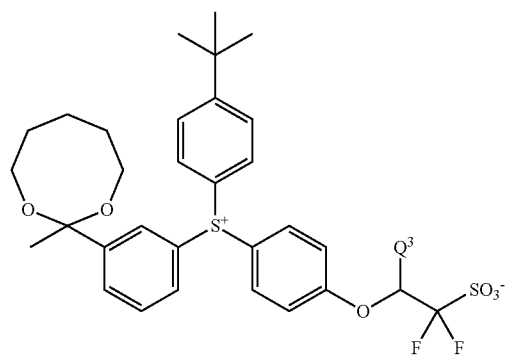
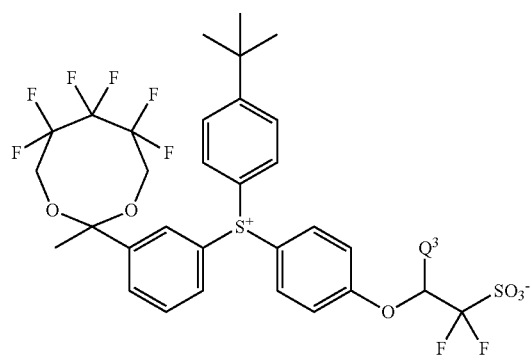
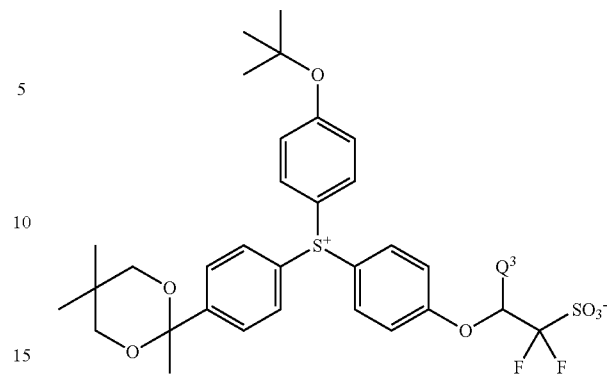
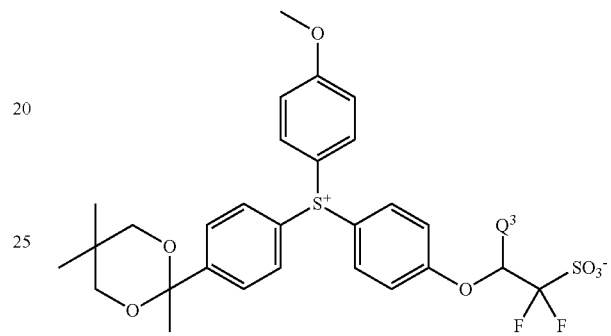
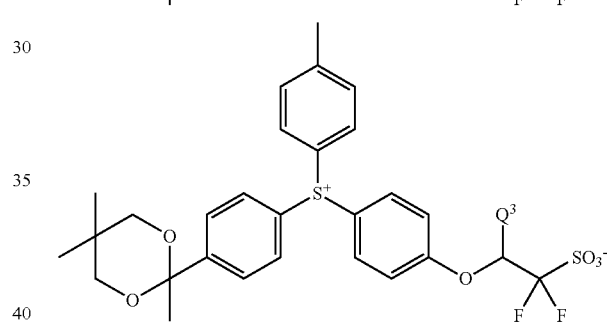
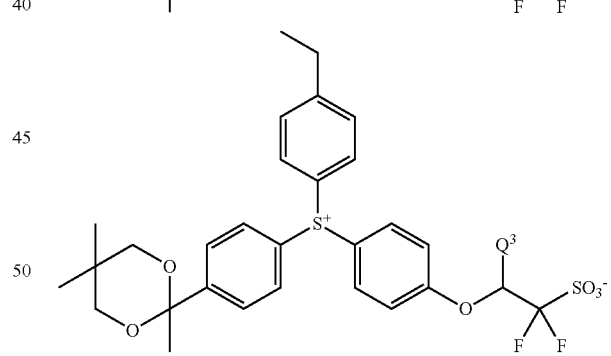
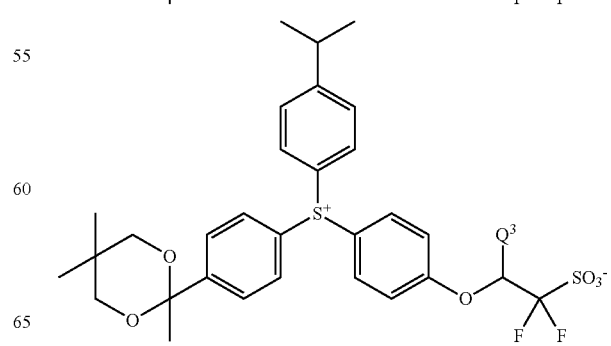

95
-continued
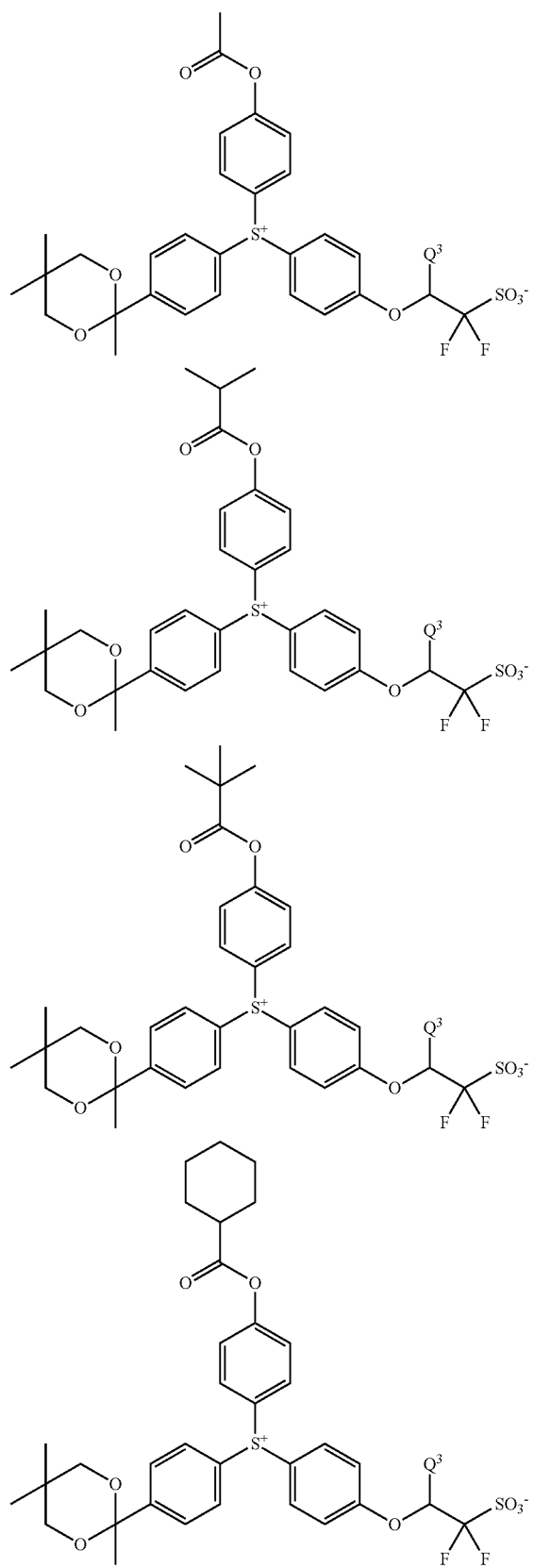
96
-continued
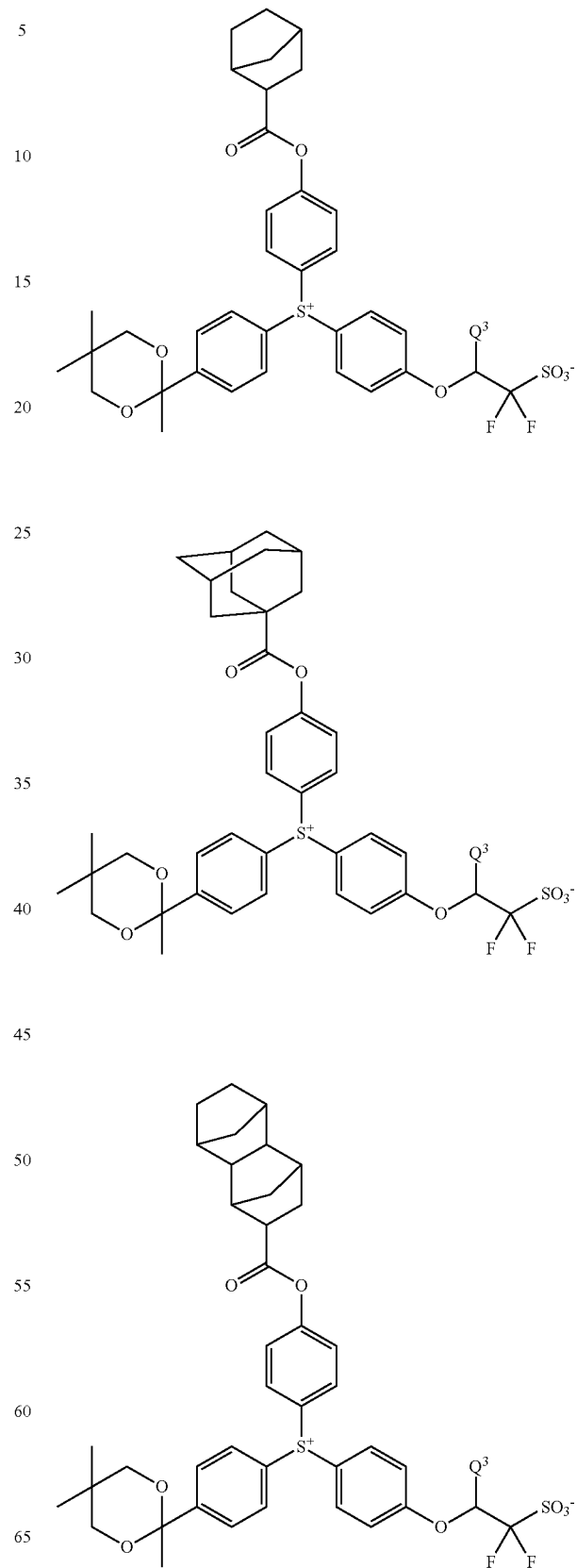

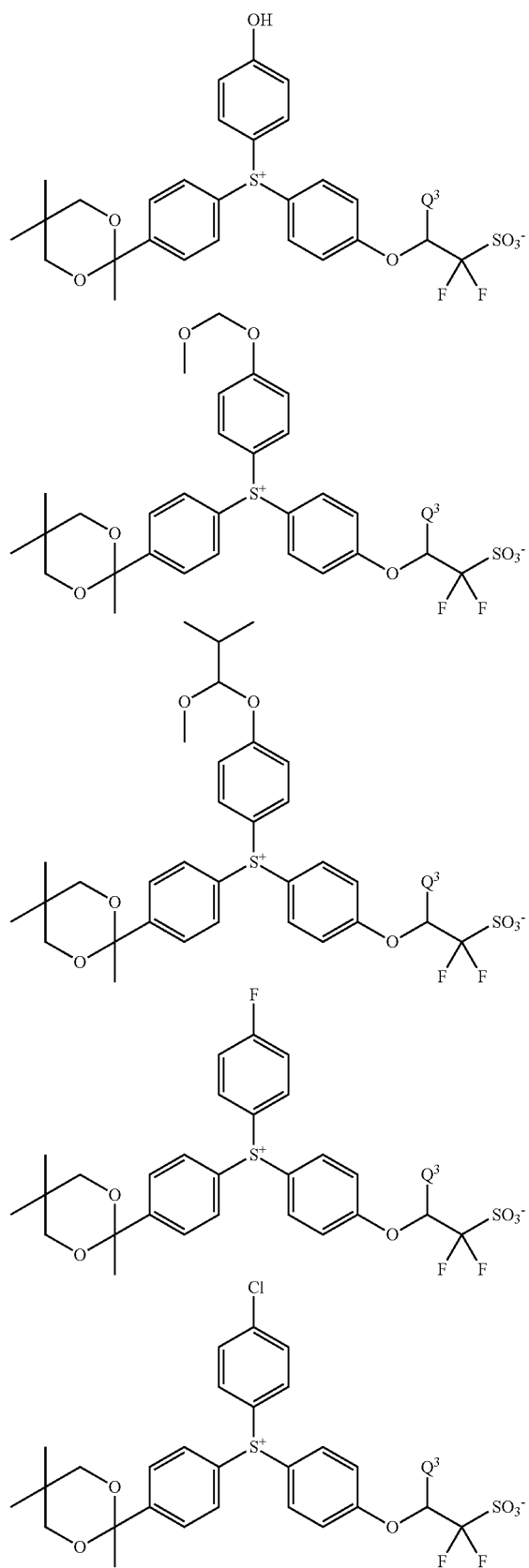
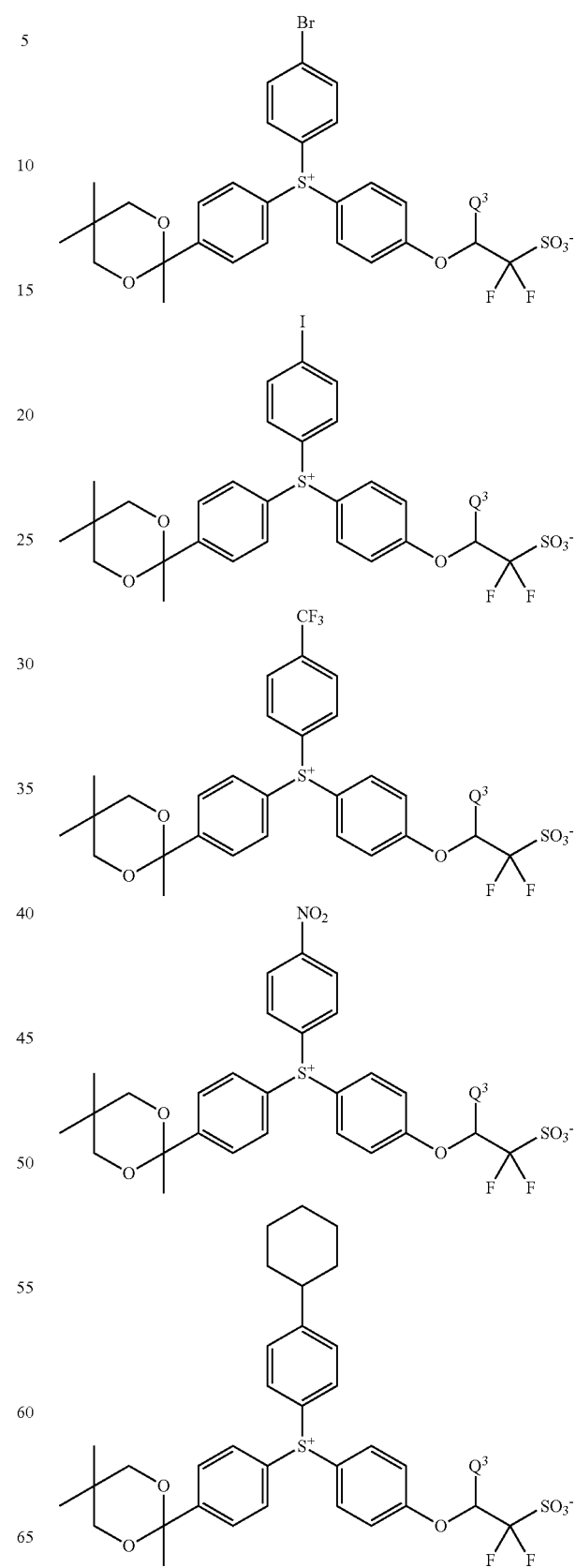

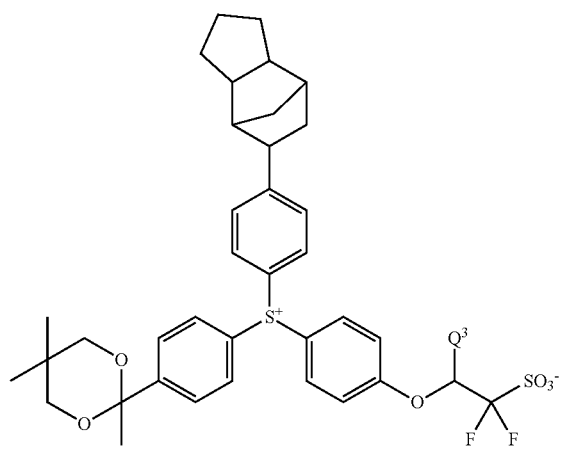
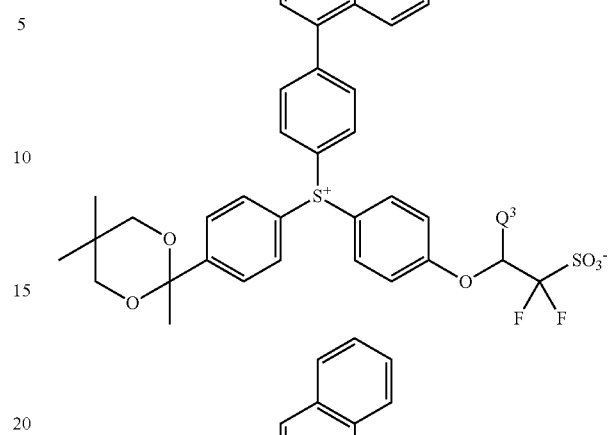
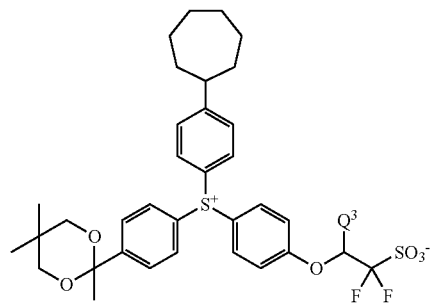
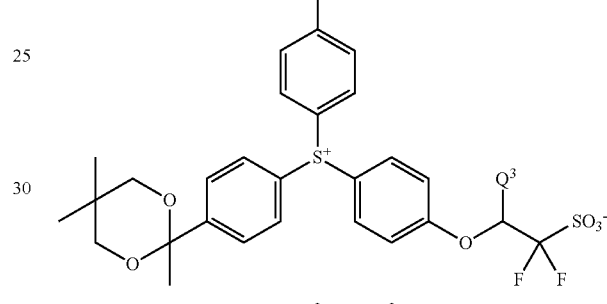
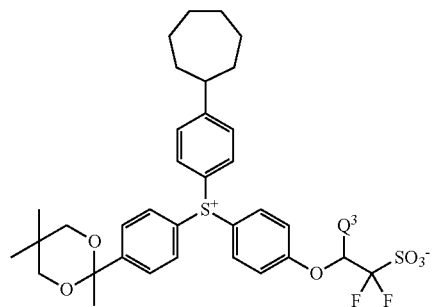
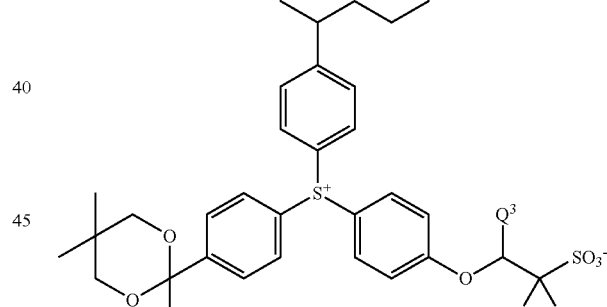
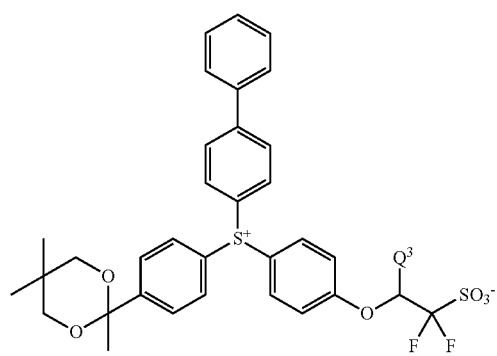
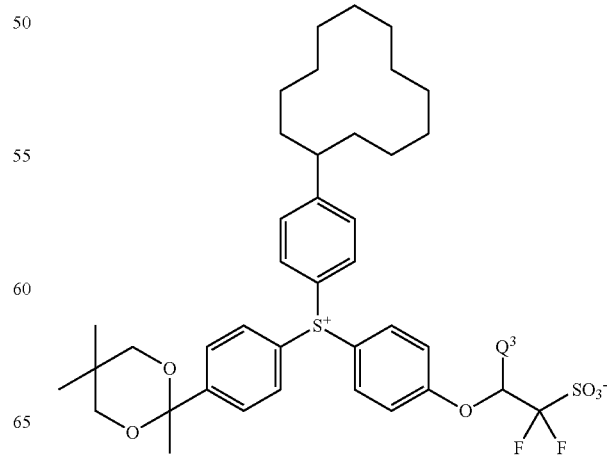

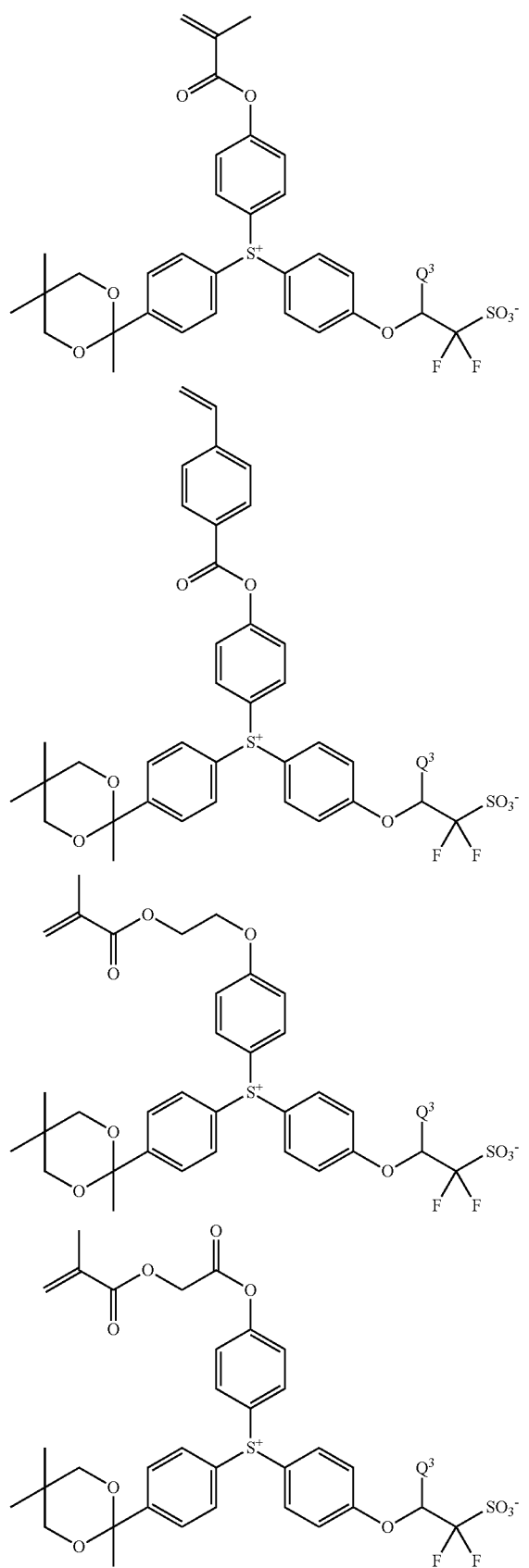
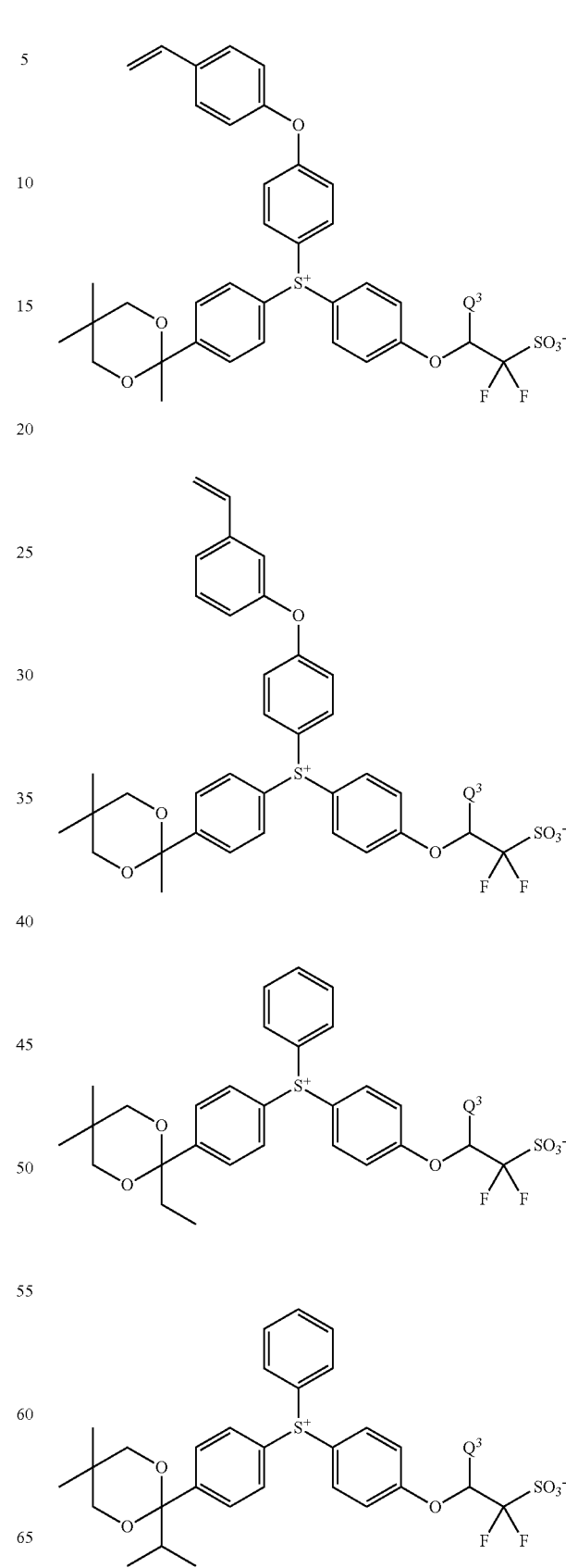

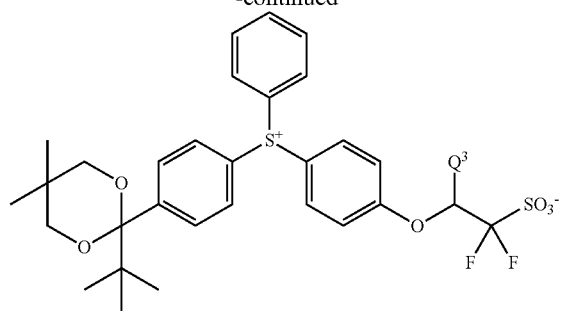
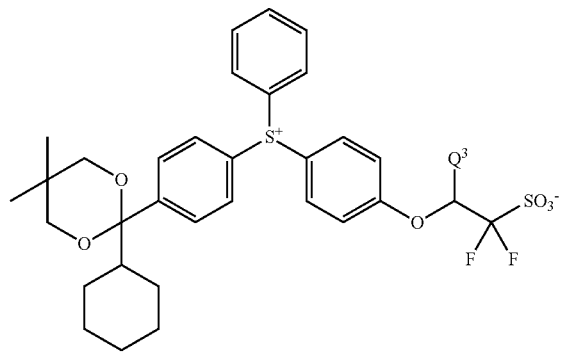
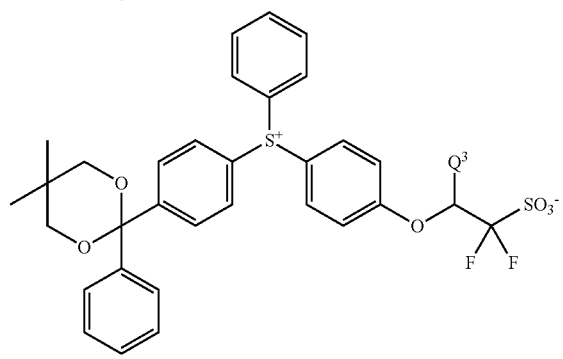
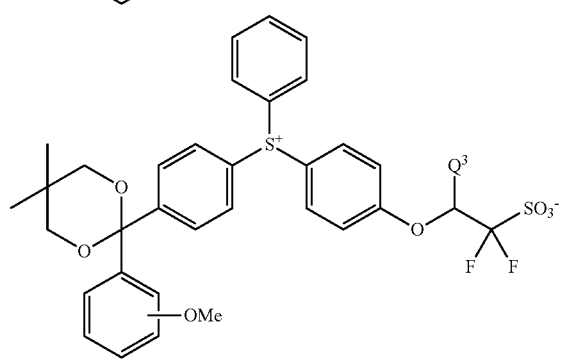
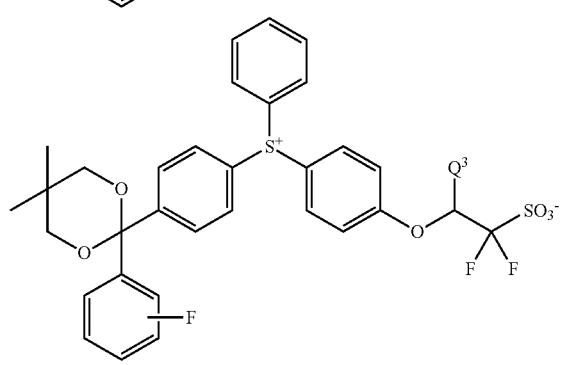
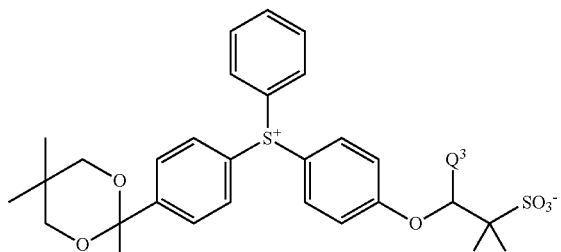
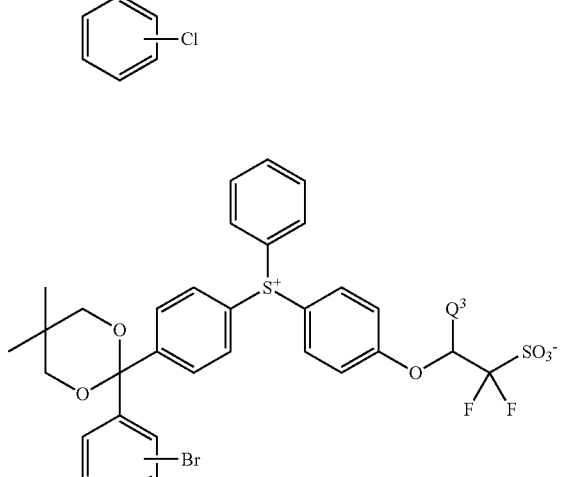
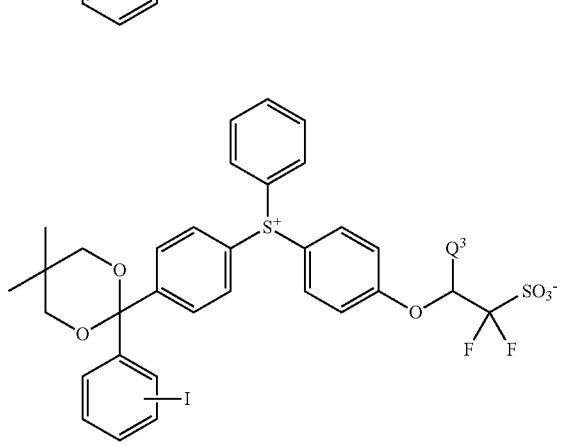
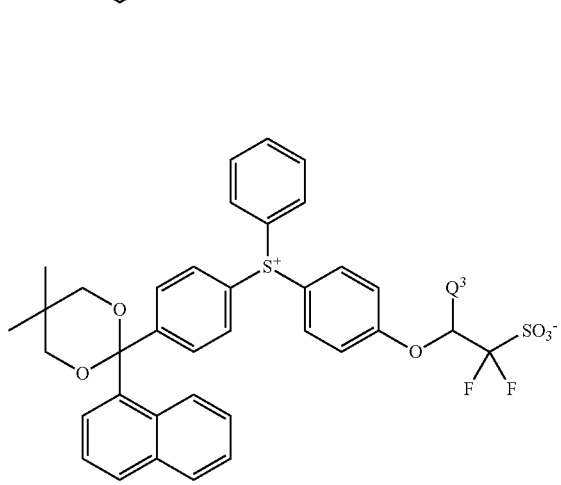

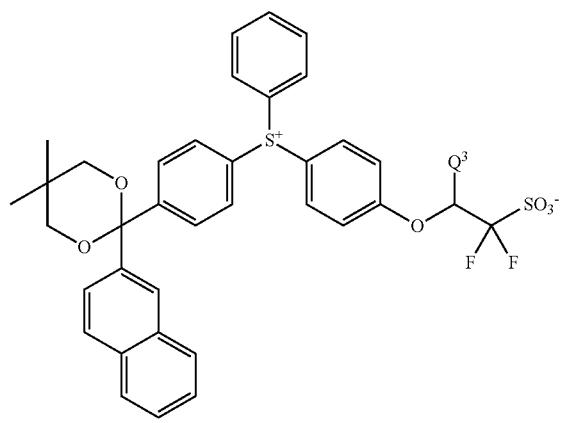
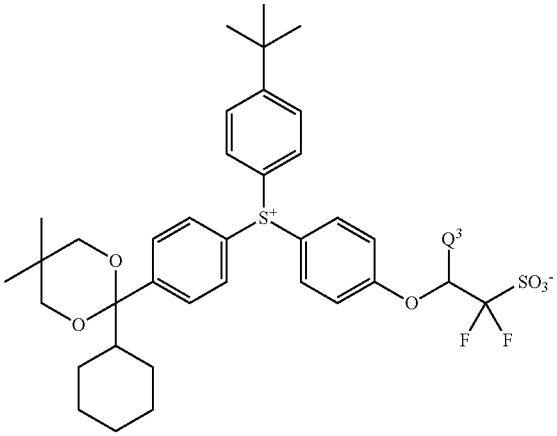
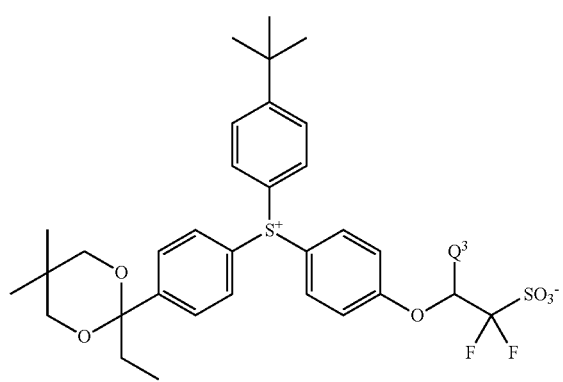
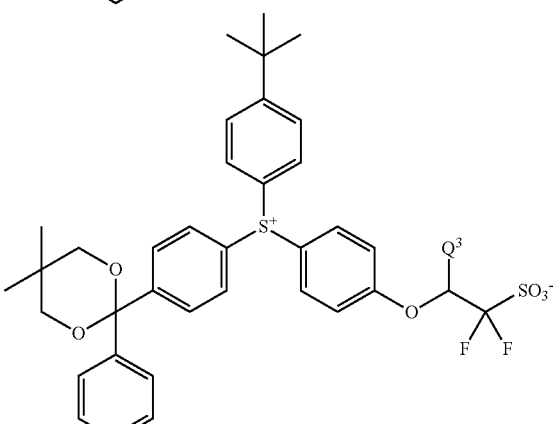
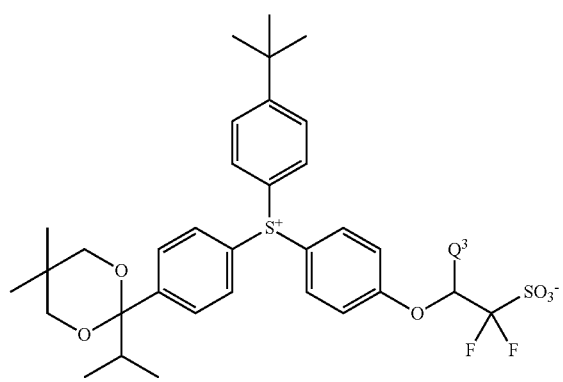
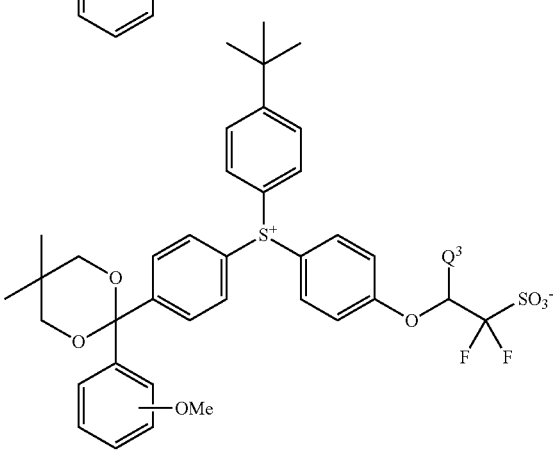
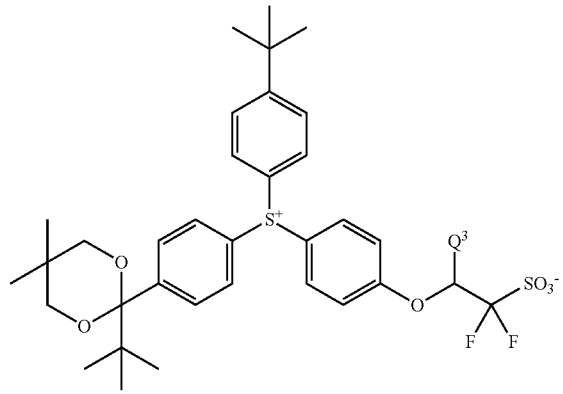
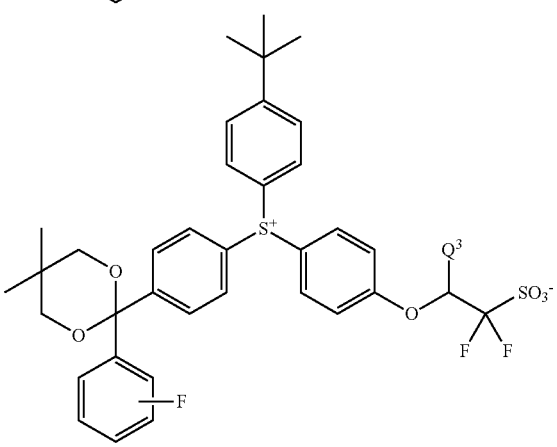

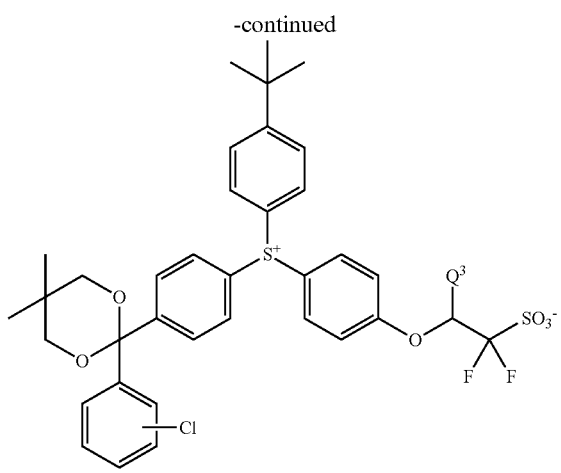

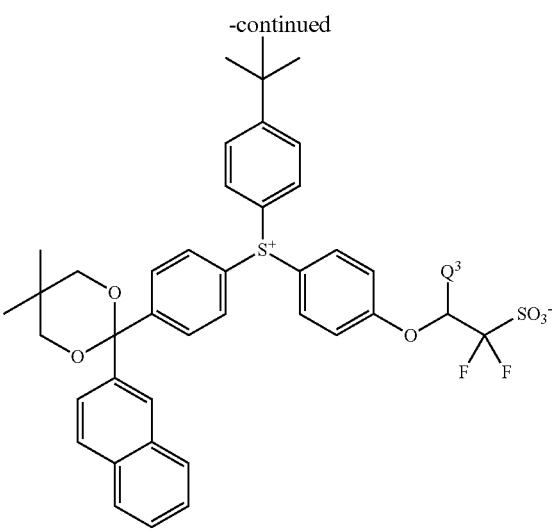

The inventive sulfonium compound is a useful PAG. The sulfonium compound is structurally characterized by a betaine structure possessing cation and anion moieties within a common molecule, and an acetal structure in the molecule. After an acid is generated upon exposure, a salt compound is formed between molecules and when another PAG is co-present, a salt compound is formed between the acid and the other PAG, probably assuming an apparently giant compound. After the acid generation, not only decomposition of the cation moiety, but also acid-catalyzed deprotection reaction of the acetal structure takes place. It is presumed that the acetal structure converts to a ketone (or aldehyde) structure which is a polar group, whereby the dissolution contrast increases.

For the same reason, the behavior that acid diffusion is suppressed is presumed. This leads to improvements in EL, MEF and LWR as well as DOF and CDU. Heretofore, DOF and CDU are in a tradeoff relationship as a result of scramble for resolution performance or acid diffusion control. By contrast, the inventive resist composition is successful in improving both the factors at the same time, and thus useful. The conversion of the acetal structure to a polar ketone (or aldehyde) structure ensures that in the positive tone alkaline development process, the affinity to alkaline developer is improved and development defectivity in the exposed region is reduced. Inversely in the negative tone organic solvent development process, the solubility in the organic solvent lowers, and percent film retention in the exposed region is improved.

The inventive sulfonium compound may be prepared according to the scheme shown below. Although reference is made to the synthesis of a sulfonium compound of cyclic acetal structure having formula (A-a), the synthesis method is not limited thereto.

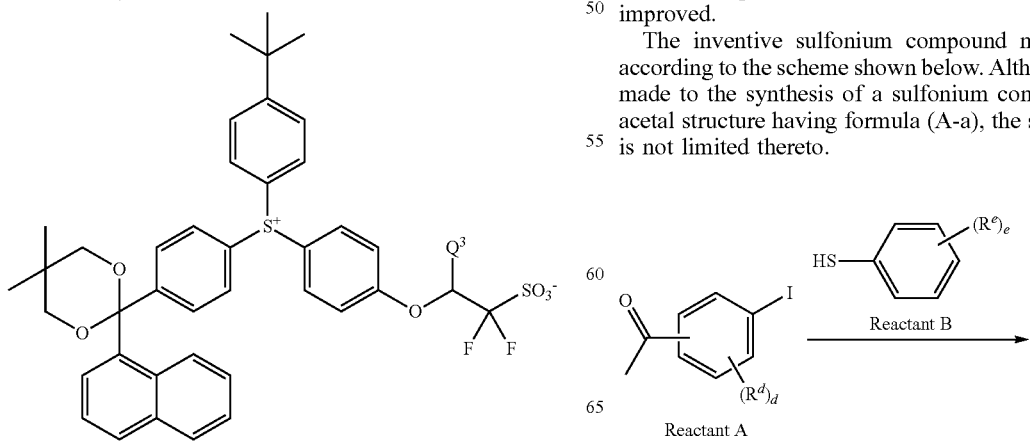

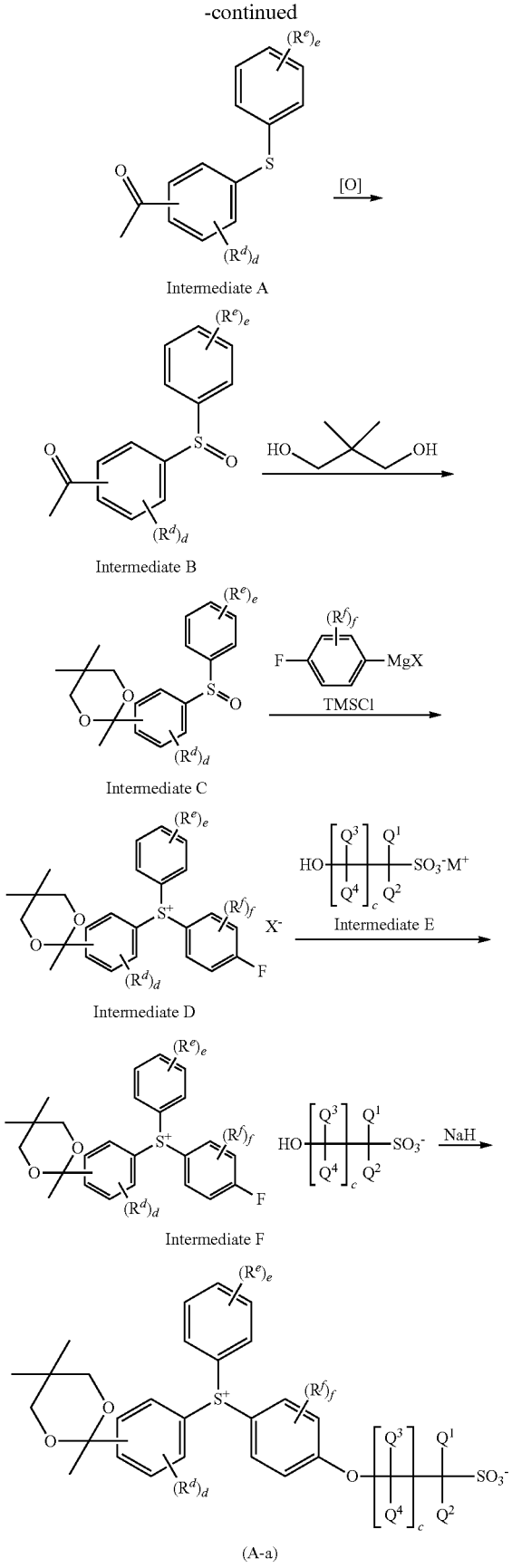

Herein $R^d$, $R^e$, $R^f$, $Q^1$ to $Q^4$, c, d, e and f are as defined above, X is a halogen atom, X⁻ is a halide ion, and M⁺ is a counter cation.

In the first step, coupling reaction is performed between Reactant A and Reactant B to form Intermediate A, diaryl sulfide. Reactants A and B are available as commercial products or can be synthesized by a standard method.

The reaction may be performed by a well-known organic synthesis method, specifically by dissolving Reactants A and B in a solvent such as N-methylpyrrolidone, dimethylformamide or dimethylacetamide, and adding a copper catalyst and a base to the solution. Examples of the copper catalyst used herein include copper(I) iodide, copper(I) bromide, and copper(I) chloride. Examples of the base used herein include organic bases such as triethylamine, pyridine and diisopropylethylamine and inorganic bases such as sodium hydroxide, potassium carbonate and lithium hydroxide. The reaction temperature may be from 80° C. to about the boiling point of the solvent. It is desirable from the standpoint of yield that the reaction time is determined so as to drive the reaction to completion by monitoring the reaction process by gas chromatography (GC) or silica gel thin-layer chromatography (TLC). Usually, the reaction time is about 6 to 24 hours. At the end of reaction, Intermediate A is recovered from the reaction mixture through an ordinary aqueous workup. If necessary, Intermediate A may be purified by a standard technique such as distillation, silica gel column chromatography or recrystallization.

In the second step, Intermediate A, diaryl sulfide is oxidized into diaryl sulfoxide.

The reaction may be performed by a well-known organic synthesis method, specifically by dissolving the sulfide (Intermediate A) in formic acid, acetic acid or the like, and adding aqueous hydrogen peroxide thereto. An amount of aqueous hydrogen peroxide in excess of the sulfide is accompanied by excessive oxidation to sultone. The reaction may also be performed by dissolving the sulfide in methylene chloride and adding m-chloroperbenzoic acid thereto. The reaction temperature is typically room temperature to about 50° C. It is desirable from the standpoint of yield that the reaction time is determined so as to drive the reaction to completion by monitoring the reaction process by GC or TLC. Usually, the reaction time is about 6 to 24 hours. At the end of reaction, Intermediate B is recovered from the reaction mixture through an ordinary aqueous workup. If necessary, Intermediate B may be purified by a standard technique such as silica gel column chromatography or recrystallization.

In the third step, a diol is reacted with the carbonyl group on Intermediate B to form cyclic acetal Intermediate C.

The reaction may be performed by a well-known organic synthesis method, specifically by dissolving Intermediate B in toluene, xylene or the like and adding a corresponding diol thereto. The reaction rate may be increased by adding an acid catalyst to the reaction solution. Exemplary of the acid catalyst are hydrochloric acid, sulfuric acid, nitric acid, p-toluenesulfonic acid, methanesulfonic acid, and trifluoromethanesulfonic acid. Also, the reaction time may be shortened by removing the water of reaction out of the reaction system to bias the equilibrium of the reaction system to the product side. The reaction temperature is typically about 80 to 150° C. It is desirable from the standpoint of yield that the reaction time is determined so as to drive the reaction to completion by monitoring the reaction process by GC or TLC. Usually, the reaction time is about 6 to 24 hours. At the end of reaction, Intermediate C is recovered from the reaction mixture through an ordinary aqueous workup. If necessary, Intermediate C may be purified by a standard technique such as silica gel column chromatography or recrystallization.

In the 4-th step, a Grignard reagent prepared from halogenated fluorobenzene is added to Intermediate C to form Intermediate D or triarylsulfonium salt.

The reaction may be performed by a well-known organic synthesis method, specifically by preparing a Grignard reagent from halogenated fluorobenzene in a standard way, adding a solution of Intermediate C in a solvent such as methylene chloride or tetrahydrofuran (THF) thereto, and adding dropwise trimethylsilyl chloride to the solution. The reaction temperature is typically about 10 to 30° C. It is desirable from the standpoint of yield that the reaction time is determined so as to drive the reaction to completion by monitoring the reaction process by TLC. Usually, the reaction time is about 1 to 2 hours. At the end of reaction, Intermediate D is recovered from the reaction mixture through an ordinary aqueous workup. If necessary, Intermediate D may be purified by a standard technique such as silica gel column chromatography or recrystallization. Notably, X⁻ in Intermediate D is preferably chloride or bromide ion.

The 5-th step is a salt exchange between Intermediate D and Intermediate E to form Intermediate F.

The reaction may be performed by a well-known organic synthesis method, specifically by dissolving or suspending Intermediate D and Intermediate E in methylene chloride or methyl isobutyl ketone, adding water thereto, and stirring the solution or suspension. It is desirable from the standpoint of yield to monitor the reaction process by TLC. At the end of reaction, Intermediate F is recovered from the reaction mixture through an ordinary aqueous workup. If necessary, Intermediate F may be purified by a standard technique such as chromatography or recrystallization.

In the above scheme, the 5-th step of ion exchange may be readily performed by any well-known method, for example, according to the teaching of JP-A 2007-145797.

The 6-th step is an aromatic nucleophilic displacement reaction of Intermediate F to yield the desired sulfonium compound (A-a).

Specifically, the reaction is performed by suspending sodium hydride in THF, cooling the suspension, and adding dropwise a THF solution of Intermediate F to the system. It is desirable from the standpoint of yield to monitor the reaction process by TLC. At the end of reaction, the sulfonium compound (A-a) is recovered from the reaction mixture through an ordinary aqueous workup. If necessary, the compound may be purified by a standard technique such as chromatography or recrystallization.

While the procedure according to the above scheme is merely exemplary, the preparation of the inventive sulfonium compound is not limited thereto. While the scheme refers to the synthesis of a compound having an ether bond, it is possible for the skilled artisan to synthesize sulfonium compounds having an ester bond, sulfonic ester bond, carbonate bond, and carbamate bond using any of organic chemistry methods commonly known in the art.

Resist Composition

Another embodiment of the invention is a chemically amplified resist composition comprising (A) a photoacid generator in the form of the sulfonium compound having formula (A) and (B) a base resin as essential components, and (C) an organic solvent as optional component. If necessary, the resist composition may further comprise at least one component selected from (D) another photoacid generator, (E) a quencher, (F) a surfactant, and (G) another component.

The amount of the PAG in the form of the sulfonium compound having formula (A) as component (A) is preferably 0.1 to 20 parts by weight, more preferably 0.5 to 10 parts by weight per 80 parts by weight of the base resin as component (B). As long as the amount of component (A) is in the range, good sensitivity and resolution are achievable and the risk of foreign particles being formed after development or during stripping of resist film is avoided. The PAG may be used alone or in admixture as component (A).

(B) Base Resin

The base resin as component (B) preferably contains recurring units having the formula (a1) or recurring units having the formula (a2).

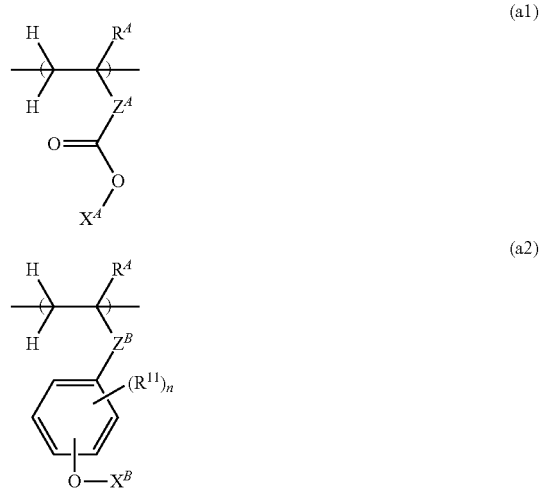

In formulae (a1) and (a2), $R^A$ is each independently hydrogen, fluorine, methyl or trifluoromethyl. $Z^A$ is a single bond, phenylene, naphthylene or (backbone)-C(=O)—O—$Z^{41}$—, wherein $Z^{41}$ is a $C_1$-$C_{10}$ alkanediyl group which may contain a hydroxyl moiety, ether bond, ester bond or lactone ring, or a phenylene or naphthylene group. $Z^B$ is a single bond or (backbone)-C(=O)—O—. $X^A$ and $X^B$ are each independently an acid labile group. $R^{11}$ is a $C_1$-$C_{20}$ monovalent hydrocarbon group which may contain a heteroatom, and n is an integer of 0 to 4.

Examples of the structure of formula (a1) wherein $Z^A$ is a variant are illustrated below, but not limited thereto. Herein $R^A$ and $X^A$ are as defined above.

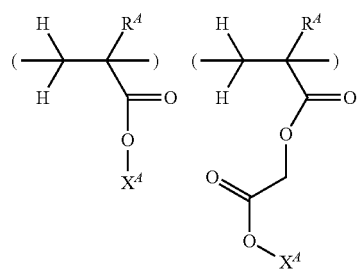

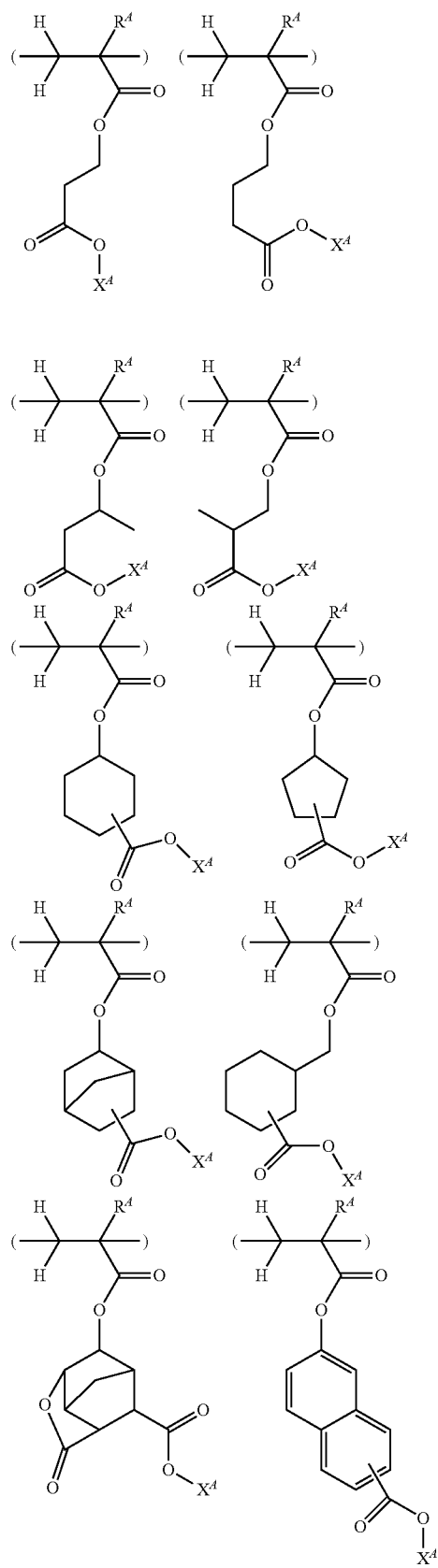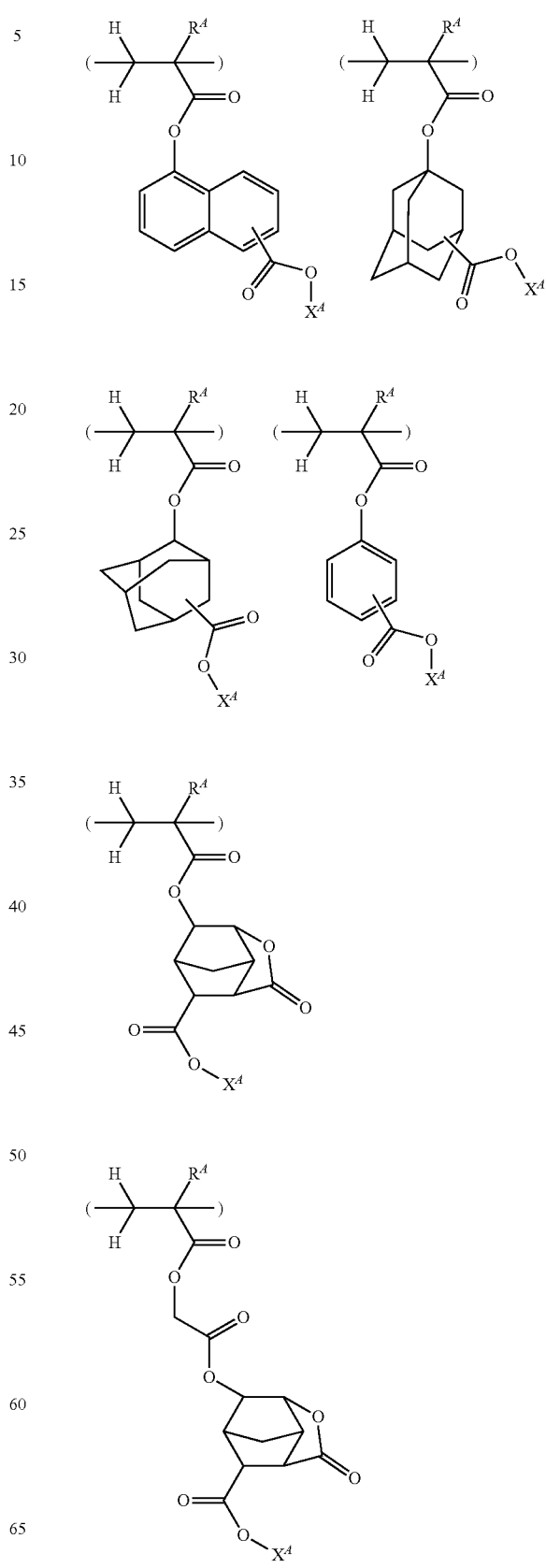

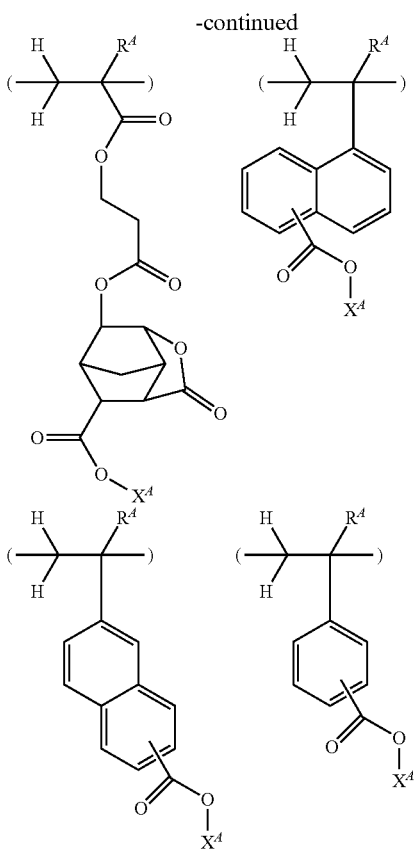

A polymer comprising recurring units having formula (a1) turns alkali soluble through the mechanism that it is decomposed under the action of acid to generate a carboxyl group.

The acid labile groups represented by $X^A$ and $X^B$ may be selected from a variety of such groups. Examples of the acid labile group are groups of the following formulae (L1) to (L4), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxo-containing alkyl groups.

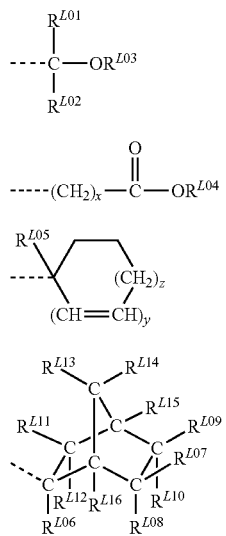

In formula (L1), $R^{L01}$ and $R^{L02}$ are each independently hydrogen or a $C_1$-$C_{18}$, preferably $C_1$-$C_{10}$ alkyl group. The alkyl group may be straight, branched or cyclic and examples thereof include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a $C_1$-$C_{18}$, preferably $C_1$-$C_{10}$ monovalent hydrocarbon group which may contain a moiety containing a heteroatom such as oxygen. Examples of the monovalent hydrocarbon group include straight, branched or cyclic alkyl groups and such groups in which some hydrogen is substituted by hydroxyl, alkoxy, oxo, amino, alkylamino or the like, or some carbon is replaced by a moiety containing a heteroatom such as oxygen. Suitable alkyl groups are as exemplified above for $R^{L01}$ and $R^{L02}$. Examples of the substituted alkyl groups are shown below.

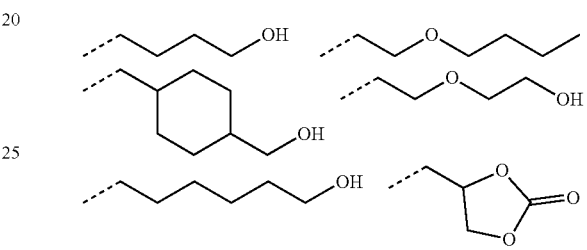

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a $C_1$-$C_{18}$, preferably $C_1$-$C_{10}$ straight or branched alkanediyl group when they form a ring.

In formula (L2), $R^{L04}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxo-containing alkyl group, or a group of formula (L1). Exemplary tertiary alkyl groups include tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups include trimethylsilyl, triethylsilyl, and dimethyl-tert-butylsilyl. Exemplary oxo-containing alkyl groups include 3-oxocyclohexyl, 4-methyl-2-oxooxan-4-yl, and 5-methyl-2-oxooxolan-5-yl. Letter x is an integer of 0 to 6.

In formula (L3), $R^{L05}$ is an optionally substituted $C_1$-$C_8$ alkyl group or an optionally substituted $C_6$-$C_{20}$ aryl group. The optionally substituted alkyl group may be straight, branched or cyclic and examples thereof include methyl, ethyl, propyl, isopropyl, n-butyl, sec-butyl, tert-butyl, tert-pentyl, n-pentyl, n-hexyl, cyclopentyl and cyclohexyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Letter y is equal to 0 or 1, z is an integer of 0 to 3, and 2y+z is equal to 2 or 3.

In formula (L4), $R^{L06}$ is an optionally substituted $C_1$-$C_8$ alkyl group or an optionally substituted $C_6$-$C_{20}$ aryl group. The alkyl group may be straight, branched or cyclic. Examples of the alkyl and aryl groups are the same as exemplified for $R^{L05}$.

$R^{L07}$ to $R^{L16}$ are each independently hydrogen or an optionally substituted $C_1$-$C_{15}$ monovalent hydrocarbon group. Suitable hydrocarbon groups include straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents $C_1$-$C_{15}$ divalent hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups having formula (L1), the straight and branched ones are exemplified by the following groups, but not limited thereto.

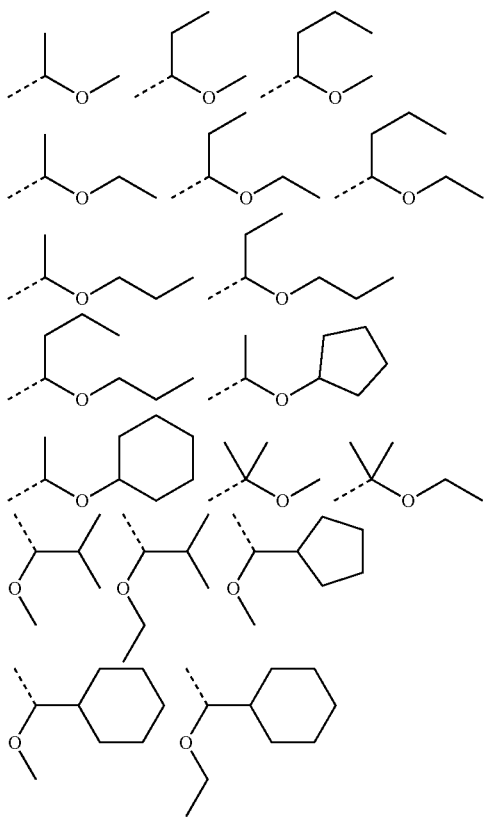

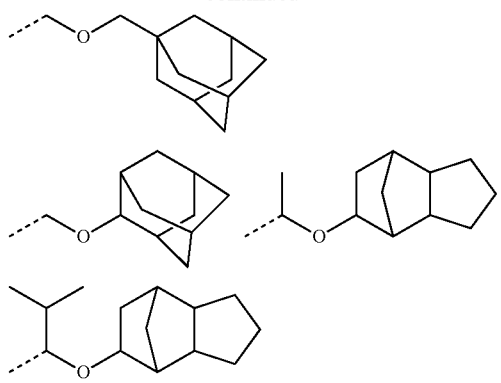

Of the acid labile groups having formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile group having formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile group having formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

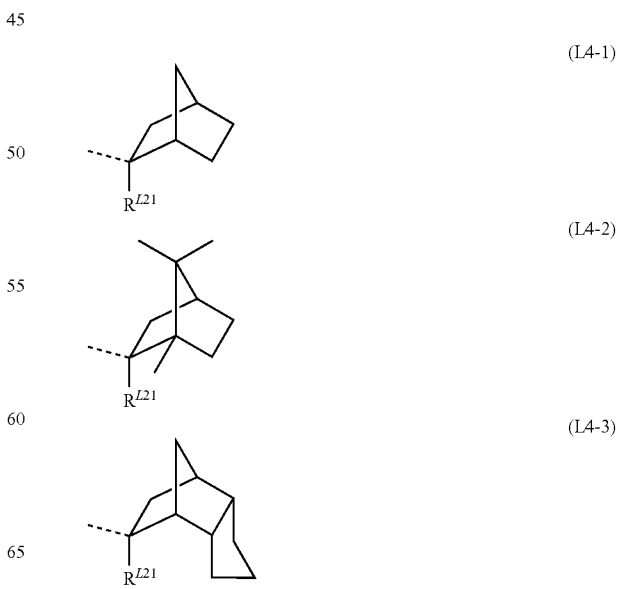

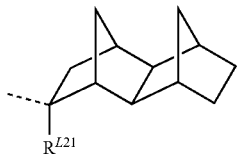
(L4-4)

In formulas (L4-1) to (L4-4), the broken line denotes a bonding site and direction. $R^{L21}$ is each independently a $C_1$-$C_{10}$ monovalent hydrocarbon group. The monovalent hydrocarbon group may be straight, branched or cyclic, and examples thereof include alkyl groups such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist stereoisomers (enantiomers or diastereomers). Each of formulae (L4-1) to (L4-4) collectively represents all such stereoisomers. When the acid labile group $X^A$ is of formula (L4), there may be contained a plurality of stereoisomers.

For example, the formula (L4-3) represents one or a mixture of two selected from groups having the following formulas (L4-3-1) and (L4-3-2).

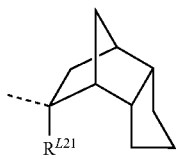
(L4-3-1)

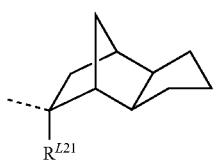
(L4-3-2)

Herein $R^{L21}$ is as defined above.

Similarly, the formula (L4-4) represents one or a mixture of two or more selected from groups having the following formulas (L4-4-1) to (L4-4-4).

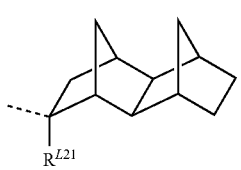
(L4-4-1)

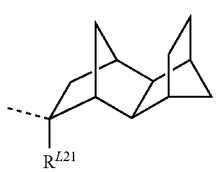
(L4-4-2)

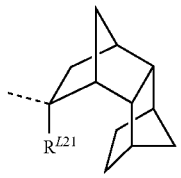
(L4-4-3)

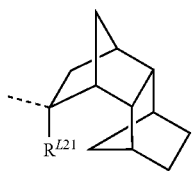
(L4-4-4)

Herein $R^{L21}$ is as defined above.

Each of formulas (L4-1) to (L4-4), (L4-3-1), (L4-3-2), and (L4-4-1) to (L4-4-4) collectively represents an enantiomer thereof and a mixture of enantiomers.

It is noted that in the above formulas (L4-1) to (L4-4), (L4-3-1), (L4-3-2), and (L4-4-1) to (L4-4-4), the bond direction is on the exo side relative to the bicyclo[2.2.1] heptane ring, which ensures high reactivity for acid catalyzed elimination reaction (see JP-A2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

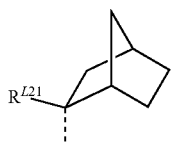
(L4-1-endo)

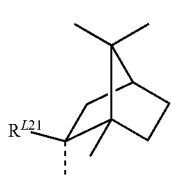
(L4-2-endo)

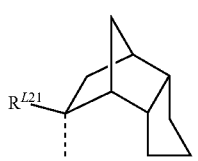
(L4-3-endo)

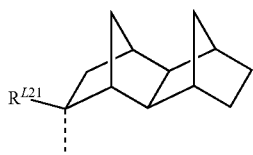
(L4-4-endo)

Herein $R^{L21}$ is as defined above.

Illustrative examples of the acid labile group having formula (L4) are given below.

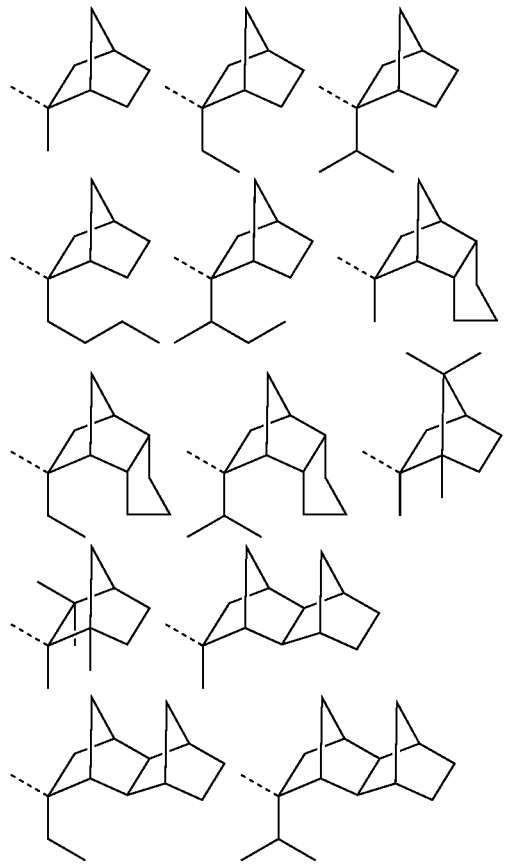

Examples of the tertiary $C_4$-$C_{20}$ alkyl groups, trialkylsilyl groups in which each alkyl moiety has 1 to 6 carbon atoms, and $C_4$-$C_{20}$ oxo-containing alkyl groups, represented by $X^A$, are as exemplified for $R^{L04}$.

Illustrative examples of the recurring units of formula (a1) are given below, but not limited thereto. Herein $R^A$ is as defined above.

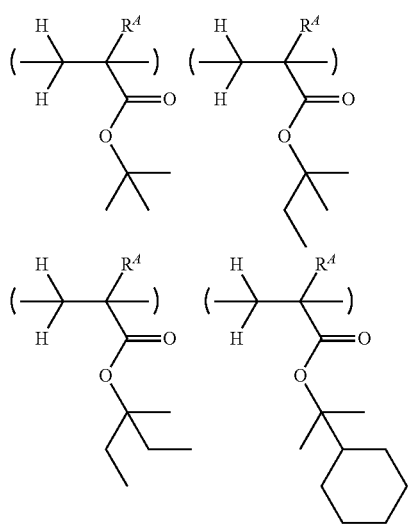

-continued

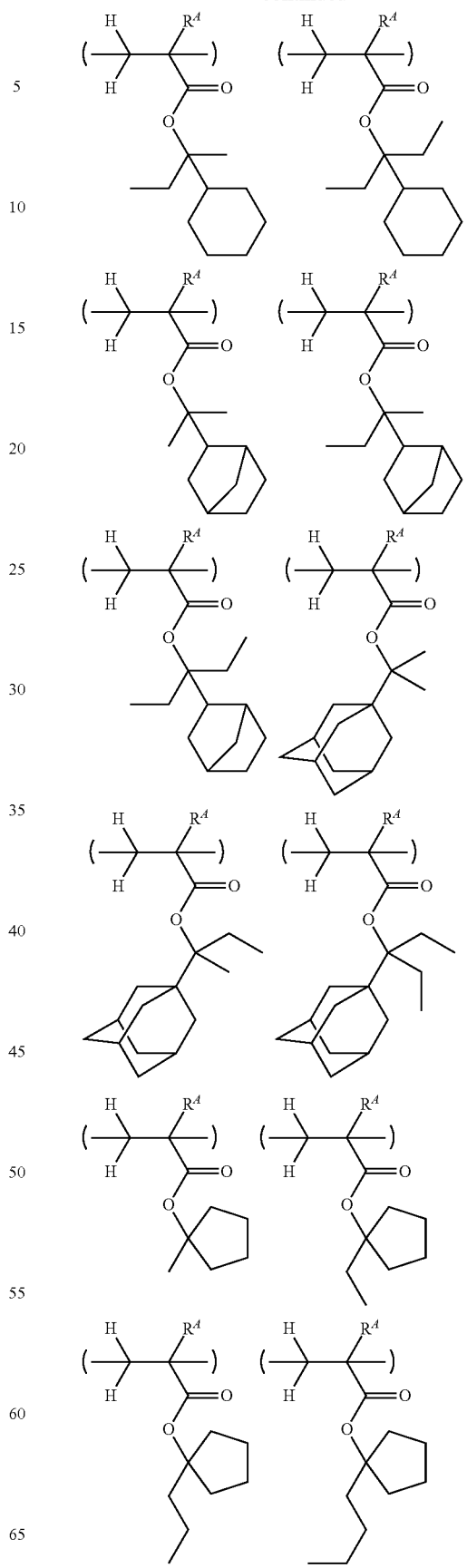

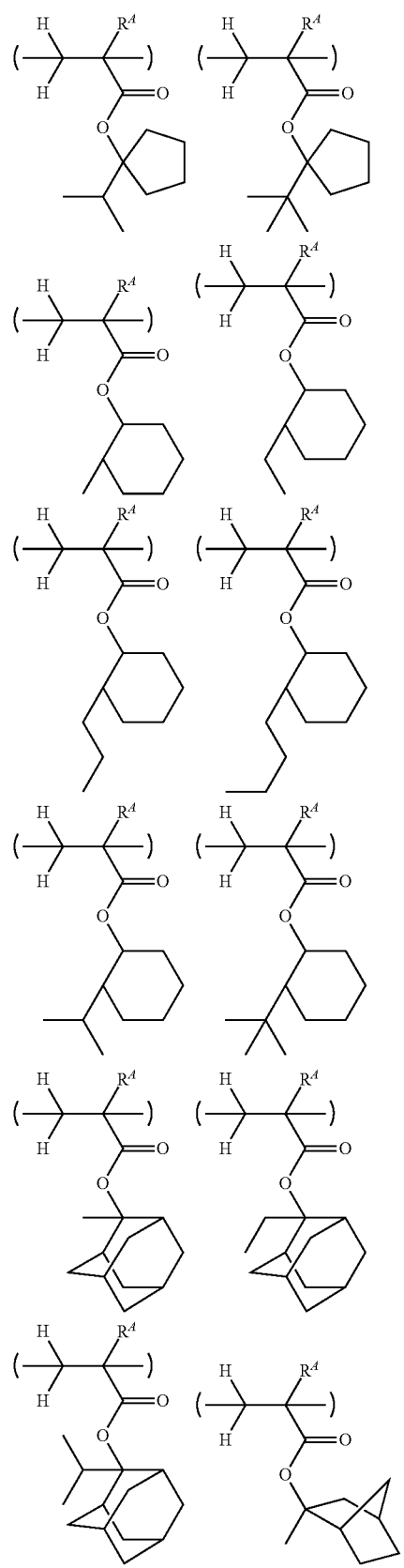
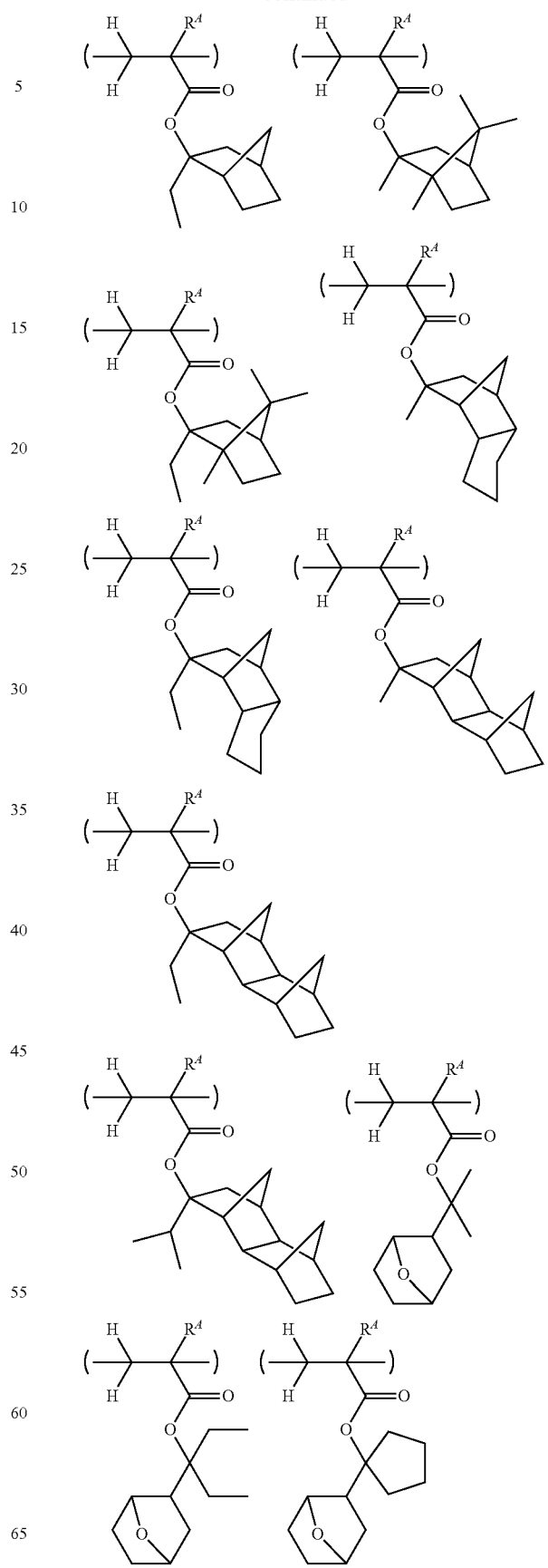

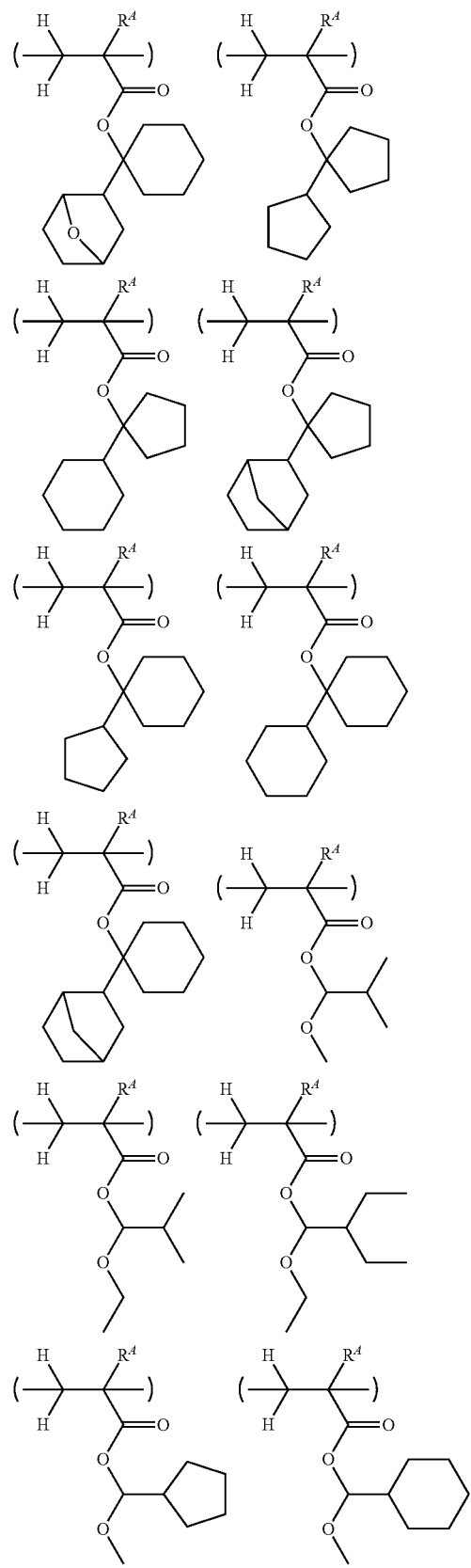
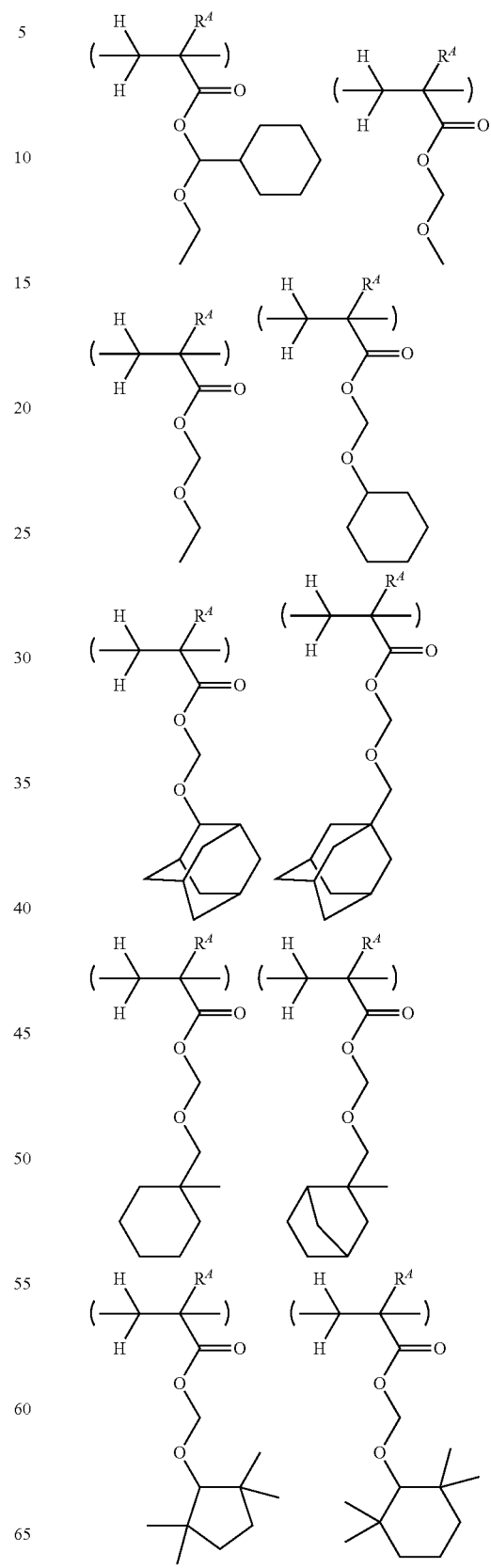

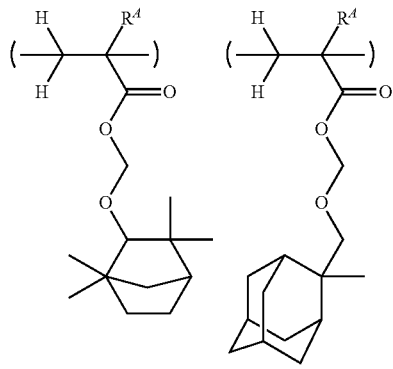
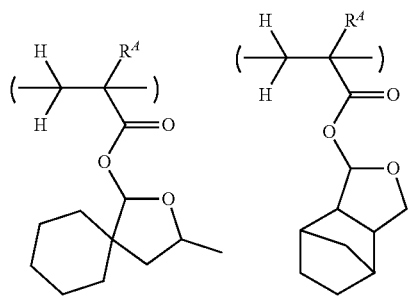
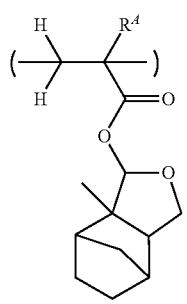
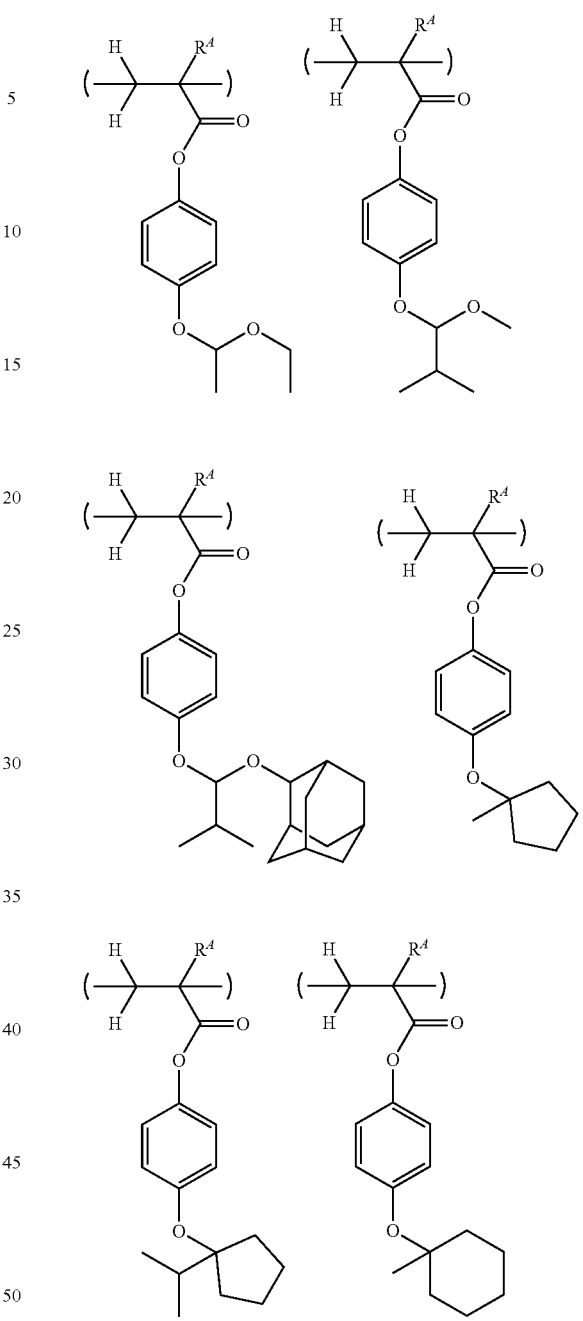

The above examples correspond to those units of formula (a1) wherein $Z^A$ is a single bond. Where $Z^A$ is other than a single bond, a combination with a similar acid labile group is possible. Thus examples of the recurring units of formula (a1) wherein $Z^A$ is other than a single bond are as illustrated above.

In formula (a2), the subscript n is an integer of 0 to 4, preferably 0 or 1.

Like the recurring units having formula (a1), a polymer comprising recurring units having formula (a2) turns alkali soluble through the mechanism that it is decomposed under the action of acid to generate a hydroxyl group.

Illustrative examples of the recurring units of formula (a2) are given below, but not limited thereto. Herein $R^A$ is as defined above.

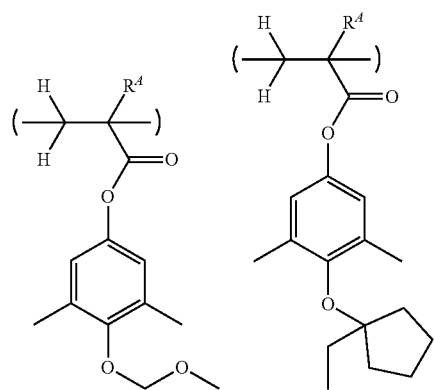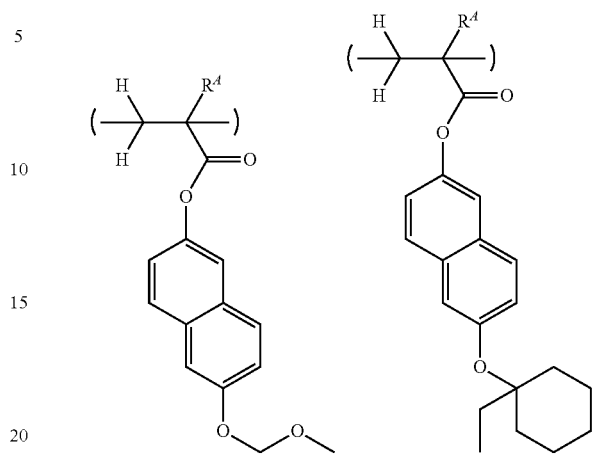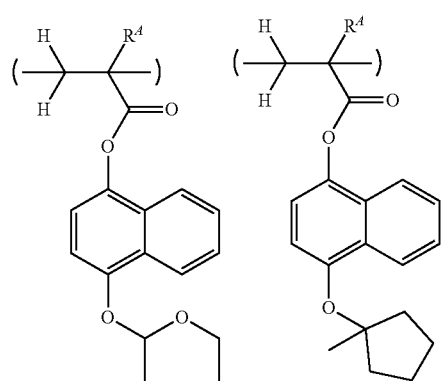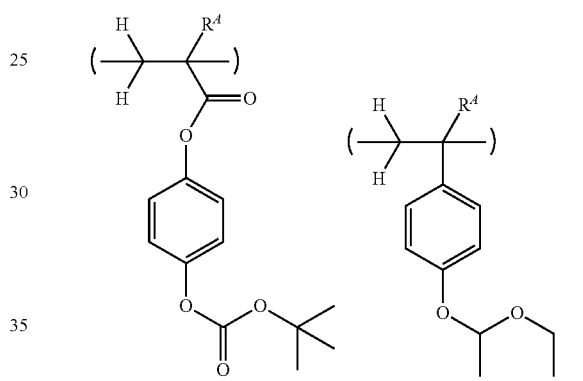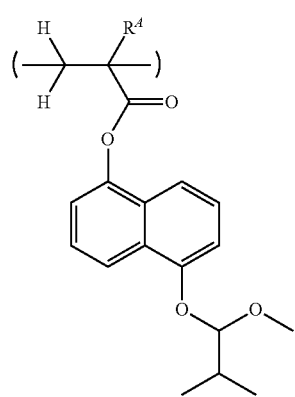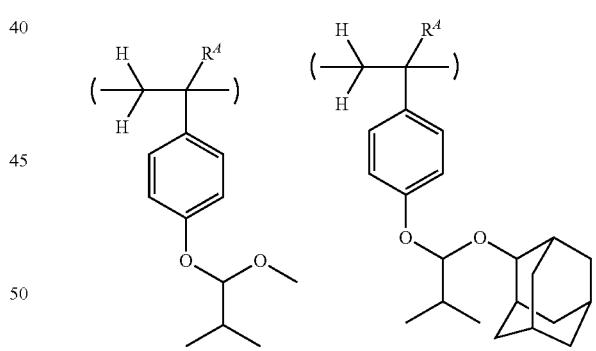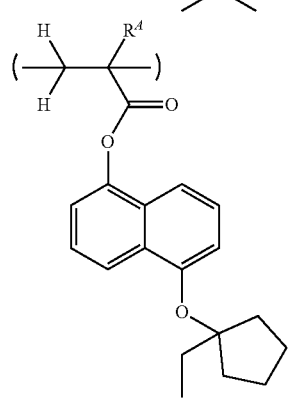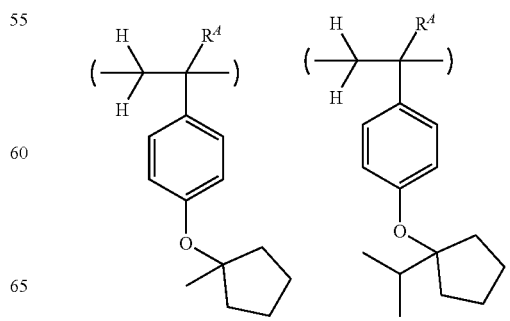

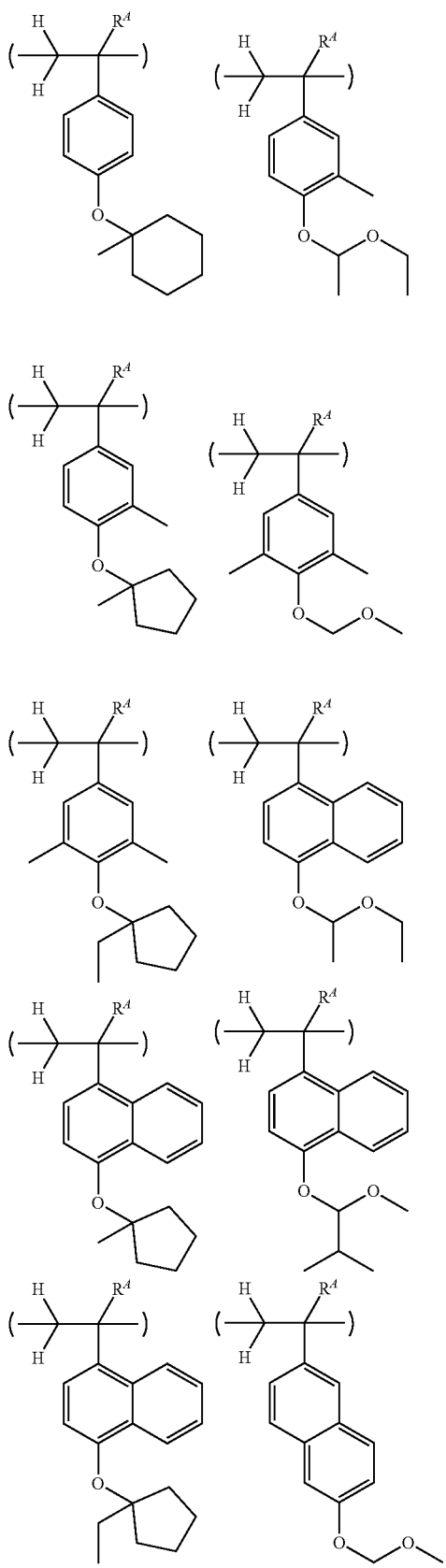

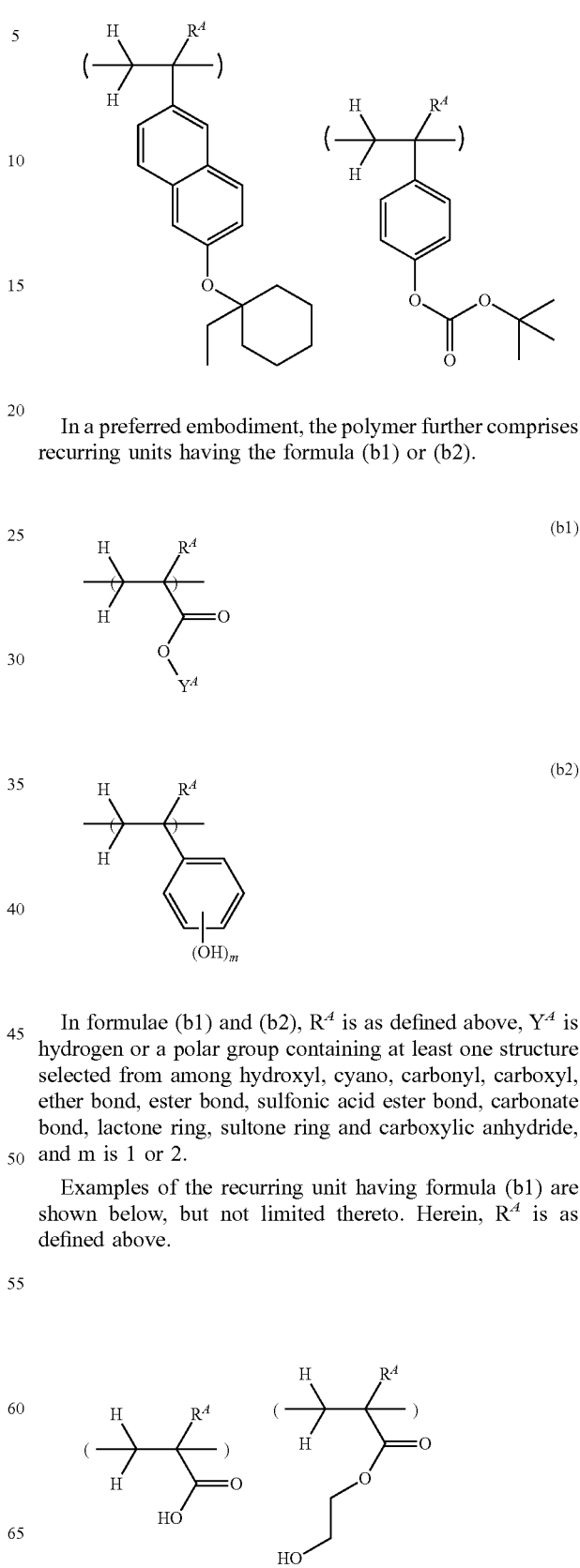

In a preferred embodiment, the polymer further comprises recurring units having the formula (b1) or (b2).

In formulae (b1) and (b2), $R^A$ is as defined above, $Y^A$ is hydrogen or a polar group containing at least one structure selected from among hydroxyl, cyano, carbonyl, carboxyl, ether bond, ester bond, sulfonic acid ester bond, carbonate bond, lactone ring, sultone ring and carboxylic anhydride, and m is 1 or 2.

Examples of the recurring unit having formula (b1) are shown below, but not limited thereto. Herein, $R^A$ is as defined above.

-continued
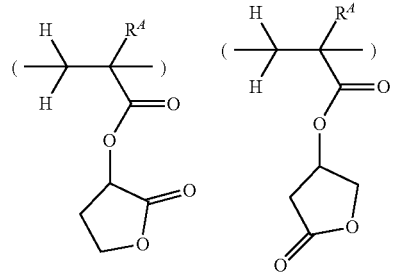
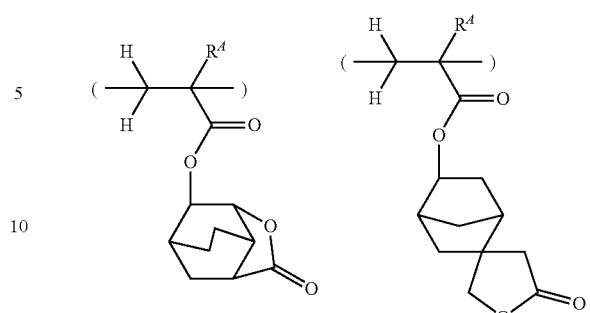
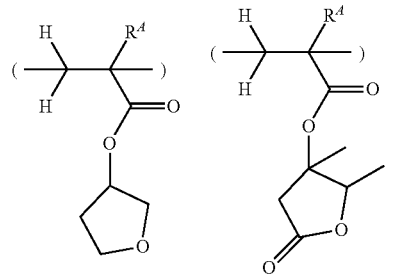
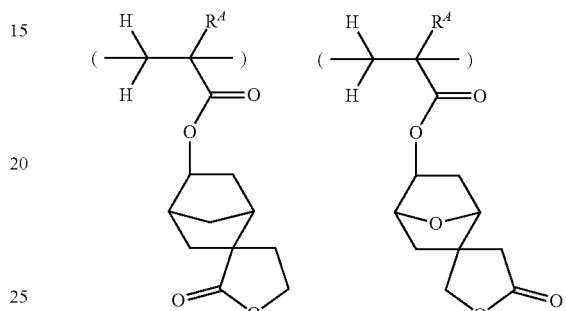
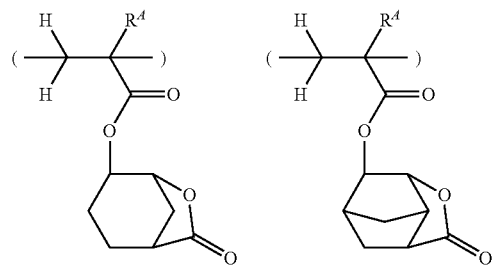
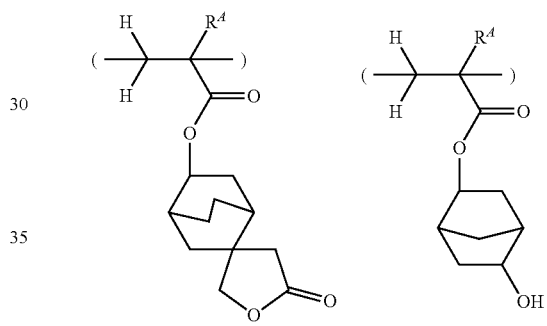
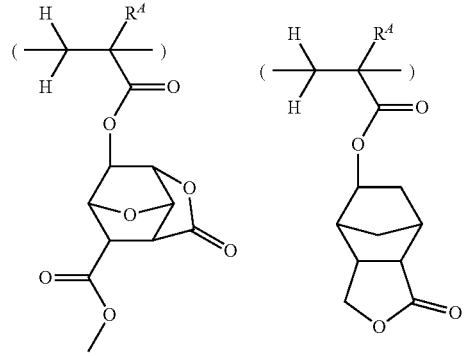
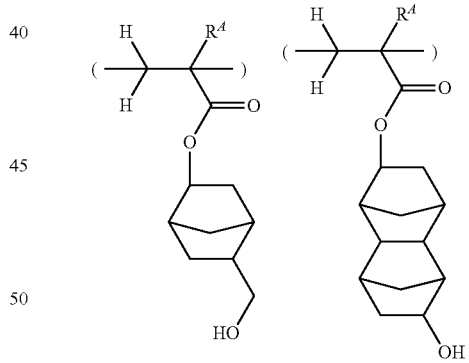
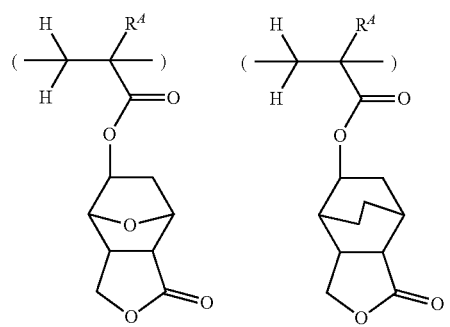
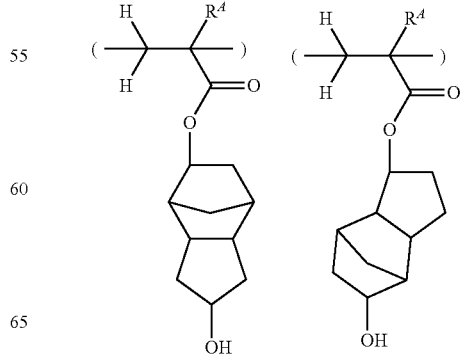

135
-continued
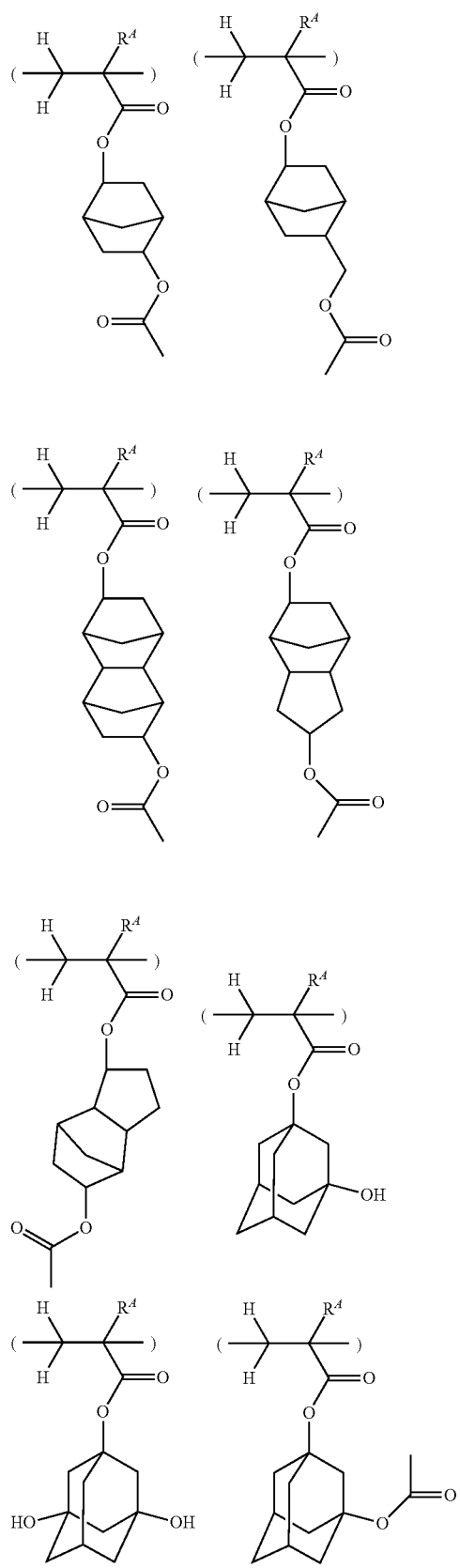
136
-continued
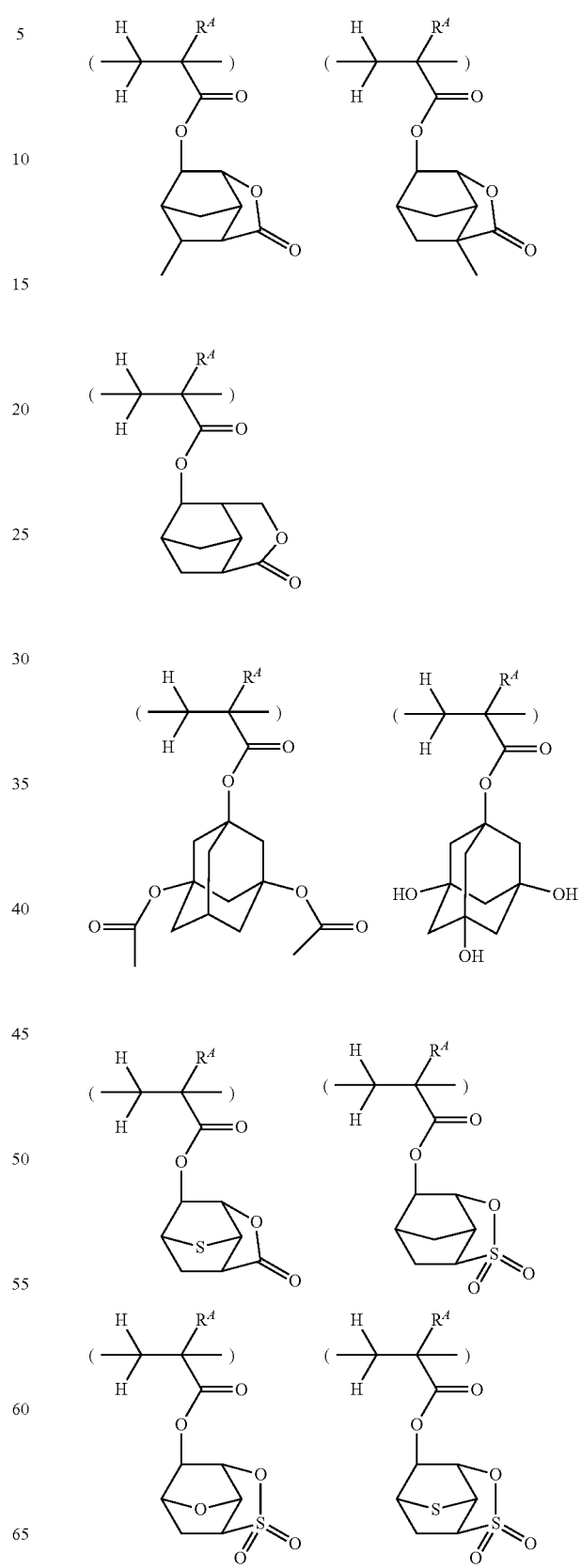

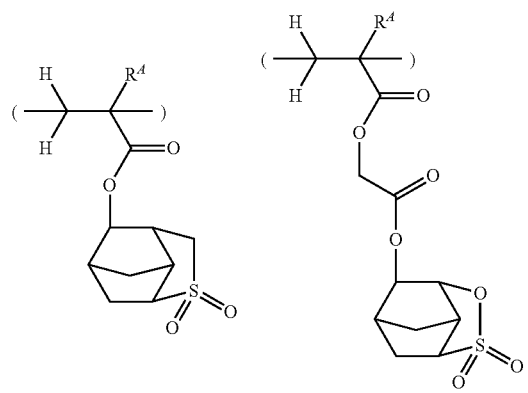
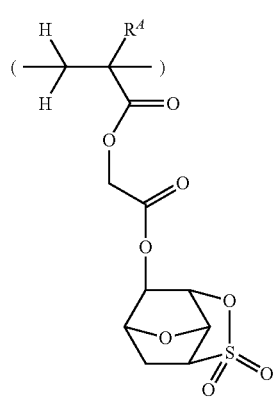
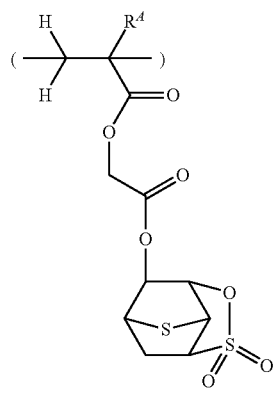
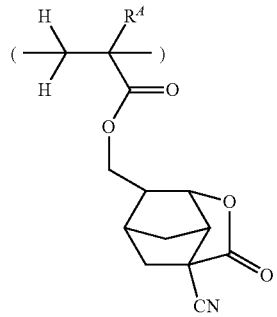
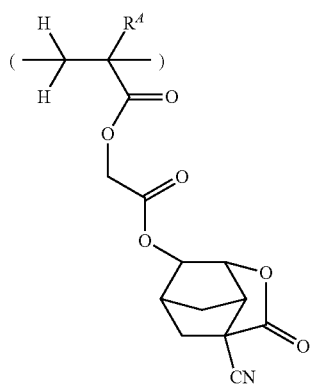
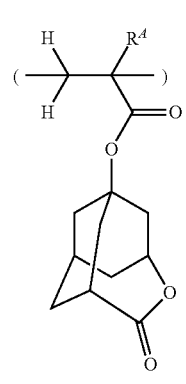
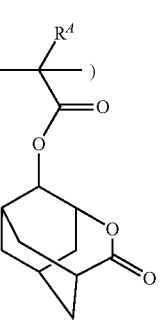
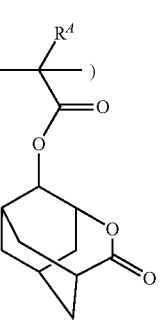
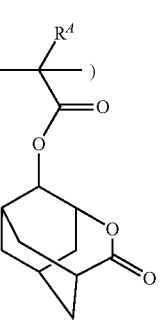
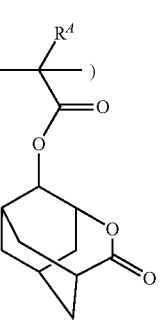
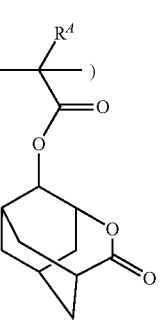

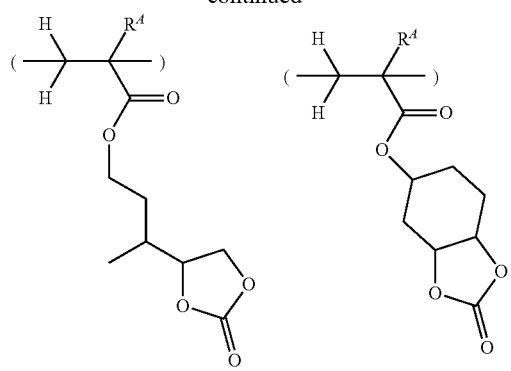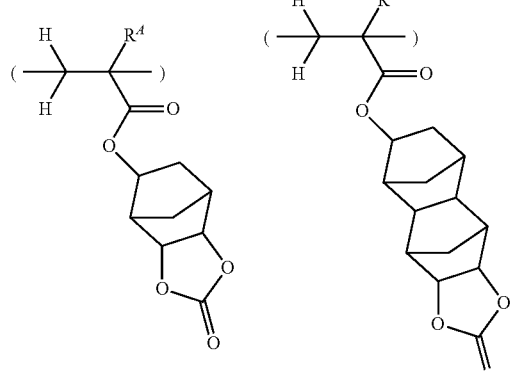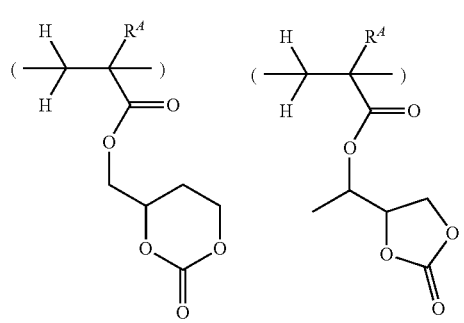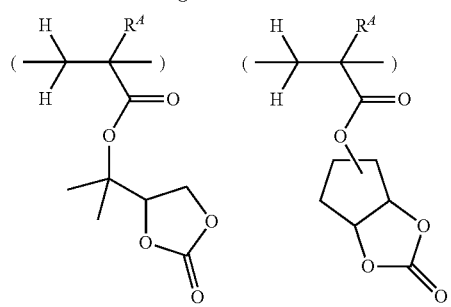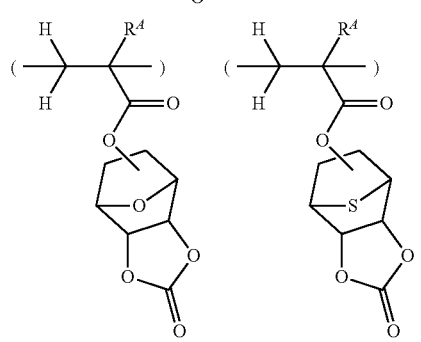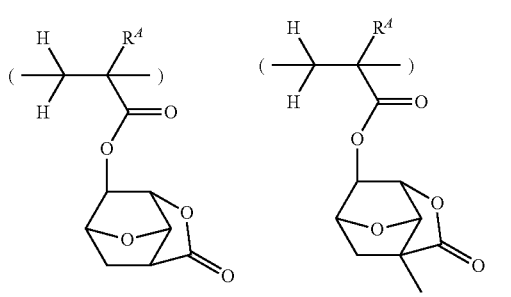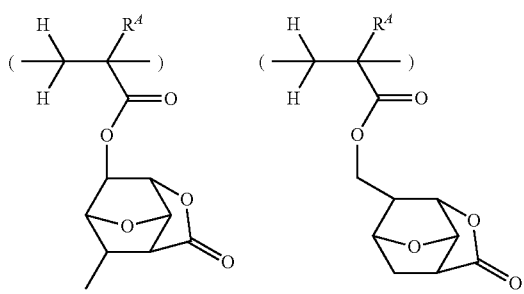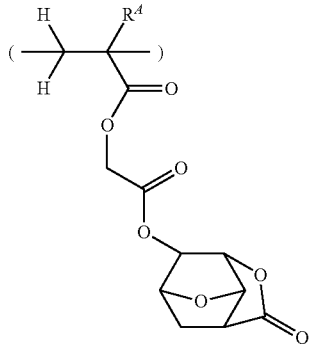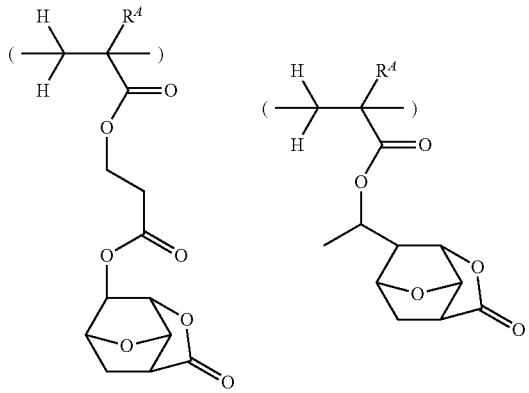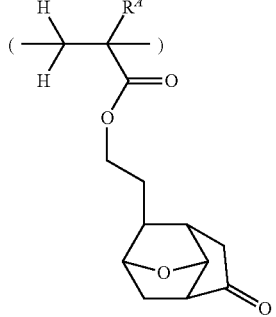

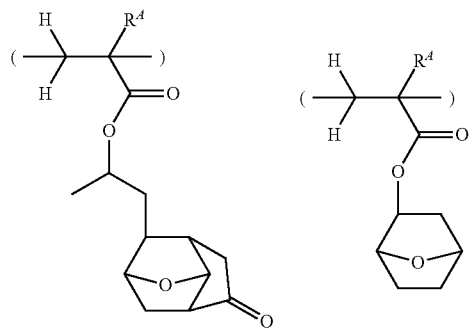
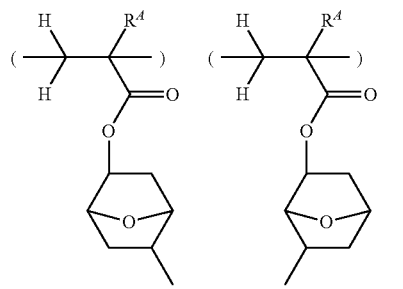
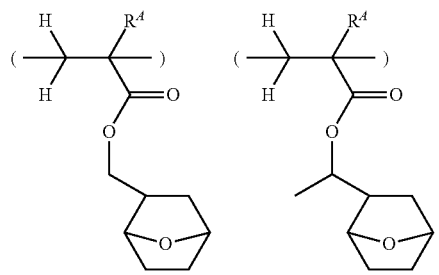
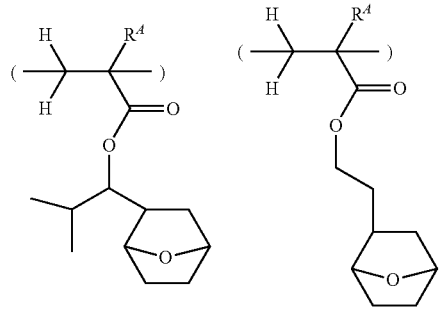
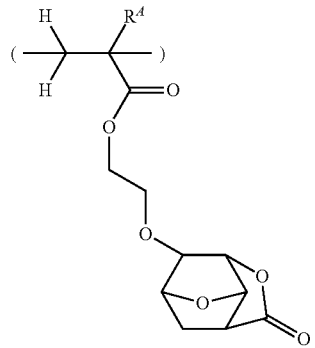
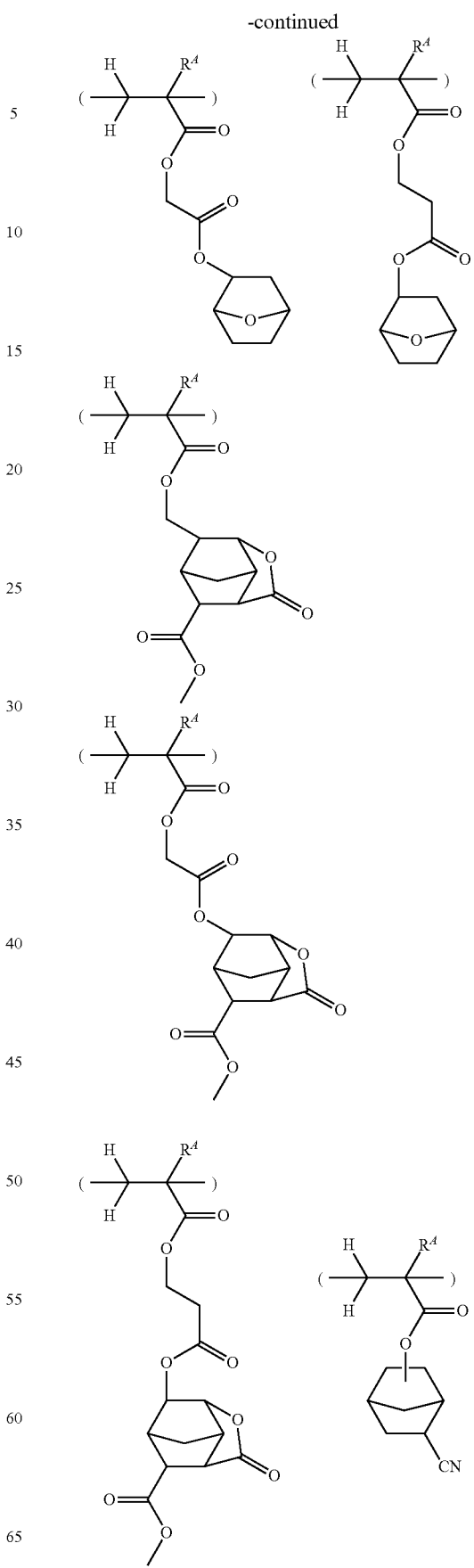

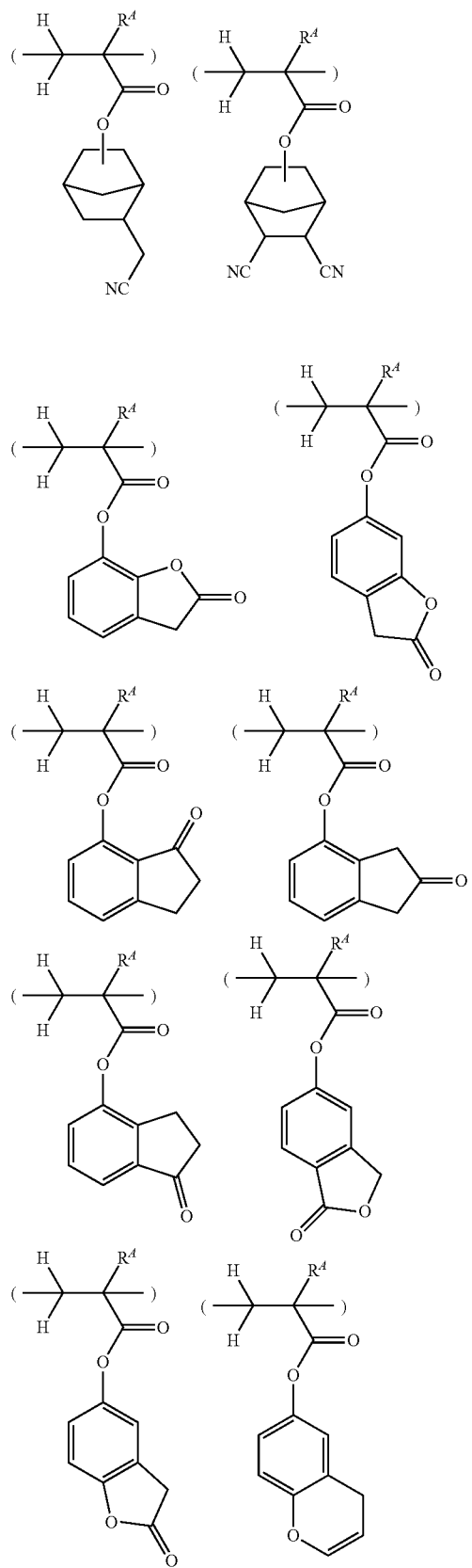
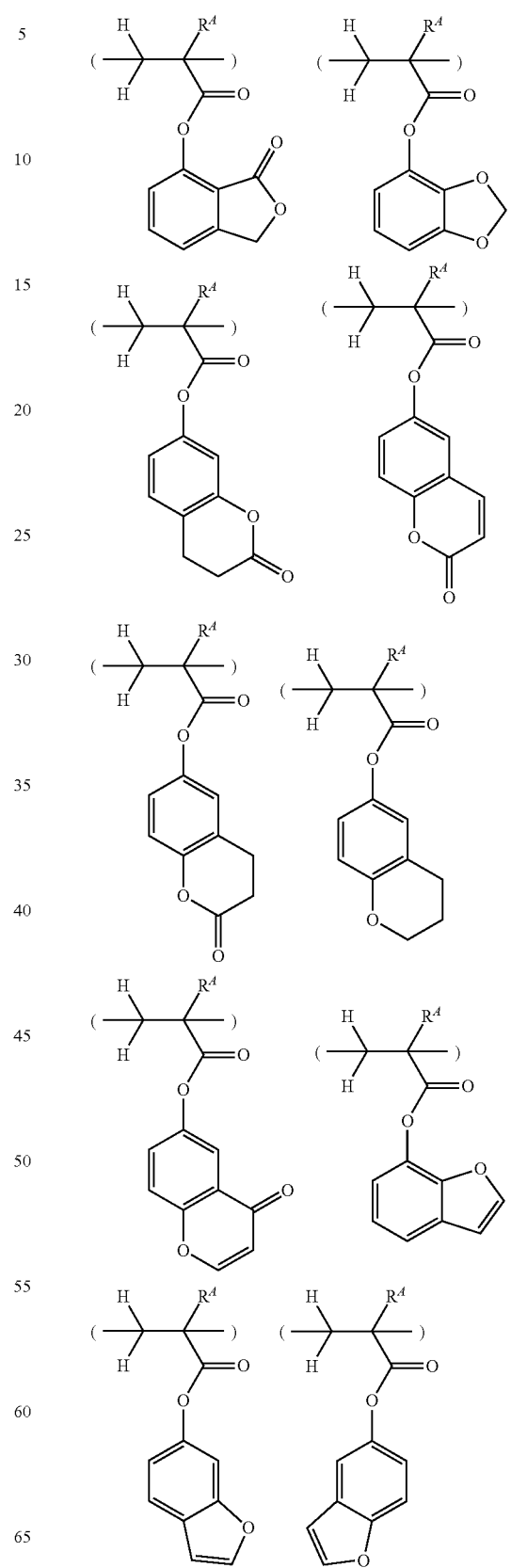

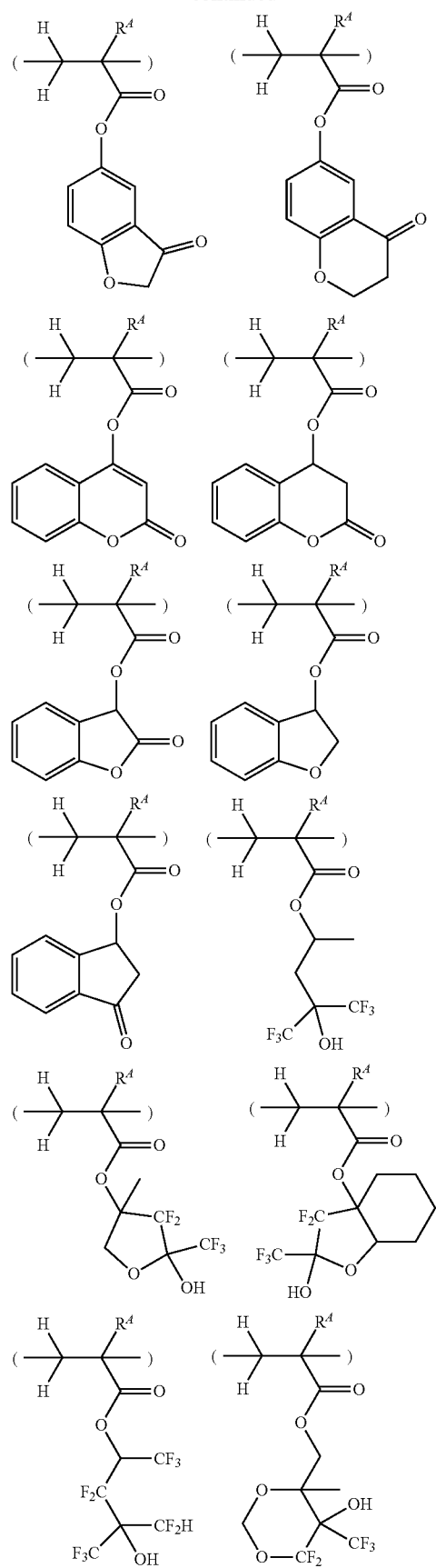
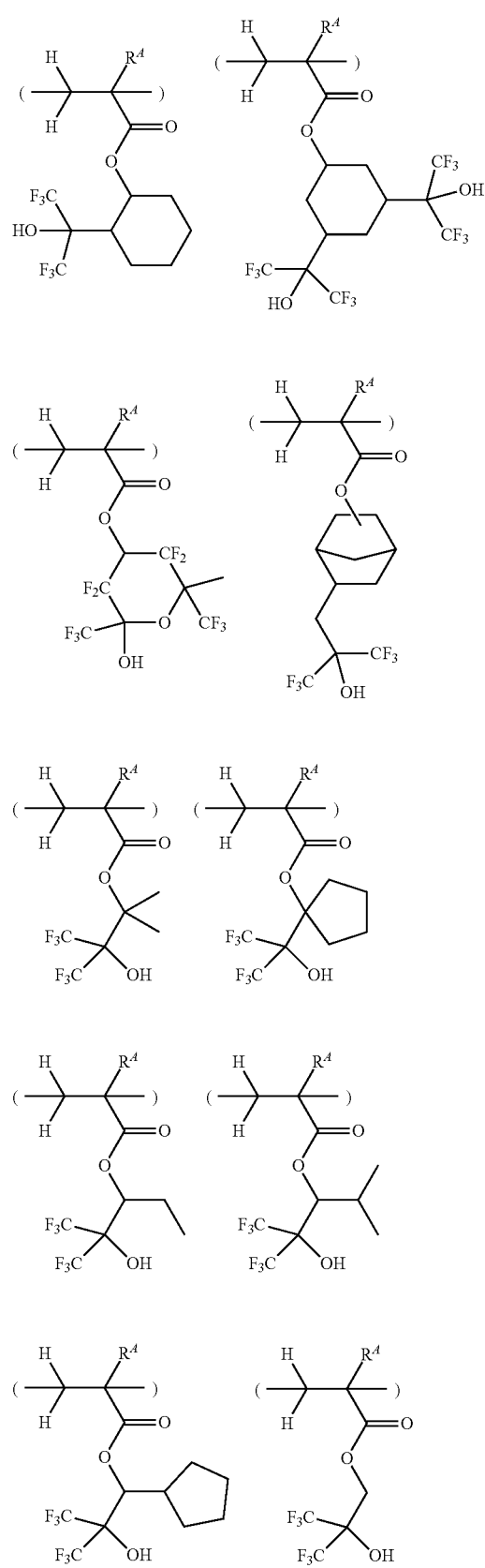

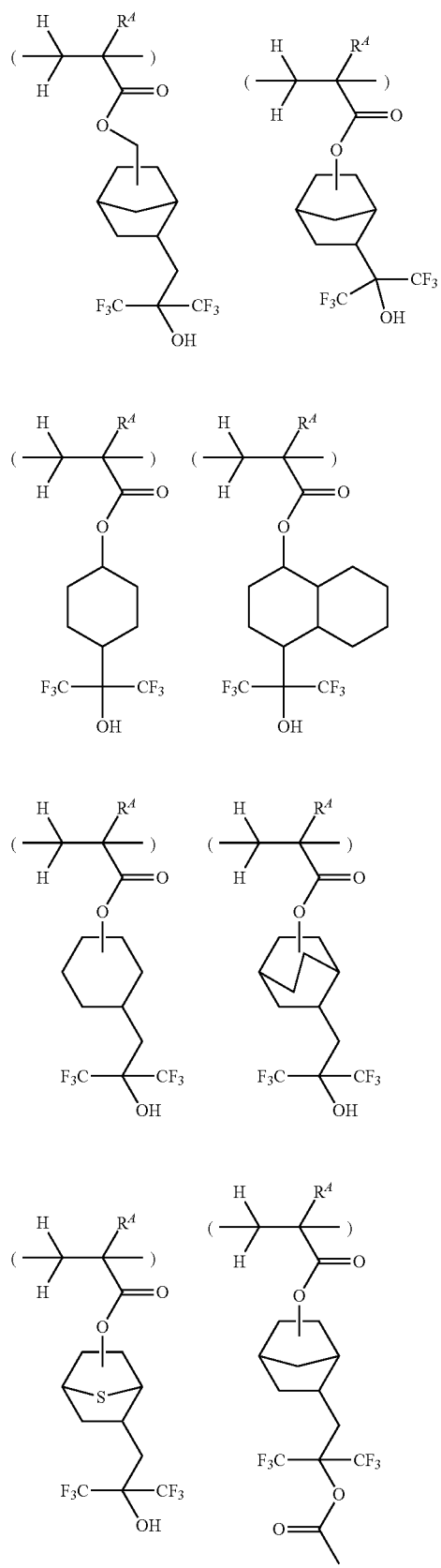
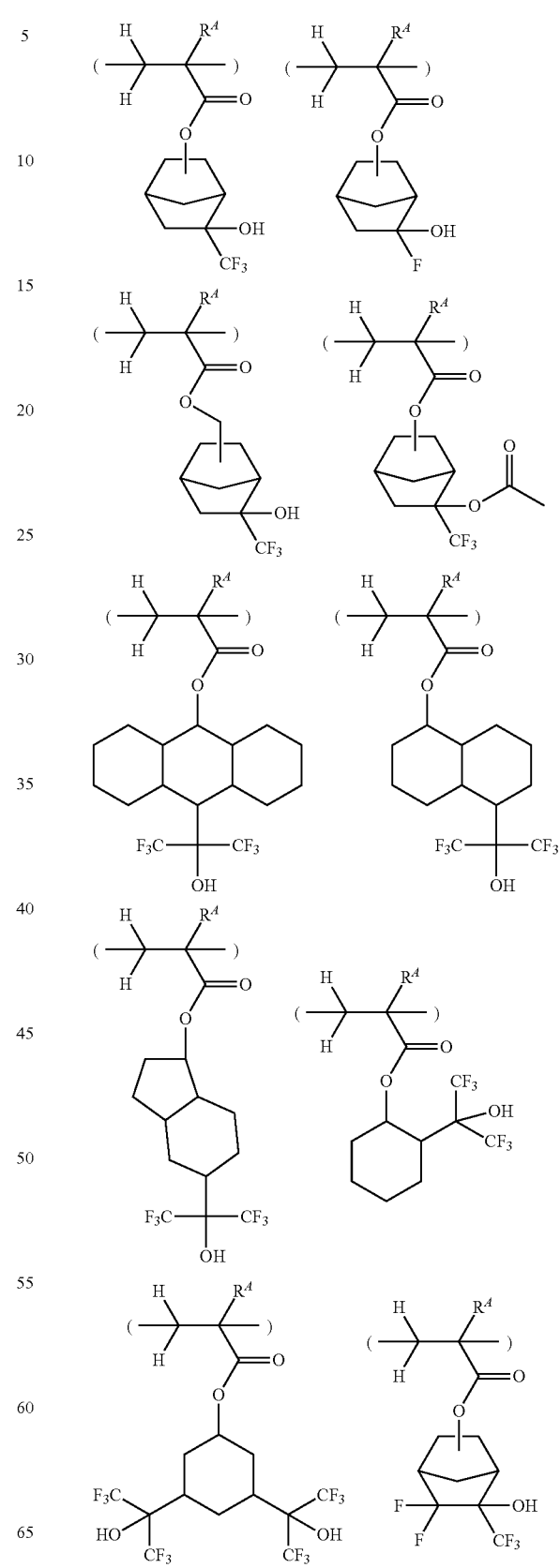

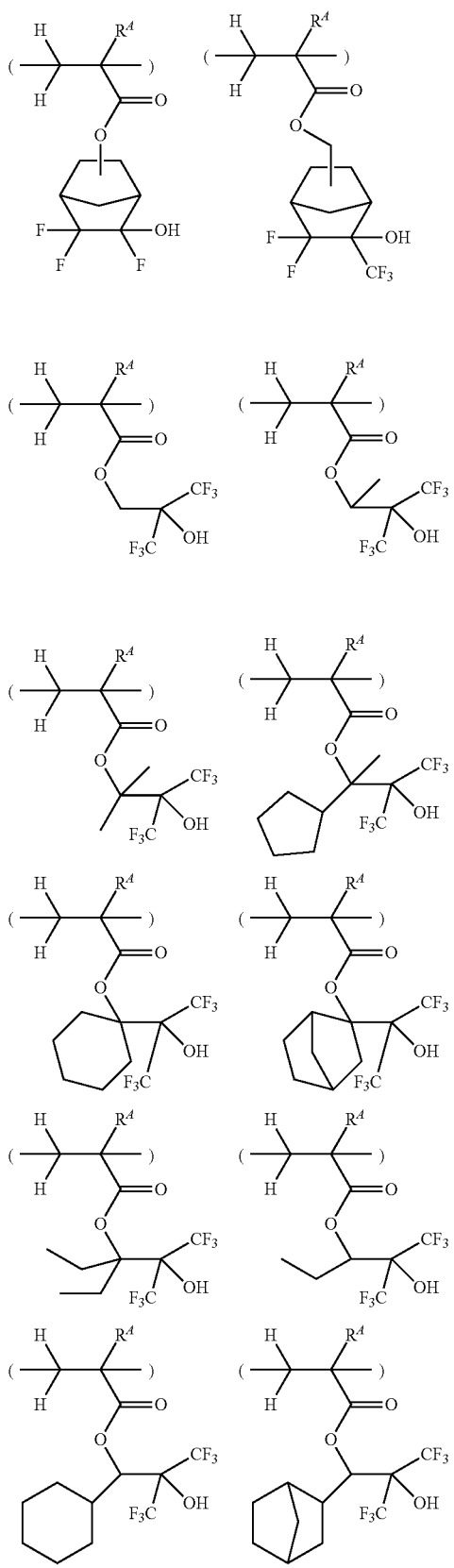
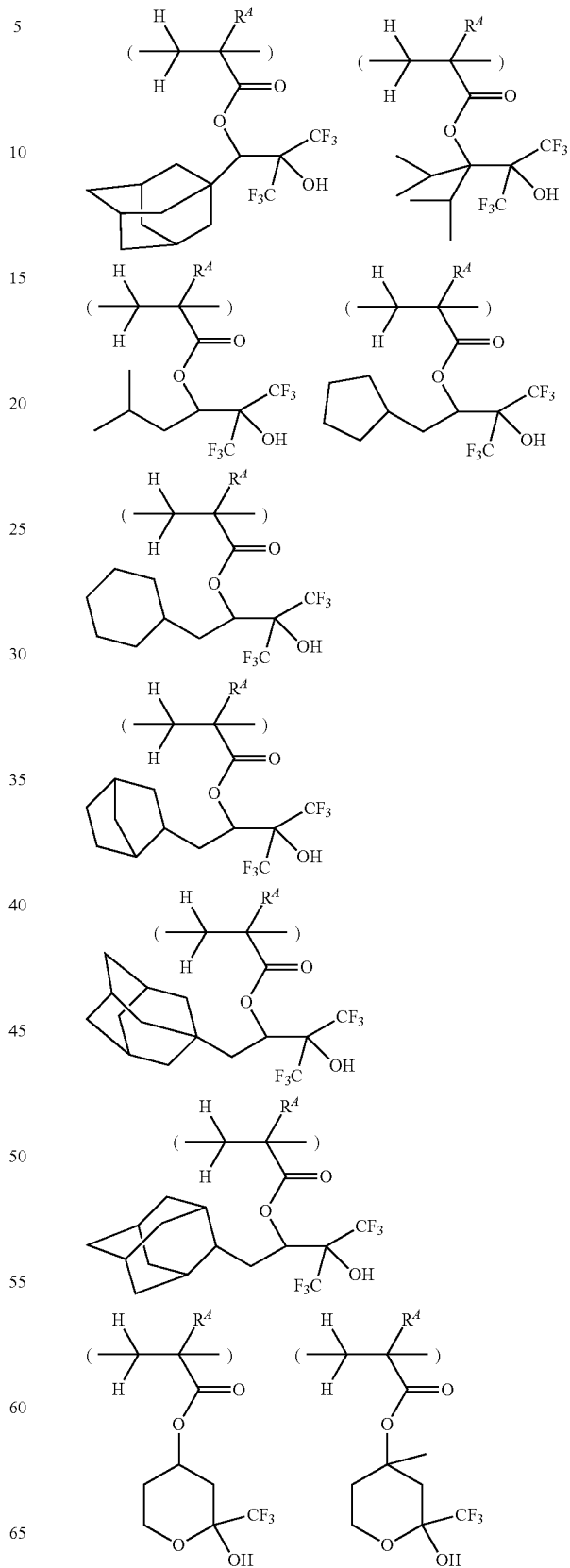

151
-continued
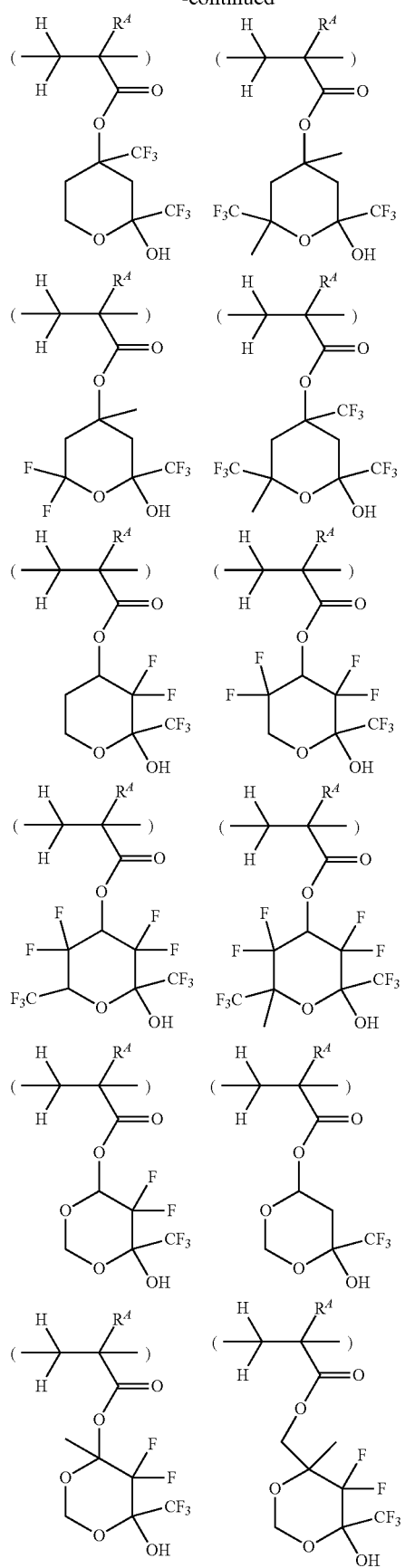
152
-continued
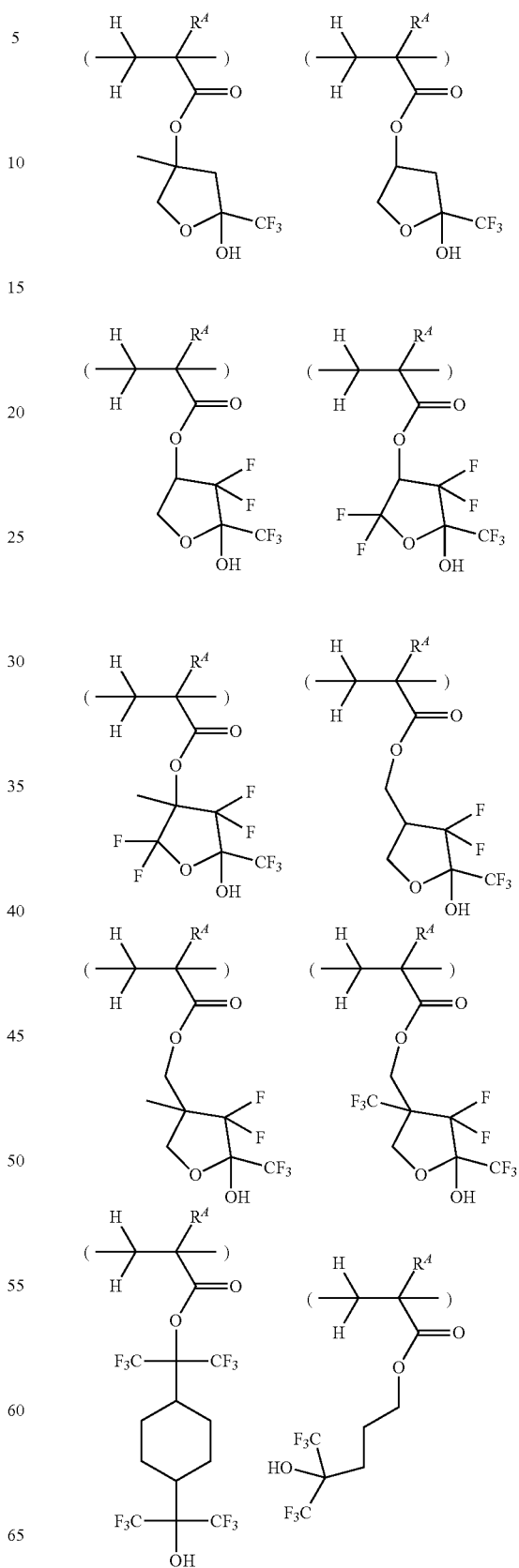

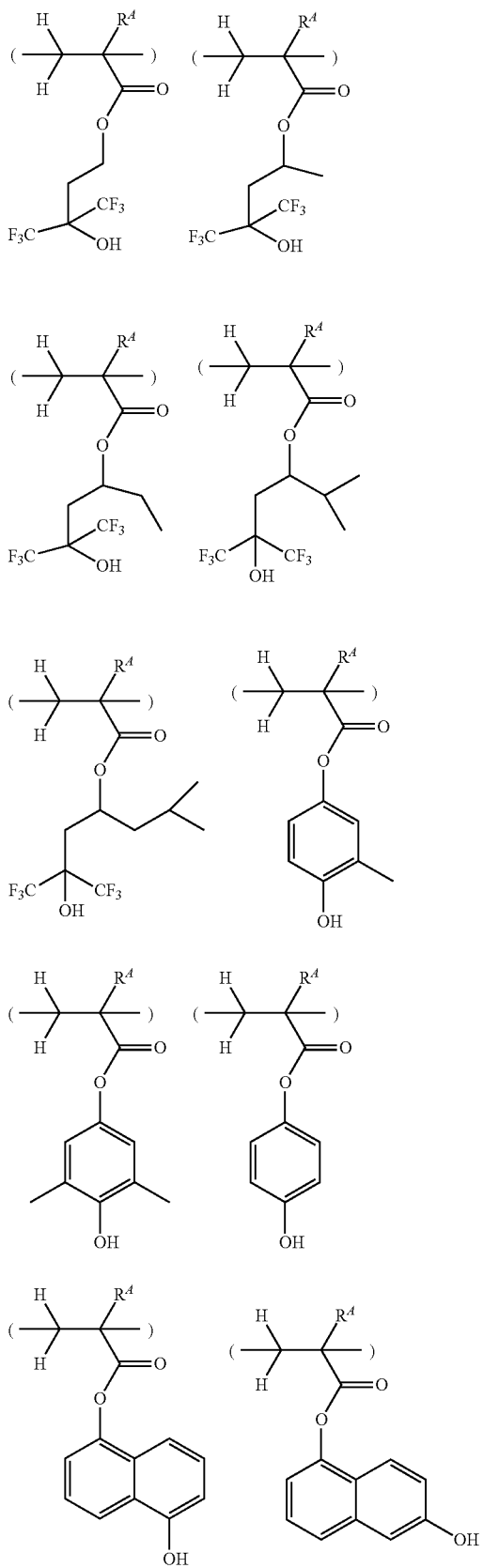
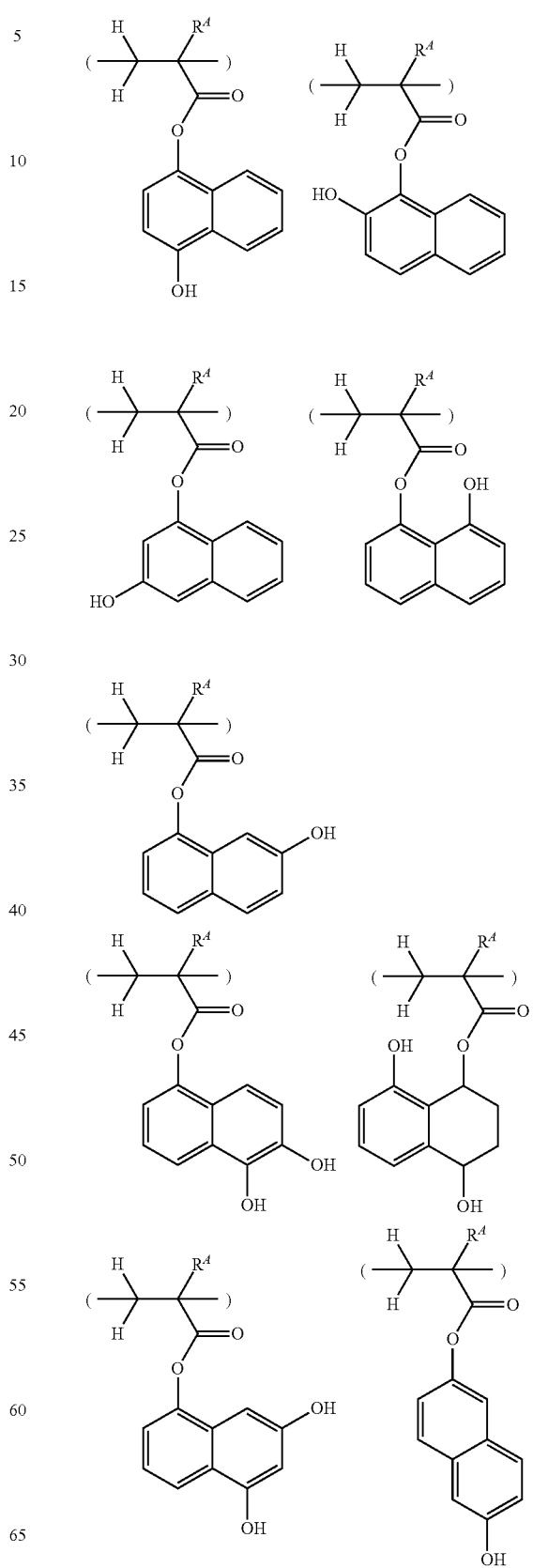

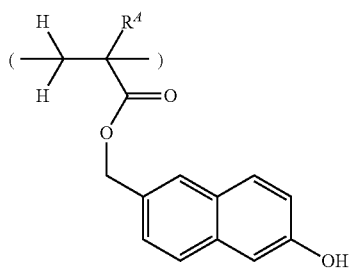

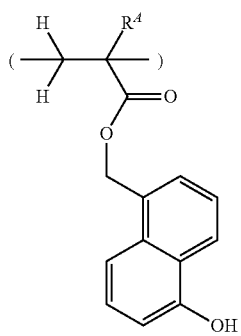

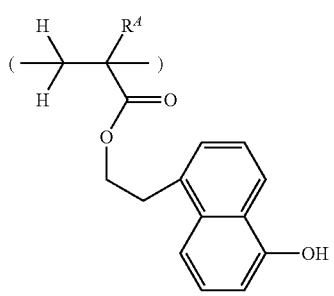

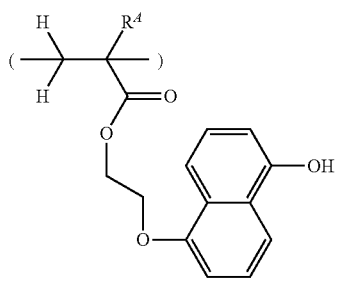

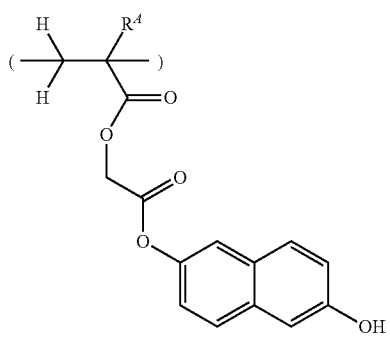

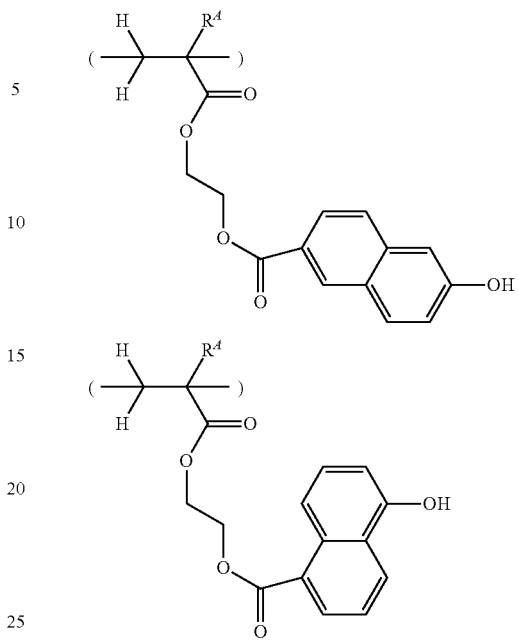

Examples of the recurring unit having formula (b2) are shown below, but not limited thereto. Herein, $R^A$ is as defined above.

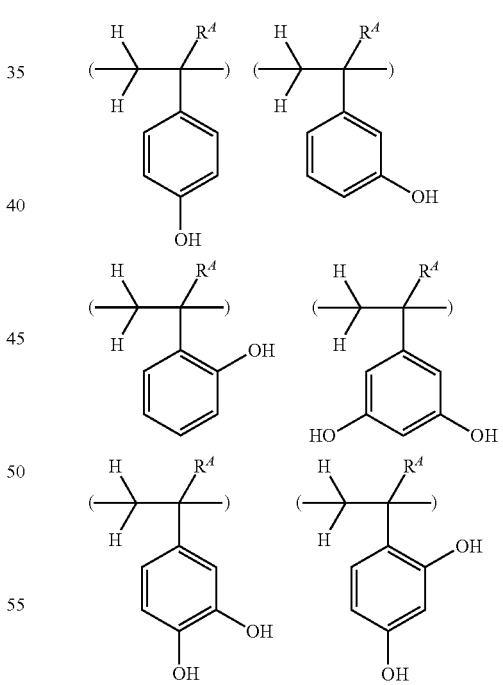

Of the recurring units having formula (b1) or (b2), those units having a lactone ring as the polar group are preferred in the ArF lithography and those units having a phenolic site are preferred in the KrF, EB and EUV lithography.

The polymer may further comprise recurring units of at least one type selected from recurring units having the formulae (c1) to (c3).

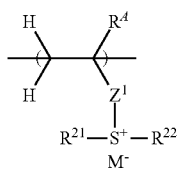
(c1)

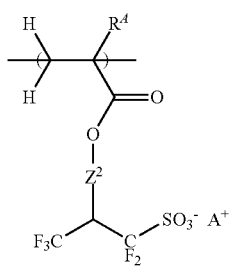
(c2)

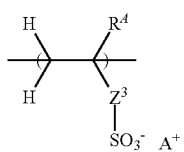
(c3)

In formulae (c1) to (c3), $R^4$ is as defined above. $Z^1$ is a single bond, phenylene, —O—$Z^{11}$—, —C(=O)—O—$Z^{11}$— or —C(=O)—NH—$Z^{11}$—, wherein $Z^{11}$ is a $C_1$-$C_{20}$ alkanediyl group, $C_2$-$C_{20}$ alkenediyl group or phenylene group, which may contain a carbonyl moiety (—CO—), ester bond (—COO—), ether bond (—O—) or hydroxyl moiety. $Z^2$ is a single bond or —$Z^{21}$—C(=O)—O— wherein $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$— or —C(=O)—NH—$Z^{31}$—, wherein $Z^{31}$ is a $C_1$-$C_6$ alkanediyl group, $C_2$-$C_6$ alkenediyl group or phenylene group, which may contain a carbonyl moiety, ester bond, ether bond or hydroxyl moiety.

In formula (c1), $R^{21}$ and $R^{22}$ are each independently a $C_1$-$C_{20}$ monovalent hydrocarbon group which may contain a heteroatom. $R^{21}$ and $R^{22}$ may bond together to form a ring with the sulfur atom to which they are attached.

Examples of the monovalent hydrocarbon group represented by $R^{21}$ and $R^{22}$ include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, hexenyl, and cyclohexenyl, aryl groups such as phenyl, naphthyl, and thienyl, and aralkyl groups such as benzyl, 1-phenylethyl and 2-phenylethyl. Inter alia, aryl groups are preferred. In these hydrocarbon groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

In formula (c1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and non-afluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide.

Also included are a sulfonate anion which is fluorinated at α-position as represented by the formula (c1-1) and a sulfonate anion which is fluorinated at α- and β-positions as represented by the formula (c1-2).

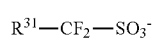
(c1-1)

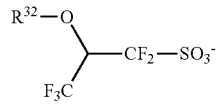
(c1-2)

In formula (c1-1), $R^{31}$ is hydrogen, or a $C_1$-$C_{20}$ alkyl group, $C_2$-$C_{20}$ alkenyl group or $C_6$-$C_{20}$ aryl group, which may contain an ether bond, ester bond, carbonyl moiety, lactone ring or fluorine atom. The alkyl and alkenyl groups may be straight, branched or cyclic.

In formula (c1-2), $R^{32}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl, acyl, and alkenyl groups may be straight, branched or cyclic.

In formula (c2) wherein $Z^2$ is —$Z^{21}$—C(=O)—O—, $Z^{21}$ is a $C_1$-$C_{20}$ divalent hydrocarbon group which may contain a heteroatom. Examples of the divalent hydrocarbon group are shown below, but not limited thereto.

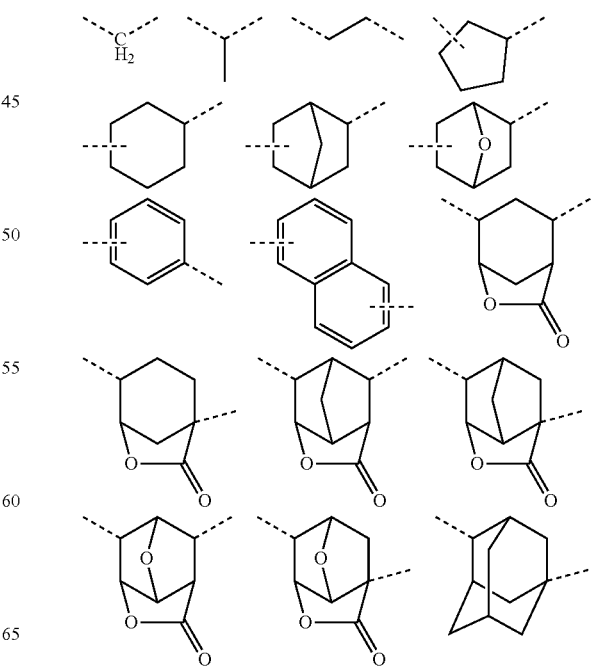

-continued

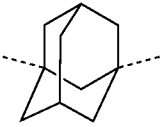

In formulae (c2) and (c3), A⁺ is a sulfonium cation or iodonium cation. Suitable examples of the sulfonium or iodonium cation include sulfonium cations having the formula (c4) or iodonium cations having the formula (c5).

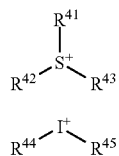

In formula (c4), $R^{41}$, $R^{42}$ and $R^{43}$ are each independently a $C_1$-$C_{20}$ monovalent hydrocarbon group which may contain a heteroatom. Any two of $R^{41}$, $R^{42}$ and $R^{43}$ may bond together to form a ring with the sulfur atom to which they are attached. In formula (c5), $R^{44}$ and $R^{45}$ are each independently a $C_1$-$C_{20}$ monovalent hydrocarbon group which may contain a heteroatom.

The monovalent hydrocarbon group may be straight, branched or cyclic. Examples include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, hexenyl, and cyclohexenyl, aryl groups such as phenyl, naphthyl, and thienyl, and aralkyl groups such as benzyl, 1-phenylethyl and 2-phenylethyl. Inter alia, aryl groups are preferred. In these monovalent hydrocarbon groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

When any two of $R^{41}$, $R^{42}$ and $R^{43}$ bond together to form a ring with the sulfur atom to which they are attached, examples of the sulfonium cation having formula (c4) are shown below.

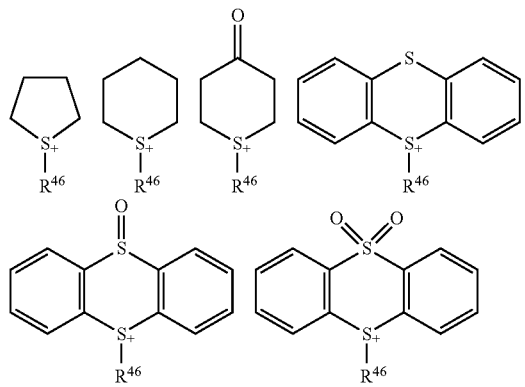

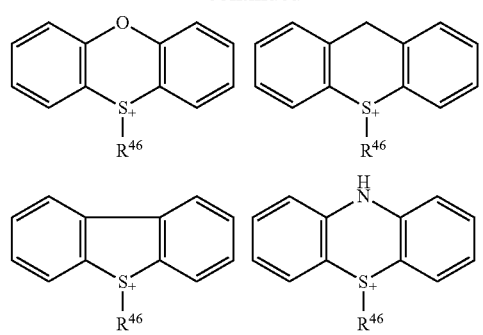

Herein $R^{46}$ is a $C_1$-$C_{20}$ monovalent hydrocarbon group which may contain a heteroatom.

Examples of the sulfonium cation having formula (c4) are given below, but not limited thereto.

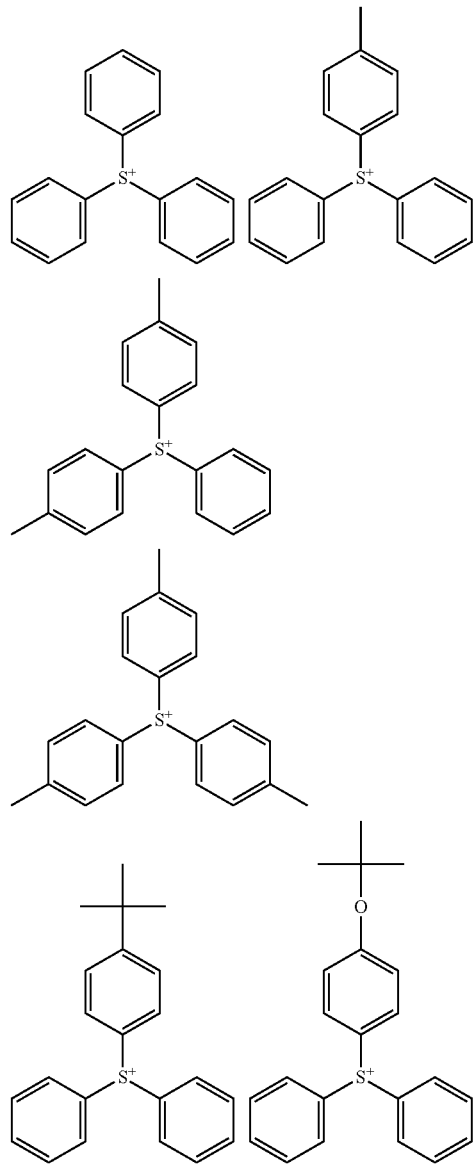

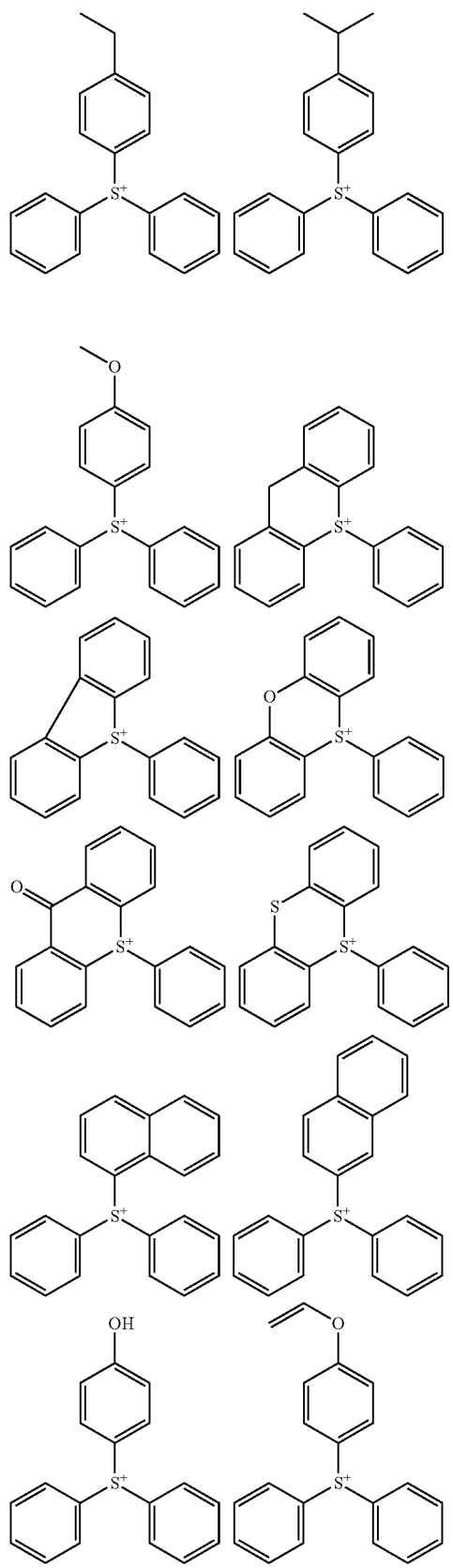
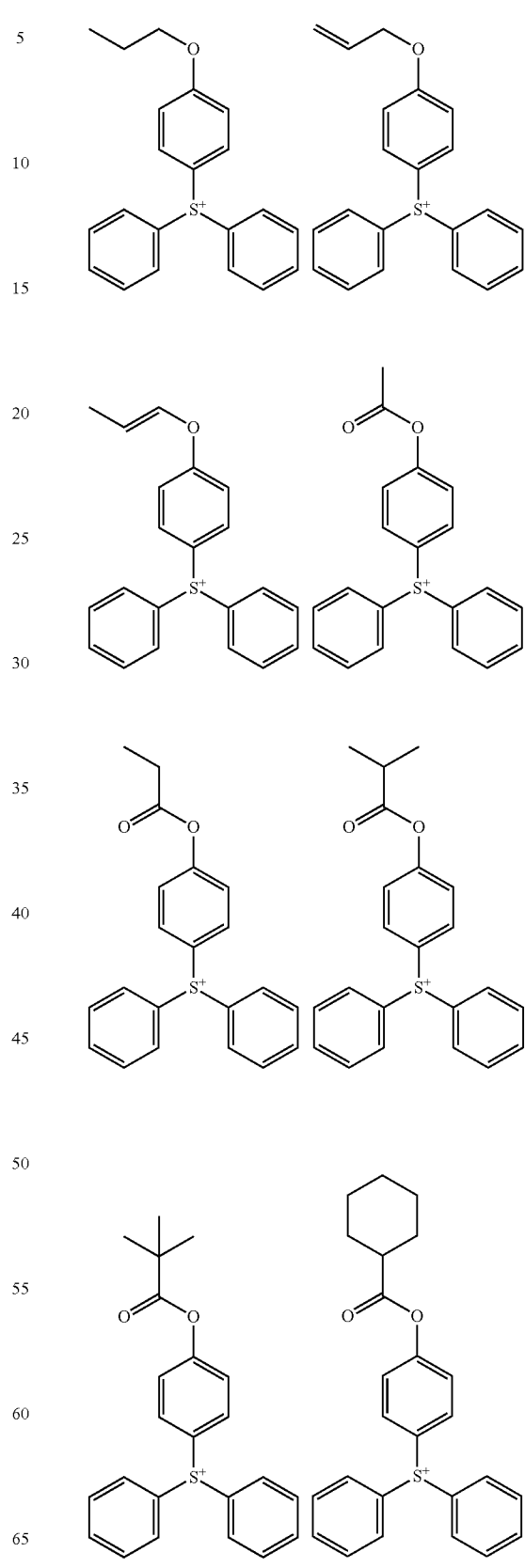

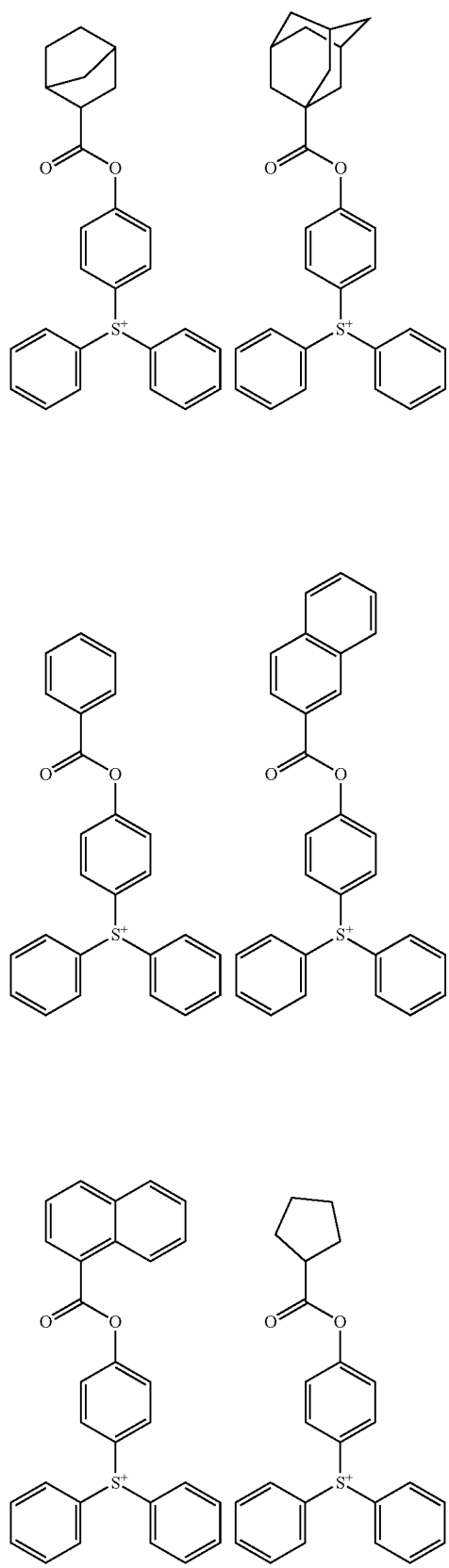
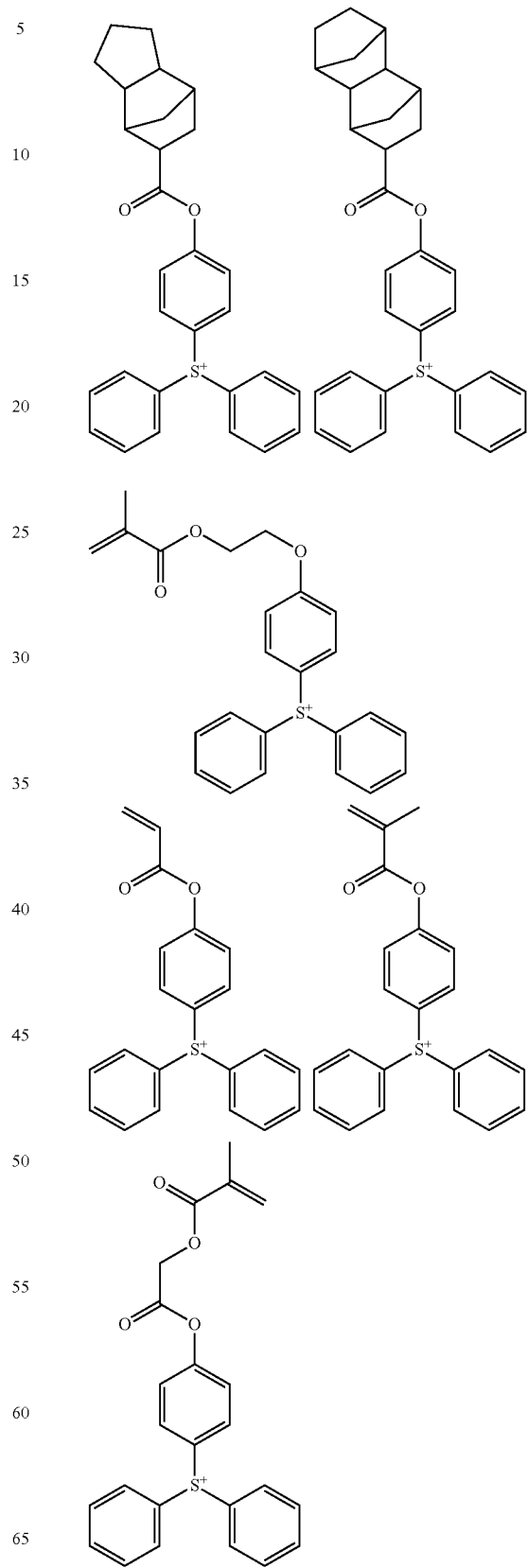

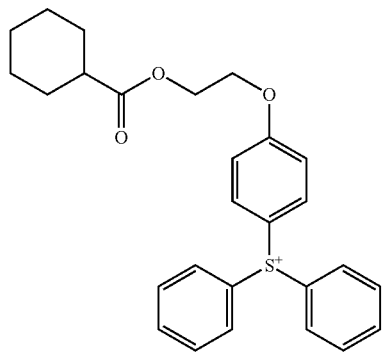
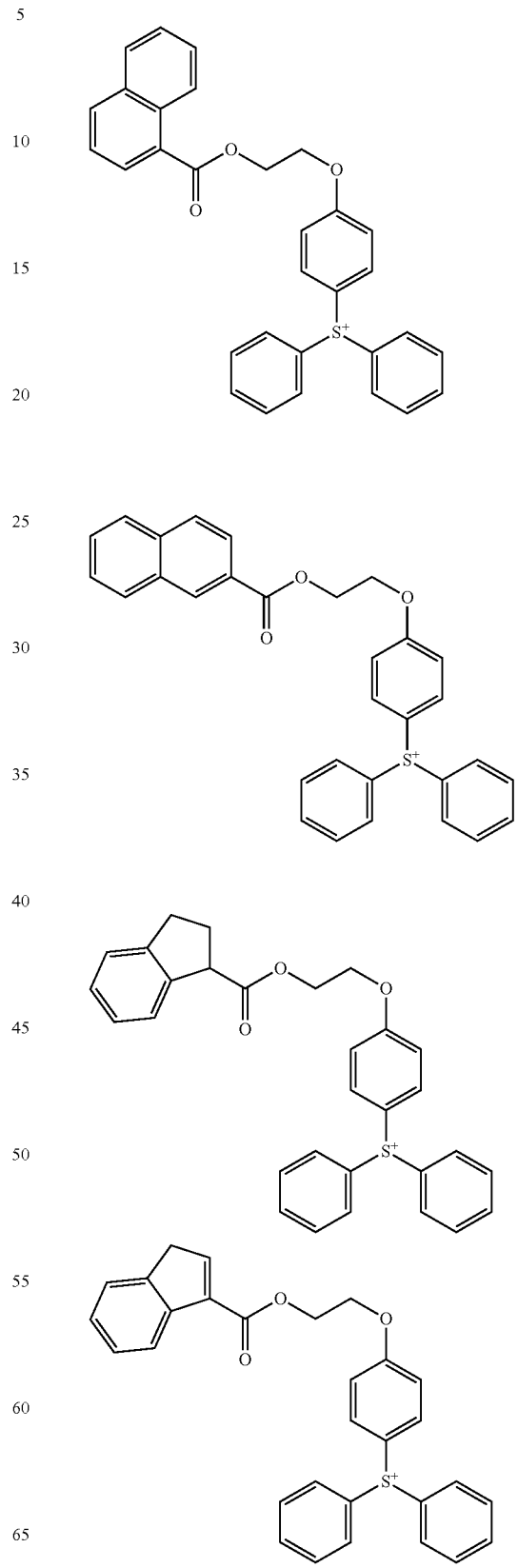

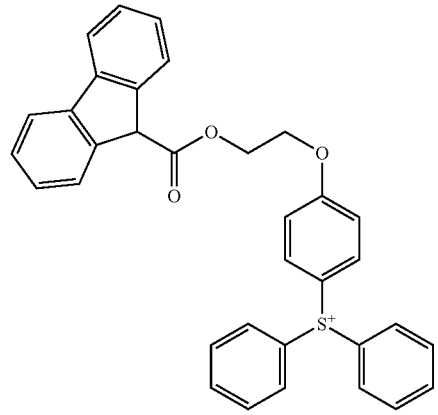
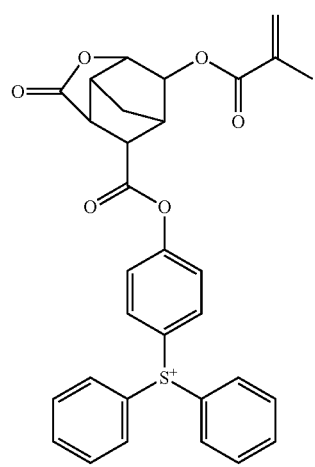
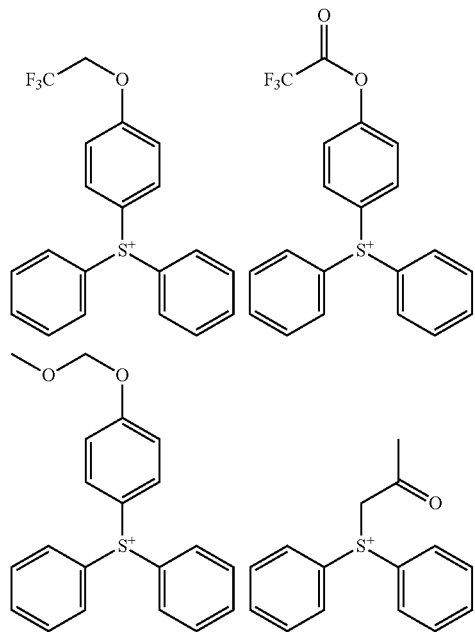
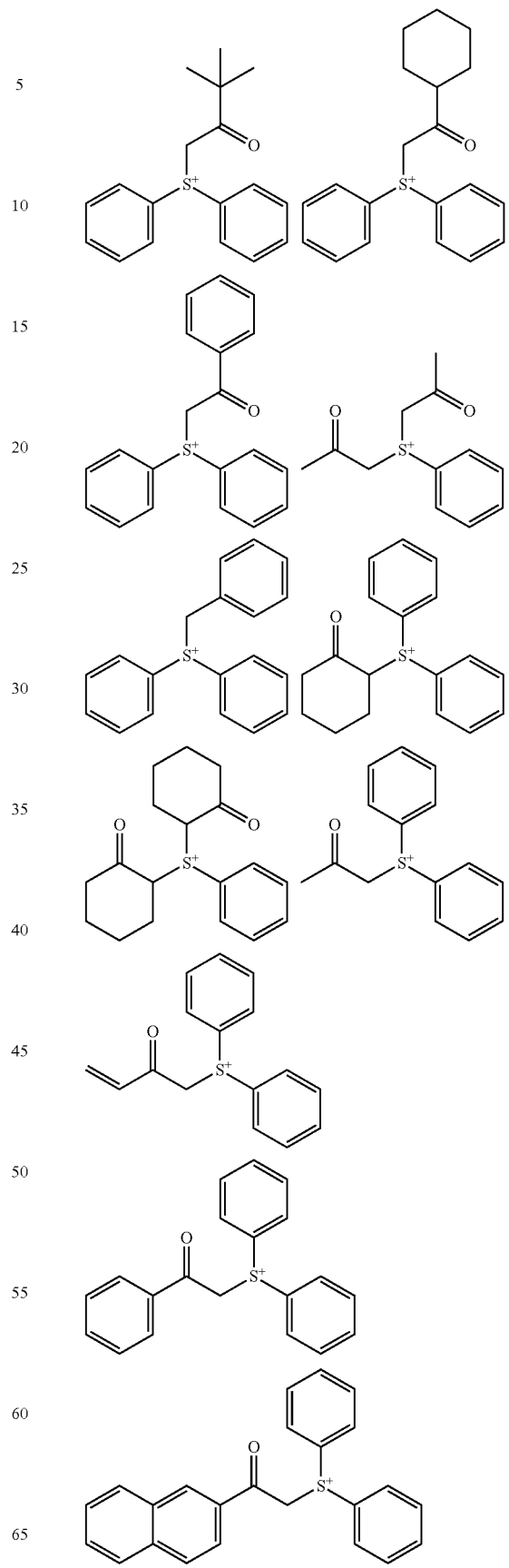

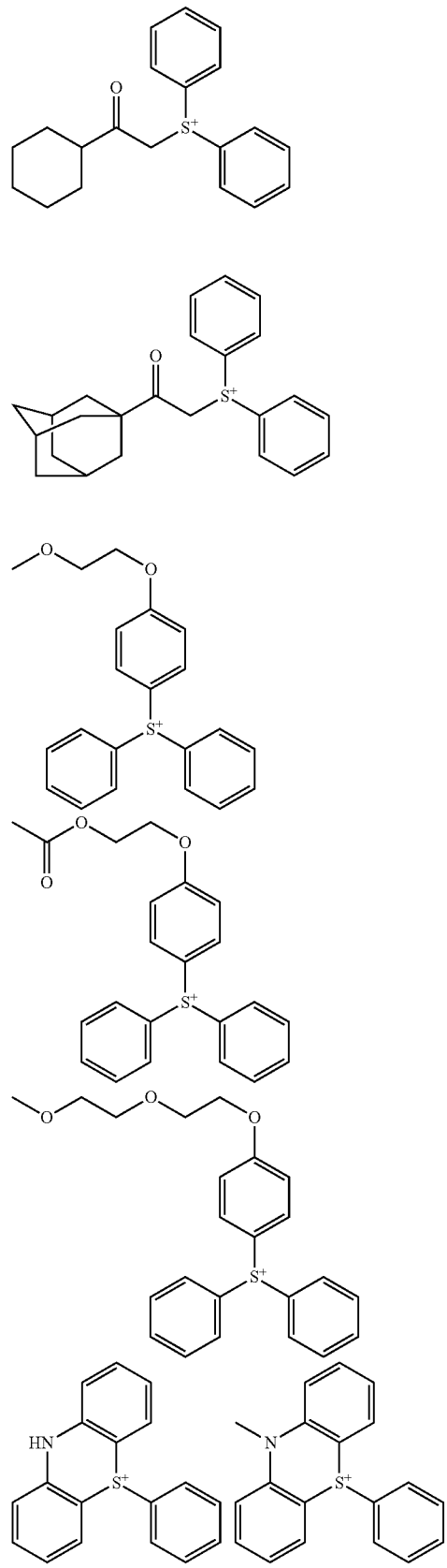
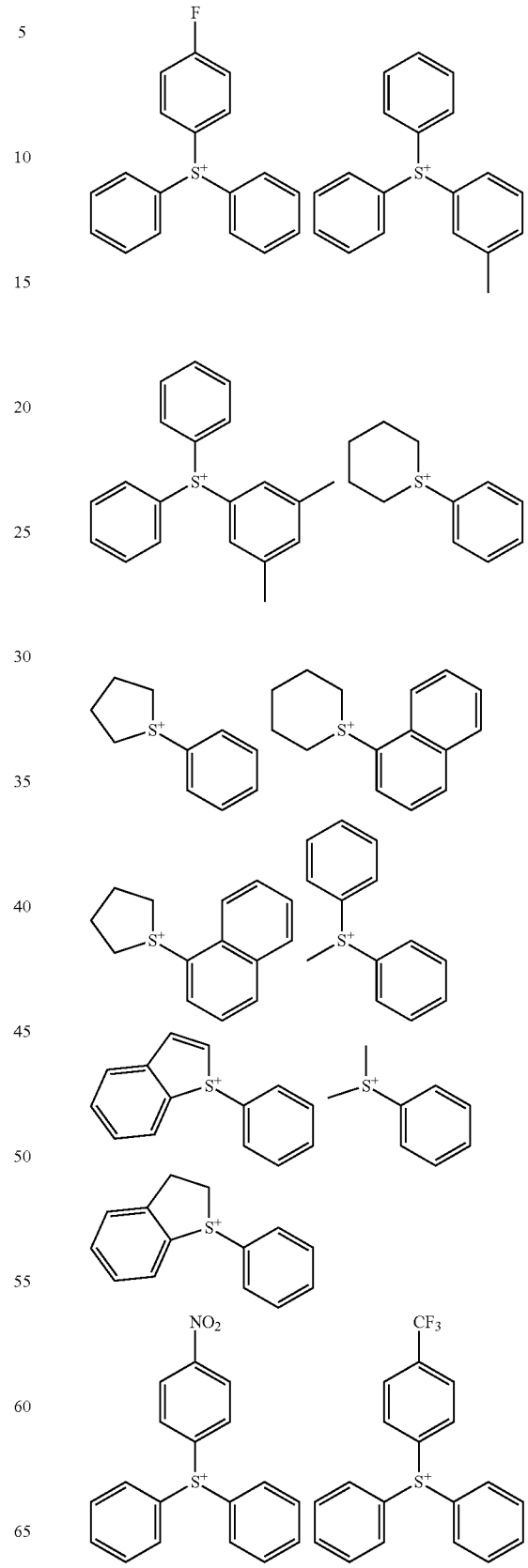

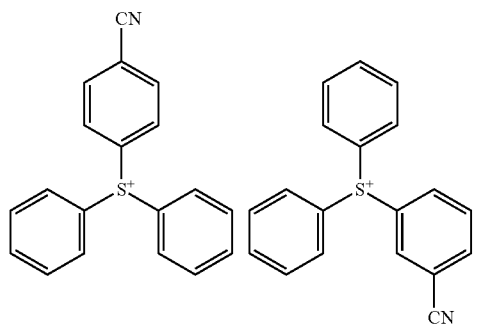
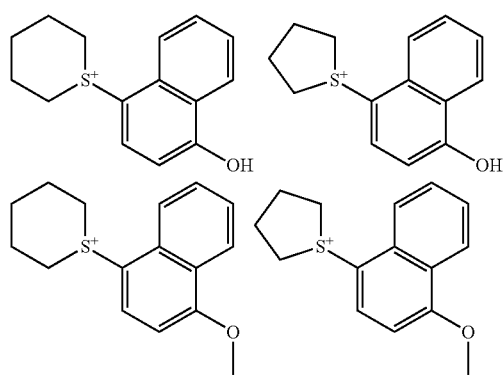
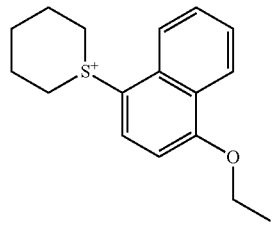
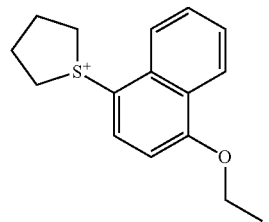
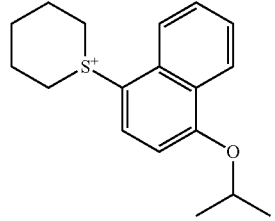
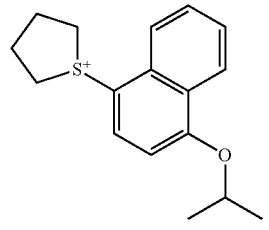
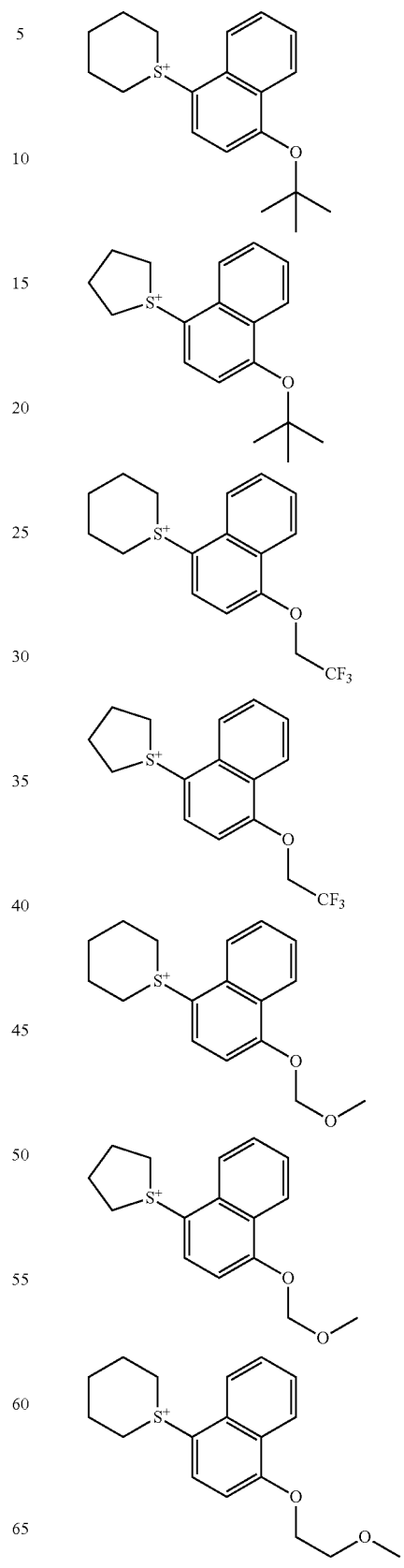

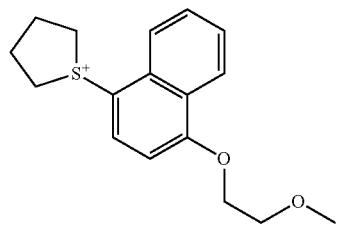
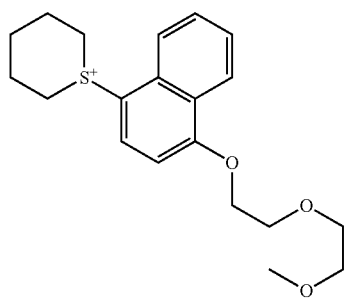
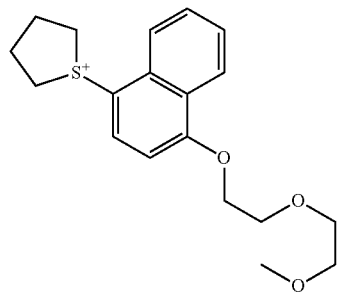
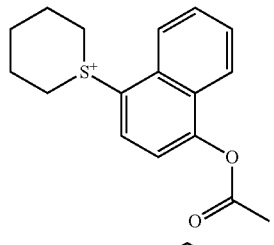
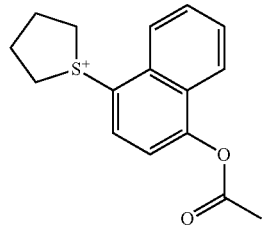
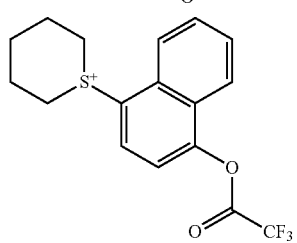
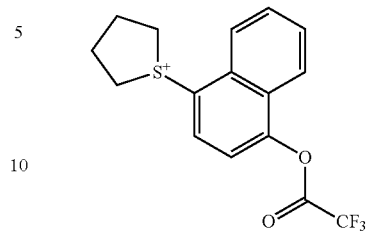
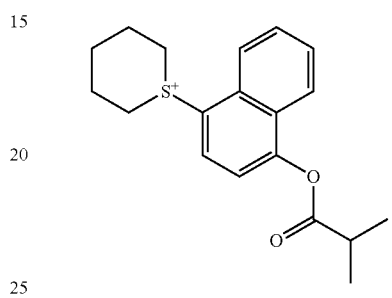
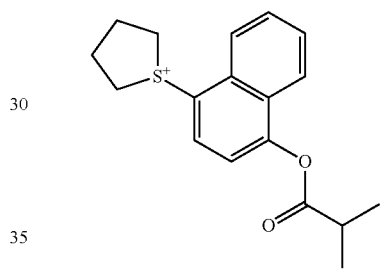
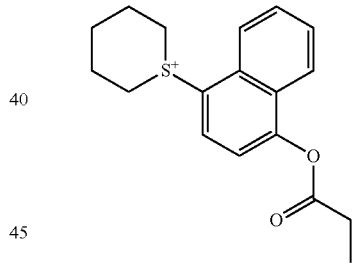
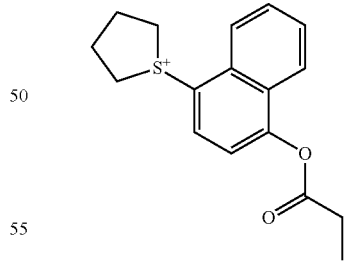
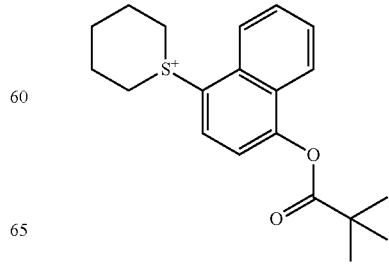

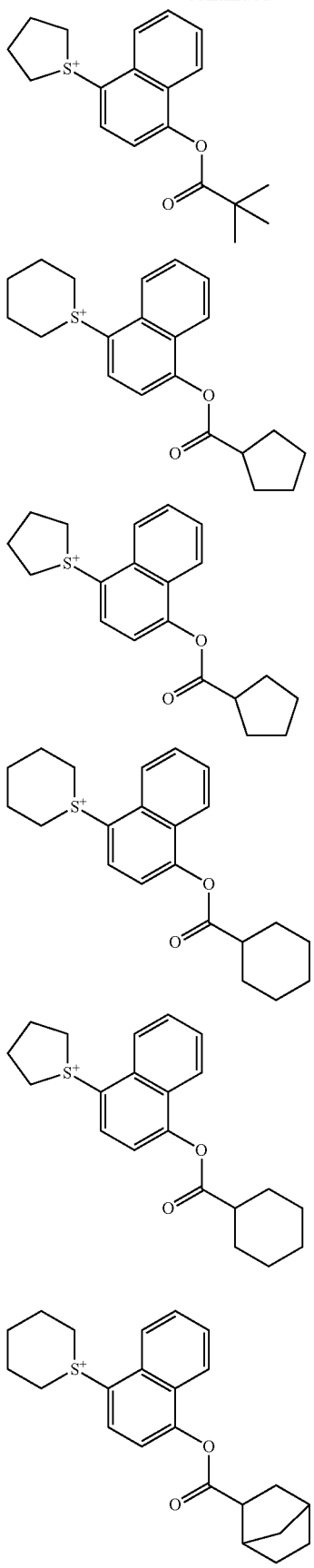
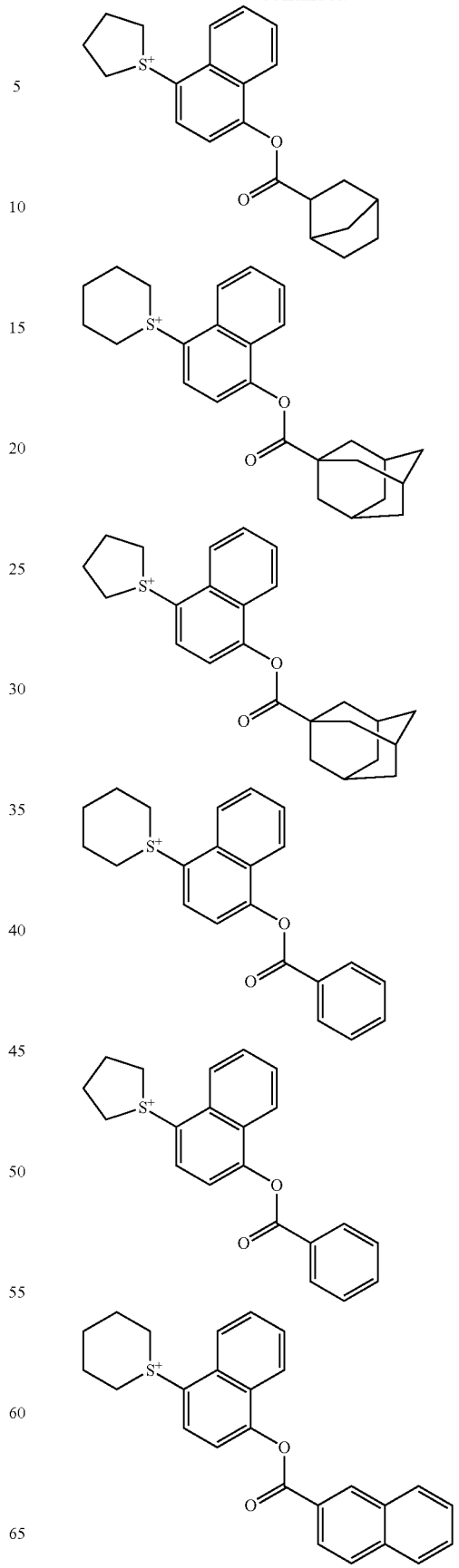

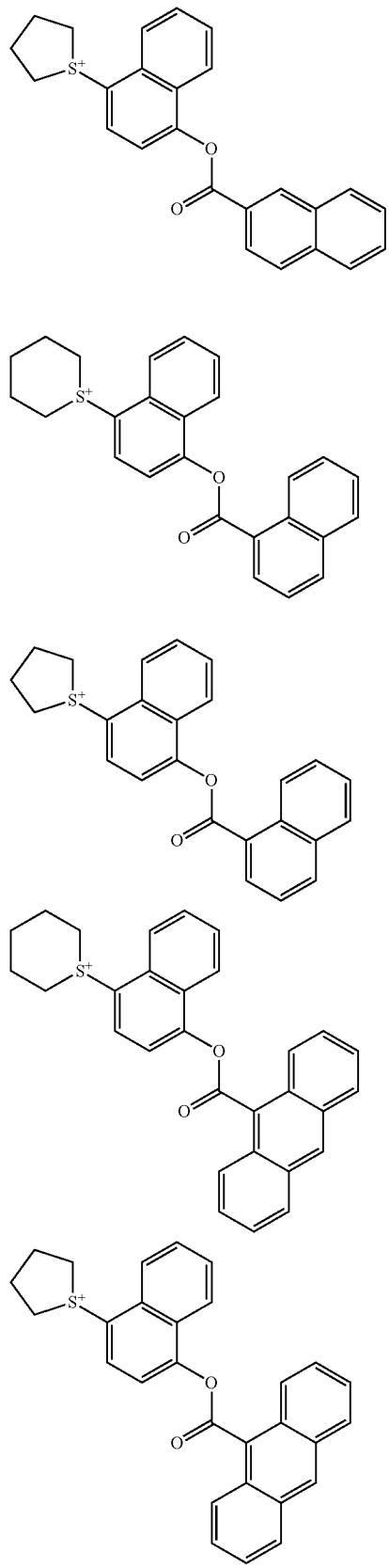
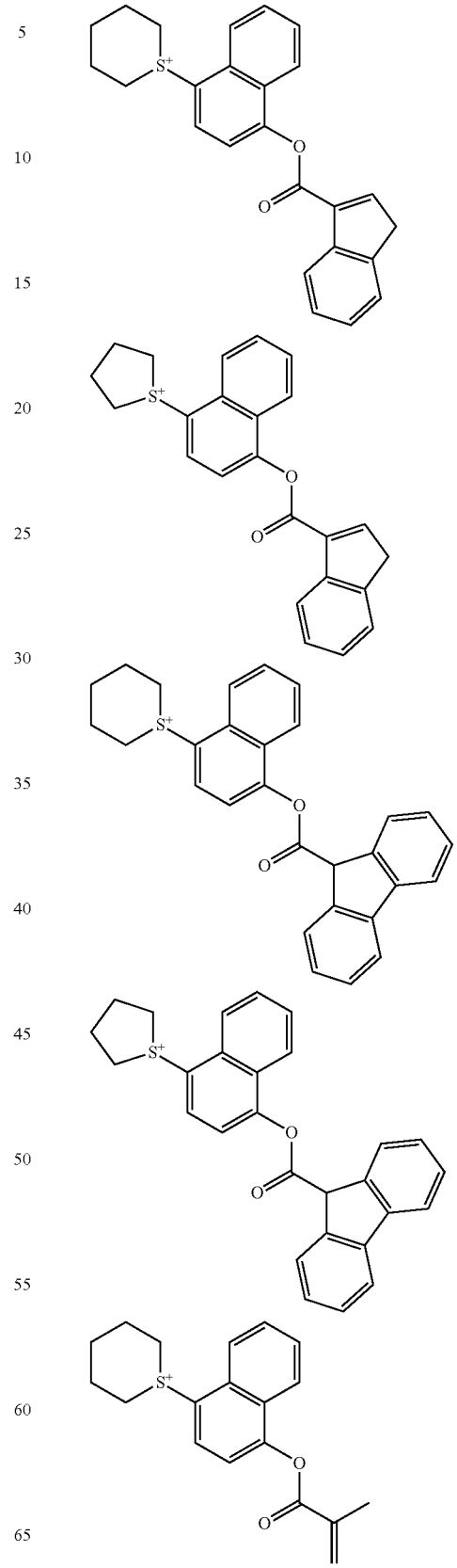

179
-continued
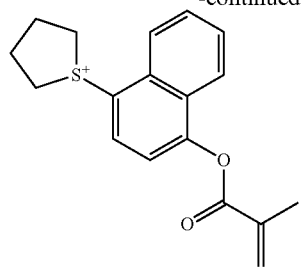
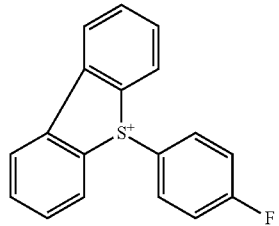
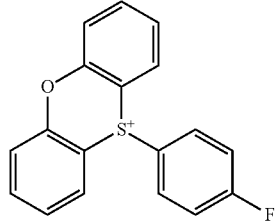
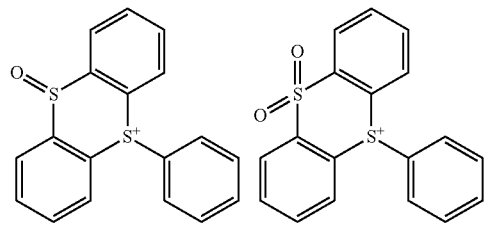
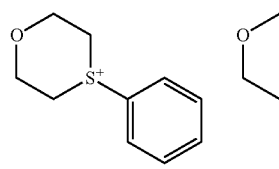
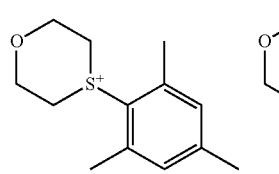
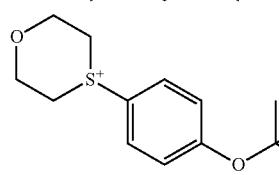
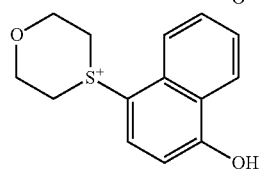
180
-continued
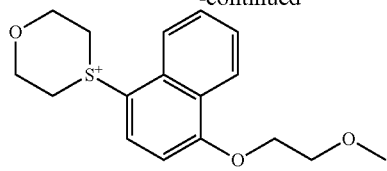
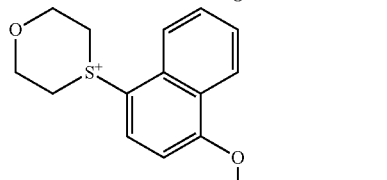
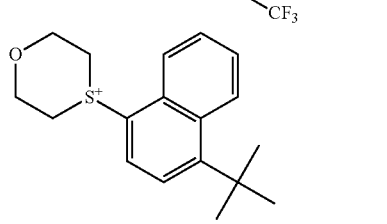
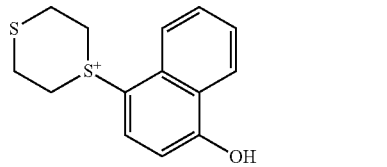
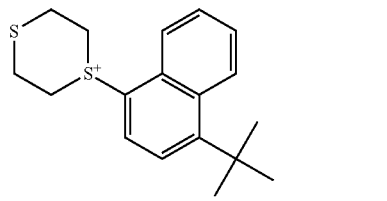
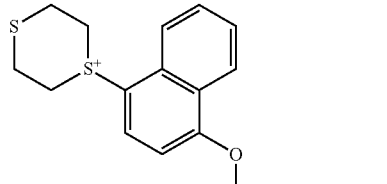
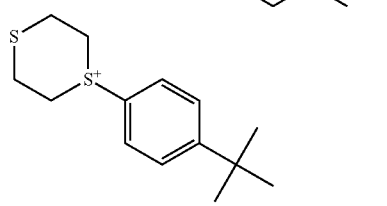
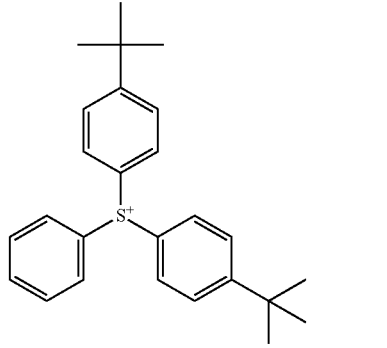

181
-continued
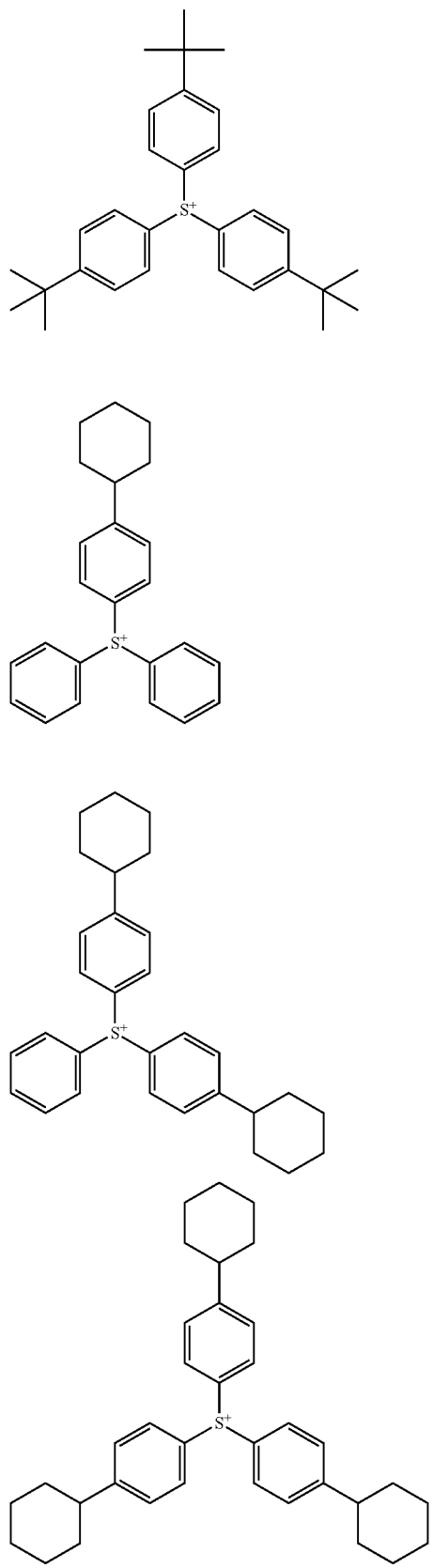
182
-continued
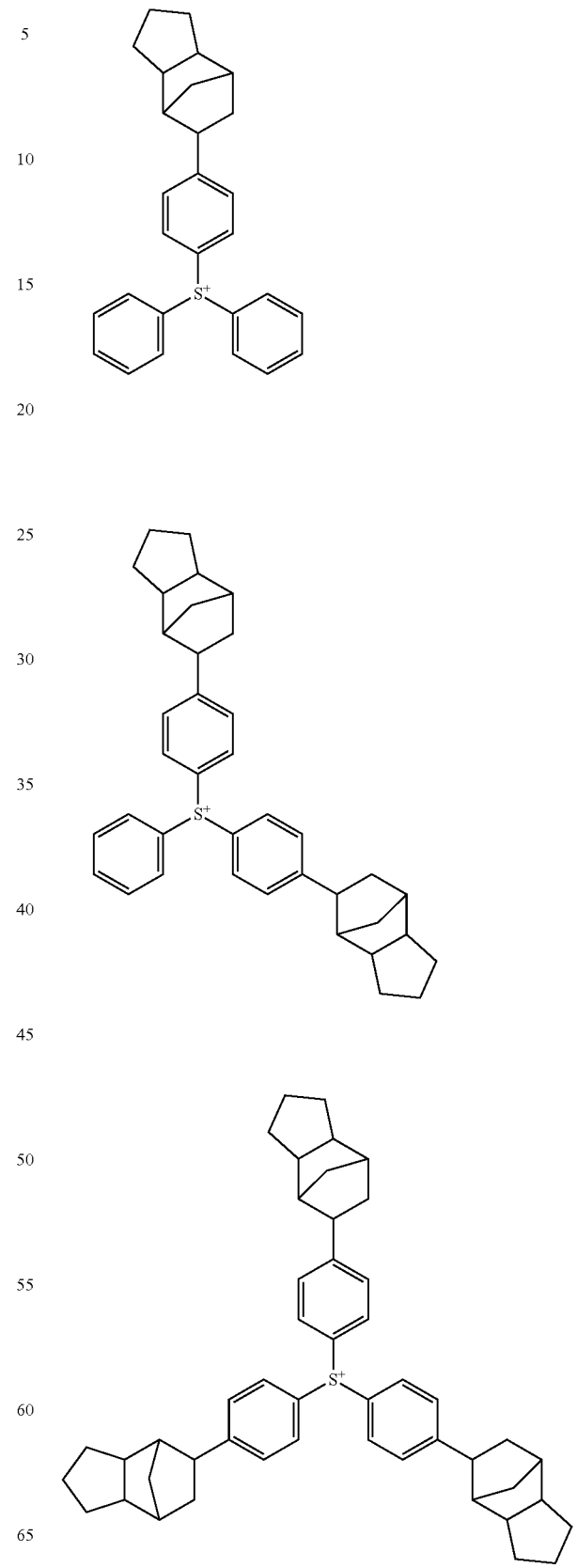

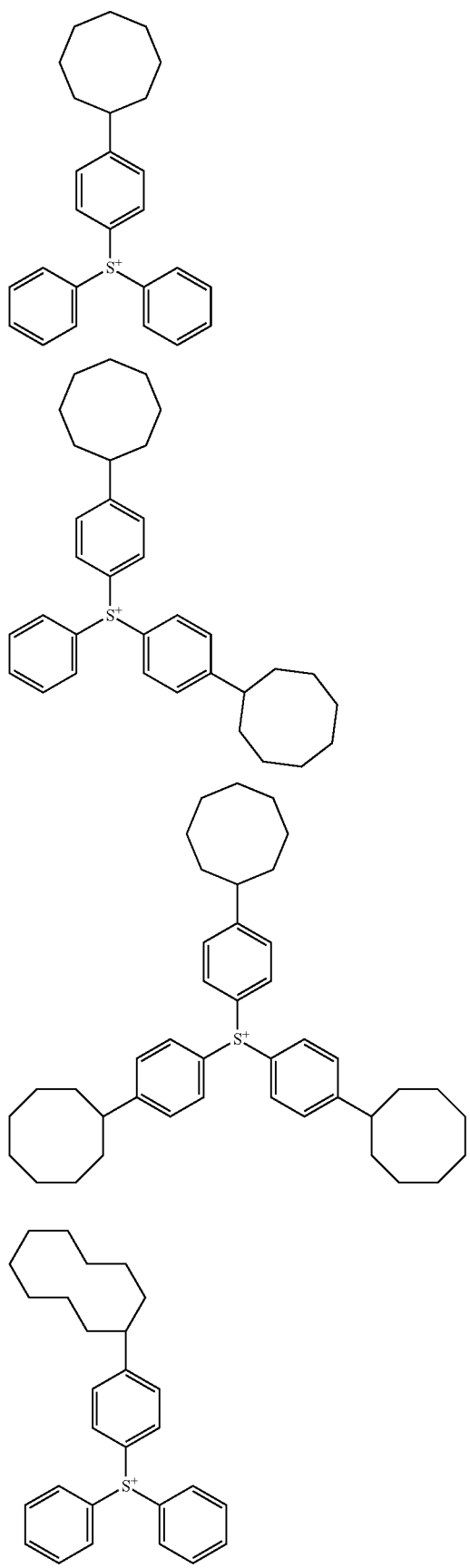
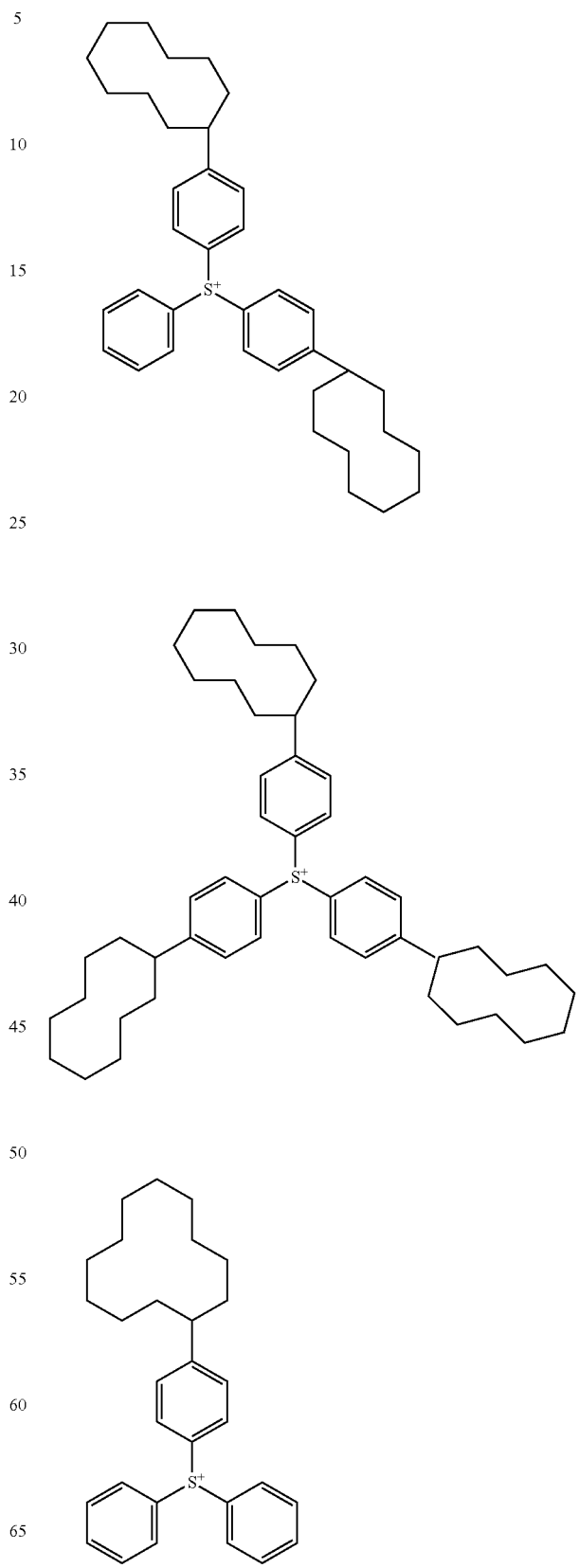

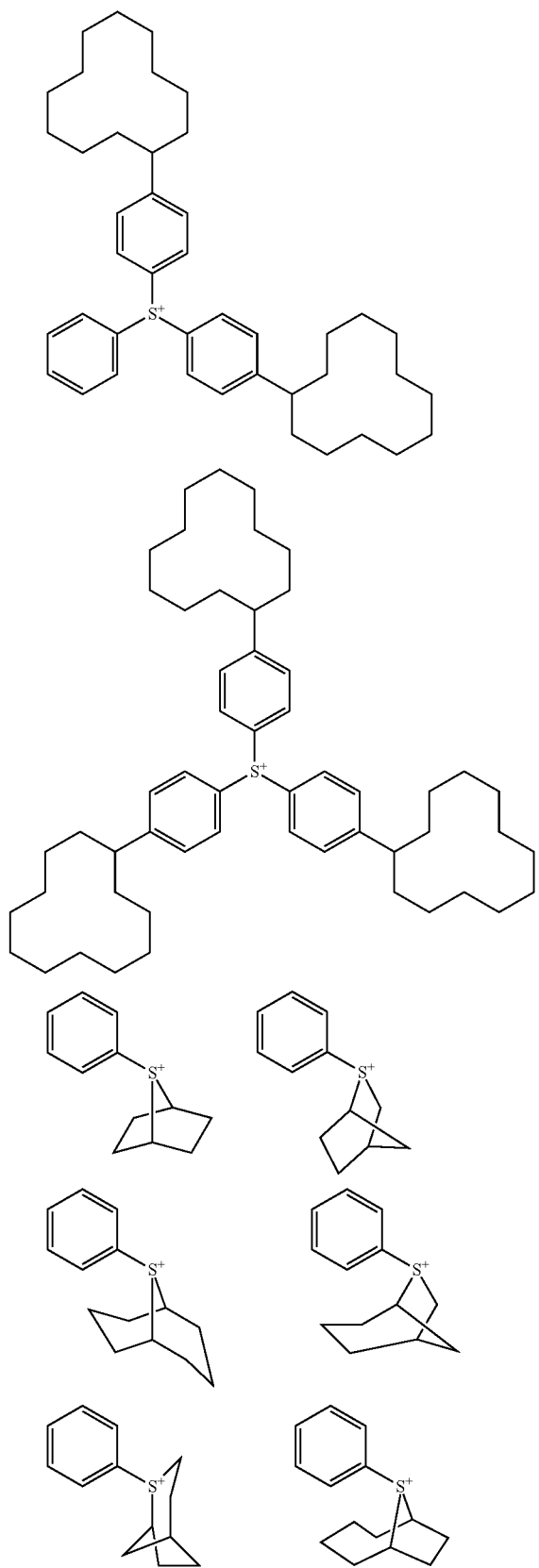
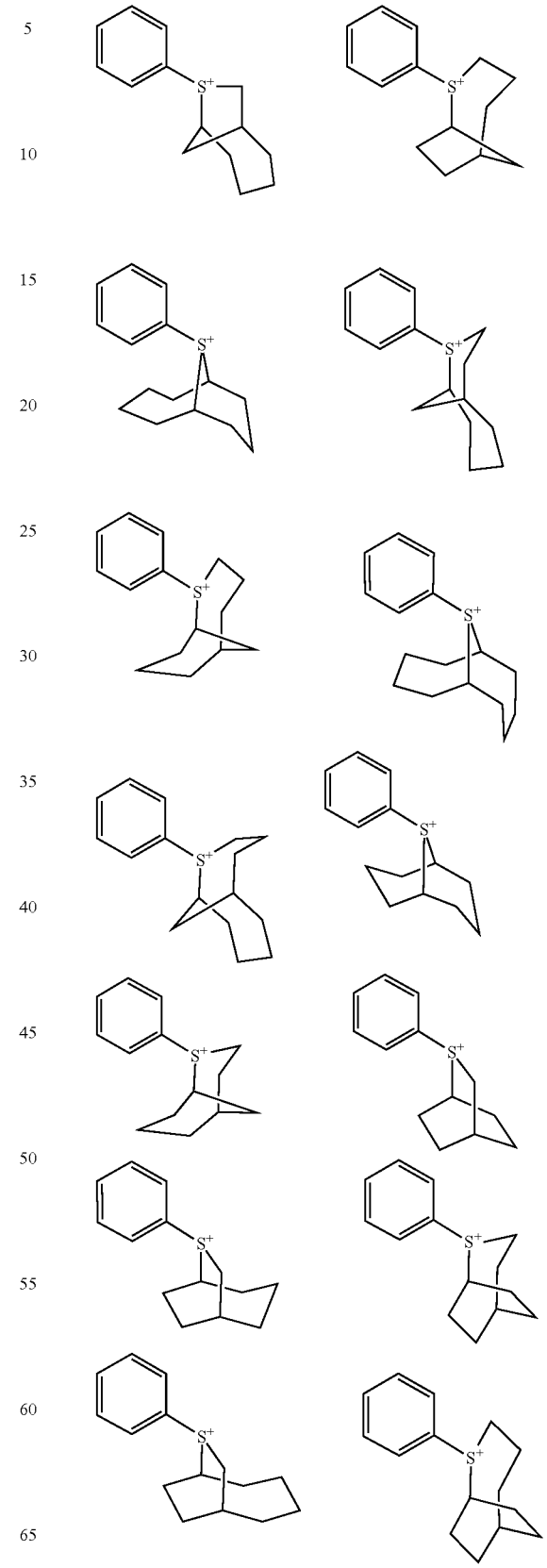

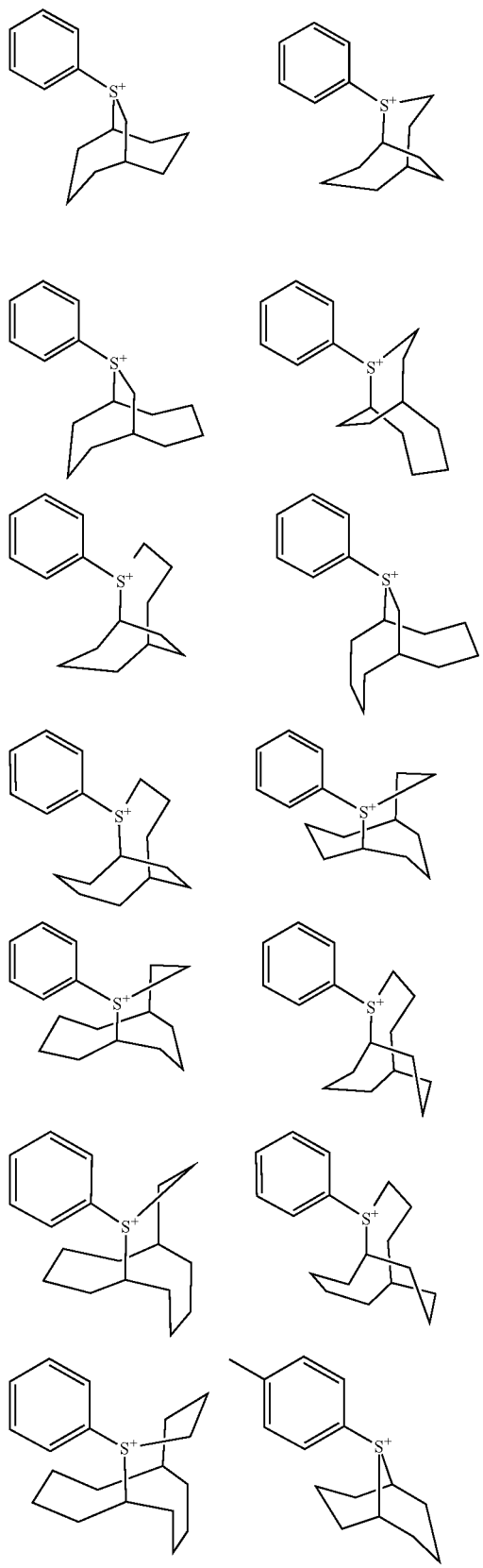
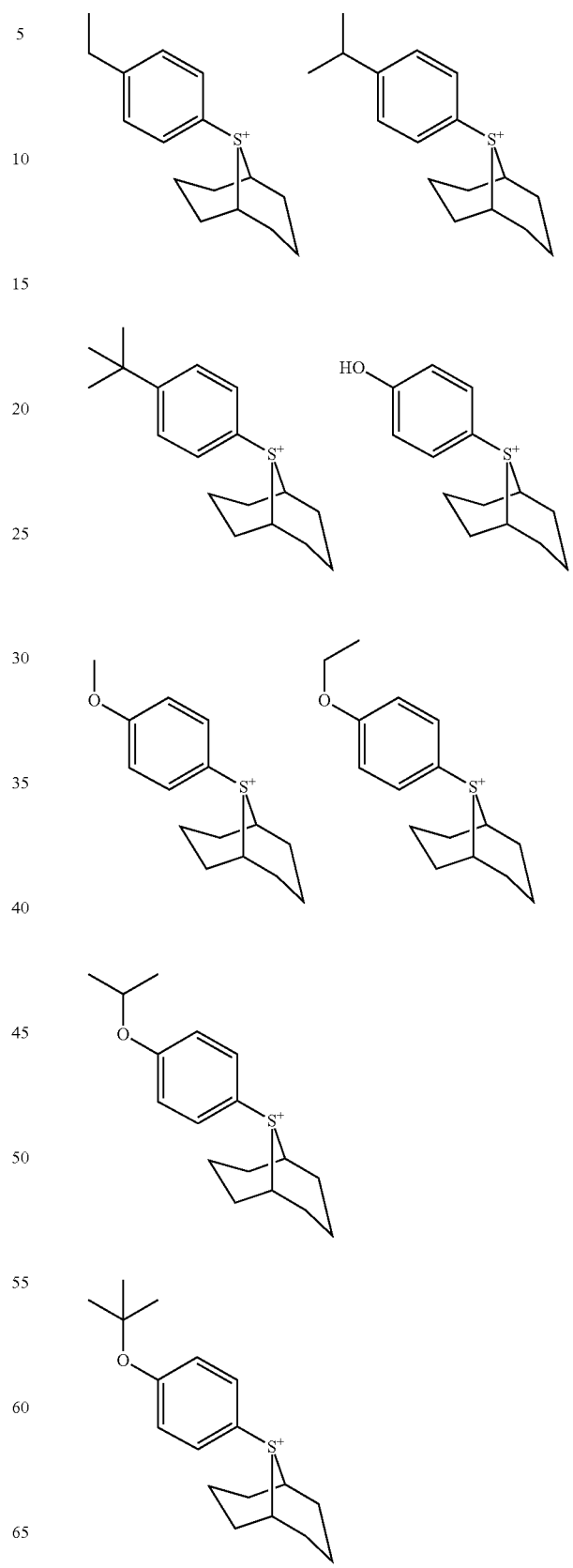

189
190
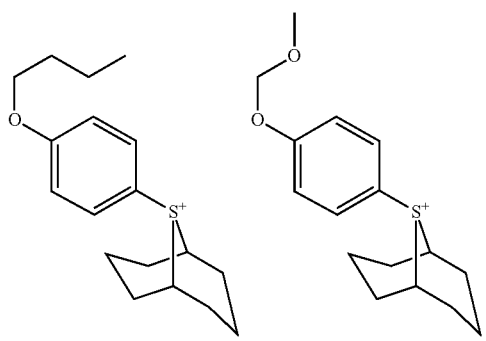
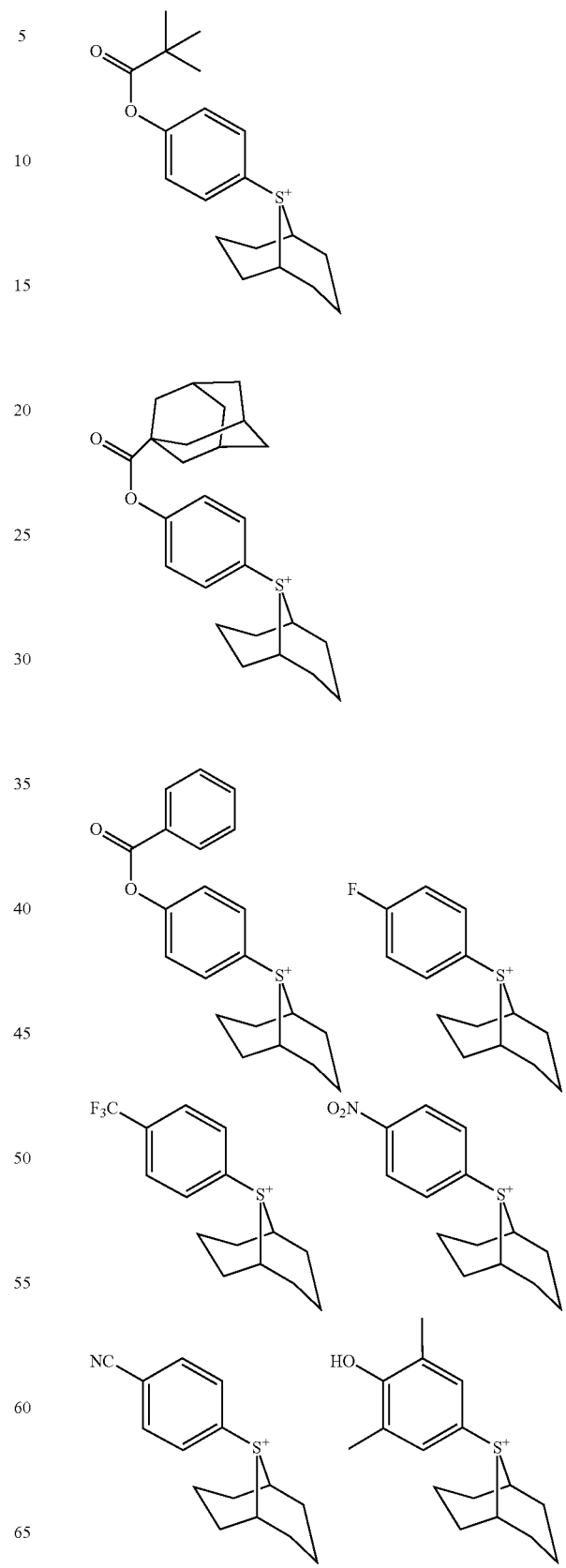

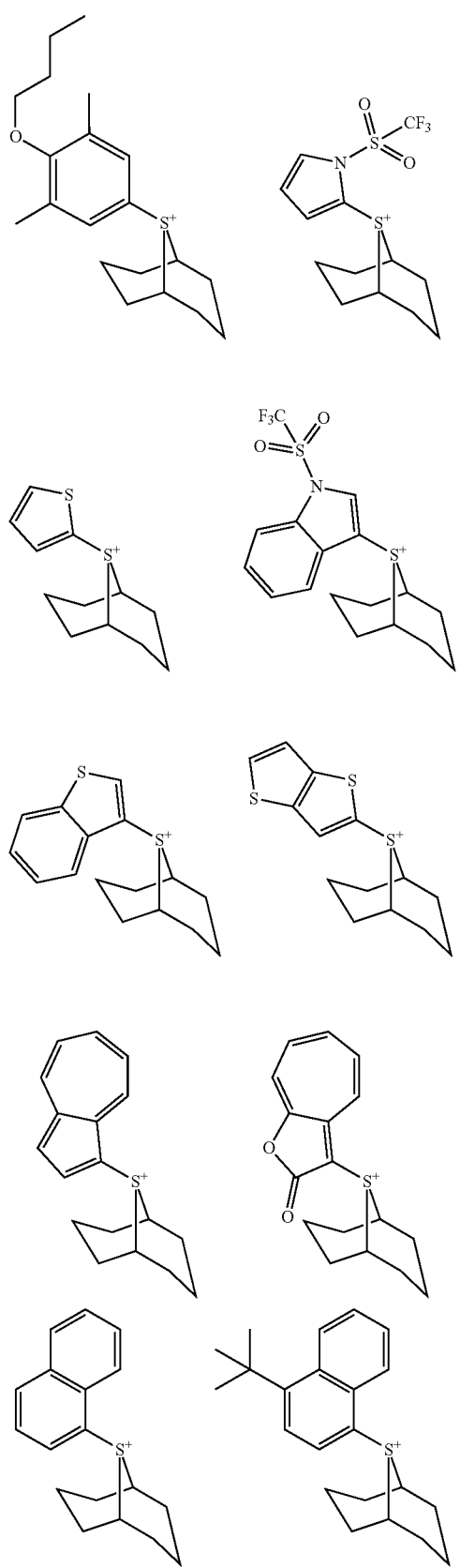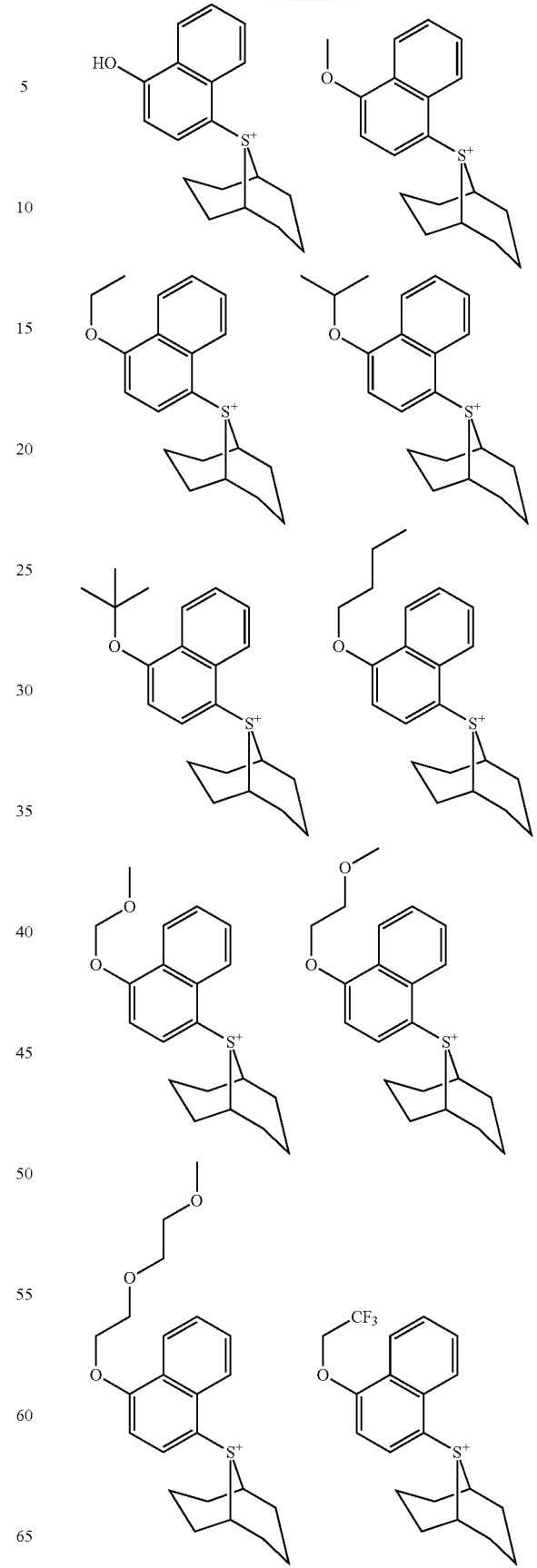

193
-continued
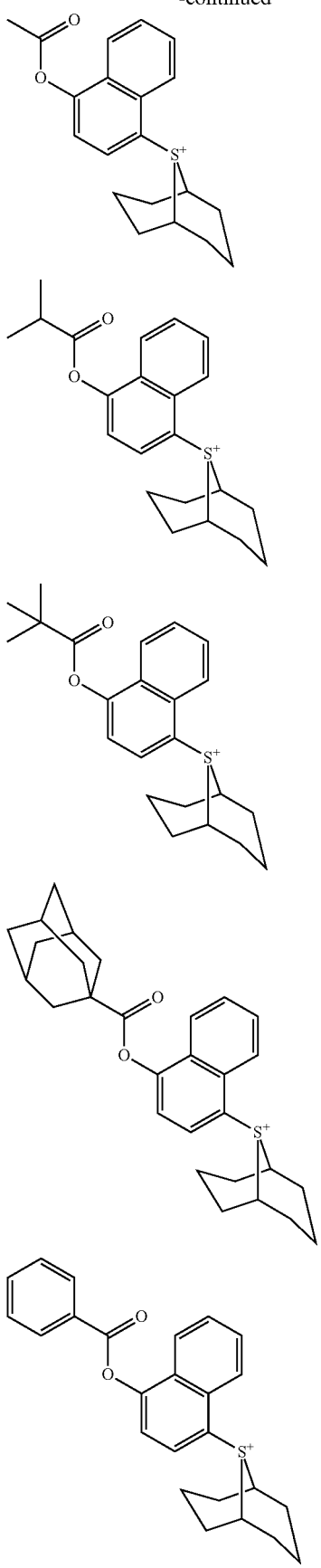
194
-continued
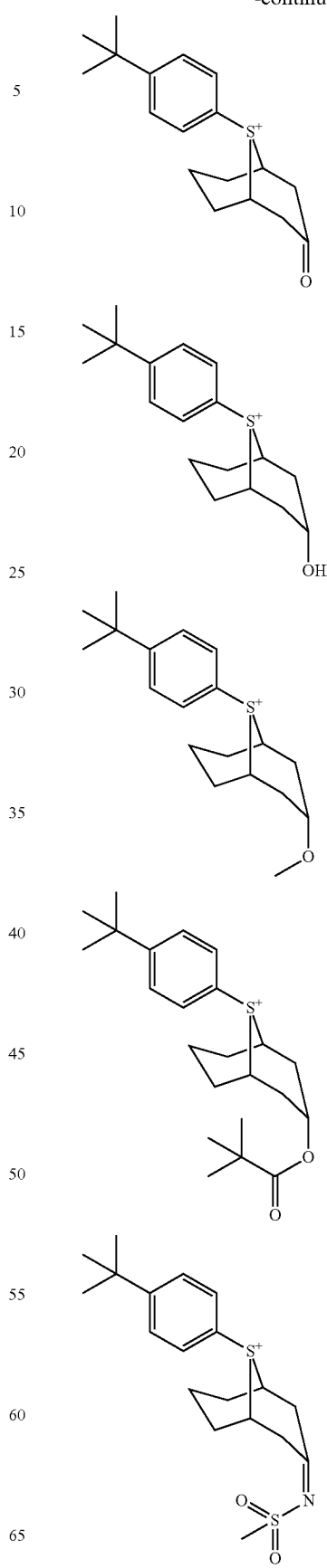

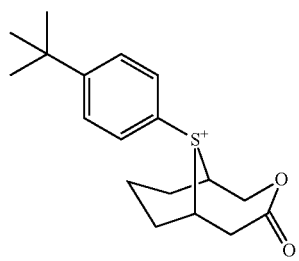
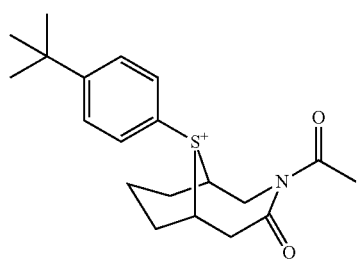
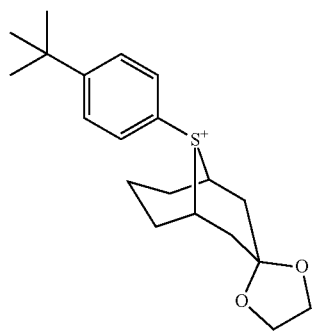
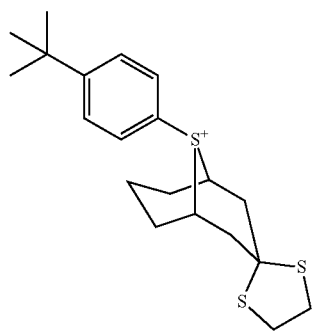
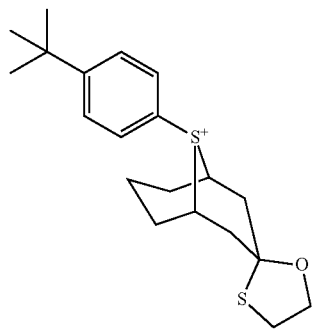
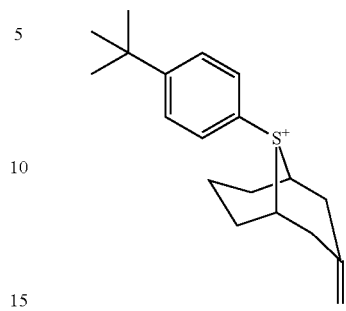
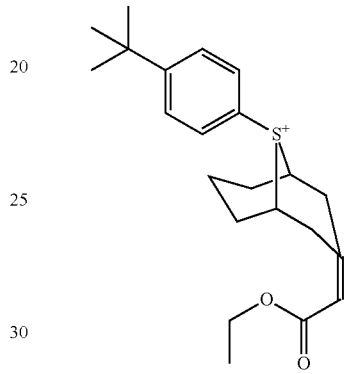
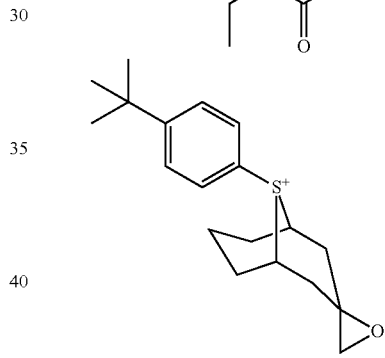
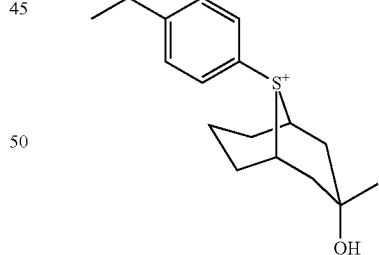
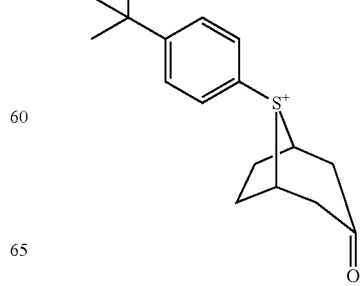

197
-continued
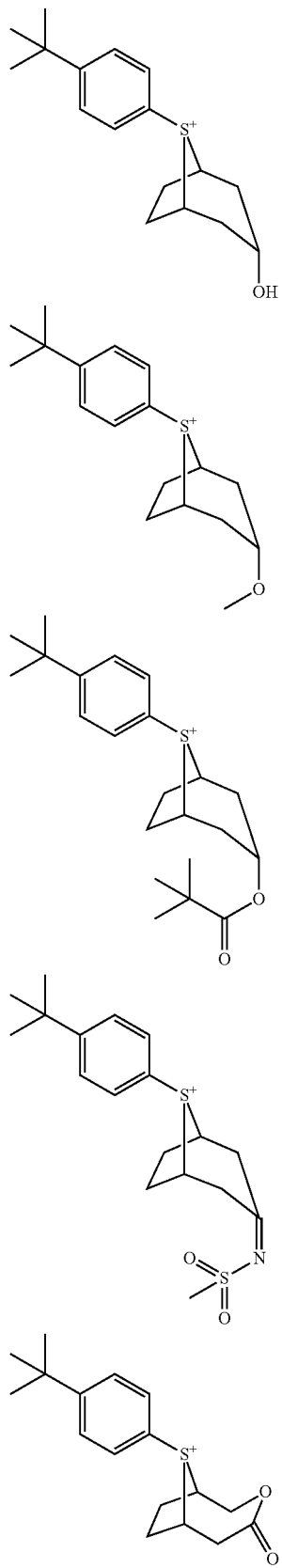
198
-continued
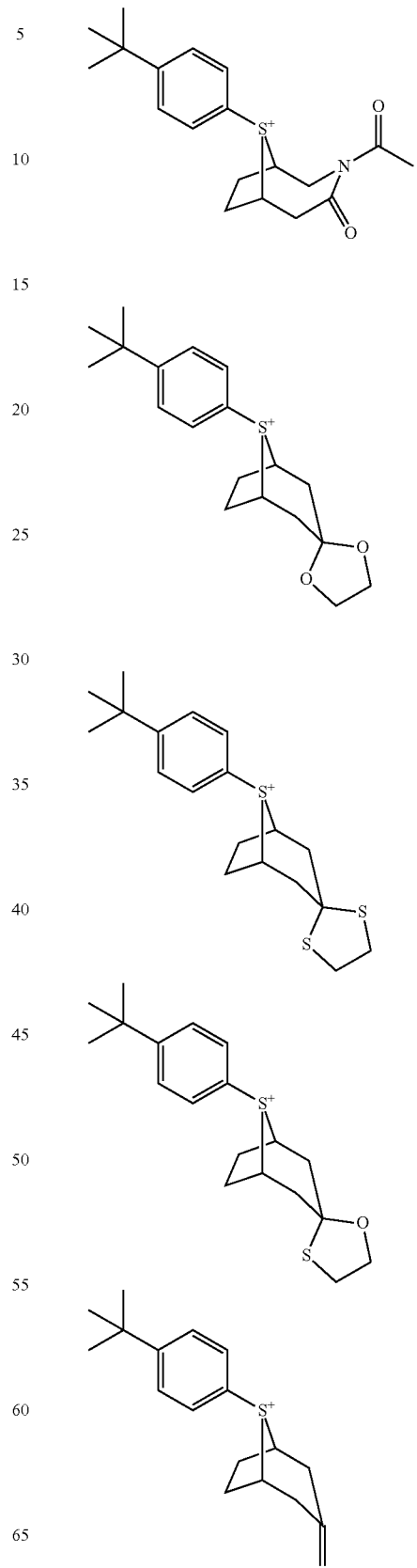

199
-continued
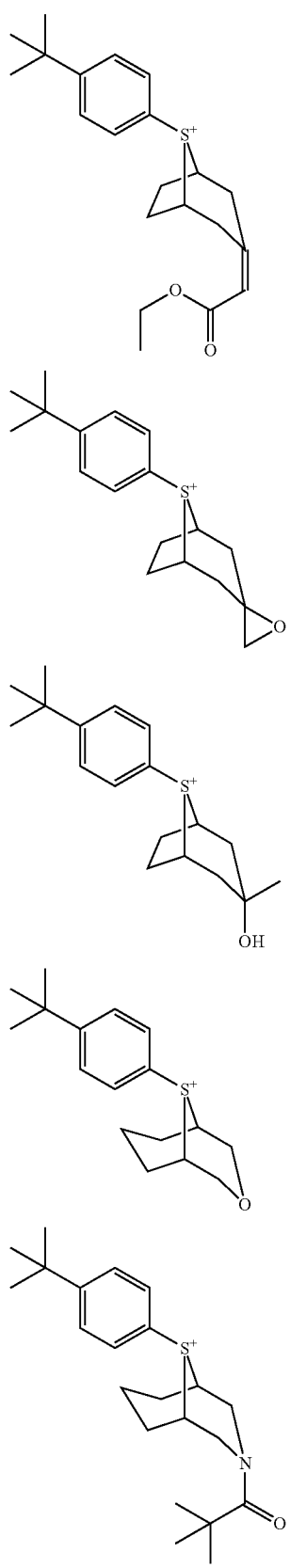
200
-continued
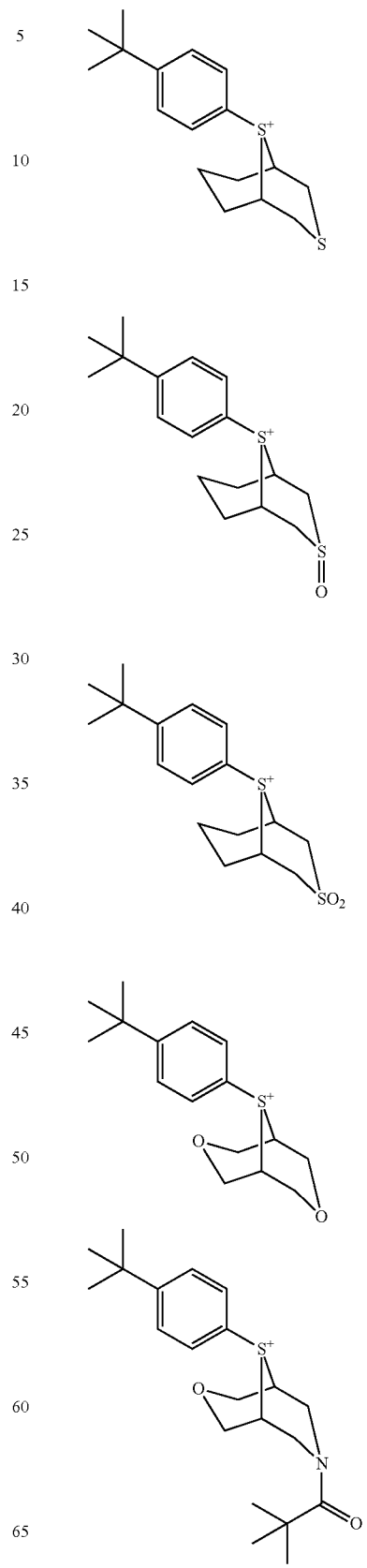

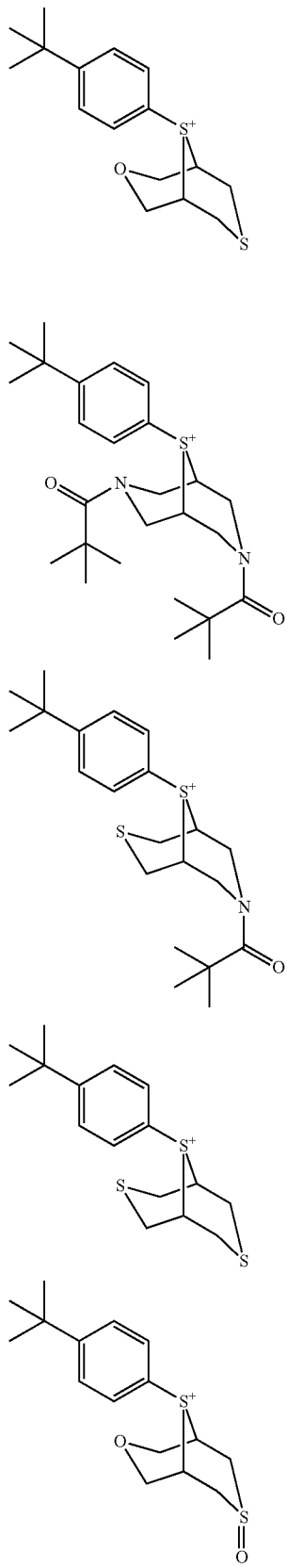
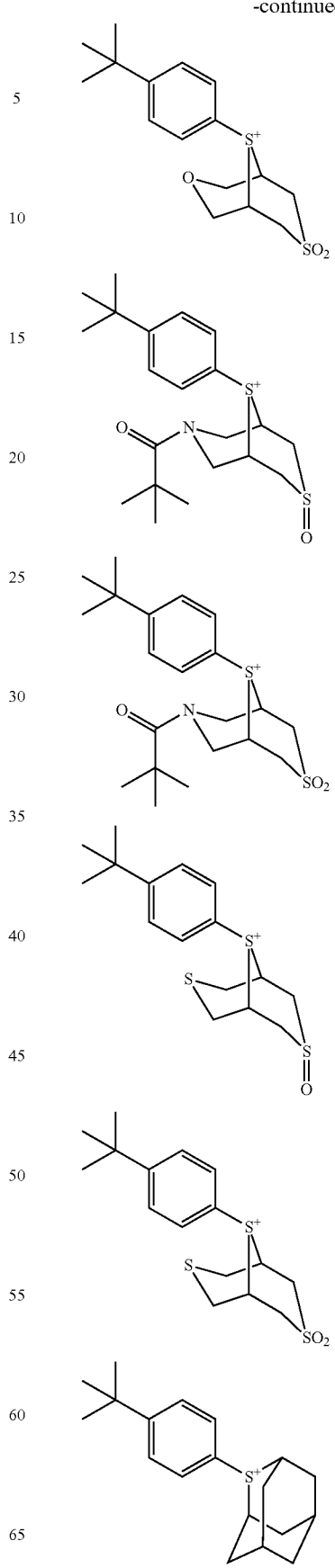

203
-continued
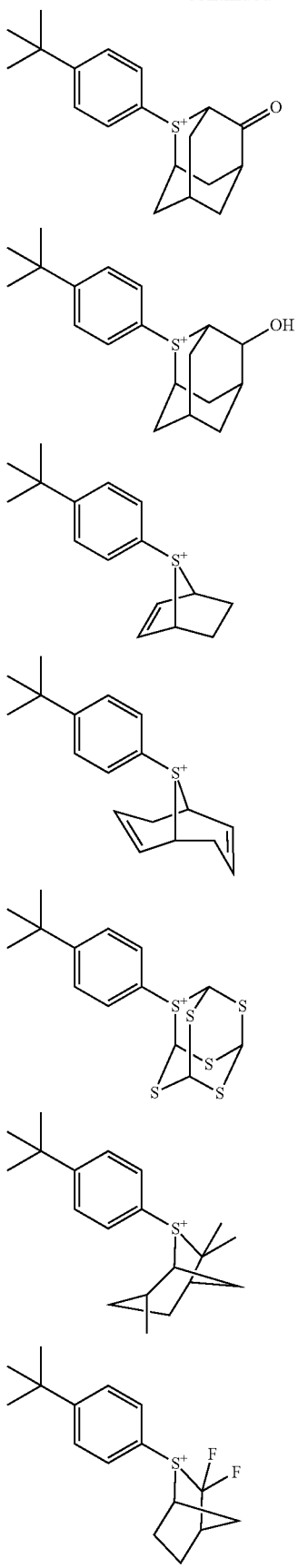
204
-continued
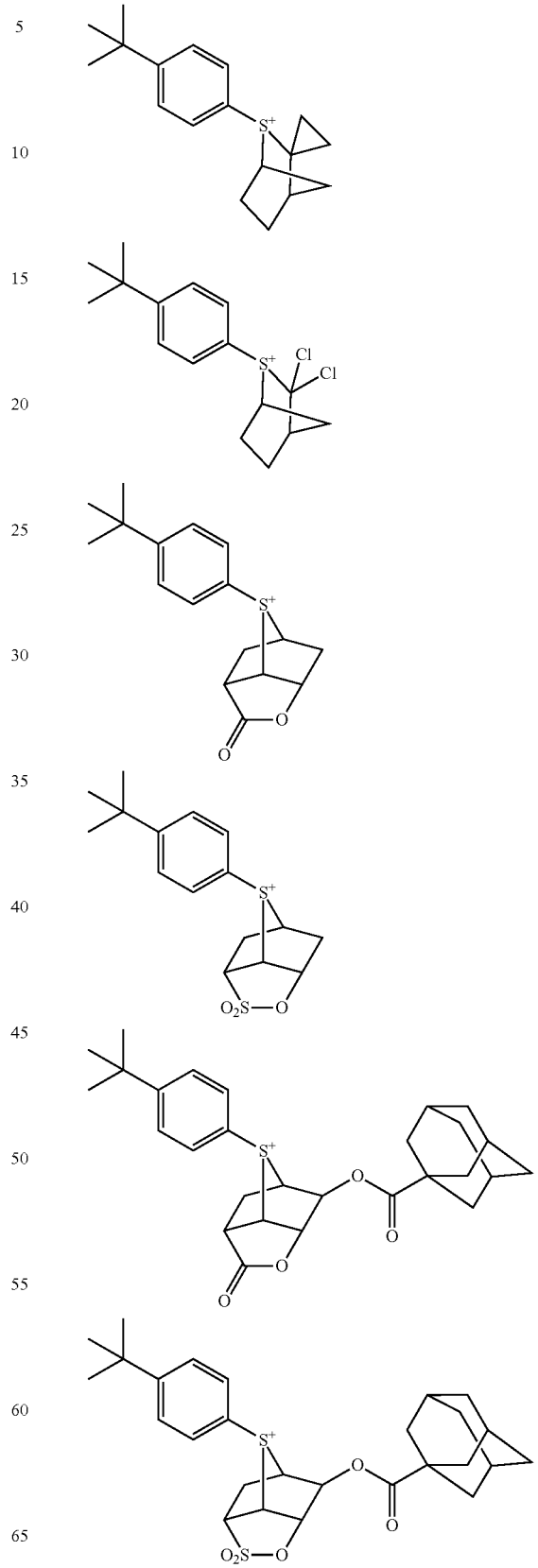

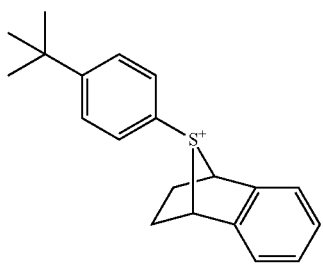

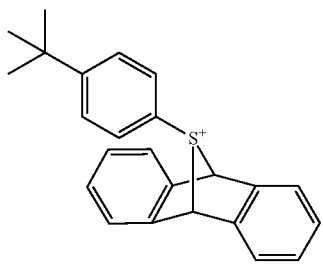

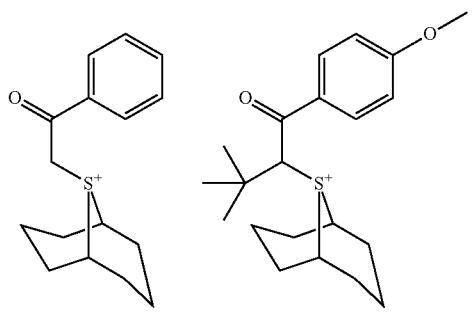

Examples of the iodonium cation having formula (c5) are given below, but not limited thereto.

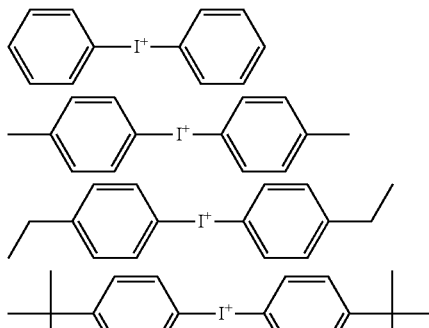

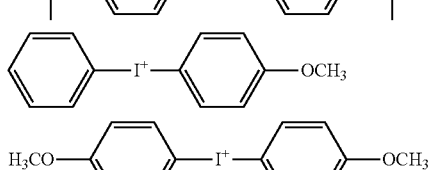

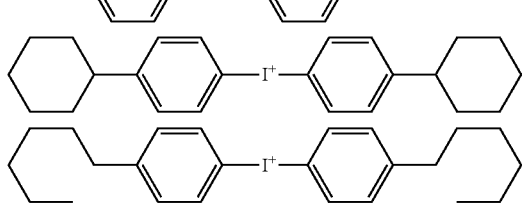

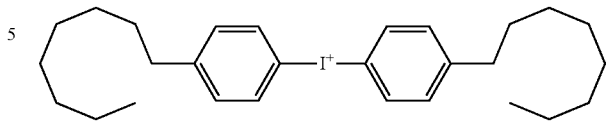

The polymer may further comprise recurring units of a structure having a hydroxyl group protected with an acid labile group. These recurring units are not particularly limited as long as the unit includes one or more structures having a hydroxyl group protected with a protective group such that the protective group is decomposed to generate the hydroxyl group under the action of acid. Recurring units having the formula (d1) are preferred.

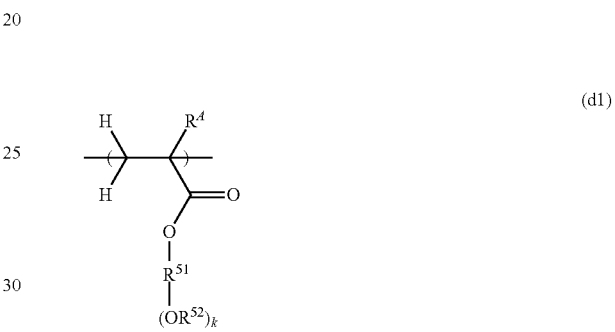

(d1)

In formula (d1), $R^A$ is as defined above. $R^{51}$ is a $C_1$-$C_{30}$ (j+1)-valent hydrocarbon group which may contain a heteroatom. $R^{52}$ is an acid labile group, and j is an integer of 1 to 4.

Examples of the recurring units having formula (d1) are shown below, but not limited thereto. Herein $R^A$ and $R^{52}$ are as defined above.

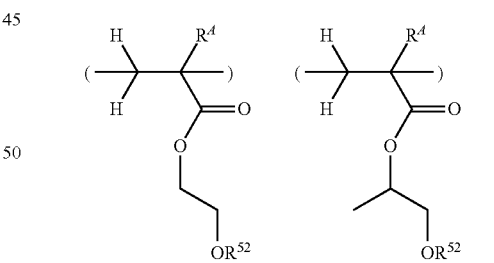

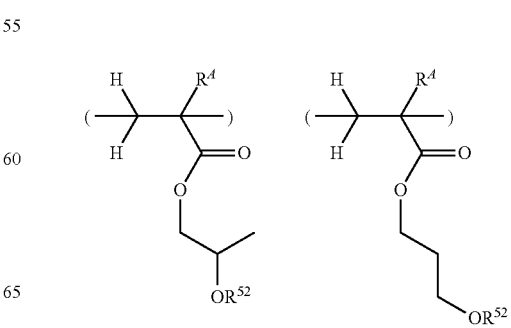

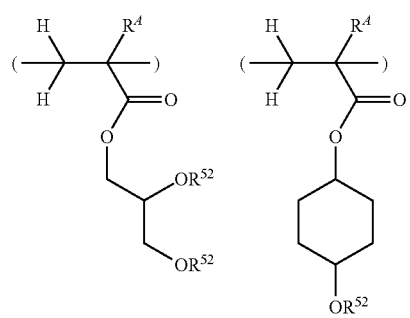
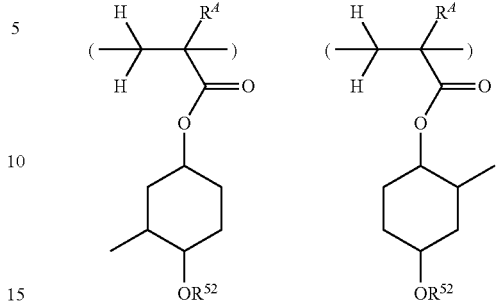
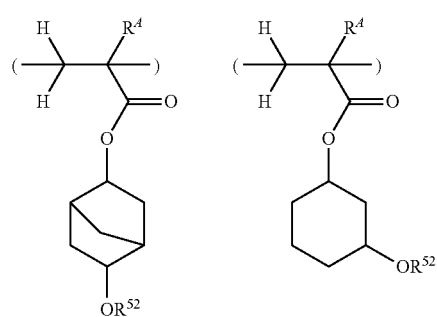
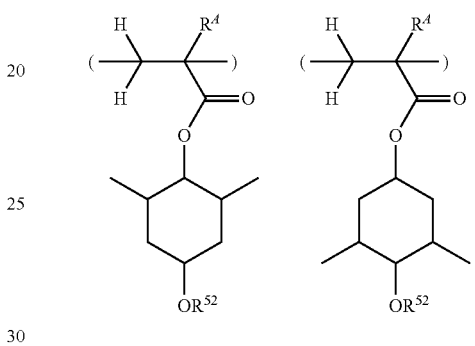
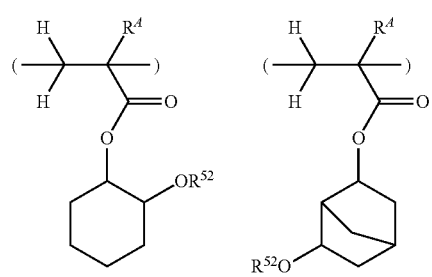
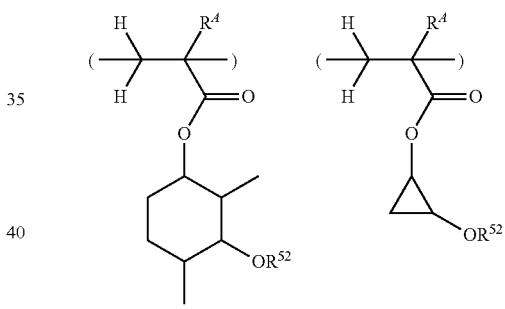
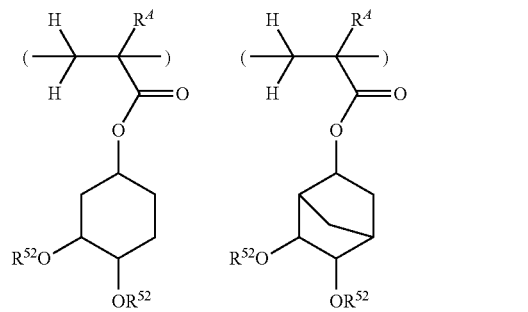
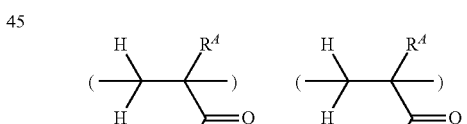
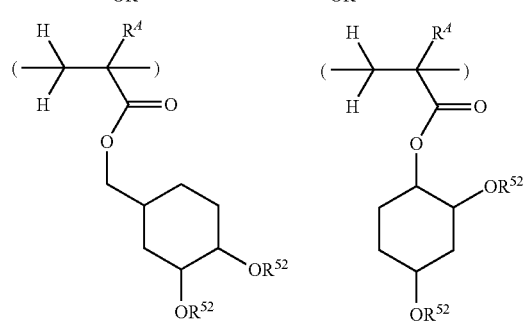
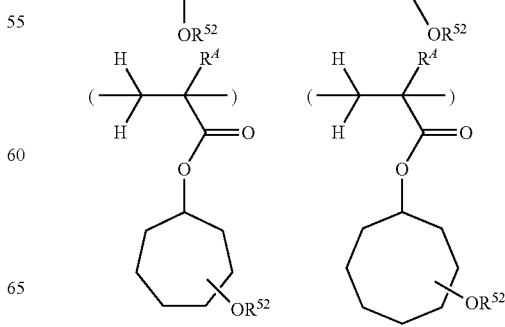

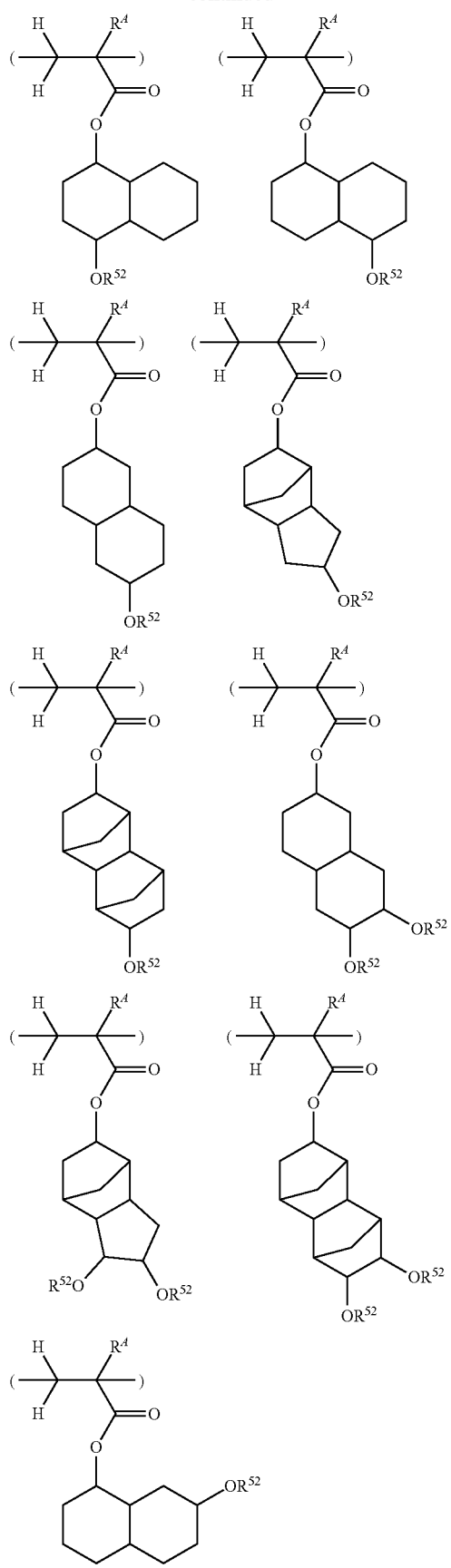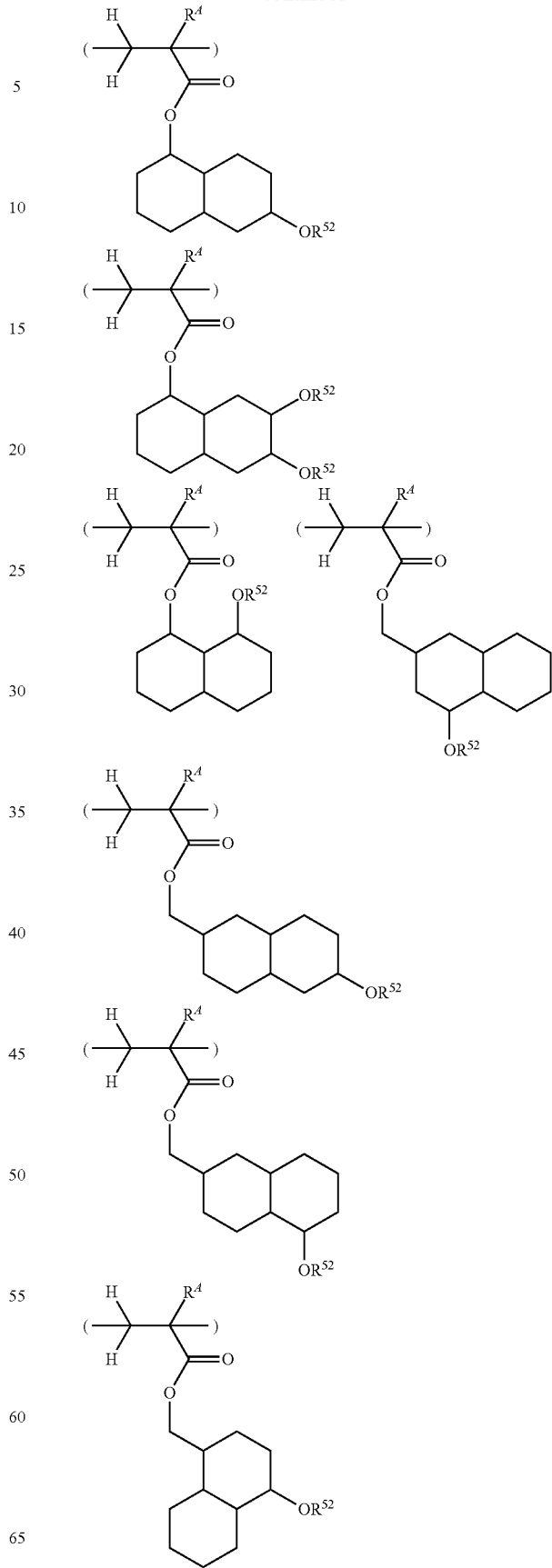

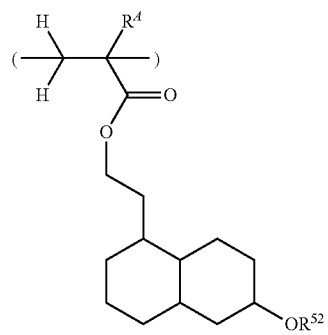
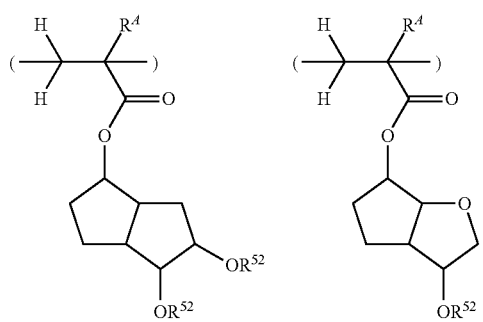
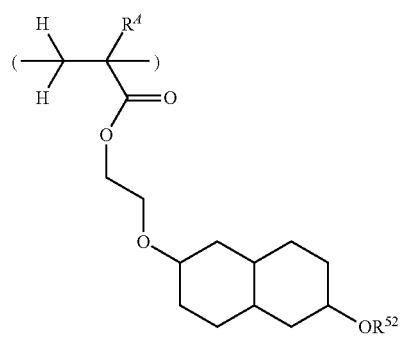
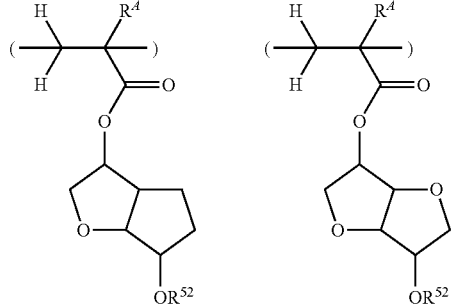
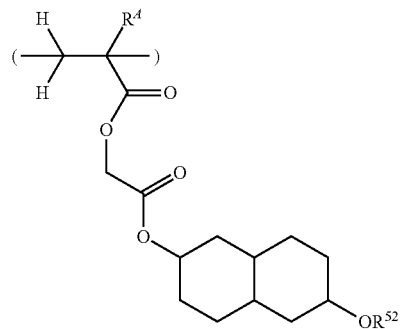
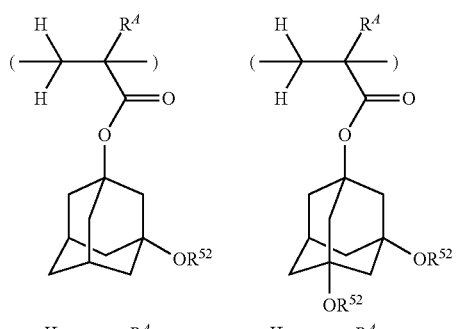
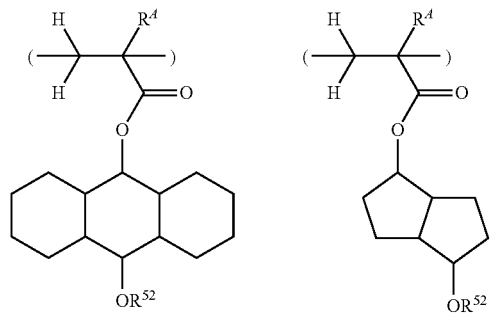
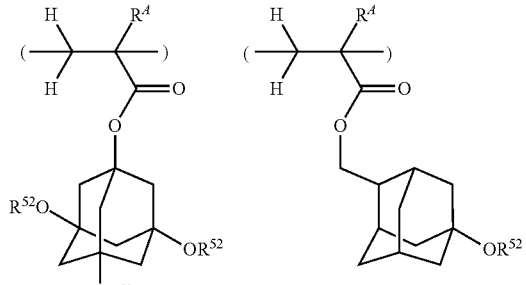
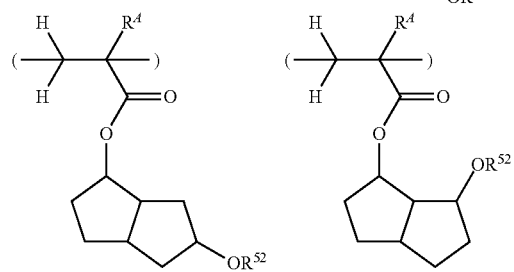
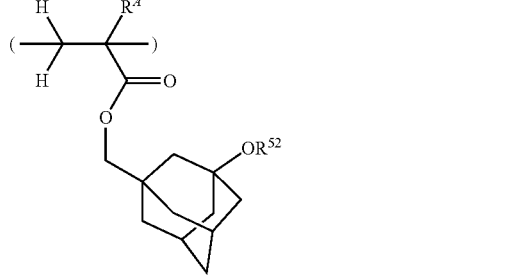
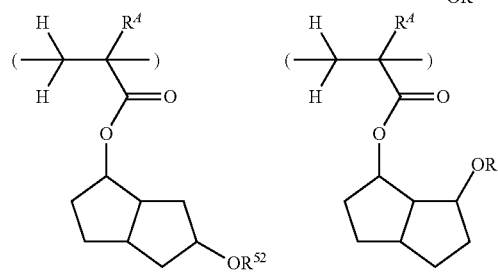
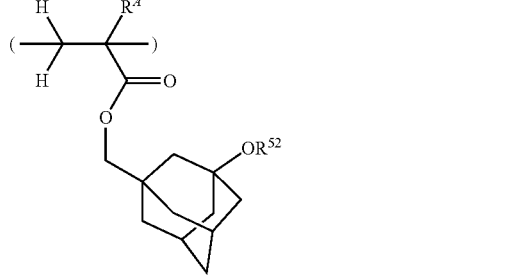
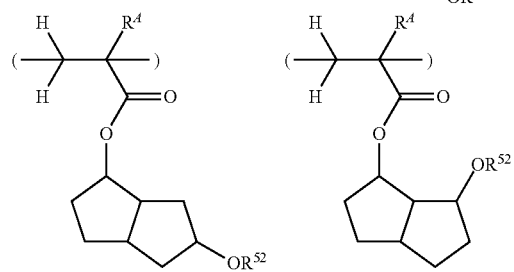
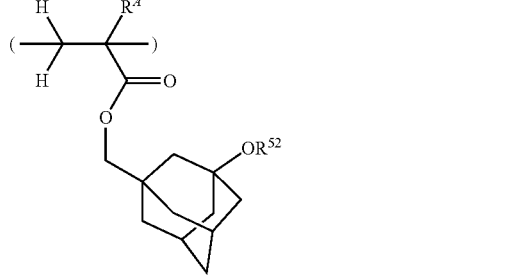

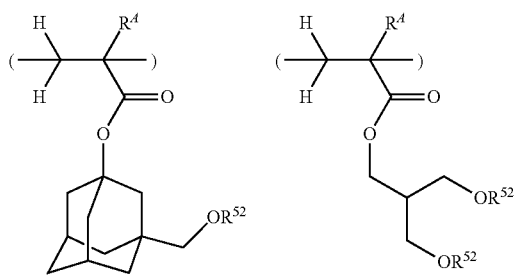
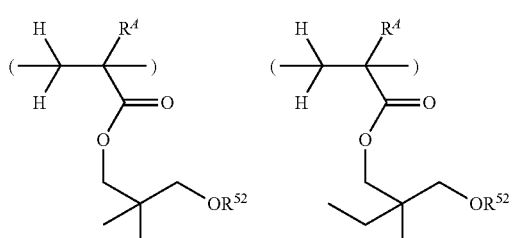
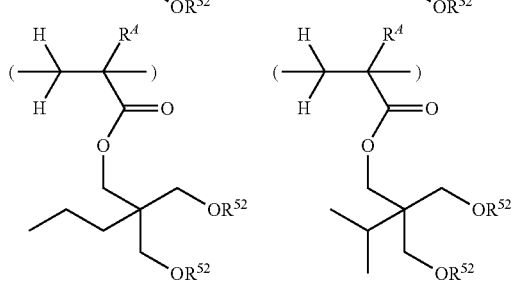
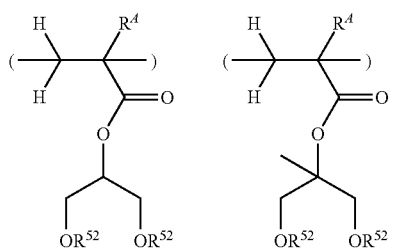
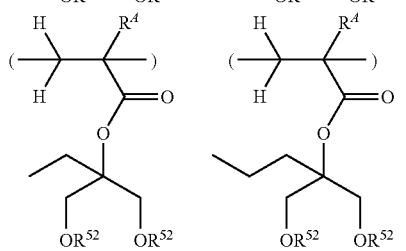
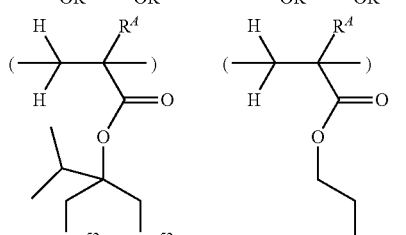
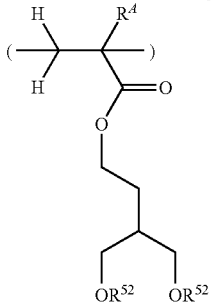
The acid labile group $R^{52}$ in formula (d1) is not particularly limited as long as it is deprotected to generate a hydroxyl group under the action of acid. Typical, non-limiting acid labile groups are groups of acetal or ketal structure and alkoxycarbonyl groups, with examples being shown below.
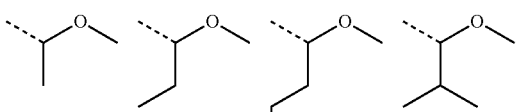
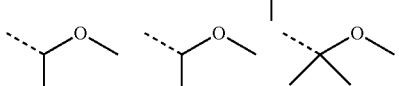
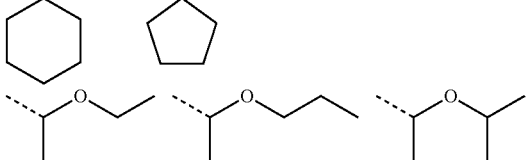
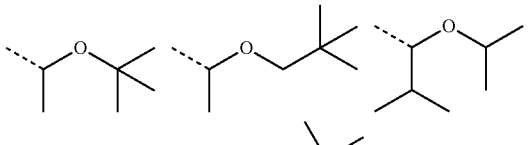
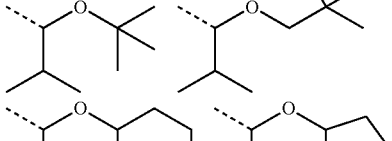
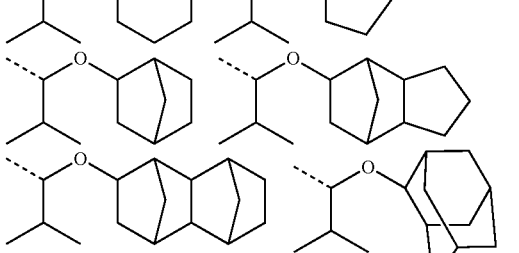
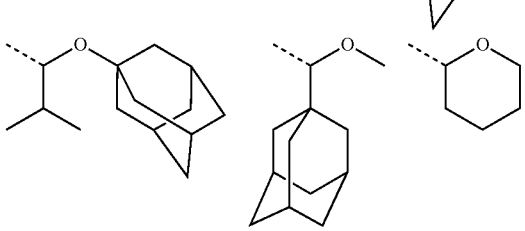

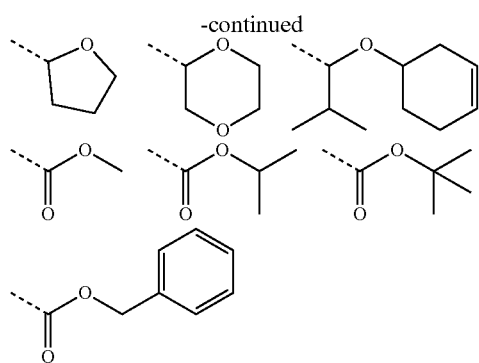
Of the acid labile groups R⁵², alkoxymethyl groups having the formula (d2) are preferred.
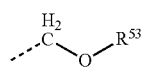  (d2)
Herein $R^{53}$ is a $C_1$-$C_{15}$ monovalent hydrocarbon group.
Examples of the acid labile group having formula (d2) are shown below, but not limited thereto.
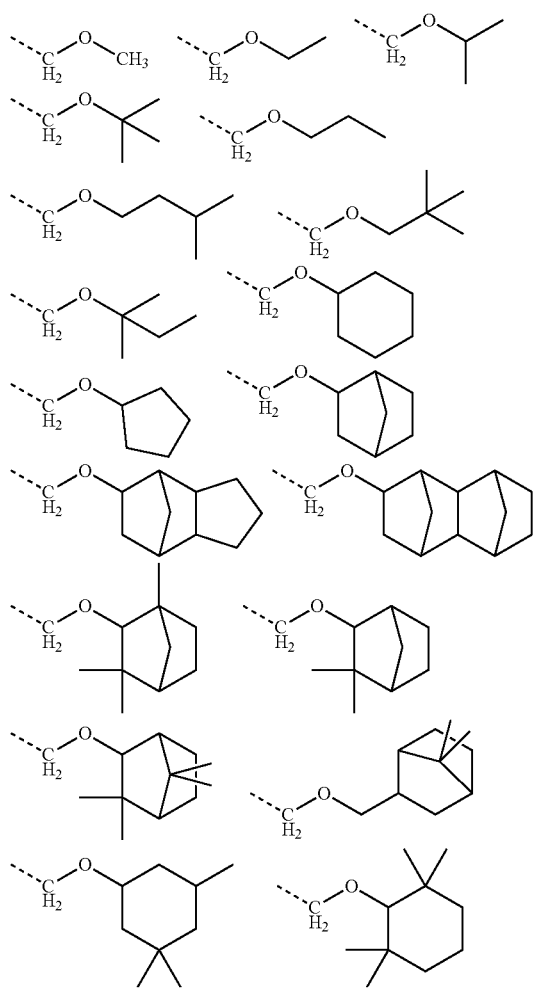
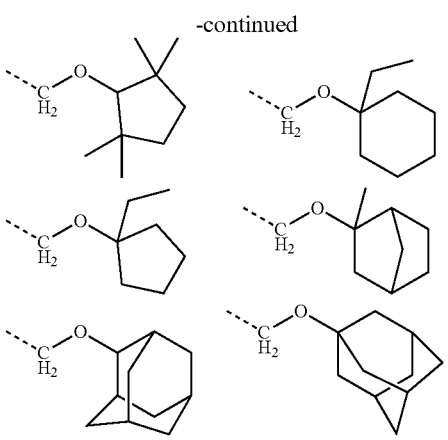
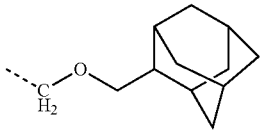
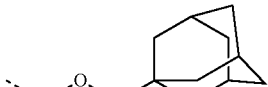
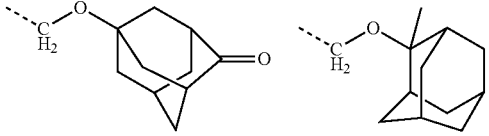
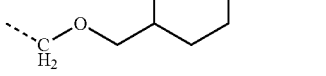
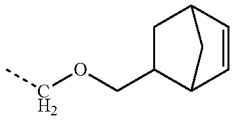
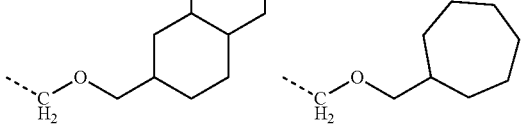
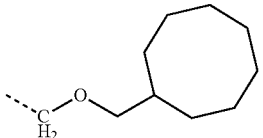
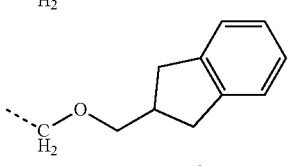
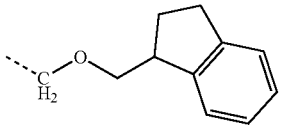

-continued

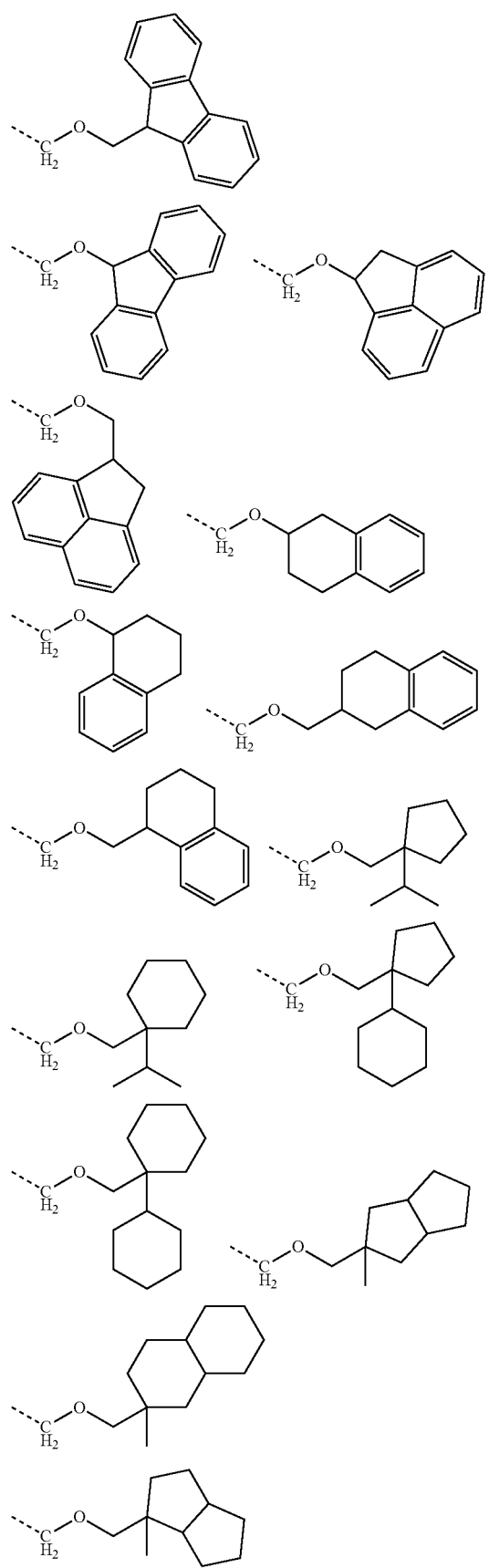

-continued

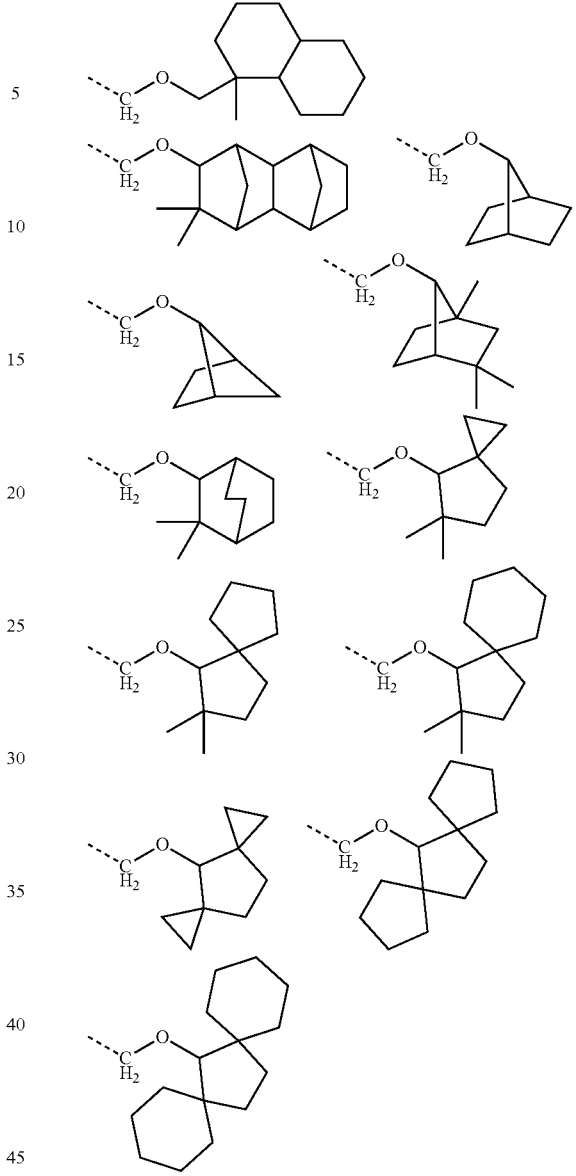

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo [$6.2.1.1^{3,6}.0^{2,7}$]dodecene derivatives, and unsaturated acid anhydrides such as itaconic anhydride.

The polymer preferably has a weight average molecular weight (Mw) of 1,000 to 500,000, and more preferably 3,000 to 100,000, as measured versus polystyrene standards by gel permeation chromatography (GPC) using tetrahydrofuran (THF) as solvent. The above range of Mw ensures satisfactory etch resistance and eliminates the risk of resolution being reduced due to difficulty to gain a dissolution rate difference before and after exposure.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the polymer should preferably have a narrow dispersity (Mw/Mn) of 1.0 to 2.0 in order to provide a resist composition suitable for micropatterning to a small feature size.

The method of synthesizing the polymer is, for example, by dissolving one or more unsaturated bond-bearing monomers in an organic solvent, adding a radical initiator, and heating for polymerization. Examples of the organic solvent which can be used for polymerization include toluene, benzene, THF, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C. The reaction time is preferably 2 to 100 hours, more preferably 5 to 20 hours. The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:
(I) 1 to 60 mol %, more preferably 5 to 50 mol %, even more preferably 10 to 50 mol % of recurring units of at least one type having formula (a1) or (a2),
(II) 40 to 99 mol %, more preferably 50 to 95 mol %, even more preferably 50 to 90 mol % of recurring units of at least one type having formula (b1) or (b2), and optionally,
(III) 0 to 30 mol %, more preferably 0 to 20 mol %, and even more preferably 0 to 10 mol % of recurring units of at least one type selected from formulae (c1) to (c3), and optionally,
(IV) 0 to 80 mol %, more preferably 0 to 70 mol %, and even more preferably 0 to 50 mol % of recurring units of at least one type derived from another monomer(s).

The polymers may be used as the base resin (B) alone or in a combination of two or more polymers which are different in compositional ratio, Mw and/or Mw/Mn. In addition to the foregoing polymer, the base resin (B) may contain a hydrogenated ROMP polymer as described in JP-A 2003-066612.

(C) Organic Solvent

Any organic solvent may be used as long as the foregoing components and other additives are soluble therein. Examples of the organic solvent are described in JP-A 2008-111103, paragraphs [0144]-[0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use DAA, 1-ethoxy-2-propanol, PGMEA, cyclohexanone, GBL, and mixtures thereof because the PAG (A) is most soluble therein.

An appropriate amount of the organic solvent used is 200 to 5,000 parts, more preferably 400 to 3,000 parts by weight per 80 parts by weight of the base resin (B).

(D) Other Photoacid Generator

The chemically amplified resist composition may comprise (D) a photoacid generator other than component (A). The other photoacid generator is not particularly limited as long as it is capable of generating an acid upon exposure to high-energy radiation. The preferred other photoacid generator is a salt having the formula (1).

In formula (1), $R^{101}$, $R^{102}$ and $R^{103}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic and examples thereof areas exemplified above in conjunction with formula (c4). Examples of the cation in the sulfonium salt of formula (1) are as exemplified above for the sulfonium cation having formula (c4).

In formula (1), $X^-$ is an anion selected from the formulae (1A) to (1D).

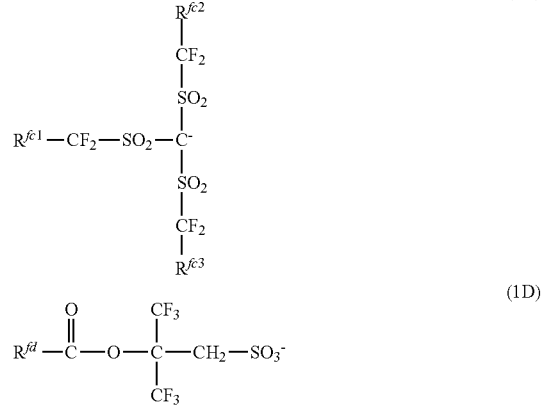

In formula (1A), $R^{fa}$ is fluorine or a $C_1$-$C_{40}$ monovalent hydrocarbon group which may contain a heteroatom. The monovalent hydrocarbon group may be straight, branched or cyclic and examples thereof are as will be exemplified later for $R^{112}$ in formula (1A').

Of the anions having formula (1A), a structure having the formula (1A') is preferred.

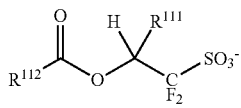
(1A')

In formula (1A'), $R^{111}$ is hydrogen or trifluoromethyl, preferably trifluoromethyl.

$R^{112}$ is a $C_1$-$C_{38}$ monovalent hydrocarbon group which may contain a heteroatom.

Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. The monovalent hydrocarbon group may be straight, branched or cyclic. Examples include methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

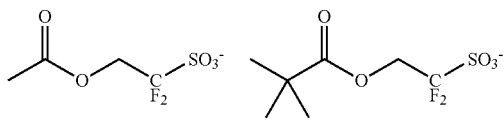

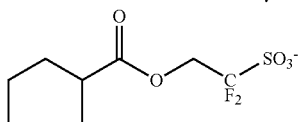

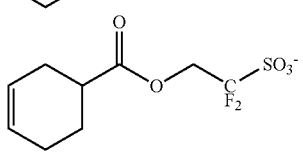

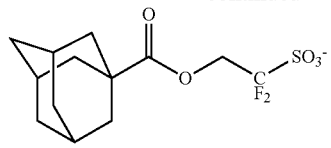

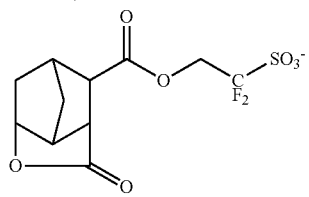

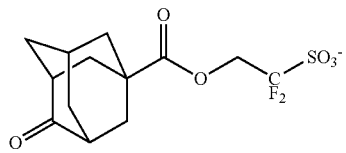

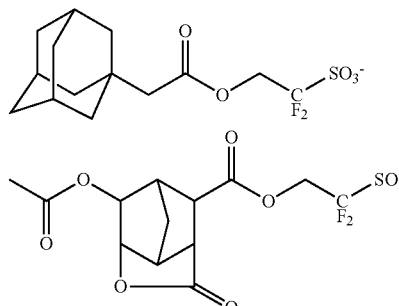

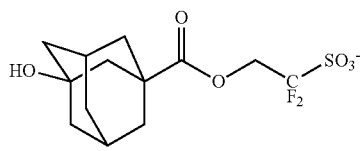

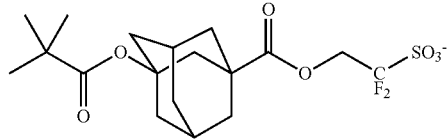

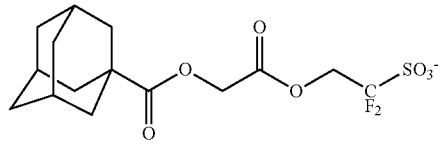

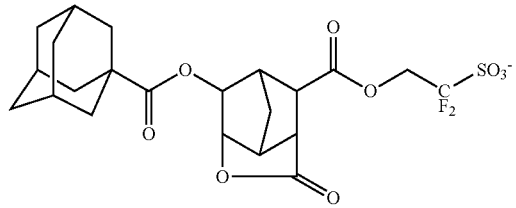

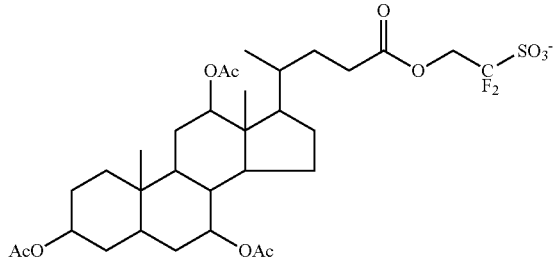

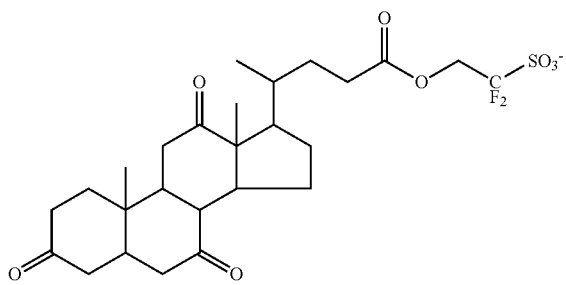
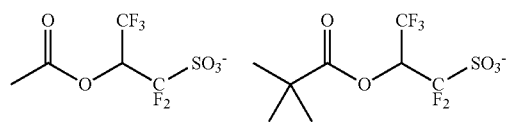
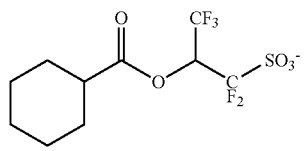
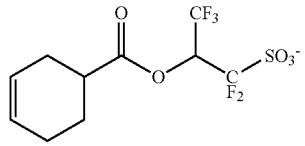
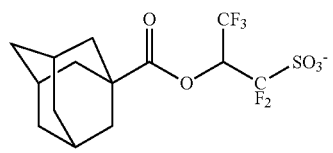
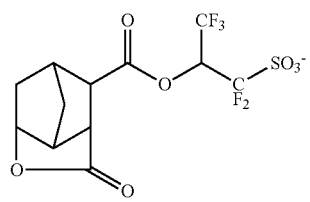
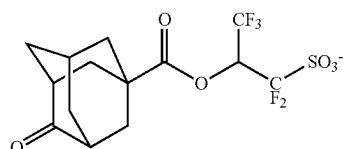
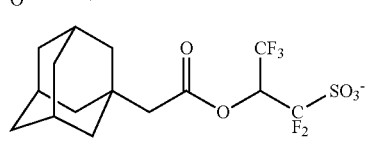
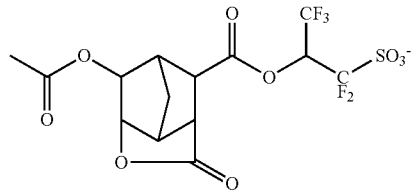
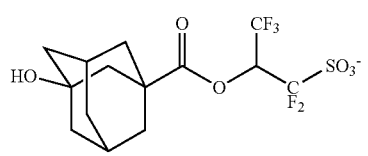
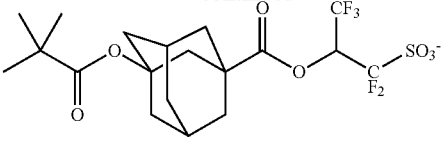
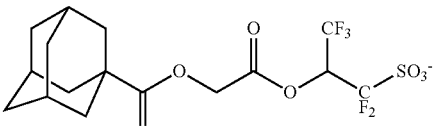
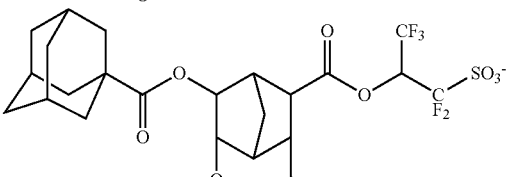
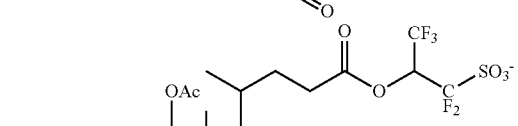
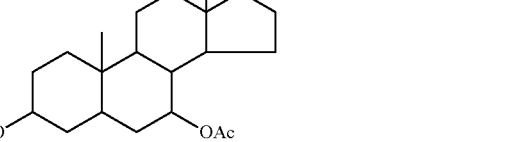
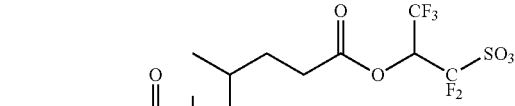
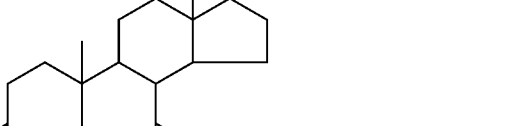
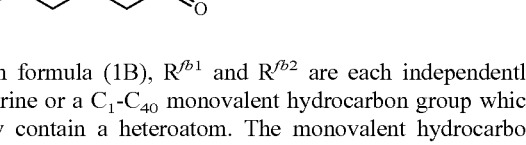

In formula (1B), $R^{fb1}$ and $R^{fb2}$ are each independently fluorine or a $C_1$-$C_{40}$ monovalent hydrocarbon group which may contain a heteroatom. The monovalent hydrocarbon groups may be straight, branched or cyclic, and examples thereof are as exemplified above for $R^{112}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic, and examples thereof are as exemplified above for $R^{112}$. Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group.

In formula (1D), $R^{fd}$ is a $C_1$-$C_{40}$ monovalent hydrocarbon group which may contain a heteroatom. The monovalent hydrocarbon group may be straight, branched or cyclic, and examples thereof are as exemplified above for $R^{112}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

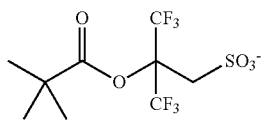

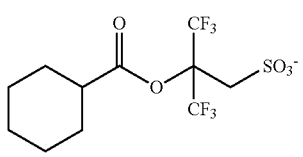

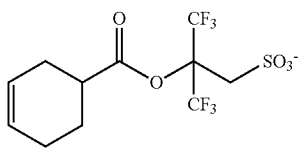

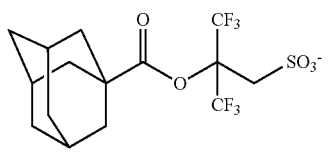

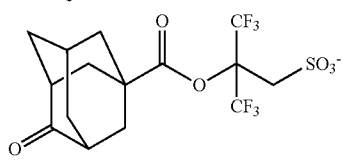

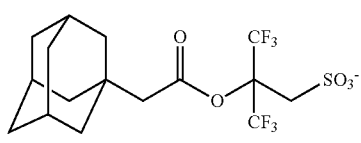

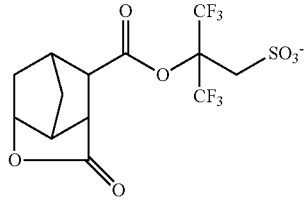

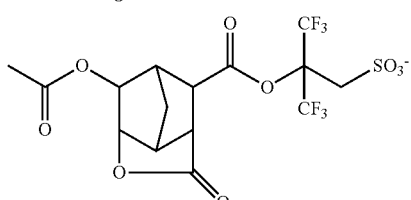

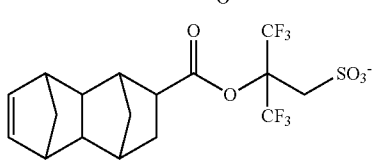

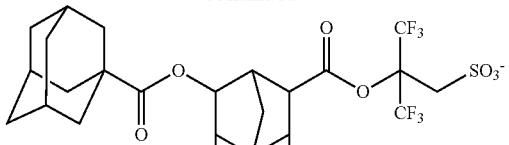

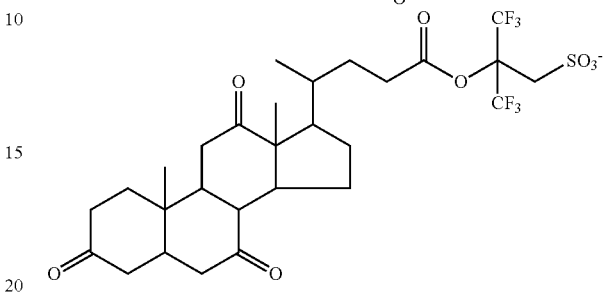

The compound having the anion of formula (1D) has a sufficient acid strength to cleave acid labile groups in the resist polymer because it is free of fluorine at α-position of sulfo group, but has two trifluoromethyl groups at β-position. Thus the compound is a useful PAG.

Further, compounds having the formula (2) are also useful as the PAG (D).

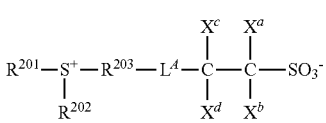

(2)

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond or ether bond, or a $C_1$-$C_{20}$ divalent hydrocarbon group which may contain a heteroatom. $X^a$, $X^b$, $X^c$ and $X^d$ are each independently hydrogen, fluorine or trifluoromethyl, with the proviso that at least one of $X^a$, $X^b$, $X^c$ and $X^d$ is fluorine or trifluoromethyl.

The monovalent hydrocarbon groups represented by $R^{201}$ and $R^{202}$ may be straight, branched or cyclic, and examples thereof include methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl, and anthracenyl. Also included are the foregoing groups in which some hydrogen is substituted by a moiety containing a heteroatom such as oxygen, sulfur, nitrogen or halogen, or in which a moiety containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

The divalent hydrocarbon groups represented by $R^{203}$ include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; arylene groups such as cyclopentanediyl, cyclohexanediyl, norbornanediyl, and adamantanediyl; and divalent unsaturated cyclic hydrocarbon groups such as phenylene and naphthylene. Also included are the foregoing groups in which some hydrogen is substituted by an alkyl group such as methyl, ethyl, propyl, n-butyl or tert-butyl, or in which some hydrogen is substituted by a moiety containing a heteroatom such as oxygen, sulfur, nitrogen or halogen, or in which a moiety containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety. The preferred heteroatom is oxygen.

Of the PAGs having formula (2), those compounds having formula (2') are preferred.

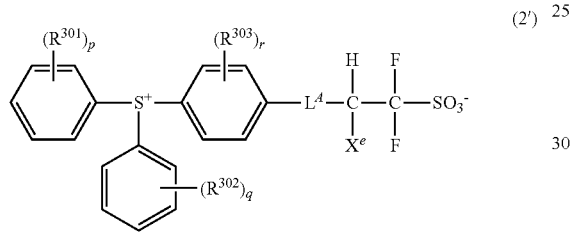

(2')

In formula (2'), $L^A$ is as defined above. $X^e$ is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon group may be straight, branched or cyclic, and examples thereof are as exemplified above for $R^{112}$. The subscripts p and q each are an integer of 0 to 5, and r is an integer of 0 to 4.

Examples of the PAG having formula (2) are shown below, but not limited thereto. Herein $X^e$ is as defined above.

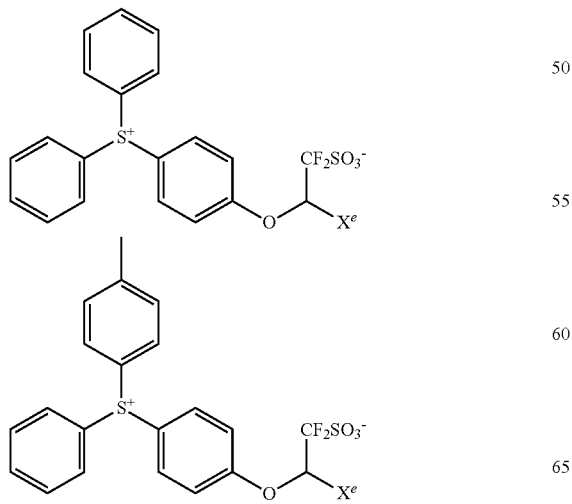

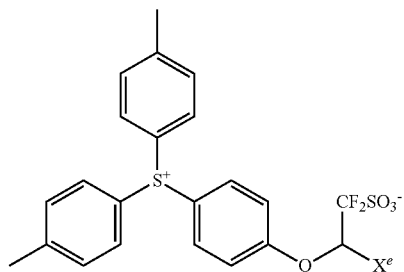

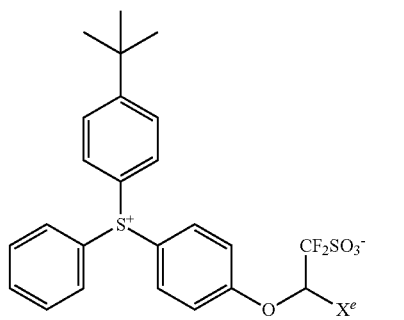

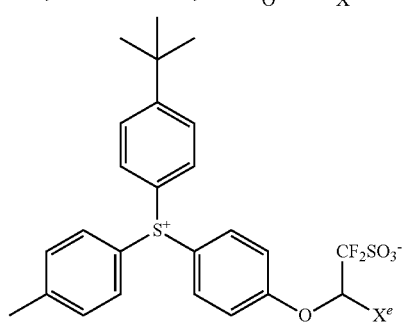

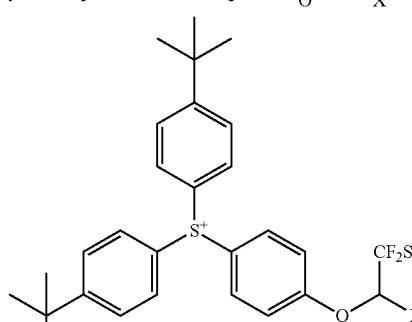

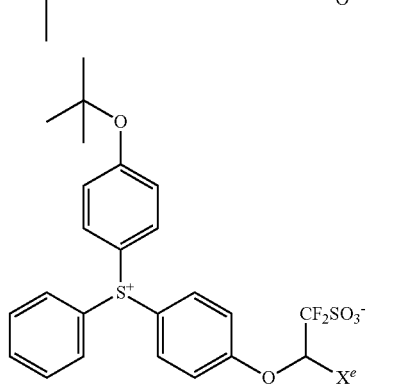

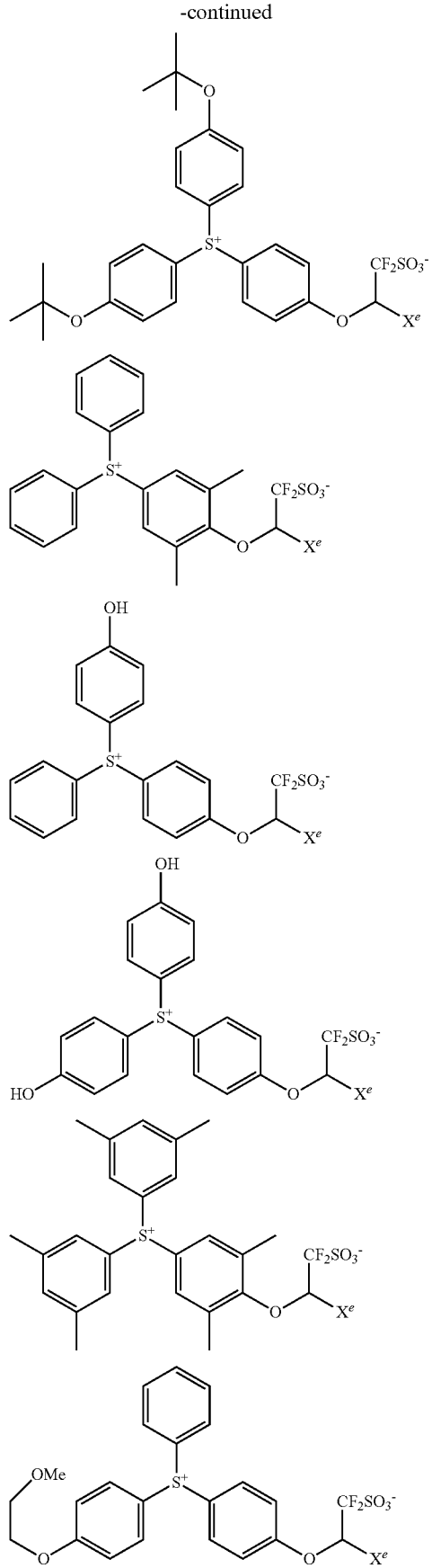
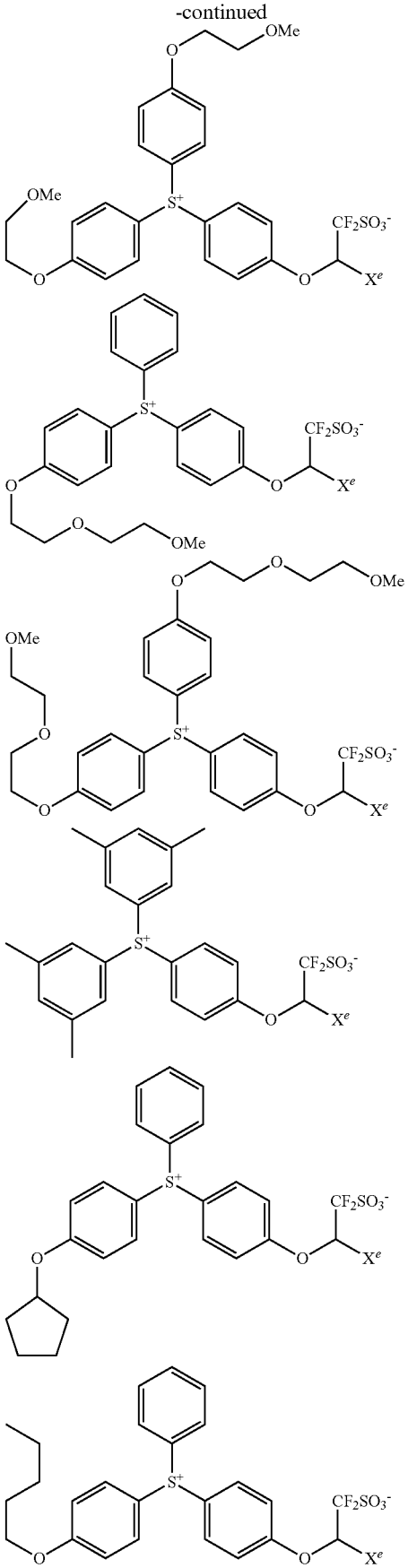

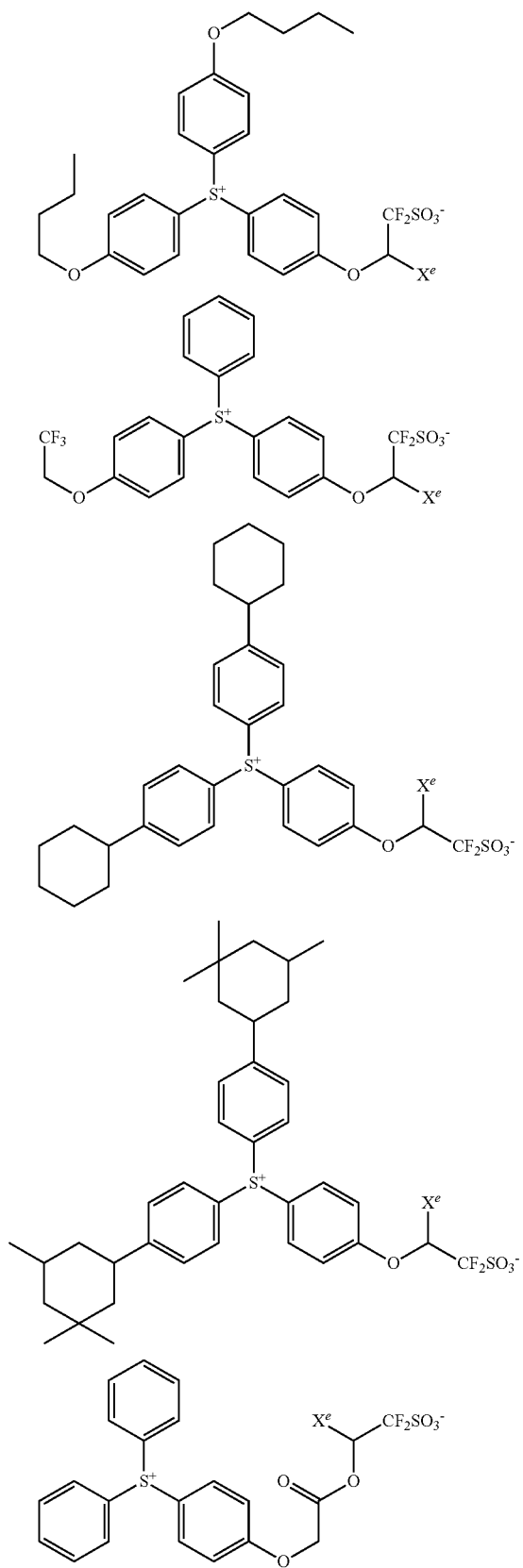
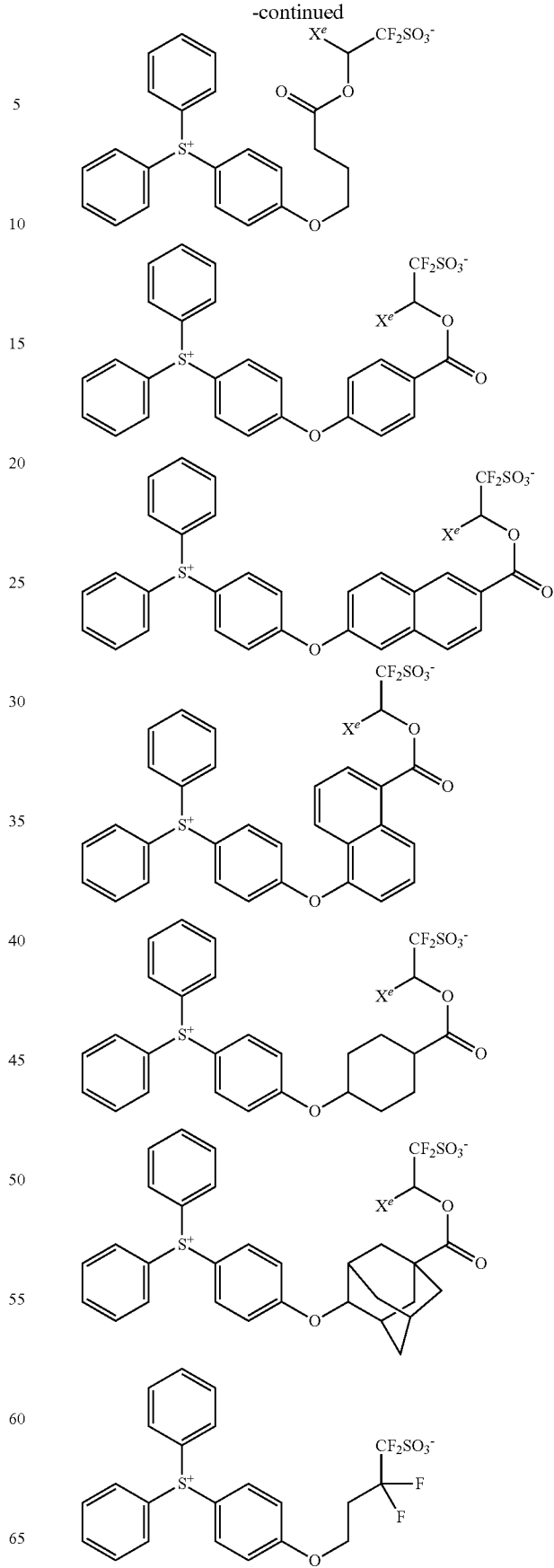

-continued

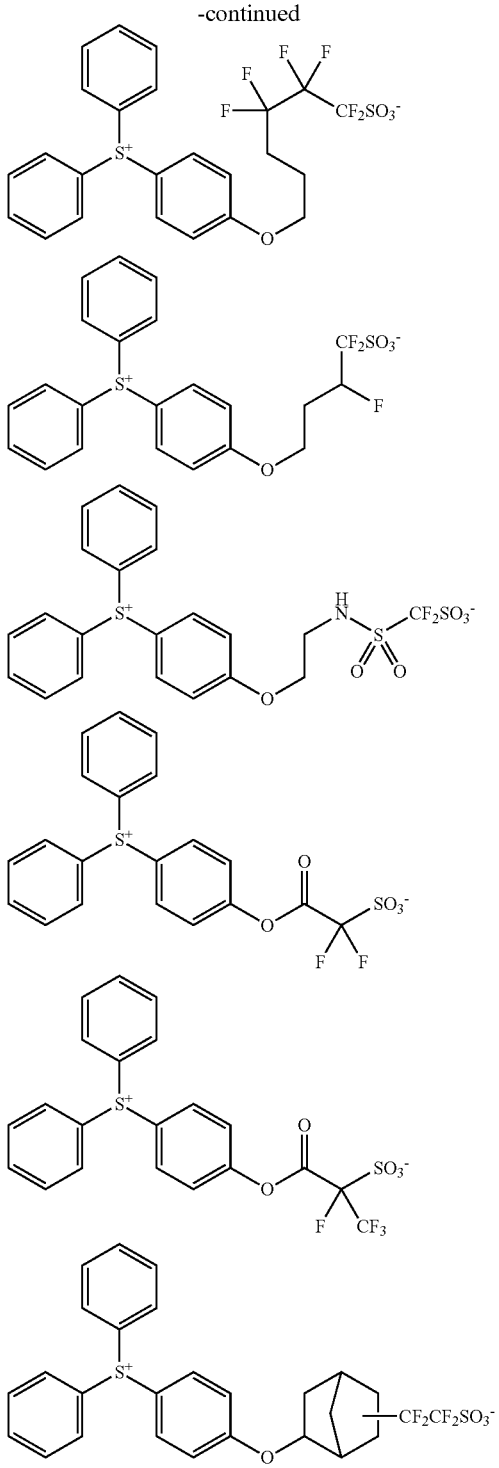

Of the other PAGs, those compounds having an anion of formula (1A') or (1D) are especially preferred because of reduced acid diffusion and high solubility in resist solvent, and those compounds having an anion of formula (2') are especially preferred because of minimized acid diffusion.

When the resist composition contains the other PAG (D), an appropriate amount of the PAG added is 0.1 to 40 parts, more preferably 0.5 to 20 parts by weight per 80 parts by weight of the base resin (B). As long as the amount of component (D) is in the range, good resolution is achievable and the risk of foreign particles being formed after development or during stripping of resist film is avoided. The other PAG may be used alone or in admixture as component (D).

(E) Quencher

The chemically amplified resist composition may further include (E) a quencher or acid diffusion controlling agent. As used herein, the "quencher" refers to a compound capable of trapping the acid generated by the PAG in the resist film to prevent the acid from diffusing to the unexposed region thereof, for thereby forming the desired pattern.

Typical of the quencher (E) are onium salts having the formulae (3) and (4).

In formula (3), $R^{q1}$ is hydrogen or a $C_1$-$C_{40}$ monovalent hydrocarbon group which may contain a heteroatom, exclusive of the group wherein hydrogen bonded to the carbon atom at α-position relative to the sulfo group is substituted by fluorine or fluoroalkyl. In formula (4), $R^{q2}$ is hydrogen or a $C_1$-$C_{40}$ monovalent hydrocarbon group which may contain a heteroatom. The monovalent hydrocarbon group may be straight, branched or cyclic and examples thereof are as exemplified above for $R^{112}$ in formula (1A').

Examples of the monovalent hydrocarbon group $R^{q1}$ include methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl, and anthracenyl.

In these groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

Examples of the monovalent hydrocarbon group $R^{q2}$ include fluoroalkyl groups such as trifluoromethyl and trifluoroethyl and fluoroaryl groups such as pentafluorophenyl and 4-trifluoromethylphenyl as well as the substituents exemplified above for $R^{q1}$.

Examples of the anion in the onium salt having formula (3) are shown below, but not limited thereto.

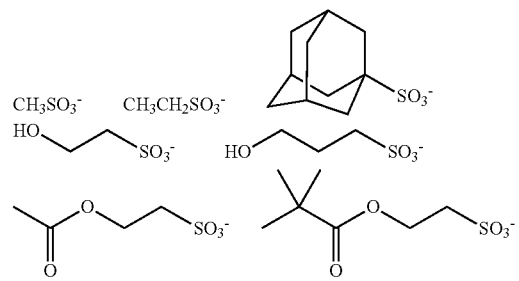

235
-continued
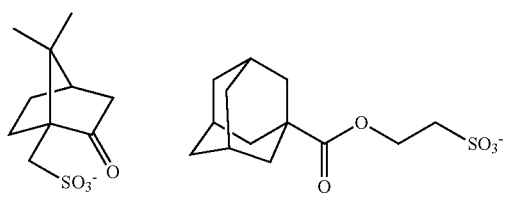
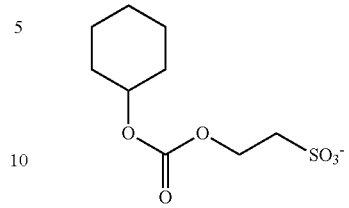
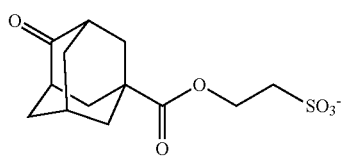
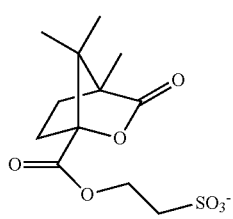
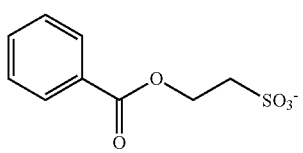
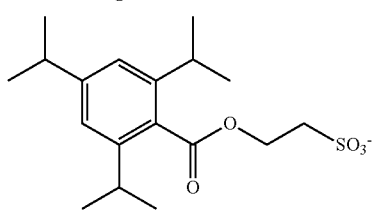
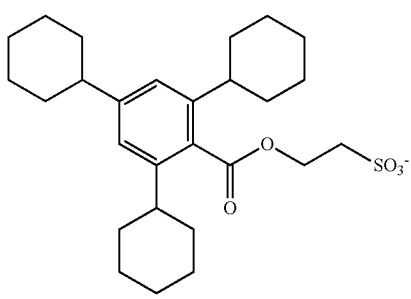
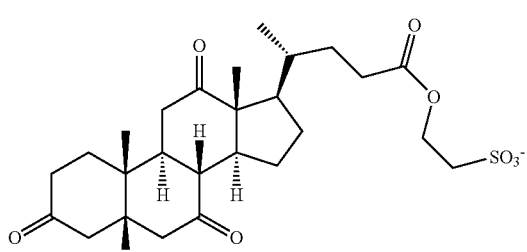
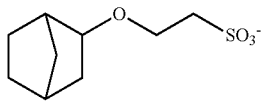
236
-continued
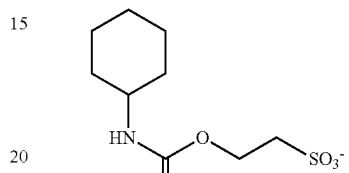
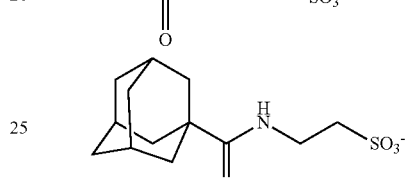
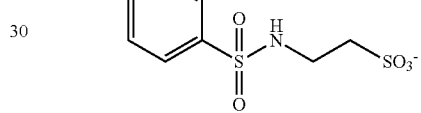
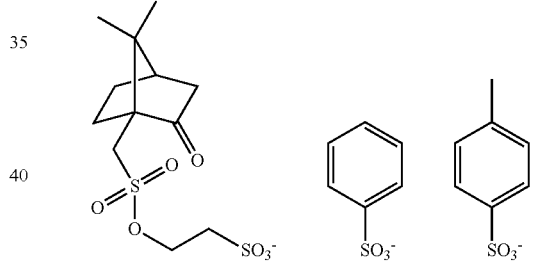
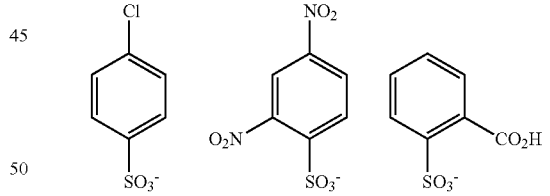
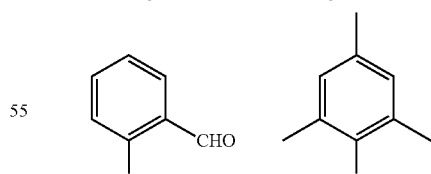
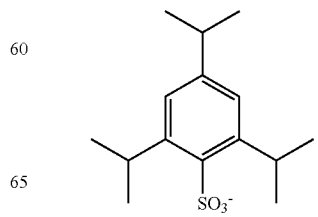

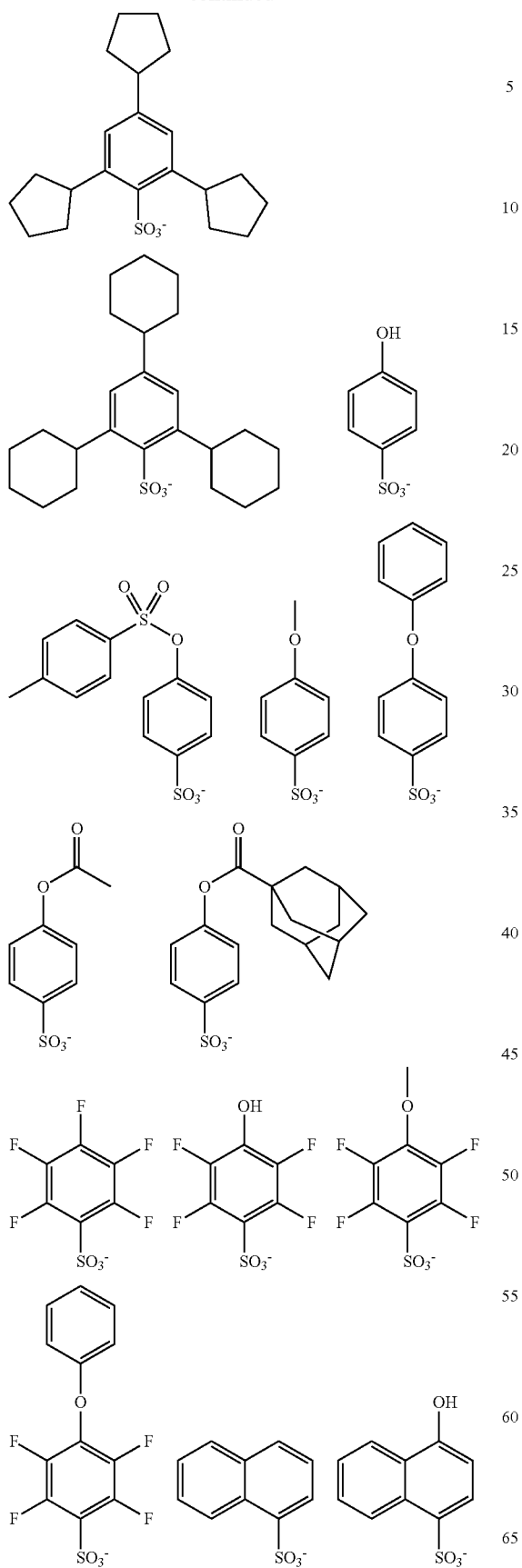
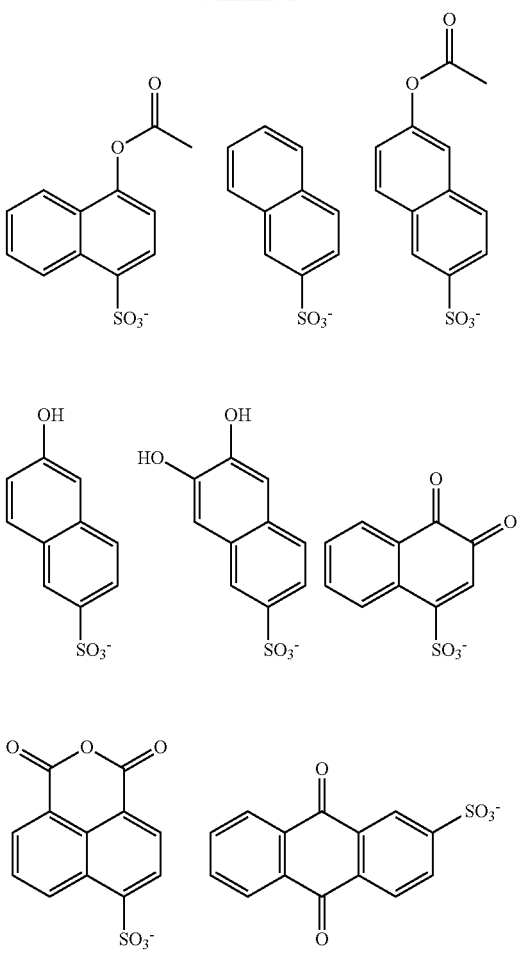
Examples of the anion in the onium salt having formula (4) are shown below, but not limited thereto.
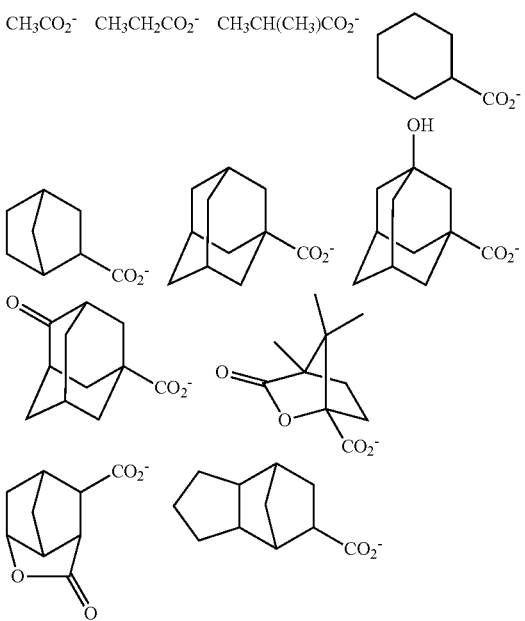

-continued

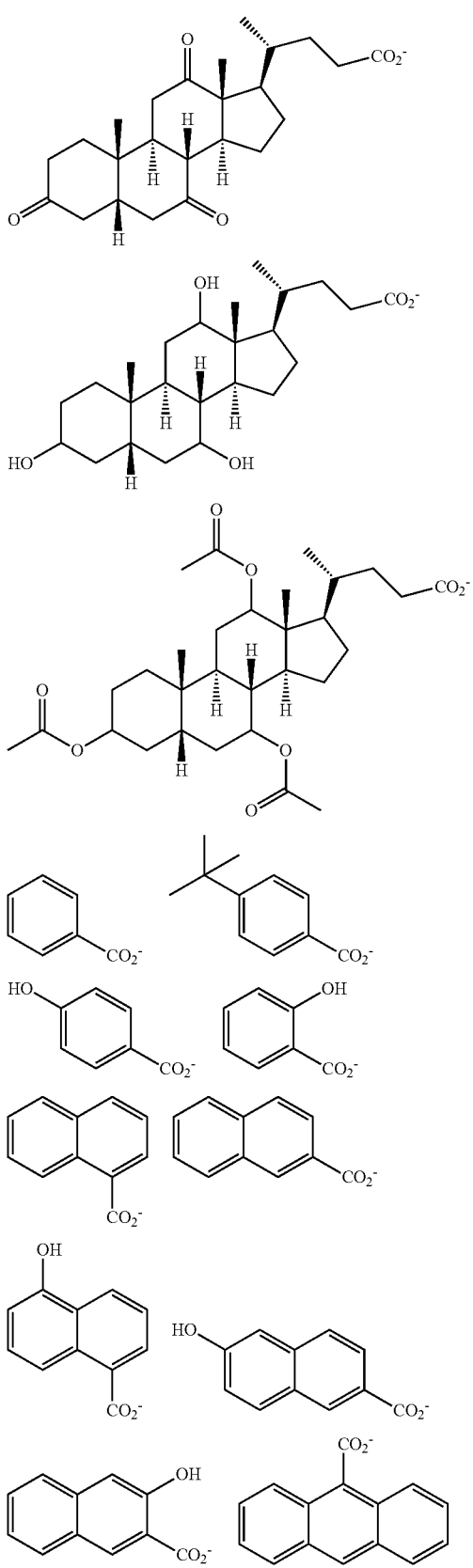

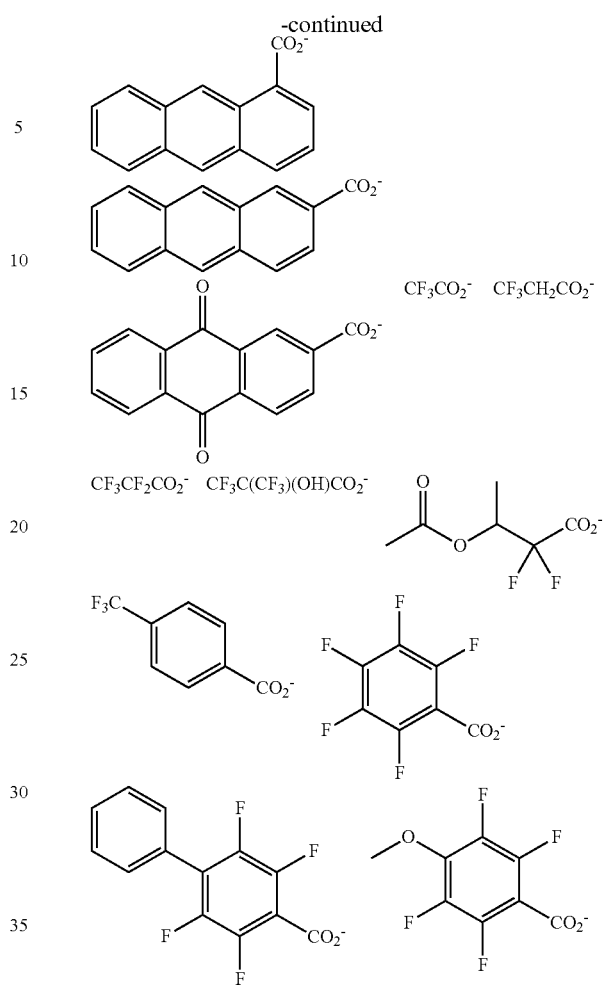

In formulae (3) and (4), $Mq^+$ is an onium cation, which is preferably selected from cations having the formulae (5a), (5b) and (5c).

 (5a)

 (5b)

 (5c)

In formulae (5a) to (5c), $R^{q11}$ to $R^{q19}$ are each independently a $C_1$-$C_{40}$ monovalent hydrocarbon group which may contain a heteroatom. A pair of $R^{q11}$ and $R^{q12}$ may bond together to form a ring with the sulfur atom to which they are attached. A pair of $R^{q16}$ and $R^{q17}$ may bond together to form a ring with the nitrogen atom to which they are attached. Examples of the monovalent hydrocarbon group are as exemplified above for $R^{q1}$ in formula (3).

Examples of the onium cation represented by $Mq^+$ are shown below, but not limited thereto.

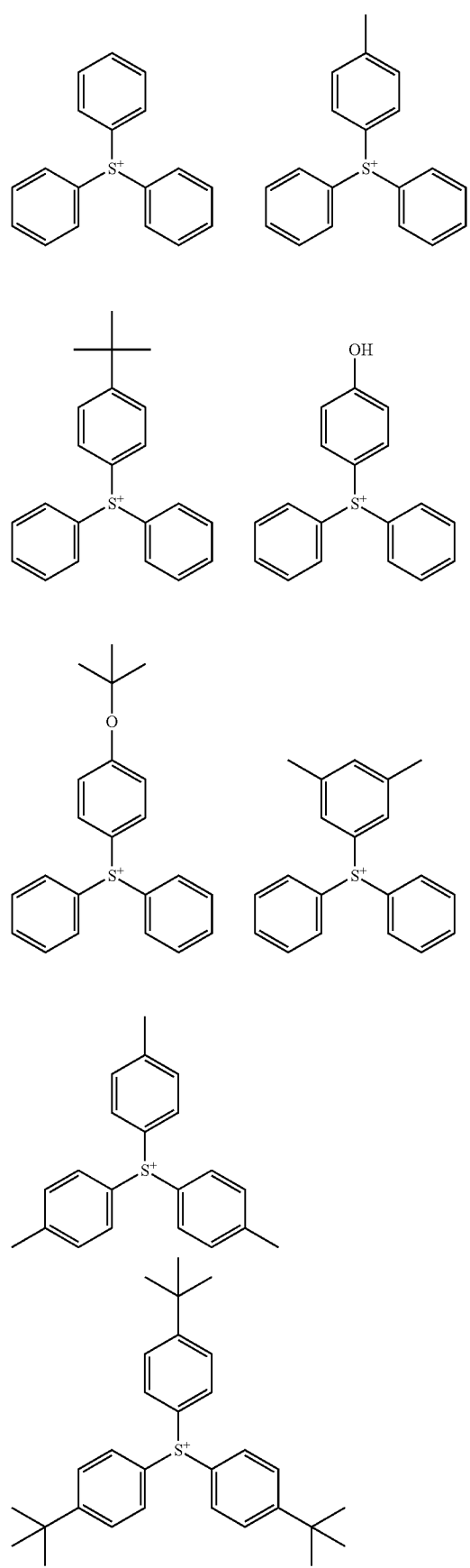
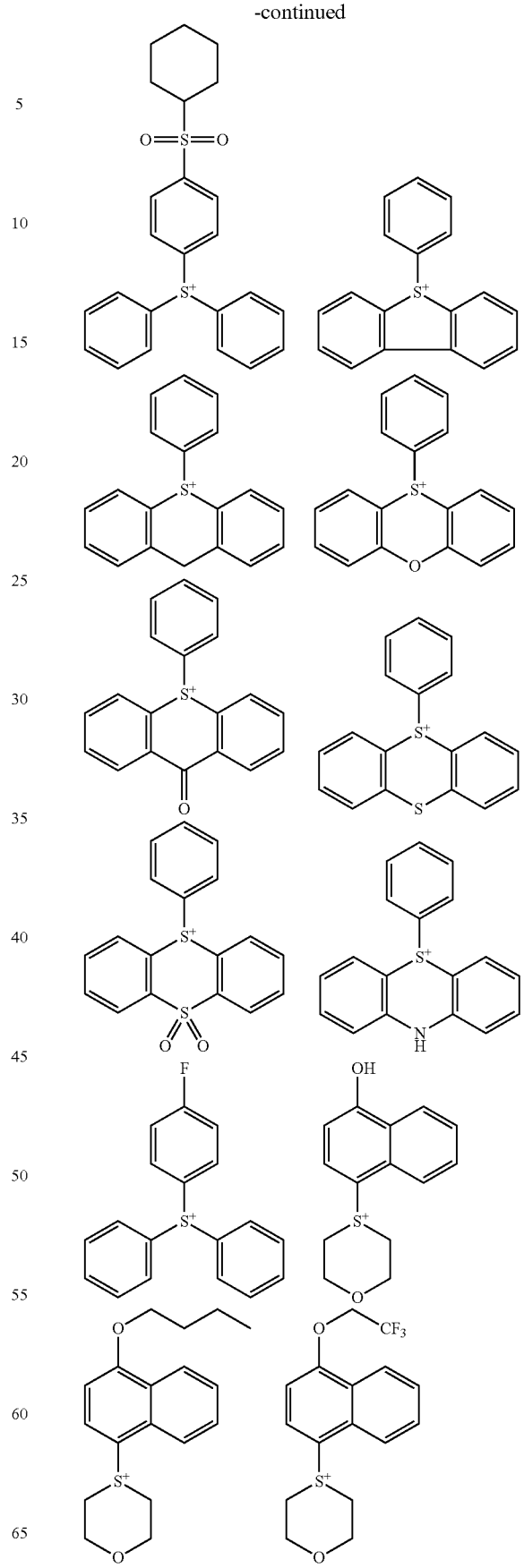

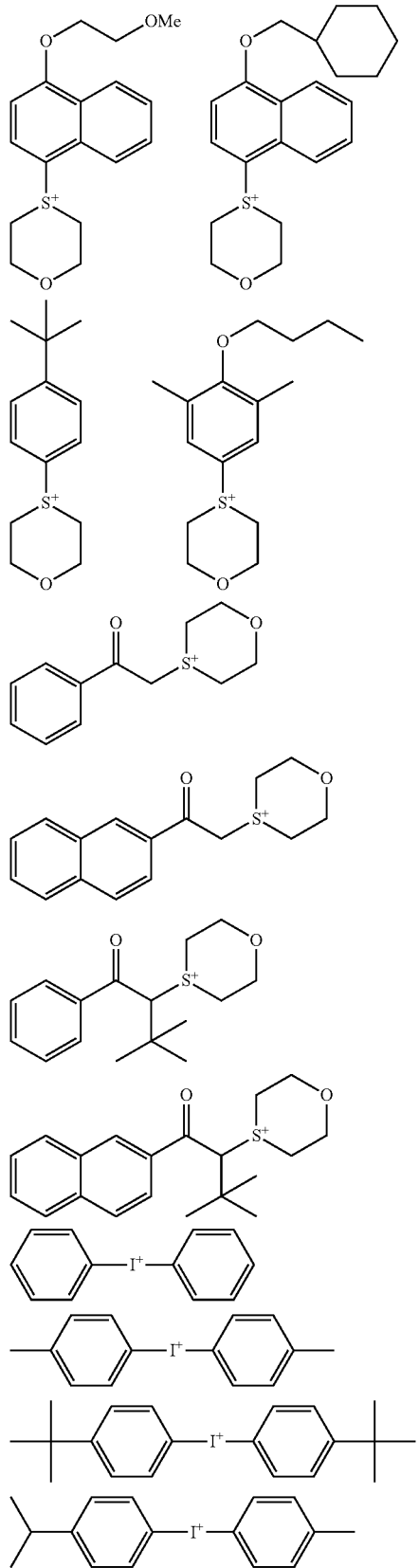

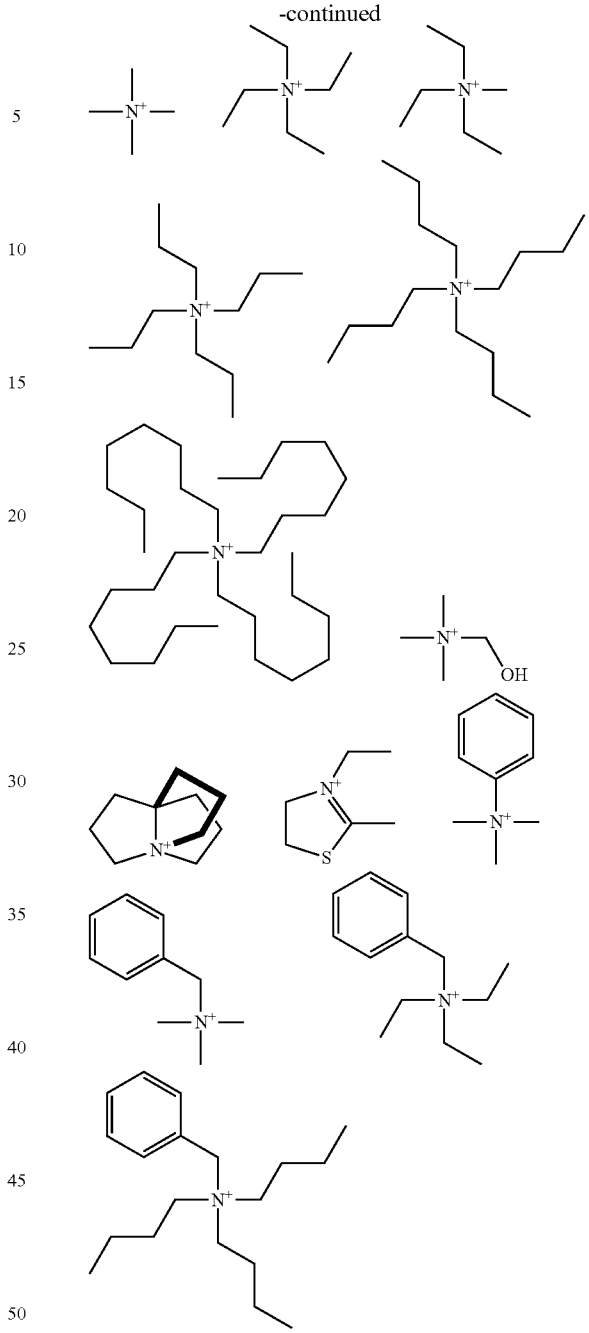

Examples of the onium salt having formula (3) or (4) include arbitrary combinations of anions with cations, both as exemplified above. These onium salts may be readily obtained from ion exchange reaction using any well-known organic chemistry technique. For the ion exchange reaction, reference may be made to JP-A 2007-145797, for example.

The onium salt having formula (3) or (4) functions as a quencher in the chemically amplified resist composition because the counter anion of the onium salt is a conjugated base of a weak acid. As used herein, the weak acid indicates an acidity insufficient to deprotect an acid labile group from an acid labile group-containing unit in the base resin. The onium salt having formula (3) or (4) functions as a quencher when used in combination with an onium salt type PAG having a conjugated base of a strong acid (typically a sulfonic acid which is fluorinated at α-position) as the counter anion. In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

When the onium salt having formula (3) or (4) is used as the quencher (E), the amount of the onium salt used is preferably 0.1 to 10 parts by weight, more preferably 0.1 to 5 parts by weight per 80 parts by weight of the base resin (B). As long as the amount of component (E) is in the range, a satisfactory resolution is available without a substantial lowering of sensitivity. The onium salt having formula (3) or (4) may be used alone or in admixture.

Also nitrogen-containing compounds may be used as the quencher (E). Suitable nitrogen-containing compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146]-[0164] (U.S. Pat. No. 7,537,880), and primary or secondary amine compounds protected with a carbamate group, as described in JP 3790649.

A sulfonic acid sulfonium salt having a nitrogen-containing substituent may also be used as the nitrogen-containing compound. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and JP-A 2012-046501, for example.

When the nitrogen-containing compound is used as the quencher (E), the amount of the nitrogen-containing compound used is preferably 0.001 to 12 parts by weight, more preferably 0.01 to 8 parts by weight per 80 parts by weight of the base resin (B). The nitrogen-containing compound may be used alone or in admixture.

(F) Surfactant

The resist composition may further include (F) a surfactant which is insoluble or substantially insoluble in water and soluble in alkaline developer, and/or a surfactant (hydrophobic resin) which is insoluble or substantially insoluble in water and alkaline developer. For the surfactant, reference should be made to those compounds described in JP-A 2010-215608 and JP-A 2011-016746.

While many examples of the surfactant which is insoluble or substantially insoluble in water and alkaline developer are described in the patent documents cited herein, preferred examples are fluorochemical surfactants FC-4430 (3M), Olfine® E1004 (Nissin Chemical Co., Ltd.), Surflon® S-381, KH-20 and KH-30 (AGC Seimi Chemical Co., Ltd.). Partially fluorinated oxetane ring-opened polymers having the formula (surf-1) are also useful.

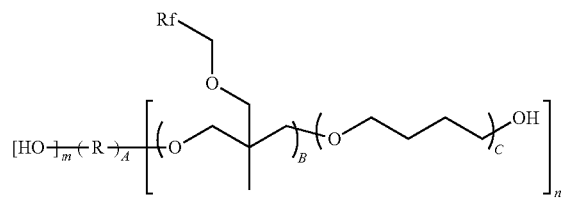

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

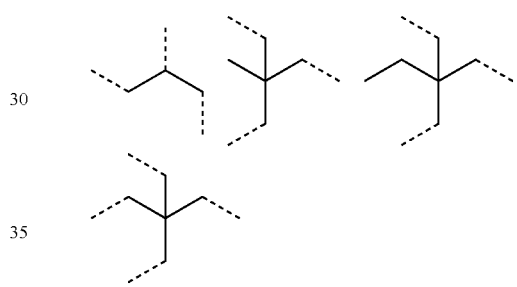

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing recurring units of at least one type selected from the formulae (6A) to (6E).

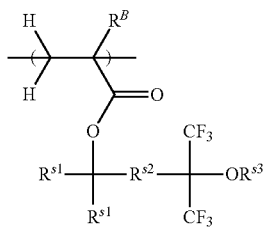
(6A)

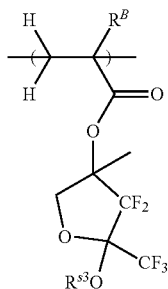
(6B)

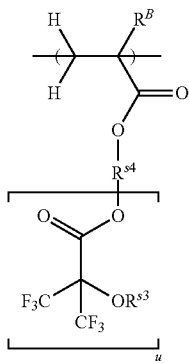
(6C)

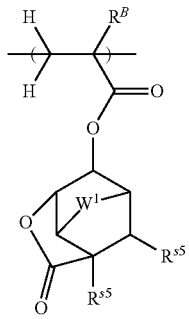
(6D)

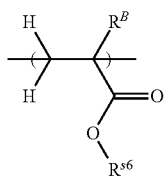
(6E)

Herein, $R^B$ is hydrogen, fluorine, methyl or trifluoromethyl. $W^1$ is —$CH_2$—, —$CH_2CH_2$— or —O—, or two separate —H. $R^{s1}$ is each independently hydrogen or a $C_1$-$C_{10}$ monovalent hydrocarbon group. $R^{s2}$ is a single bond or a $C_1$-$C_5$ straight or branched divalent hydrocarbon group. $R^{s3}$ is each independently hydrogen, a $C_1$-$C_{15}$ monovalent hydrocarbon or fluorinated hydrocarbon group, or an acid labile group. When $R^{s3}$ is a monovalent hydrocarbon or fluorinated hydrocarbon group, an ether bond (—O—) or carbonyl moiety (—C(=O)—) may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group having the formula: —C(=O)—O—$R^{sa}$ wherein $R^{sa}$ is a $C_1$-$C_{20}$ fluorinated hydrocarbon group. $R^{s6}$ is a $C_1$-$C_{15}$ monovalent hydrocarbon or fluorinated hydrocarbon group in which an ether bond (—O—) or carbonyl moiety (—C(=O)—) may intervene in a carbon-carbon bond.

The monovalent hydrocarbon group represented by $R^{s1}$ may be straight, branched or cyclic and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbomyl. Inter alia, $C_1$-$C_6$ hydrocarbon groups are preferred.

The divalent hydrocarbon group represented by $R^{s2}$ may be straight, branched or cyclic and examples thereof include methylene, ethylene, propylene, butylene, and pentylene.

The monovalent hydrocarbon group represented by $R^{s3}$ or $R^{s6}$ may be straight, branched or cyclic and examples thereof include alkyl, alkenyl, and alkynyl groups, with the alkyl groups being preferred. Suitable alkyl groups include those exemplified for the monovalent hydrocarbon group represented by $R^{s1}$ as well as n-undecyl, n-dodecyl, tridecyl, tetradecyl, and pentadecyl. Examples of the monovalent fluorinated hydrocarbon group represented by $R^{s3}$ or $R^{s6}$ include the foregoing monovalent hydrocarbon groups in which some or all carbon-bonded hydrogen atoms are substituted by fluorine atoms. In these groups, an ether bond (—O—) or carbonyl moiety (—C(=O)—) may intervene in a carbon-carbon bond as mentioned above.

Examples of the acid labile group represented by $R^{s3}$ include groups of the above formulae (L1) to (L4), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxo-containing alkyl groups.

The (u+1)-valent hydrocarbon or fluorinated hydrocarbon group represented by $R^{s4}$ may be straight, branched or cyclic and examples thereof include the foregoing monovalent hydrocarbon or fluorinated hydrocarbon groups from which the number (u) of hydrogen atoms are eliminated.

The fluorinated hydrocarbon group represented by $R^{sa}$ may be straight, branched or cyclic and examples thereof include the foregoing monovalent hydrocarbon groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the recurring units having formulae (6A) to (6E) are shown below, but not limited thereto. Herein $R^B$ is as defined above.
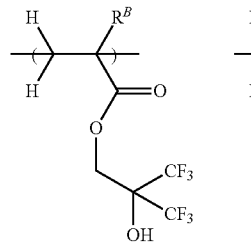
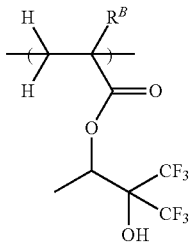
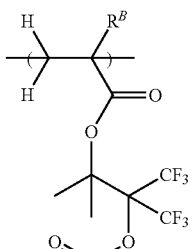
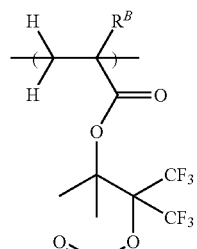
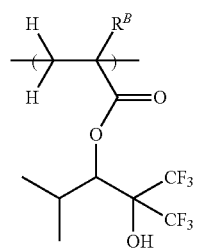
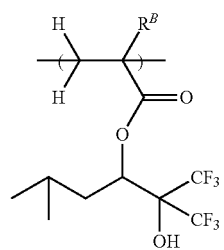
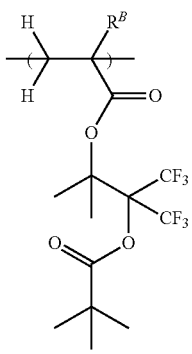
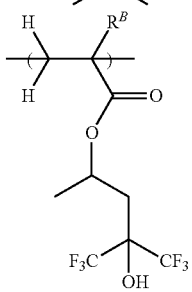
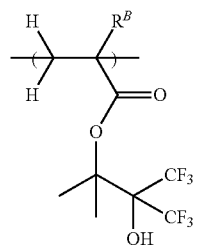
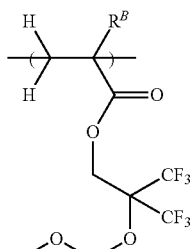
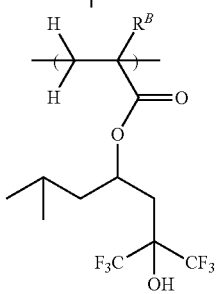
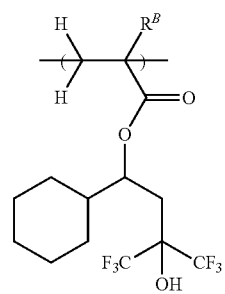
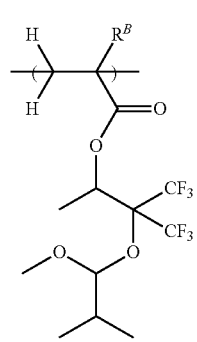
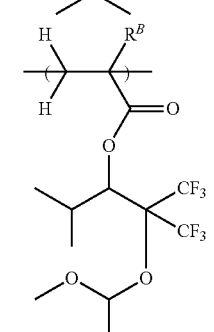
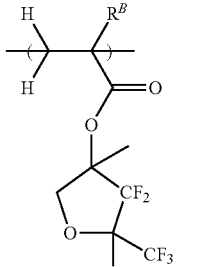
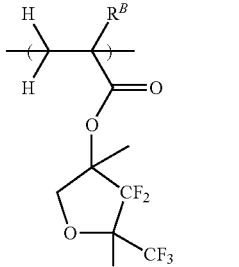
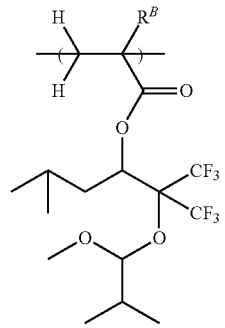
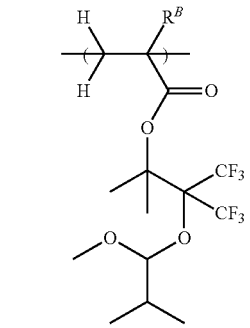
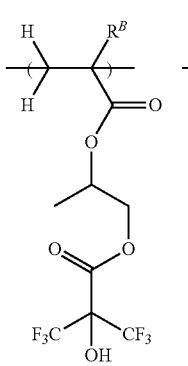
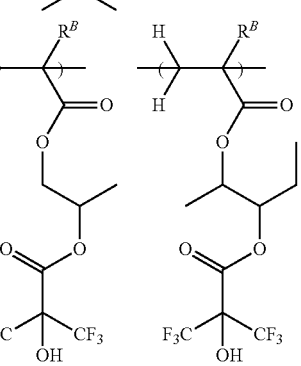

251
-continued
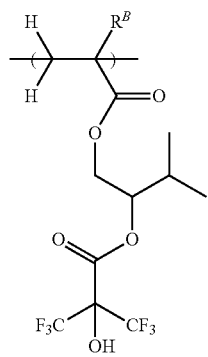 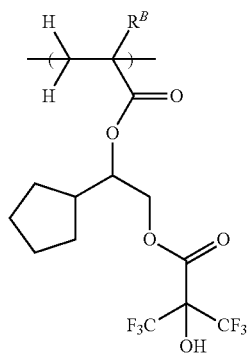
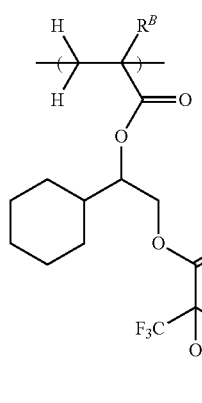 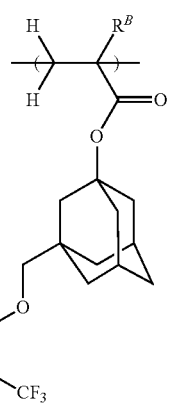
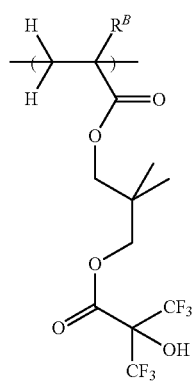 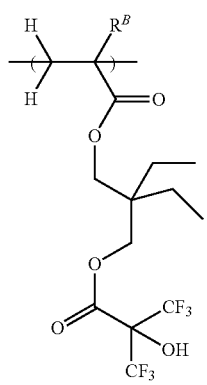
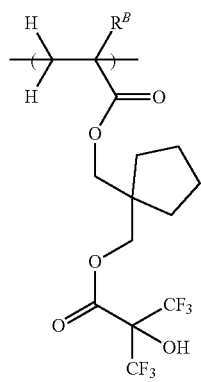
252
-continued
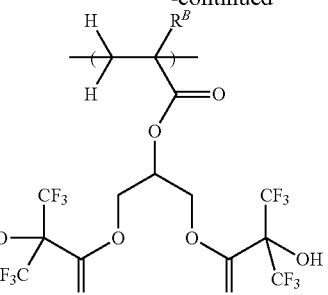
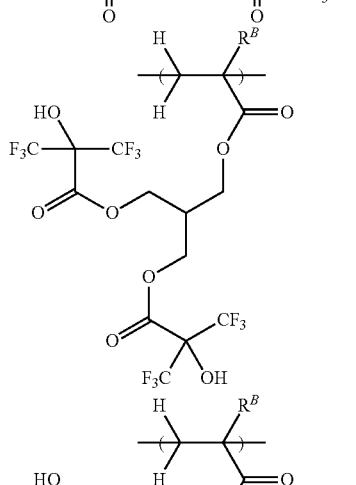
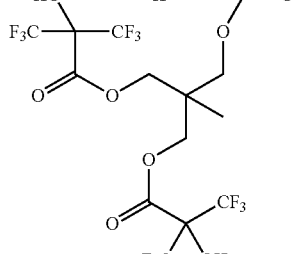
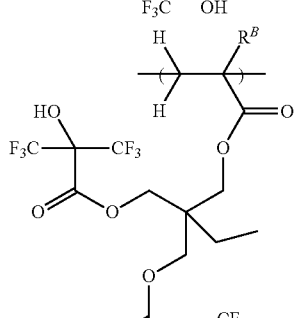
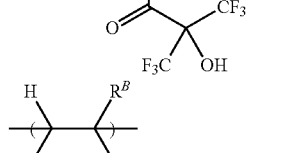
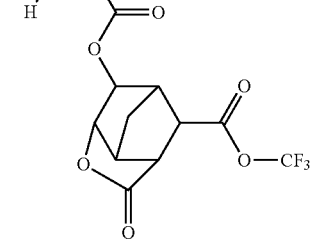

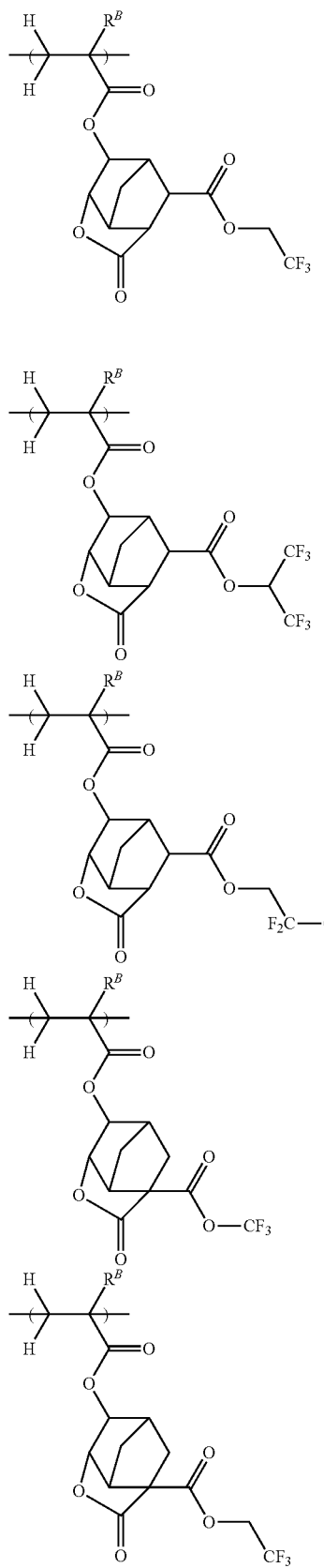
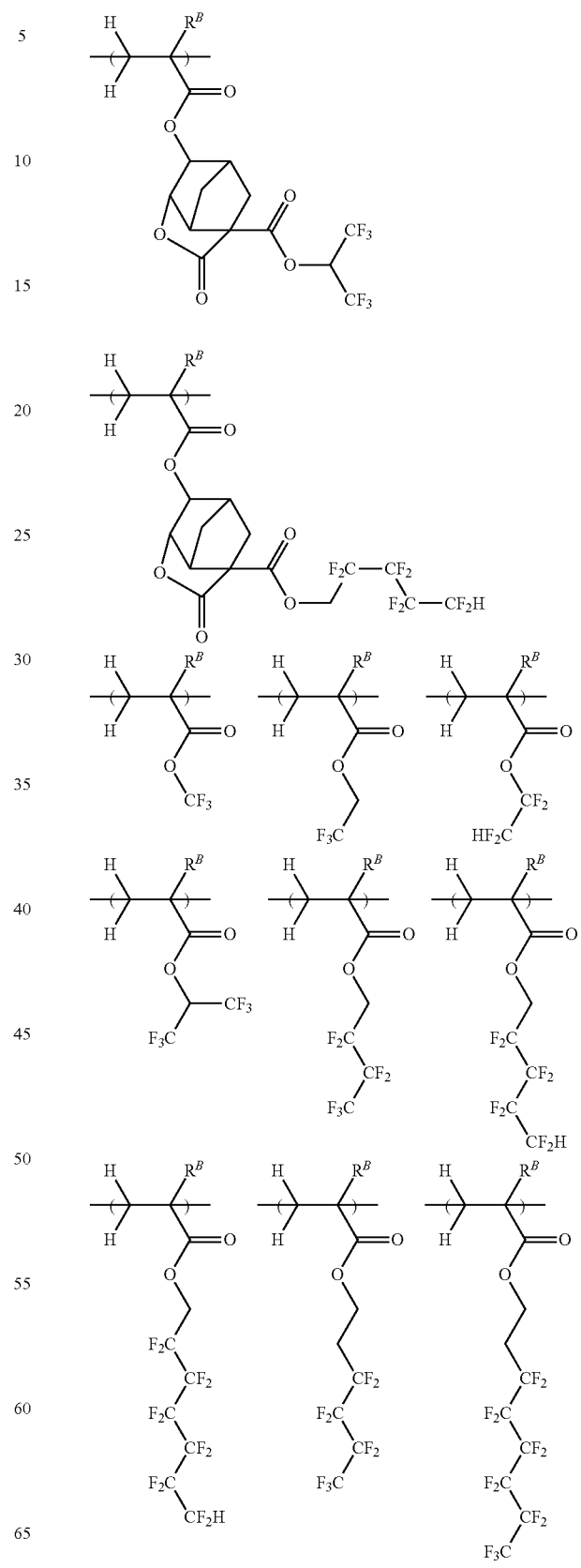

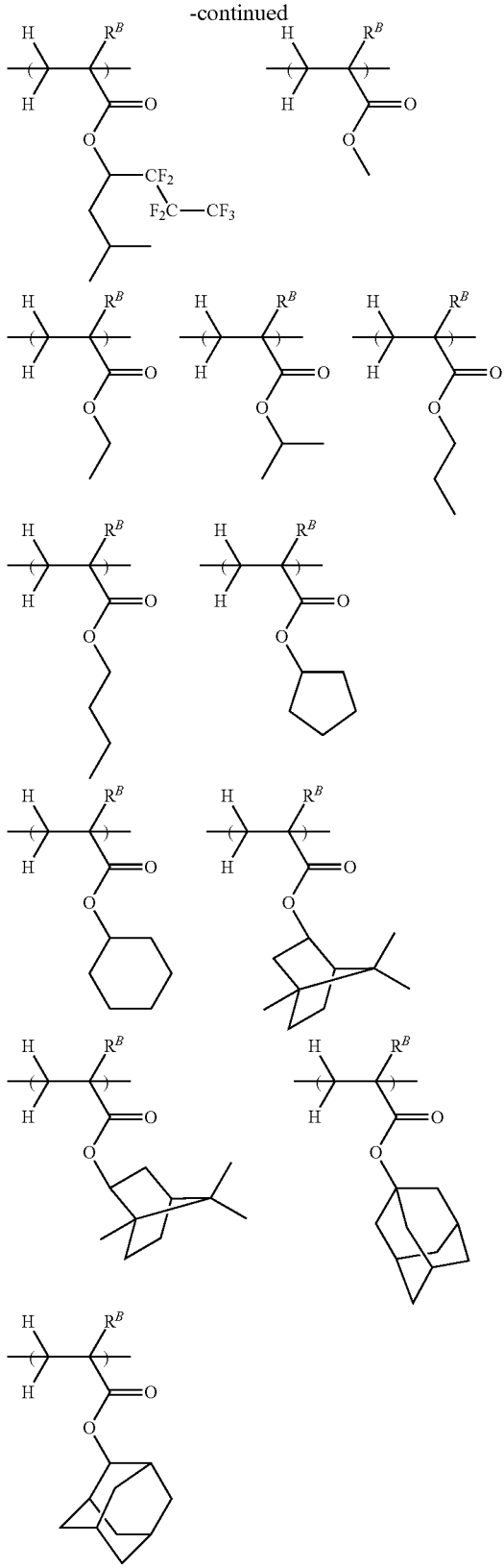

The polymeric surfactant may further contain recurring units other than the recurring units having formulae (6A) to (6E). Typical other recurring units are those derived from methacrylic acid and α-trifluoromethylacrylic acid derivatives. In the polymeric surfactant, the content of the recurring units having formulae (6A) to (6E) is preferably at least 20 mol %, more preferably at least 60 mol %, most preferably 100 mol % of the overall recurring units.

The polymeric surfactant preferably has a Mw of 1,000 to 500,000, more preferably 3,000 to 100,000 and a Mw/Mn of 1.0 to 2.0, more preferably 1.0 to 1.6.

The polymeric surfactant may be synthesized by any desired method, for example, by dissolving an unsaturated bond-containing monomer or monomers providing recurring units having formula (6A) to (6E) and optionally other recurring units in an organic solvent, adding a radical initiator, and heating for polymerization. Suitable organic solvents used herein include toluene, benzene, THF, diethyl ether, and dioxane. Examples of the polymerization initiator used herein include AIBN, 2,2'-azobis(2,4-dimethylvaleronitrile), dimethyl 2,2-azobis(2-methylpropionate), benzoyl peroxide, and lauroyl peroxide. Preferably the reaction temperature is 50 to 100° C. and the reaction time is 4 to 24 hours. The acid labile group that has been incorporated in the monomer may be kept as such, or the polymer may be protected or partially protected therewith at the end of polymerization.

During the synthesis of polymeric surfactant, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

When the resist composition contains a surfactant (F), the amount thereof is preferably 0.1 to 50 parts by weight, and more preferably 0.5 to 10 parts by weight per 80 parts by weight of the base resin (B). At least 0.1 part of the surfactant is effective in improving the receding contact angle with water of the resist film at its surface. Up to 50 parts of the surfactant is effective in forming a resist film having a low rate of dissolution in an alkaline developer and capable of maintaining the height of a fine pattern formed therein.

(G) Other Components

The resist composition may further comprise (G) another component, for example, a compound which is decomposed with an acid to generate another acid (i.e., acid amplifier compound), an organic acid derivative, a fluorinated alcohol, and a compound having a Mw of up to 3,000 which changes its solubility in developer under the action of an acid (i.e., dissolution inhibitor). Specifically, the acid amplifier compound is described in JP-A 2009-269953 and JP-A 2010-215608 and preferably used in an amount of 0 to 5 parts, more preferably 0 to 3 parts by weight per 80 parts by weight of the base resin (B). An extra amount of the acid amplifier compound can make the acid diffusion control difficult and cause degradations to resolution and pattern profile. With respect to the remaining additives, reference should be made to JP-A 2009-269953 and JP-A 2010-215608.

Process

A further embodiment of the invention is a pattern forming process using the chemically amplified resist composition defined above. A pattern may be formed from the resist composition using any well-known lithography process. The preferred process includes the steps of applying the resist composition to form a resist film on a substrate, exposing a selected region of the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 150° C. for 1 to 10 minutes, more preferably at 80 to 140° C. for 1 to 5 minutes. The resulting resist film preferably has a thickness of 0.05 to 2 µm.

Then the resist film is exposed patternwise to excimer laser, EUV or EB. On use of KrF excimer laser, ArF excimer laser or EUV of wavelength 13.5 nm, the resist film is exposed through a mask having a desired pattern, preferably in a dose of 1 to 200 $mJ/cm^2$, more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, negative tone development may also be used. That is, an organic solvent may be used instead of the aqueous alkaline solution as the developer for developing and dissolving away the unexposed region of the resist film.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLES

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, and PGMEA for propylene glycol monomethyl ether acetate. Analysis is made by IR spectroscopy, $^1$H-NMR spectroscopy, and liquid chromatography-mass spectrometry (LC-MS) using analytic instruments as shown below.

IR: NICOLET 6700 by Thermo Fisher Scientific Inc.

$^1$H-NMR: ECA-500 by JEOL Ltd.

LC-MS: Acquity UPLC H-Class system and Acquity QDa by Waters Corp.

[1] Synthesis of Sulfonium Compounds

Example 1-1

Synthesis of PAG-1

PAG-1 was synthesized according to the following scheme.

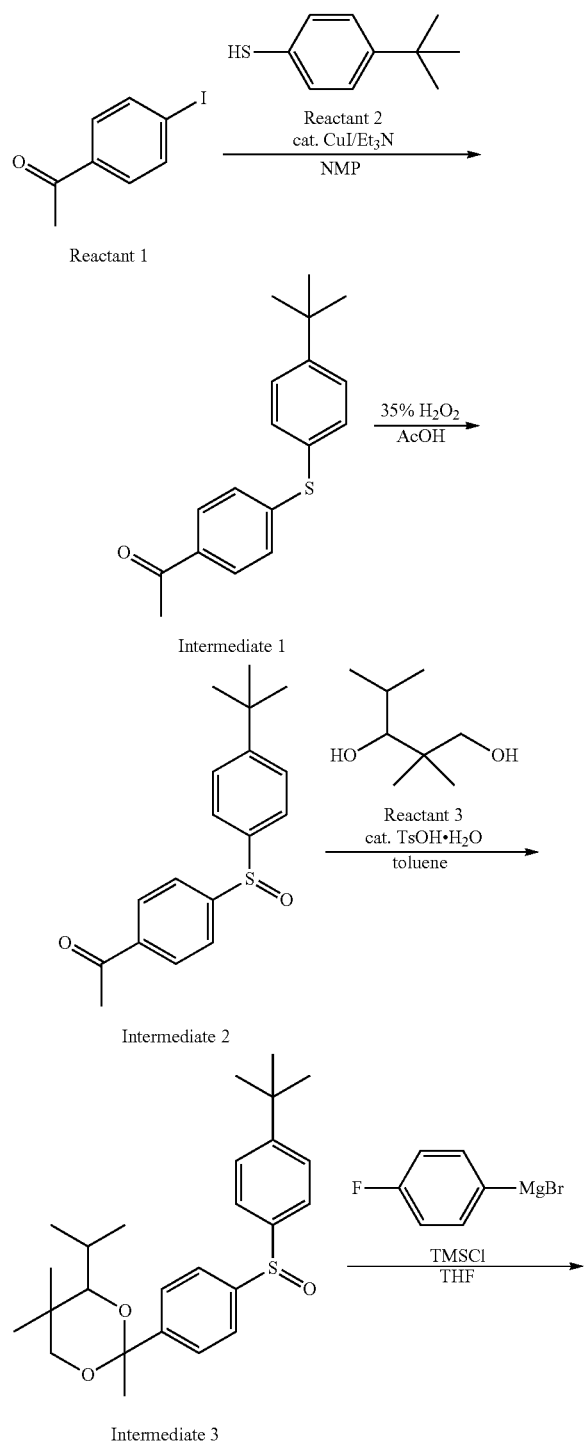

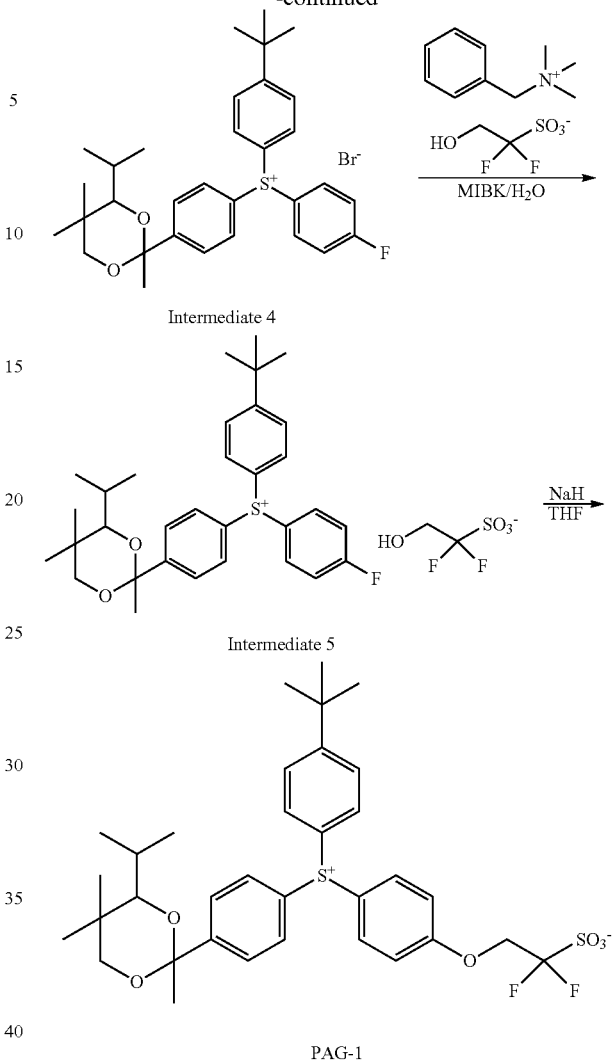

Example 1-1-1

Synthesis of Intermediate 1

In a flask under nitrogen atmosphere, 225 g of Reactant 1, 182 g of Reactant 2, and 4.4 g of copper(I) iodide were dissolved in 700 g of N-methylpyrrolidone, which was heated at 70° C. Thereafter, 102 g of triethylamine was added dropwise to the solution, which was aged at 80° C. for 24 hours. After the disappearance of Reactant 1 was confirmed by GC, the reaction system was cooled and 1,000 g of water was added dropwise to quench the reaction. The reaction solution was extracted with 2,000 mL of toluene, followed by ordinary aqueous workup, solvent distillation, and recrystallization from hexane. There was obtained Intermediate 1 as white crystals (amount 233 g, yield 90%).

Example 1-1-2

Synthesis of Intermediate 2

Under nitrogen atmosphere, a flask was charged with 119 g of Intermediate 1 and 500 g of acetic acid and heated at 30°

C. for dissolution. With the temperature kept below 40° C., 41 g of 35 wt % aqueous hydrogen peroxide was added dropwise to the solution. At the end of dropwise addition, the solution was aged at 40° C. for 20 hours. After aging, the reaction system was cooled, a solution of 20 g of sodium thiosulfate pentahydrate in 400 g of water was added dropwise to quench the reaction. Thereafter, 1,300 mL of toluene and 300 mL of ethyl acetate were added to the reaction solution to extract the desired compound, followed by ordinary aqueous workup, solvent distillation, and recrystallization from hexane. There was obtained Intermediate 2 as white crystals (amount 115 g, yield 92%).

Example 1-1-3

Synthesis of Intermediate 3

Under nitrogen atmosphere, a flask was charged with 15.6 g of Intermediate 2, 1.0 g of p-toluenesulfonic acid monohydrate, 15.2 g of Reactant 3, and 70 g of toluene, which were heated under reflux at 105° C. for 7 hours. After the disappearance of Intermediate 2 was confirmed by TLC, the reaction solution was ice cooled and 1.0 g of triethylamine was added to quench the reaction. Further, 50 mL of saturated aqueous solution of sodium bicarbonate was added. The desired compound was extracted with 50 mL of toluene, followed by ordinary aqueous workup, solvent distillation, and purification by silica gel column chromatography (elute: 15/1 hexane/ethyl acetate). There was obtained Intermediate 3 as colorless oily matter (amount 21.8 g, yield 98%).

Example 1-1-4

Synthesis of Intermediate 4

In a flask under nitrogen atmosphere, a Grignard reagent was prepared from 26.8 g of 4-bromofluorobenzene, 3.7 g of metallic magnesium, and 60 g of THF. After the preparation, the flask was cooled, to which a solution of 21.8 g of Intermediate 3 in 25 g of THF was added. Below 20° C., 16.6 g of trimethylsilyl chloride was added dropwise to the solution, which was aged in an ice bath for 2 hours. At the end of aging, the reaction system was cooled, and 100 mL of saturated aqueous solution of ammonium chloride was added dropwise to quench the reaction. This was followed by extraction with 150 mL of methyl isobutyl ketone, ordinary aqueous workup, solvent distillation, and recrystallization from hexane. There was obtained Intermediate 4 as white crystals (amount 28.3 g, yield 94%).

Example 1-1-5

Synthesis of Intermediate 5

Under nitrogen atmosphere, 14.2 g of Intermediate 4, 9.0 g of benzyltrimethylammonium 1,1-difluoro-2-hydroxyethane-1-sulfonate, 70 g of methyl isobutyl ketone, and 50 g of water were added to a flask. After 30 minutes of stirring, the organic layer was taken out, washed with water, and concentrated under reduced pressure. The concentrate was washed with hexane, obtaining Intermediate 5 as oily matter (amount 15.2 g, yield 94%).

Example 1-1-6

Synthesis of PAG-1

In nitrogen atmosphere, 0.6 g of sodium hydride was suspended in 56 g of THF. After the suspension was cooled below 5° C., a solution of 7.9 g of Intermediate 5 in 55.5 g of THF was added dropwise thereto. The resulting solution was aged at room temperature for 12 hours. At the end of aging, the reaction system was cooled and 60 mL of water was added dropwise to quench the reaction. This was followed by extraction with 150 g of methyl isobutyl ketone, ordinary aqueous workup, solvent distillation, and recrystallization from hexane. There was obtained PAG-1 as white crystals (amount 7.1 g, yield 92%).

PAG-1 was analyzed by IR spectroscopy and LC-MS, with the data shown below. FIG. 1 is the $^1$H-NMR/DMSO-$d_6$ spectrum of PAG-1.

IR (D-ATR): v=3484, 3094, 2963, 2872, 1589, 1494, 1397, 1368, 1316, 1259, 1237, 1180, 1152, 1110, 1068, 1035, 989, 932, 879, 833, 779, 689, 667, 649, 635, 619, 591, 552, 524 cm$^{-1}$

LC-MS: positive [M+H]$^+$ 649

Example 1-2

Synthesis of PAG-2

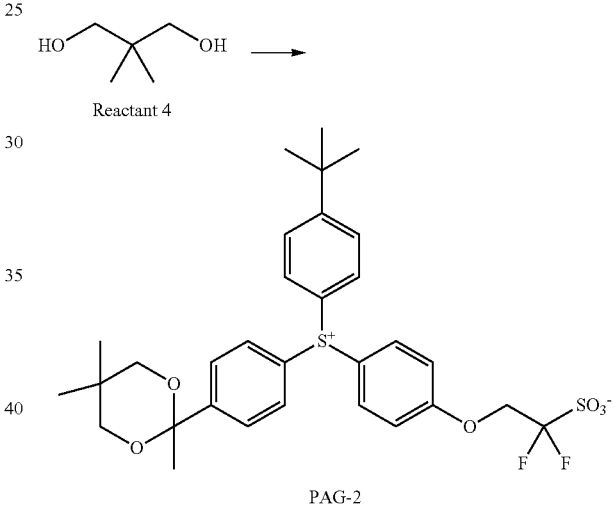

PAG-2

By following the same procedure as in Example 1-1 aside from using Reactant 4 instead of Reactant 3, PAG-2 was obtained (amount 5.0 g, final step yield 94%).

Figure 2:
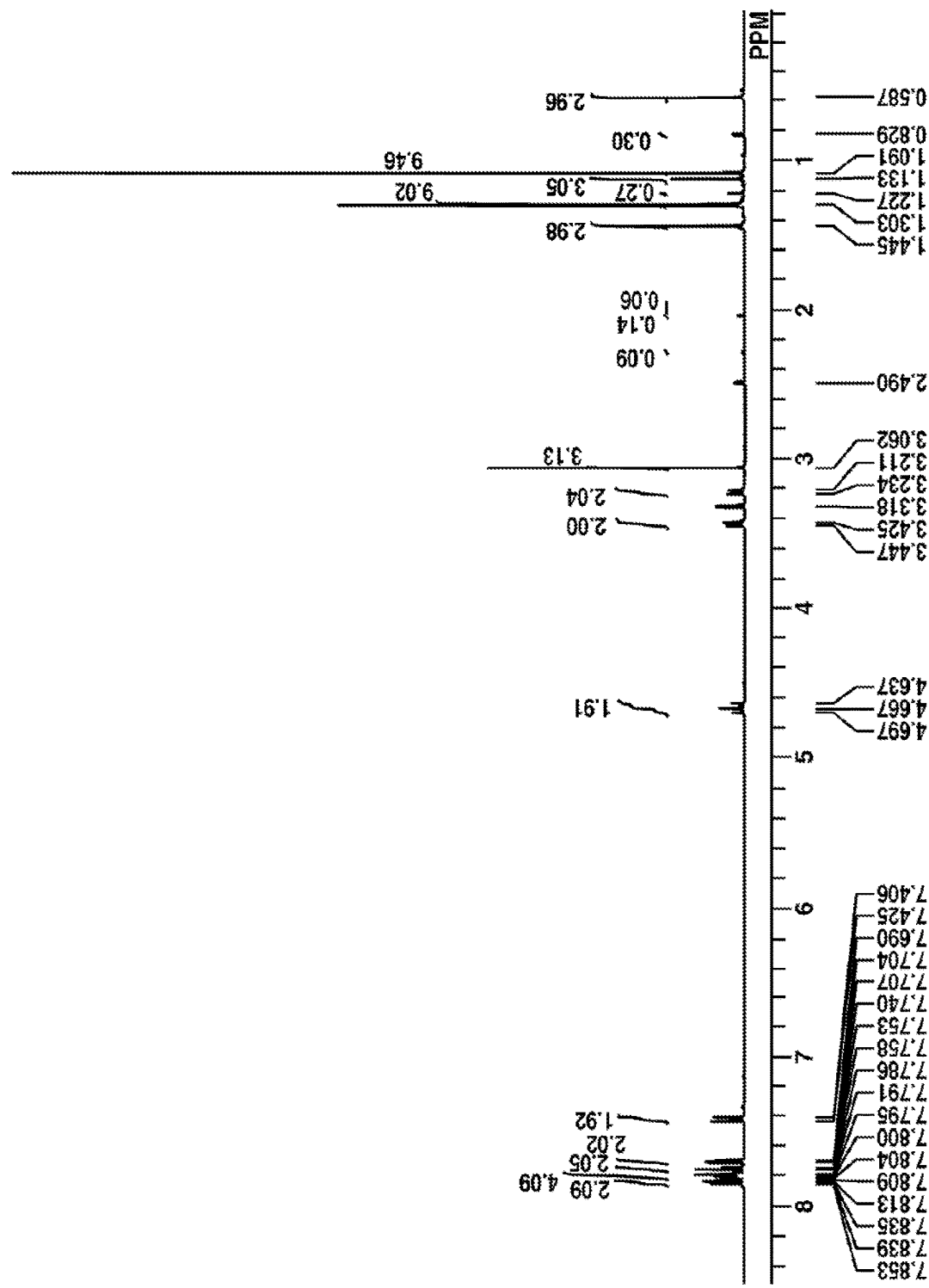
FIG. 2 is a diagram showing the $^1$H-NMR spectrum of PAG-2 in Example 1-2.

PAG-2 was analyzed by IR spectroscopy and LC-MS, with the data shown below. FIG. 2 is the $^1$H-NMR/DMSO-$d_6$ spectrum of PAG-2.

IR (D-ATR): v=3492, 3064, 2963, 2870, 1589, 1494, 1398, 1365, 1317, 1256, 1237, 1215, 1181, 1125, 1104, 1078, 1034, 1009, 988, 949, 914, 876, 834, 777, 743, 726, 670, 651, 635, 619, 590, 552, 524 cm$^{-1}$

LC-MS: positive [M+H]$^+$ 607

Example 1-3

Synthesis of PAG-3

Example 1-5

Synthesis of PAG-5

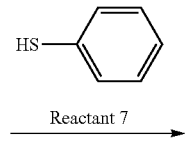

Reactant 1

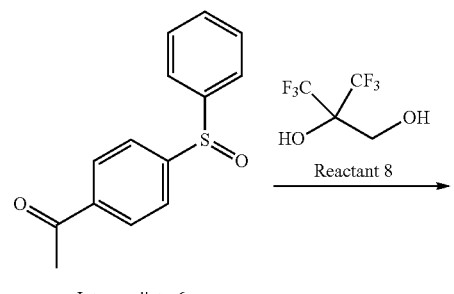

Intermediate 6

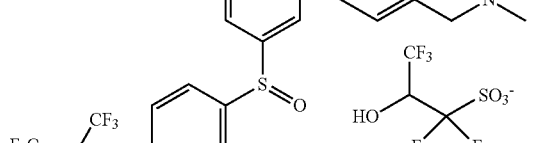

Intermediate 7

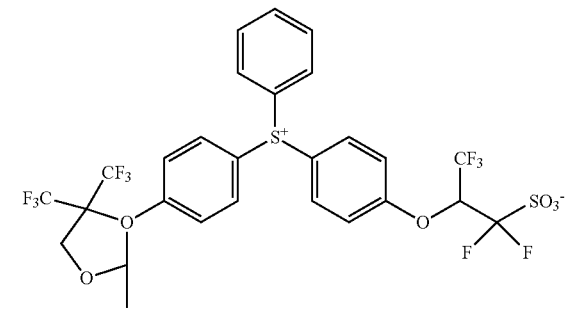

PAG-5

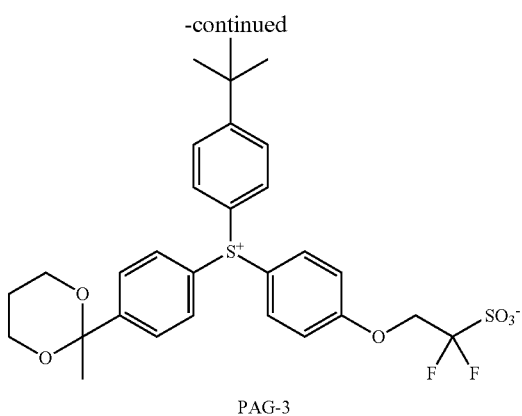

PAG-3

By following the same procedure as in Example 1-1 aside from using Reactant 5 instead of Reactant 3, PAG-3 was obtained (amount 4.3 g, final step yield 95%).

PAG-3 was analyzed by LC-MS, with the data shown below.

LC-MS: positive $[M+H]^+$ 579

Example 1-4

Synthesis of PAG-4

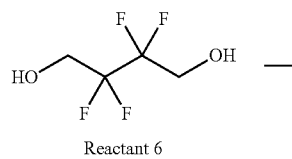

Reactant 6

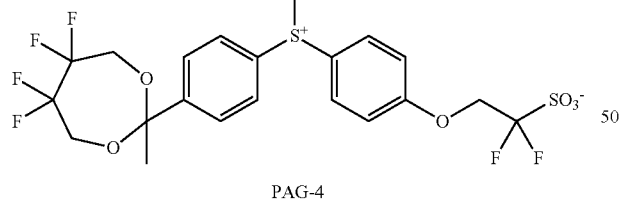

PAG-4

By following the same procedure as in Example 1-1 aside from using Reactant 6 instead of Reactant 3, PAG-4 was obtained (amount 8.4 g, final step yield 78%).

Figure 3:
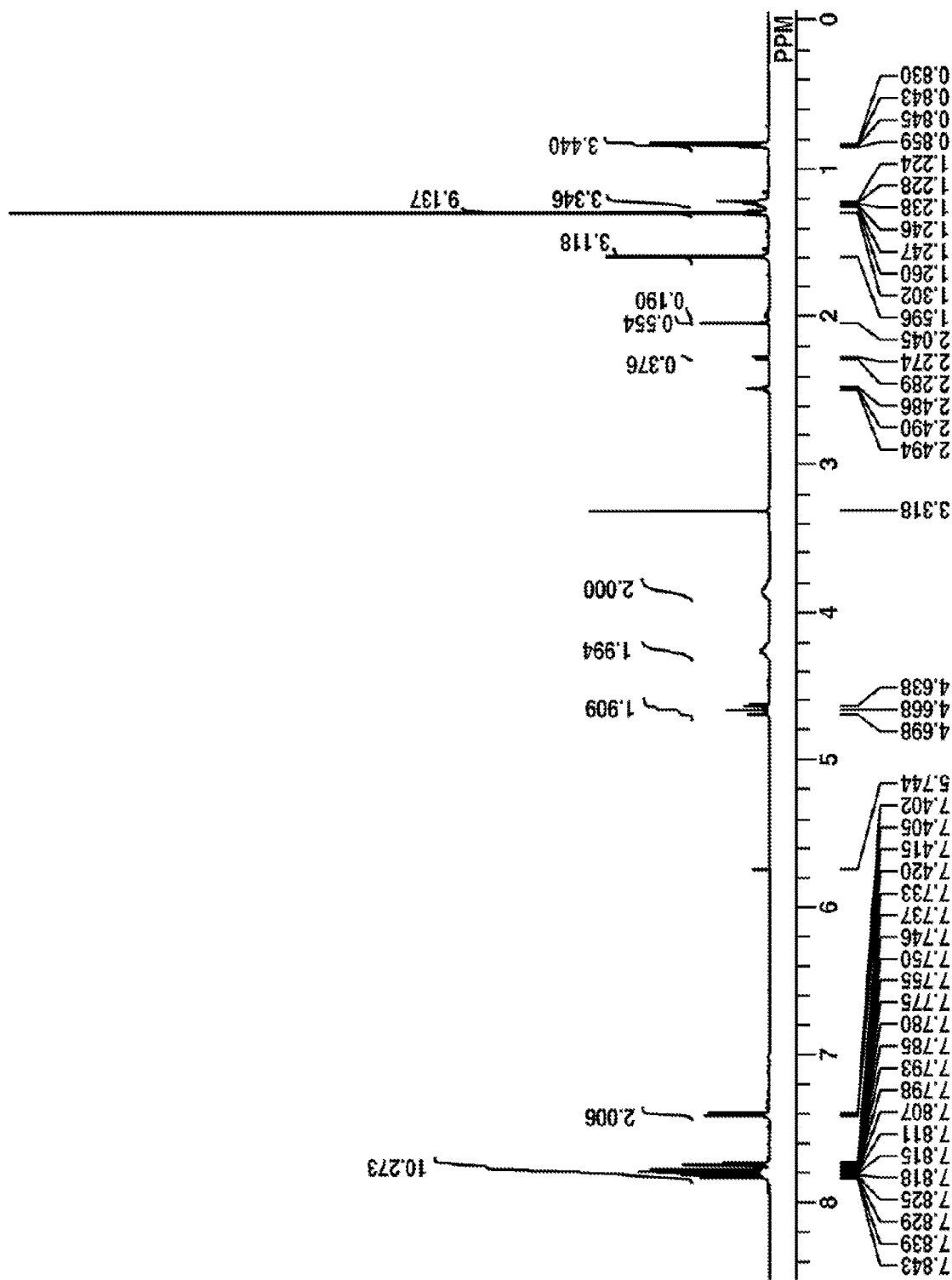
FIG. 3 is a diagram showing the $^1$H-NMR spectrum of PAG-4 in Example 1-4.

PAG-4 was analyzed by IR spectroscopy and LC-MS, with the data shown below. FIG. 3 is the $^1$H-NMR/DMSO-$d_6$ spectrum of PAG-4.

IR (D-ATR): ν=3488, 3096, 2961, 2873, 1589, 1494, 1454, 1399, 1315, 1261, 1236, 1172, 1135, 1115, 1073, 1032, 1009, 989, 935, 834, 778, 712, 678, 651, 636, 620, 591, 573, 545, 524 cm$^{-1}$

LC-MS: positive $[M+H]^+$ 665

Example 1-5-1

Synthesis of Intermediate 6

Intermediate 6 was synthesized by the same procedure as in Examples 1-1-1 to 1-1-2 aside from using Reactant 7 instead of Reactant 2.

Example 1-5-2

Synthesis of Intermediate 7

Intermediate 7 was synthesized by the same procedure as in Example 1-1-3 aside from using Reactant 8 instead of Reactant 3.

Example 1-5-3

Synthesis of PAG-5

PAG-5 was synthesized by the same procedure as in Examples 1-1-4 to 1-1-6 aside from using benzyltrimethylammonium 1,1,3,3,3-pentafluoro-2-hydroxypropane-1-sulfonate instead of benzyltrimethylammonium 1,1-difluoro-2-hydroxyethane-1-sulfonate.

Figure 4:
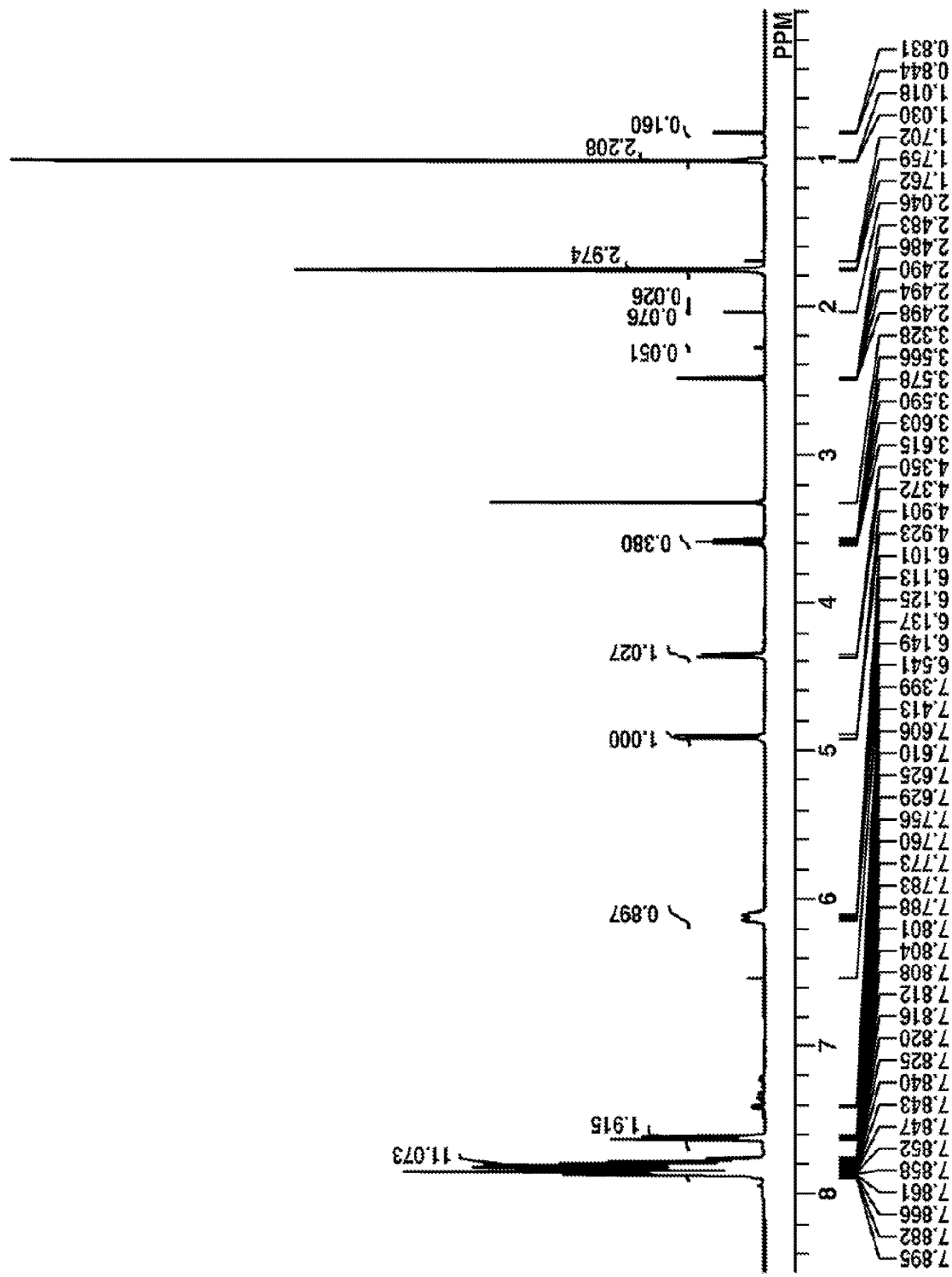
FIG. 4 is a diagram showing the $^1$H-NMR spectrum of PAG-5 in Example 1-5-3.

PAG-5 was analyzed by IR spectroscopy and LC-MS, with the data shown below. FIG. 4 is the $^1$H-NMR/DMSO-$d_6$ spectrum of PAG-5.

IR (D-ATR): ν=3486, 3097, 2976, 1587, 1493, 1448, 1401, 1369, 1318, 1245, 1161, 1107, 1087, 1060, 1012, 998, 913, 884, 834, 751, 741, 690, 642, 593, 553, 525 cm$^{-1}$

LC-MS: positive [M+H]$^+$ 713

Examples 1-6 to 1-11

Synthesis of PAG-6 to PAG-11

PAG-6

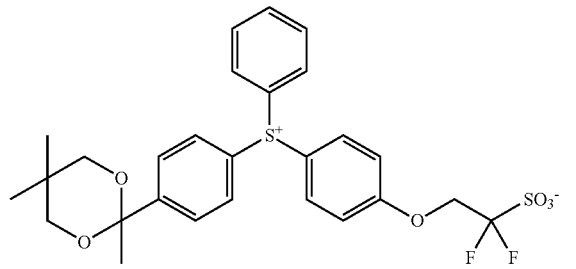

PAG-7

PAG-8

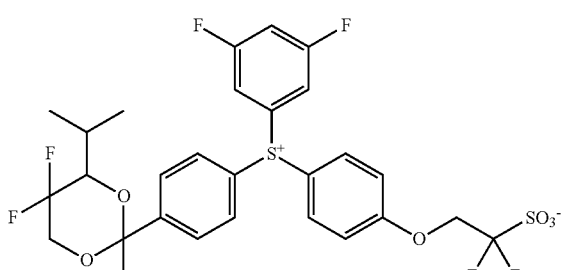

PAG-9

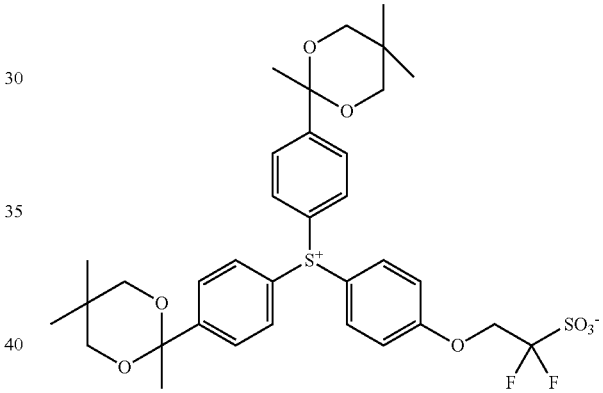

PAG-10

PAG-11

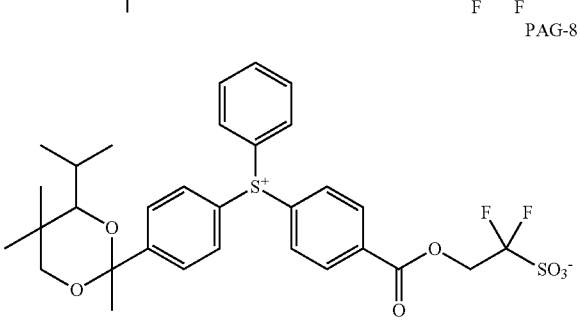

PAG-6 to PAG-11 were synthesized by any well-known organic chemistry methods using corresponding reactants.

[2] Synthesis of Base Resins

Base resins (or polymers) used in resist compositions were synthesized by the following procedure.

Synthesis Example 1

Synthesis of Polymer P-1

In a funnel under nitrogen atmosphere, 5.0 g of 3-hydroxy-1-adamantyl methacrylate, 14.4 g of α-methacryloxy-γ-butyrolactone, 20.8 g of 1-isopropylcyclopentyl methacrylate, 0.49 g of dimethyl 2,2′-azobis(2-methylpropionate) (V-601 by Wako Pure Chemical Industries, Ltd.), 0.41 g of 2-mercaptoethanol, and 56 g of PGMEA were combined to form a monomer/initiator solution. A flask in nitrogen atmosphere was charged with 19 g of PGMEA, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining Polymer P-1 in white powder form (amount 35.3 g, yield 88%). On GPC analysis, Polymer P-1 had a Mw of 8,500 and a Mw/Mn of 1.58.

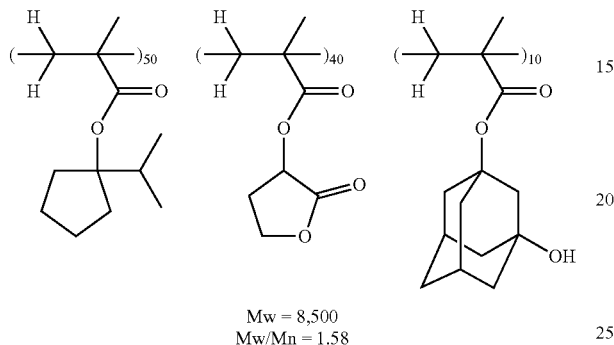

Mw = 8,500
Mw/Mn = 1.58

P-1

Synthesis Examples 2 to 6

Synthesis of Polymers P-2 to P-6

Polymers P-2 to P-6 were synthesized by the same procedure as in Synthesis Example 1 aside from changing the type and amount of monomers.

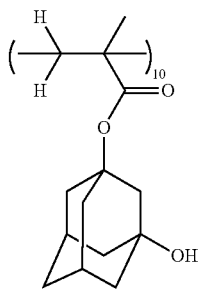

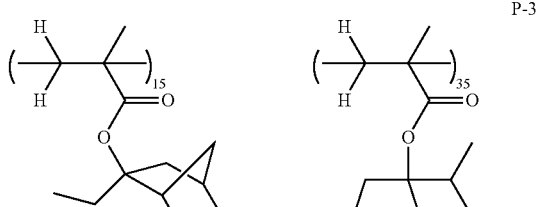

Mw = 8,100
Mw/Mn = 1.73

P-3

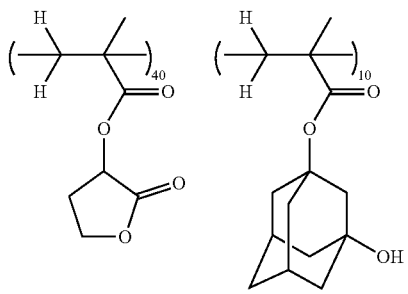

Mw = 8,300
Mw/Mn = 1.67

P-2

P-4

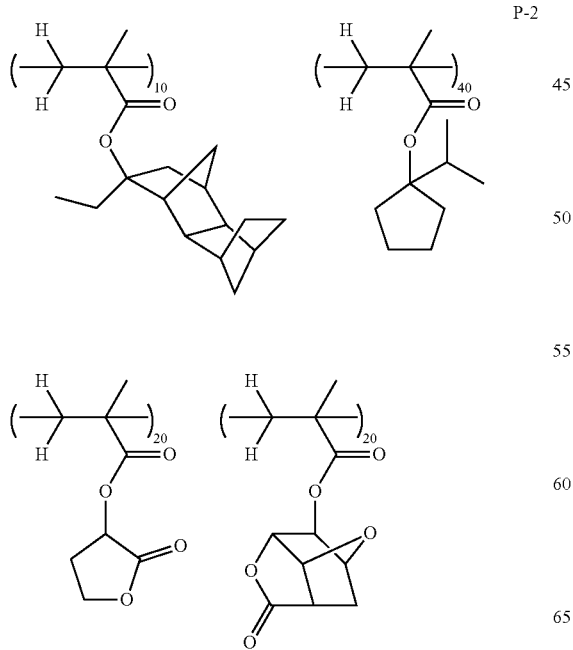

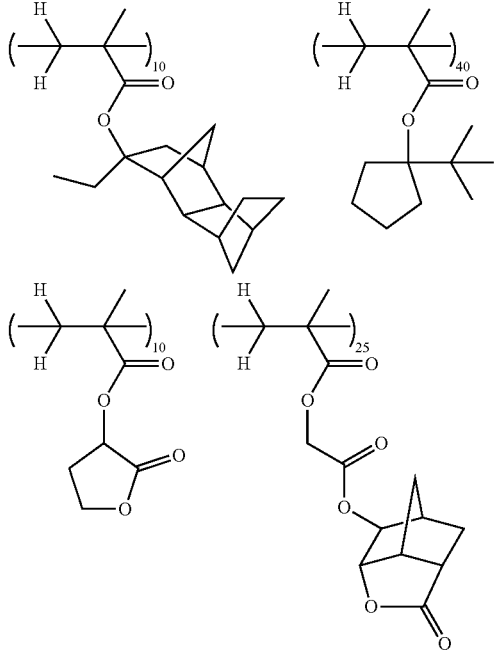

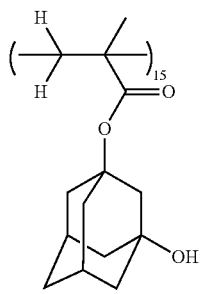

Mw = 9,400
Mw/Mn = 1.71

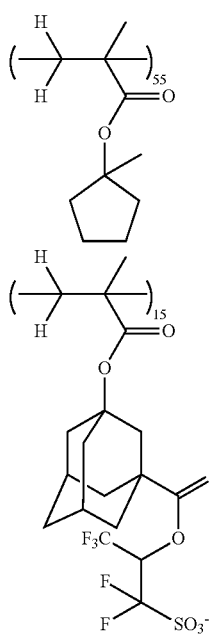

Mw = 11,400
Mw/Mn = 2.07

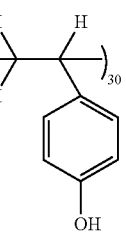

P-5

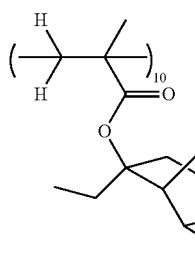

P-6

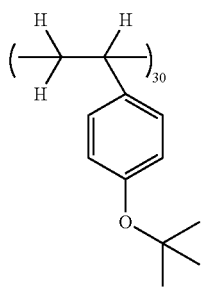

Mw = 10,800
Mw/Mn = 2.14

[3] Preparation of Resist Composition

Examples 2-1 to 2-44 and Comparative Examples 1-1 to 1-18

Chemically amplified resist compositions in solution form were prepared by dissolving a sulfonium compound (PAG-1 to PAG-11) or comparative photoacid generator (PAG-A to PAG-E), base resin (Polymers P-1 to P-6), other photoacid generator (PAG-X, PAG-Y), quencher (Q-1 to Q-4), and alkali-soluble surfactant (SF-1) in a solvent containing 0.01 wt % of surfactant A in accordance with the formulation shown in Tables 1 to 3, and filtering through a Teflon® filter with a pore size of 0.2 μm.

TABLE 1

| | | Resist composition | Base resin (pbw) | Photoacid generator (pbw) | Other photoacid generator (pbw) | Quencher (pbw) | Surfactant (pbw) | Solvent 1 (pbw) | Solvent 2 (pbw) |
|---|---|---|---|---|---|---|---|---|---|
| Example | 2-1 | R-01 | P-1 (80) | PAG-1 (4.0) | PAG-X (5.0) | Q-1 (7.0) | SF-1 (3.0) | PGMEA (1,728) | GBL (192) |
| | 2-2 | R-02 | P-1 (80) | PAG-2 (4.0) | PAG-X (5.0) | Q-1 (7.0) | SF-1 (3.0) | PGMEA (1,728) | GBL (192) |
| | 2-3 | R-03 | P-1 (80) | PAG-3 (4.0) | PAG-X (5.0) | Q-1 (7.0) | SF-1 (3.0) | PGMEA (1,728) | GBL (192) |
| | 2-4 | R-04 | P-1 (80) | PAG-4 (4.0) | PAG-X (5.0) | Q-1 (7.0) | SF-1 (3.0) | PGMEA (1,728) | GBL (192) |

TABLE 1-continued

|  | Resist composition | Base resin (pbw) | Photoacid generator (pbw) | Other photoacid generator (pbw) | Quencher (pbw) | Surfactant (pbw) | Solvent 1 (pbw) | Solvent 2 (pbw) |
|---|---|---|---|---|---|---|---|---|
| 2-5 | R-05 | P-1 (80) | PAG-6 (4.0) | PAG-X (5.0) | Q-1 (7.0) | SF-1 (3.0) | PGMEA (1,728) | GBL (192) |
| 2-6 | R-06 | P-1 (80) | PAG-7 (4.0) | PAG-X (5.0) | Q-1 (7.0) | SF-1 (3.0) | PGMEA (1,728) | GBL (192) |
| 2-7 | R-07 | P-1 (80) | PAG-8 (4.0) | PAG-X (5.0) | Q-1 (7.0) | SF-1 (3.0) | PGMEA (1,728) | GBL (192) |
| 2-8 | R-08 | P-1 (80) | PAG-10 (4.0) | PAG-X (5.0) | Q-1 (7.0) | SF-1 (3.0) | PGMEA (1,728) | GBL (192) |
| 2-9 | R-09 | P-1 (80) | PAG-11 (4.0) | PAG-X (5.0) | Q-1 (7.0) | SF-1 (3.0) | PGMEA (1,728) | GBL (192) |
| 2-10 | R-10 | P-2 (80) | PAG-1 (4.5) | PAG-X (5.0) | Q-1 (3.5) | SF-1 (3.0) | PGMEA (1,728) | GBL (192) |
| 2-11 | R-11 | P-2 (80) | PAG-2 (4.0) | PAG-X (4.5) | Q-1 (3.5) | SF-1 (3.0) | PGMEA (1,728) | GBL (192) |
| 2-12 | R-12 | P-2 (80) | PAG-4 (3.5) | PAG-Y (5.0) | Q-1 (4.5) | SF-1 (3.0) | PGMEA (1,728) | GBL (192) |
| 2-13 | R-13 | P-2 (80) | PAG-5 (4.0) | PAG-X (5.5) | Q-2 (4.5) | SF-1 (3.0) | PGMEA (1,728) | GBL (192) |
| 2-14 | R-14 | P-2 (80) | PAG-6 (4.0) | PAG-X (4.5) | Q-1 (3.5) | SF-1 (3.0) | PGMEA (1,728) | GBL (192) |
| 2-15 | R-15 | P-2 (80) | PAG-9 (4.0) | PAG-X (5.5) | Q-1 (3.5) | SF-1 (3.0) | PGMEA (1,728) | GBL (192) |
| 2-16 | R-16 | P-2 (80) | PAG-10 (4.0) | PAG-Y (4.5) | Q-4 (3.5) | SF-1 (3.0) | PGMEA (1,728) | GBL (192) |
| 2-17 | R-17 | P-2 (80) | PAG-11 (3.0) | PAG-Y (4.0) | Q-3 (3.0) | SF-1 (3.0) | PGMEA (1,728) | GBL (192) |
| 2-18 | R-18 | P-3 (80) | PAG-1 (5.0) | PAG-Y (8.0) | Q-1 (2.5) | SF-1 (3.0) | PGMEA (1,728) | GBL (192) |
| 2-19 | R-19 | P-3 (80) | PAG-2 (5.0) | PAG-Y (8.0) | Q-1 (2.5) | SF-1 (3.0) | PGMEA (1,728) | GBL (192) |
| 2-20 | R-20 | P-3 (80) | PAG-3 (5.0) | PAG-Y (8.0) | Q-1 (2.5) | SF-1 (3.0) | PGMEA (1,728) | GBL (192) |
| 2-21 | R-21 | P-3 (80) | PAG-4 (5.0) | PAG-Y (8.0) | Q-1 (2.5) | SF-1 (3.0) | PGMEA (1,728) | GBL (192) |
| 2-22 | R-22 | P-3 (80) | PAG-5 (5.0) | PAG-Y (8.0) | Q-1 (2.5) | SF-1 (3.0) | PGMEA (1,728) | GBL (192) |

TABLE 2

|  |  | Resist composition | Base resin (pbw) | Photoacid generator (pbw) | Other photoacid generator (pbw) | Quencher (pbw) | Surfactant (pbw) | Solvent 1 (pbw) | Solvent 2 (pbw) |
|---|---|---|---|---|---|---|---|---|---|
| Example | 2-23 | R-23 | P-3 (80) | PAG-6 (5.0) | PAG-Y (8.0) | Q-1 (2.5) | SF-1 (3.0) | PGMEA (1,728) | GBL (192) |
|  | 2-24 | R-24 | P-3 (80) | PAG-7 (5.0) | PAG-Y (8.0) | Q-1 (2.5) | SF-1 (3.0) | PGMEA (1,728) | GBL (192) |
|  | 2-25 | R-25 | P-3 (80) | PAG-8 (5.0) | PAG-Y (8.0) | Q-1 (2.5) | SF-1 (3.0) | PGMEA (1,728) | GBL (192) |
|  | 2-26 | R-26 | P-3 (80) | PAG-9 (5.0) | PAG-Y (8.0) | Q-1 (2.5) | SF-1 (3.0) | PGMEA (1,728) | GBL (192) |
|  | 2-27 | R-27 | P-3 (80) | PAG-10 (5.0) | PAG-Y (8.0) | Q-1 (2.5) | SF-1 (3.0) | PGMEA (1,728) | GBL (192) |
|  | 2-28 | R-28 | P-3 (80) | PAG-11 (5.0) | PAG-Y (8.0) | Q-1 (2.5) | SF-1 (3.0) | PGMEA (1,728) | GBL (192) |
|  | 2-29 | R-29 | P-4 (80) | PAG-1 (5.0) | PAG-Y (8.0) | Q-1 (2.5) | SF-1 (3.0) | PGMEA (1,728) | GBL (192) |
|  | 2-30 | R-30 | P-4 (80) | PAG-2 (4.5) | PAG-Y (8.5) | Q-1 (3.5) | SF-1 (3.0) | PGMEA (1,728) | GBL (192) |
|  | 2-31 | R-31 | P-4 (80) | PAG-4 (5.0) | PAG-X (5.5) | Q-3 (3.0) | SF-1 (3.0) | PGMEA (1,728) | GBL (192) |
|  | 2-32 | R-32 | P-4 (80) | PAG-5 (5.5) | PAG-X (6.5) | Q-1 (3.5) | SF-1 (3.0) | PGMEA (1,728) | GBL (192) |
|  | 2-33 | R-33 | P-4 (80) | PAG-7 (4.5) | PAG-Y (7.0) | Q-1 (3.5) | SF-1 (3.0) | PGMEA (1,728) | GBL (192) |
|  | 2-34 | R-34 | P-4 (80) | PAG-9 (5.0) | PAG-Y (8.0) | Q-3 (4.0) | SF-1 (3.0) | PGMEA (1,728) | GBL (192) |
|  | 2-35 | R-35 | P-4 (80) | PAG-10 (5.0) | PAG-Y (7.5) | Q-2 (4.5) | SF-1 (3.0) | PGMEA (1,728) | GBL (192) |
|  | 2-36 | R-36 | P-4 (80) | PAG-11 (3.0) | PAG-X (6.5) | Q-4 (3.0) | SF-1 (3.0) | PGMEA (1,728) | GBL (192) |

TABLE 2-continued

|  | Resist composition | Base resin (pbw) | Photoacid generator (pbw) | Other photoacid generator (pbw) | Quencher (pbw) | Surfactant (pbw) | Solvent 1 (pbw) | Solvent 2 (pbw) |
| --- | --- | --- | --- | --- | --- | --- | --- | --- |
| 2-37 | R-37 | P-5 (80) | PAG-1 (3.0) | — | Q-1 (3.5) | SF-1 (3.0) | PGMEA (1,728) | DAA (192) |
| 2-38 | R-38 | P-5 (80) | PAG-7 (3.0) | — | Q-1 (3.5) | SF-1 (3.0) | PGMEA (1,728) | DAA (192) |
| 2-39 | R-39 | P-5 (80) | PAG-11 (3.0) | — | Q-1 (3.5) | SF-1 (3.0) | PGMEA (1,728) | DAA (192) |
| 2-40 | R-40 | P-6 (80) | PAG-1 (3.0) | PAG-Y (3.5) | Q-1 (3.5) | SF-1 (3.0) | PGMEA (1,728) | DAA (192) |
| 2-41 | R-41 | P-6 (80) | PAG-1 (3.0) | — | Q-1 (3.5) | SF-1 (3.0) | PGMEA (1,728) | DAA (192) |
| 2-42 | R-42 | P-6 (80) | PAG-7 (3.0) | — | Q-1 (3.5) | SF-1 (3.0) | PGMEA (1,728) | DAA (192) |
| 2-43 | R-43 | P-6 (80) | PAG-11 (3.0) | — | Q-1 (3.5) | SF-1 (3.0) | PGMEA (1,728) | DAA (192) |
| 2-44 | R-44 | P-1 (80) | PAG-1 (3.0) | PAG-Y (2.0) | Q-1 (3.5) | SF-1 (3.0) | PGMEA (1,728) | DAA (192) |

TABLE 3

|  |  | Resist composition | Base resin (pbw) | Photoacid generator (pbw) | Other photoacid generator (pbw) | Quencher (pbw) | Surfactant (pbw) | Solvent 1 (pbw) | Solvent 2 (pbw) |
| --- | --- | --- | --- | --- | --- | --- | --- | --- | --- |
| Comparative Example | 1-1 | R-45 | P-1 (80) | PAG-A (4.0) | PAG-X (5.0) | Q-1 (7.0) | SF-1 (3.0) | PGMEA (1,728) | GBL (192) |
|  | 1-2 | R-46 | P-1 (80) | PAG-B (4.0) | PAG-X (5.0) | Q-1 (7.0) | SF-1 (3.0) | PGMEA (1,728) | GBL (192) |
|  | 1-3 | R-47 | P-1 (80) | PAG-C (4.0) | PAG-X (5.0) | Q-1 (7.0) | SF-1 (3.0) | PGMEA (1,728) | GBL (192) |
|  | 1-4 | R-48 | P-1 (80) | PAG-D (4.0) | PAG-X (5.0) | Q-1 (7.0) | SF-1 (3.0) | PGMEA (1,728) | GBL (192) |
|  | 1-5 | R-49 | P-1 (80) | PAG-E (4.0) | PAG-X (5.0) | Q-1 (7.0) | SF-1 (3.0) | PGMEA (1,728) | GBL (192) |
|  | 1-6 | R-50 | P-3 (80) | PAG-A (5.0) | PAG-Y (8.0) | Q-1 (2.5) | SF-1 (3.0) | PGMEA (1,728) | GBL (192) |
|  | 1-7 | R-51 | P-3 (80) | PAG-B (5.0) | PAG-Y (8.0) | Q-1 (2.5) | SF-1 (3.0) | PGMEA (1,728) | GBL (192) |
|  | 1-8 | R-52 | P-3 (80) | PAG-C (5.0) | PAG-Y (8.0) | Q-1 (2.5) | SF-1 (3.0) | PGMEA (1,728) | GBL (192) |
|  | 1-9 | R-53 | P-3 (80) | PAG-D (5.0) | PAG-Y (8.0) | Q-1 (2.5) | SF-1 (3.0) | PGMEA (1,728) | GBL (192) |
|  | 1-10 | R-54 | P-3 (80) | PAG-E (5.0) | PAG-Y (8.0) | Q-1 (2.5) | SF-1 (3.0) | PGMEA (1,728) | GBL (192) |
|  | 1-11 | R-55 | P-5 (80) | PAG-B (3.0) | — | Q-1 (3.5) | SF-1 (3.0) | PGMEA (1,728) | DAA (192) |
|  | 1-12 | R-56 | P-5 (80) | PAG-C (3.0) | — | Q-1 (3.5) | SF-1 (3.0) | PGMEA (1,728) | DAA (192) |
|  | 1-13 | R-57 | P-5 (80) | PAG-D (3.0) | — | Q-1 (3.5) | SF-1 (3.0) | PGMEA (1,728) | DAA (192) |
|  | 1-14 | R-58 | P-5 (80) | — | — | Q-1 (3.5) | SF-1 (3.0) | PGMEA (1,728) | DAA (192) |
|  | 1-15 | R-59 | P-6 (80) | PAG-B (3.0) | — | Q-1 (3.5) | SF-1 (3.0) | PGMEA (1,728) | DAA (192) |
|  | 1-16 | R-60 | P-6 (80) | PAG-C (3.0) | — | Q-1 (3.5) | SF-1 (3.0) | PGMEA (1,728) | DAA (192) |
|  | 1-17 | R-61 | P-6 (80) | PAG-D (3.0) | — | Q-1 (3.5) | SF-1 (3.0) | PGMEA (1,728) | DAA (192) |
|  | 1-18 | R-62 | P-6 (80) | — | — | Q-1 (3.5) | SF-1 (3.0) | PGMEA (1,728) | DAA (192) |

The solvents, other photoacid generators PAG-X to PAG-Z, comparative photoacid generators PAG-A to PAG-E, and quenchers Q-1 to Q-4, alkali-soluble surfactant SF-1, and surfactant A in Tables 1 to 3 are identified below.

Solvent:
  PGMEA (propylene glycol monomethyl ether acetate)
  GBL (γ-butyrolactone)
  DAA (diacetone alcohol)

Other Photoacid Generator: PAG-X and PAG-Y

PAG-X

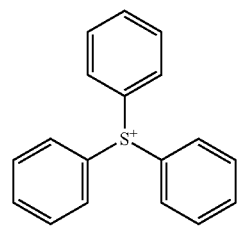

PAG-Y

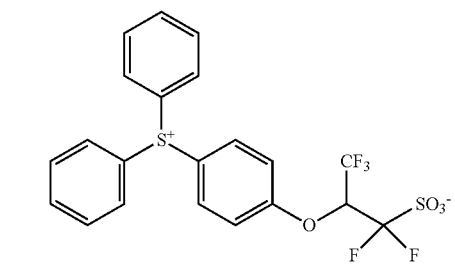

Comparative Photoacid Generator: PAG-A to PAG-E

PAG-A

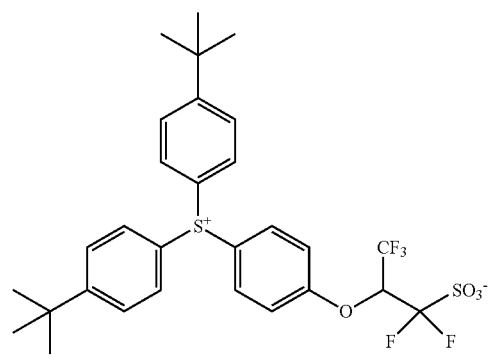

PAG-B

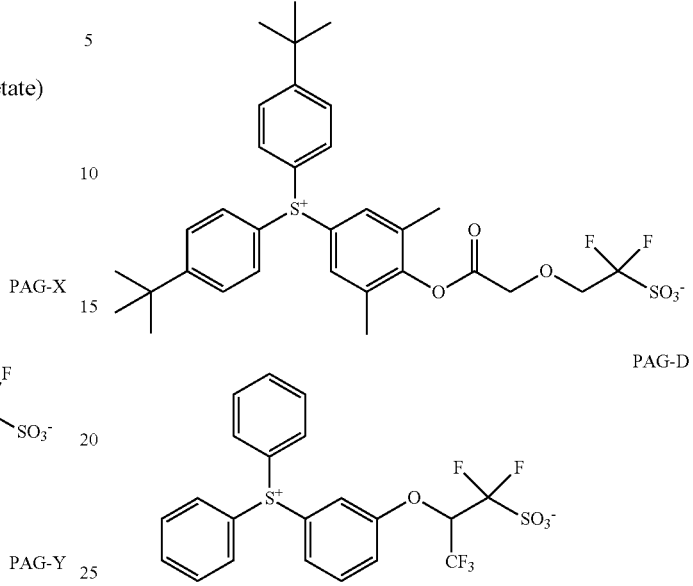

PAG-C

PAG-D

PAG-E

Quencher: Q-1 to Q-4

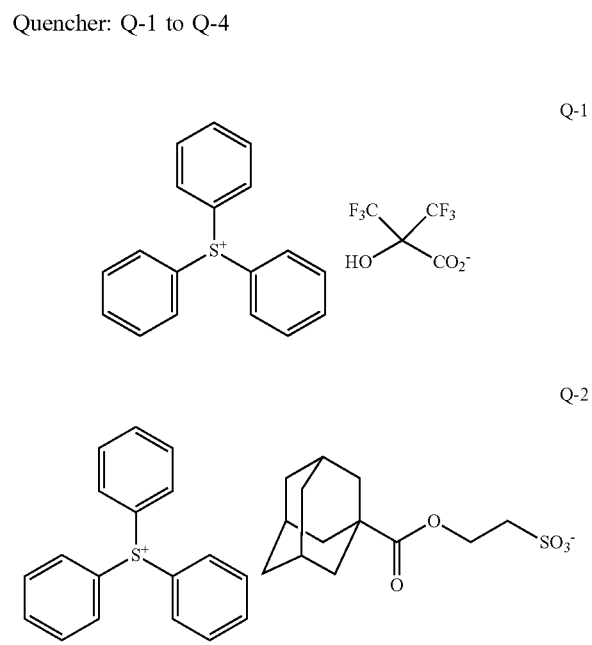

Q-1

Q-2

-continued

Q-3

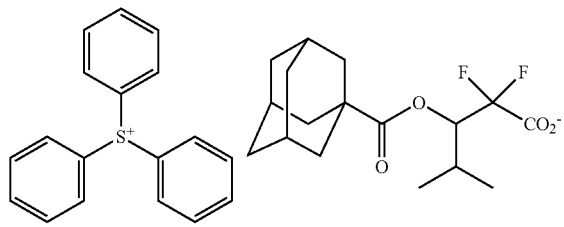

Q-4

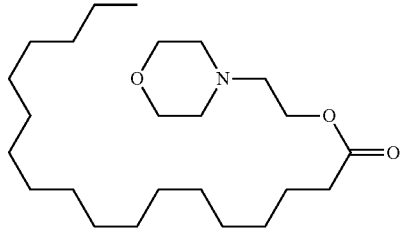

Alkali-Soluble Surfactant SF-1:

poly(2,2,3,3,4,4,4-heptafluoro-1-isobutyl-1-butyl methacrylate/9-(2,2,2-trifluoro-1-trifluoroethyloxy-carbonyl)-4-oxatricyclo[4.2.1.0$^{3,7}$]nonan-5-on-2-yl methacrylate)

Mw=7,700
Mw/Mn=1.82

SF-1

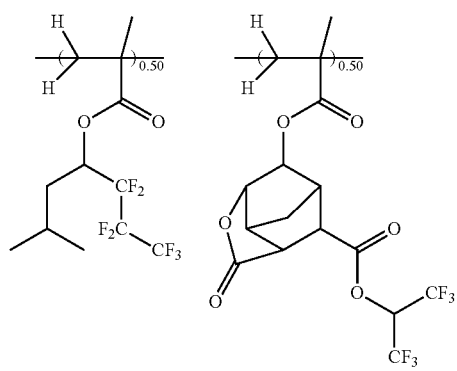

Surfactant A 3-methyl-3-(2,2,2-trifluoroethoxymethyl)oxetane/ tetrahydrofuran/2,2-dimethyl-1,3-propane diol copolymer (Omnova Solutions, Inc.)

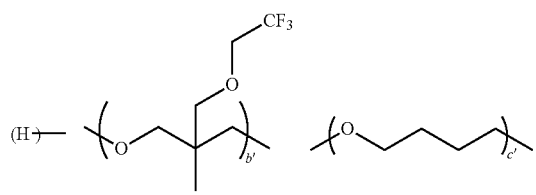

-continued

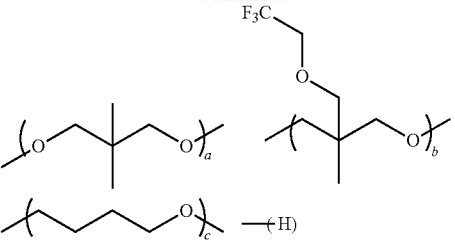

a:(b+b'):(c+c')=1:4-7:0.01-1 (molar ratio)
Mw=1,500

[4] Evaluation of Resist Composition: ArF Lithography Patterning Test 1

Examples 3-1 to 3-17 and Comparative Examples 2-1 to 2-5

On a silicon substrate, an antireflective coating solution (ARC29A, Nissan Chemical Corp.) was coated and baked at 200° C. for 60 seconds to form an ARC of 100 nm thick. Each of the resist compositions (R-01 to R-17, R-45 to R-49) was spin coated on the ARC and prebaked on a hotplate at 100° C. for 60 seconds to form a resist film of 90 nm thick on the ARC. The wafer was exposed on an ArF excimer laser immersion lithography scanner (NSR-S610C by Nikon Corp., NA 1.30, dipole illumination) through a Cr mask having a line-and-space (L/S) pattern with a line width of 40 nm and a pitch of 80 nm (on-wafer size), while varying the exposure dose and focus at a dose pitch of 1 mJ/cm$^2$ and a focus pitch of 0.025 μm. The immersion liquid used herein was water. After exposure, the resist film was baked (PEB) at the temperature shown in Table 4 for 60 seconds. The resist film was puddle developed in a 2.38 wt % tetramethylammonium hydroxide (TMAH) aqueous solution for 30 seconds, rinsed with deionized water and spin dried, forming a positive pattern. The L/S pattern after development was observed under CD-SEM (CG4000 by Hitachi High-Technologies Corp.), whereupon sensitivity, EL, MEF, LWR, and defect density were evaluated by the following methods. The results are shown in Table 4.

Evaluation of Sensitivity

The optimum exposure dose Eop (mJ/cm$^2$) which provided a L/S pattern having a line width of 40 nm and a pitch of 80 nm was determined as an index of sensitivity. A smaller dose value indicates a higher sensitivity.

Evaluation of Exposure Latitude (EL)

The exposure dose which provided a L/S pattern with a space width of 40 nm±10% (i.e., 36 nm to 44 nm) was determined. EL (%) is calculated from the exposure doses according to the following equation:

$$EL(\%)=(|E1-E2|/Eop)\times100$$

wherein E1 is an optimum exposure dose which provides a L/S pattern with a line width of 36 nm and a pitch of 80 nm, E2 is an optimum exposure dose which provides a L/S pattern with a line width of 44 nm and a pitch of 80 nm, and Eop is an optimum exposure dose which provides a L/S pattern with a line width of 40 nm and a pitch of 80 nm.

Evaluation of Mask Error Factor (MEF)

A L/S pattern was formed by exposure in the optimum dose Eop through the mask with the pitch fixed and the line width varied. MEF was calculated from the mask line width and a variation of the pattern line width according to the following equation:

MEF=(pattern line width)/(mask line width)−b wherein b is a constant. A value closer to unity (1) indicates better performance.
Evaluation of Line Width Roughness (LWR)

A L/S pattern was formed by exposure in the optimum dose Eop. The line width was measured at longitudinally spaced apart 10 points, from which a 3-fold value (3σ) of standard deviation (σ) was determined and reported as LWR. A smaller value of 3σ indicates a pattern having a lower roughness and more uniform line width.
Evaluation of Defect Density Defects in the pattern as developed were inspected by a flaw detector KLA2800 (KLA-Tencor). A defect density (count/cm$^2$) was computed by dividing the total number of detected defects by a detection area. The pattern formed was an iterated 50-nm 1:1 L/S pattern. The defect inspection conditions included light source UV, inspected pixel size 0.28 μm, and cell-to-cell mode. In this test, the sample was rated good for a defect density of less than 0.05 defect/cm$^2$ and poor for a density of equal to or more than 0.05 defect/cm$^2$.

content of 43 wt % was deposited thereon to a thickness of 35 nm. On this substrate for trilayer process, each of the resist compositions (R-18 to R-36, R-50 to R-54) was spin coated, then baked on a hot plate at 100° C. for 60 seconds to form a resist film of 100 nm thick.

Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 45 nm and a pitch of 110 nm (on-wafer size) while varying the dose and focus (dose pitch: 1 mJ/cm$^2$, focus pitch: 0.025 μm). The immersion liquid used herein was water. After the exposure, the wafer was baked (PEB) at the temperature shown in Table 5 for 60 seconds. Thereafter, the resist film was puddle developed in n-butyl acetate for 30 seconds, rinsed with 4-methyl-2-pentanol, and spin dried, obtaining a negative pattern. The CH pattern after development was observed under CD-SEM CG4000 (Hitachi High Technologies Corp.) whereupon sensitivity, MEF, CDU, and DOF were evaluated by the following methods. The results are shown in Table 5.

TABLE 4

|  |  | Resist composition | PEB temp. (° C.) | Eop (mJ/cm$^2$) | EL (%) | MEF | LWR (nm) | Defect density |
|---|---|---|---|---|---|---|---|---|
| Example | 3-1 | R-01 | 90 | 35 | 17.5 | 2.5 | 2.6 | good |
|  | 3-2 | R-02 | 90 | 38 | 18.0 | 2.4 | 2.4 | good |
|  | 3-3 | R-03 | 90 | 36 | 16.5 | 2.2 | 2.3 | good |
|  | 3-4 | R-04 | 90 | 34 | 13.5 | 2.8 | 2.9 | good |
|  | 3-5 | R-05 | 90 | 35 | 18.5 | 2.6 | 2.2 | good |
|  | 3-6 | R-06 | 90 | 34 | 14.3 | 2.7 | 2.5 | good |
|  | 3-7 | R-07 | 90 | 35 | 17.5 | 2.5 | 2.7 | good |
|  | 3-8 | R-08 | 90 | 39 | 19.2 | 2.1 | 2.3 | good |
|  | 3-9 | R-09 | 95 | 38 | 19.1 | 1.9 | 2.3 | good |
|  | 3-10 | R-10 | 95 | 35 | 18.5 | 2.4 | 2.4 | good |
|  | 3-11 | R-11 | 95 | 36 | 17.3 | 2.3 | 2.3 | good |
|  | 3-12 | R-12 | 95 | 33 | 14.1 | 2.9 | 2.8 | good |
|  | 3-13 | R-13 | 95 | 36 | 13.8 | 2.8 | 2.9 | good |
|  | 3-14 | R-14 | 95 | 38 | 19.7 | 2.4 | 2.1 | good |
|  | 3-15 | R-15 | 95 | 36 | 15.6 | 2.3 | 2.6 | good |
|  | 3-16 | R-16 | 95 | 39 | 16.9 | 1.9 | 2.5 | good |
|  | 3-17 | R-17 | 95 | 38 | 17.4 | 2.0 | 2.3 | good |
| Comparative Example | 2-1 | R-45 | 90 | 32 | 9.1 | 3.3 | 4.2 | poor |
|  | 2-2 | R-46 | 90 | 33 | 11.2 | 3.2 | 4.0 | poor |
|  | 2-3 | R-47 | 90 | 30 | 10.8 | 3.9 | 3.9 | poor |
|  | 2-4 | R-48 | 90 | 29 | 8.9 | 3.8 | 4.0 | poor |
|  | 2-5 | R-49 | 90 | 29 | 8 | 3.3 | 4.1 | poor |

As is evident from Table 4, the chemically amplified resist compositions containing sulfonium compounds within the scope of the invention exhibit a satisfactory sensitivity, improved values of EL, MEF and LWR and are effective in reducing development defects. The resist compositions are useful as the ArF immersion lithography material.

[5] Evaluation of Resist Composition: ArF Lithography Patterning Test 2

Examples 4-1 to 4-19 and Comparative Examples 3-1 to 3-5

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A941 having a silicon Evaluation of Sensitivity The optimum dose Eop (mJ/cm$^2$) which provided a CH pattern with a hole size of 45 nm and a pitch of 110 nm was determined as an index of sensitivity. A smaller dose value indicates a higher sensitivity.
Evaluation of MEF A CH pattern was formed by exposure at the optimum dose Eop by ArF lithography patterning test 2 with the pitch fixed and the mask size varied. MEF was calculated from the mask size and a variation of the CH pattern size according to the following equation:

MEF=(pattern size)/(mask size)−b wherein b is a constant. A value closer to unity (1) indicates better performance.
Evaluation of Critical Dimension Uniformity (CDU)

For the CH pattern formed by exposure at the optimum dose Eop, the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

Evaluation of Depth of Focus (DOF)

As an index of DOF, a range of focus which provided a CH pattern with a size of 45 nm±10% (i.e., 41 to 49 nm) was determined. A greater value indicates a wider DOF.

Evaluation of Film Retention

The CH pattern printed from exposure at Eop was observed in cross section under CD-SEM (S-4800 by Hitachi High-Technologies Corp.). The film thickness as developed divided by the film thickness 100 nm as spin coated is reported as an index of film retention. A greater value indicates better film retention.

$\mu C/cm^2$. The resist film was baked (PEB) at the temperature shown in Table 6 for 60 seconds. The resist film was then puddle developed in a 2.38 wt % TMAH aqueous solution for 30 seconds, rinsed with deionized water, and spin dried, yielding a positive resist pattern. The CH pattern after development was observed under CD-SEM S9380 (Hitachi High Technologies Corp.) whereupon sensitivity, EL, and CDU were evaluated by the following methods. The results are shown in Table 6.

Evaluation of Sensitivity

The optimum dose Eop ($\mu C/cm^2$) which provided a CH pattern with a hole size of 24 nm and a pitch of 48 nm was determined as an index of sensitivity. A smaller dose value indicates a higher sensitivity.

TABLE 5

|  |  | Resist composition | PEB temp. (° C.) | Eop (mJ/cm$^2$) | MEF | CDU (nm) | DOF (nm) | Film retention (%) |
|---|---|---|---|---|---|---|---|---|
| Example | 4-1 | R-18 | 95 | 35 | 2.3 | 3.1 | 150 | 71 |
|  | 4-2 | R-19 | 95 | 36 | 2.5 | 2.9 | 140 | 75 |
|  | 4-3 | R-20 | 95 | 34 | 2.2 | 3.3 | 150 | 68 |
|  | 4-4 | R-21 | 95 | 38 | 2.7 | 3.5 | 130 | 65 |
|  | 4-5 | R-22 | 95 | 40 | 2.8 | 3.4 | 120 | 70 |
|  | 4-6 | R-23 | 95 | 38 | 2.4 | 3.0 | 150 | 70 |
|  | 4-7 | R-24 | 95 | 39 | 2.7 | 3.4 | 110 | 72 |
|  | 4-8 | R-25 | 95 | 35 | 2.2 | 3.1 | 140 | 70 |
|  | 4-9 | R-26 | 95 | 38 | 2.4 | 3.1 | 130 | 69 |
|  | 4-10 | R-27 | 95 | 38 | 2.3 | 3.3 | 150 | 73 |
|  | 4-11 | R-28 | 95 | 39 | 2.4 | 2.8 | 160 | 70 |
|  | 4-12 | R-29 | 85 | 41 | 2.5 | 2.9 | 130 | 68 |
|  | 4-13 | R-30 | 85 | 42 | 2.1 | 3.1 | 140 | 69 |
|  | 4-14 | R-31 | 85 | 41 | 2.8 | 3.6 | 120 | 68 |
|  | 4-15 | R-32 | 85 | 45 | 2.8 | 3.5 | 130 | 72 |
|  | 4-16 | R-33 | 85 | 44 | 2.9 | 3.7 | 120 | 70 |
|  | 4-17 | R-34 | 85 | 43 | 2.4 | 3.1 | 150 | 70 |
|  | 4-18 | R-35 | 85 | 42 | 2.4 | 3.3 | 140 | 72 |
|  | 4-19 | R-36 | 85 | 42 | 2.3 | 3.2 | 150 | 71 |
| Comparative Example | 3-1 | R-50 | 85 | 38 | 2.5 | 4.0 | 80 | 60 |
|  | 3-2 | R-51 | 85 | 37 | 3.0 | 4.1 | 90 | 59 |
|  | 3-3 | R-52 | 85 | 35 | 2.9 | 3.8 | 70 | 63 |
|  | 3-4 | R-53 | 85 | 38 | 3.3 | 3.9 | 80 | 62 |
|  | 3-5 | R-54 | 85 | 41 | 3.4 | 4.2 | 90 | 63 |

As is evident from Table 5, the chemically amplified resist compositions containing sulfonium compounds within the scope of the invention exhibit a satisfactory sensitivity and improved values of CDU, MEF and DOF in forming negative patterns via organic solvent development. Satisfactory film retention is also confirmed. The resist compositions are also useful in the organic solvent development process.

[6] Evaluation of Resist Composition: EB Lithography Test

Examples 5-1 to 5-8 and Comparative Examples 4-1 to 4-8

An antireflective coating solution (DUV-42, Nissan Chemical Corp.) was coated on a silicon substrate and baked at 200° C. for 60 seconds to form an ARC of 61 nm thick. Each of the resist compositions (R-37 to R-44, R-55 to R-62) was spin coated on the ARC and prebaked on a hotplate at 100° C. for 60 seconds to form a resist film of 45 nm thick. Using an EB lithography system ELS-F125 (Elionix Co., Ltd., accelerating voltage 125 kV), the resist film was exposed to EB through a mask bearing a CH pattern with a hole size of 24 nm and a pitch of 48 nm (on-wafer size) while varying the dose from 50 $\mu C/cm^2$ at a step of 5

Evaluation of EL

The exposure dose which provided a CH pattern with a hole size of 24 nm±10% (i.e., 21.6 nm to 26.4 nm) was determined. EL (%) is calculated from the exposure doses according to the following equation:

$$EL(\%)=(|E1-E2|/Eop) \times 100$$

wherein E1 is an optimum exposure dose which provides a CH pattern with a hole size of 21.6 nm and a pitch of 48 nm, E2 is an optimum exposure dose which provides a CH pattern with a hole size of 26.4 nm and a pitch of 48 nm, and Eop is an optimum exposure dose which provides a CH pattern with a hole size of 24 nm and a pitch of 48 nm.

Evaluation of CDU

For the CH pattern formed by exposure at the optimum dose Eop, the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

TABLE 6

| | Resist composition | PEB temp. (° C.) | Eop (μC/cm$^2$) | EL (%) | CDU (nm) |
|---|---|---|---|---|---|
| Example | 5-1 R-37 | 105 | 153 | 13.5 | 3.3 |
| | 5-2 R-38 | 105 | 158 | 12.3 | 3.6 |
| | 5-3 R-39 | 105 | 160 | 15.6 | 3.2 |
| | 5-4 R-40 | 105 | 155 | 16.3 | 3.1 |
| | 5-5 R-41 | 105 | 157 | 15.8 | 3.5 |
| | 5-6 R-42 | 105 | 160 | 15.3 | 3.3 |
| | 5-7 R-43 | 105 | 154 | 13.2 | 3.1 |
| | 5-8 R-44 | 105 | 155 | 15.3 | 3.4 |
| Comparative Example | 4-1 R-55 | 105 | 130 | 9.0 | 4.2 |
| | 4-2 R-56 | 105 | 135 | 10.1 | 3.9 |
| | 4-3 R-57 | 105 | 145 | 8.8 | 4.3 |
| | 4-4 R-58 | 105 | 144 | 9.5 | 3.8 |
| | 4-5 R-59 | 105 | 151 | 10.2 | 4.1 |
| | 4-6 R-60 | 105 | 133 | 9.8 | 4.0 |
| | 4-7 R-61 | 105 | 142 | 8.3 | 4.2 |
| | 4-8 R-62 | 105 | 120 | 9.6 | 4.5 |

It is evident from Table 6 that the chemically amplified resist compositions containing sulfonium compounds within the scope of the invention exhibit a high sensitivity, improved EL and CDU. The resist compositions are useful EB and EUV lithography materials.

Japanese Patent Application No. 2019-072757 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium compound having the formula (A):

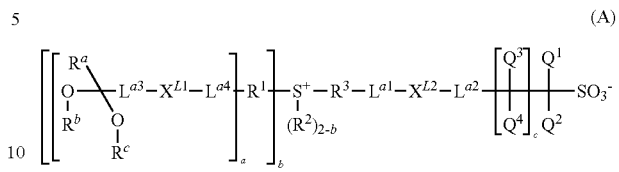

(A)

wherein $Q^1$ and $Q^2$ are each independently fluorine or a $C_1$-$C_6$ fluoroalkyl group,
$Q^3$ and $Q^4$ are each independently hydrogen, fluorine or a $C_1$-$C_6$ fluoroalkyl group,
a is an integer of 1 to 4,
b is 1 or 2,
c is an integer of 0 to 3,
$L^{a1}$ to $L^{a4}$ are each independently a single bond, ether bond, ester bond, sulfonic acid ester bond, carbonate bond or carbamate bond,
$X^{L1}$ and $X^{L2}$ are each independently a single bond or a $C_2$-$C_{40}$ divalent hydrocarbon group which may contain a heteroatom,
$R^a$ is hydrogen or a $C_1$-$C_{20}$ monovalent hydrocarbon group which may contain a heteroatom,
$R^b$ and $R^c$ are each independently a $C_2$-$C_{40}$ monovalent hydrocarbon group which may contain a heteroatom, $R^b$ and $R^c$ may bond together to form a ring with the oxygen atoms to which they are attached and the intervening carbon atom,
$R^1$ is a $C_1$-$C_{50}$ (a+1)-valent hydrocarbon group which may contain a heteroatom,
$R^2$ is a $C_1$-$C_{50}$ monovalent hydrocarbon group which may contain a heteroatom,
$R^3$ is a $C_1$-$C_{50}$ divalent hydrocarbon group which may contain a heteroatom,
in the case of b=1, $R^1$ and $R^2$, or $R^2$ and $R^3$ may bond together to form a ring with the sulfur atom to which they are attached, and in the case of b=2, $R^1$ and $R^3$, or two $R^1$ may bond together to form a ring with the sulfur atom to which they are attached.

2. The sulfonium compound of claim 1, having the formula (A-1):

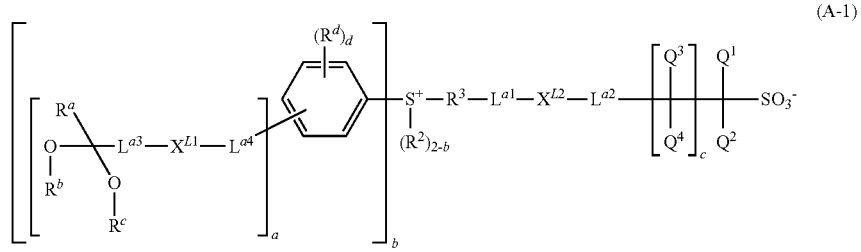

(A-1)

wherein $Q^1$ to $Q^4$, $L^{a1}$ to $L^{a4}$, $X^{L1}$, $X^{L2}$, $R^a$, $R^b$, $R^c$, $R^2$, $R^3$, a, b and c are as defined above $R^d$ is a $C_1$-$C_{20}$ monovalent hydrocarbon group which may contain a heteroatom, d is an integer of 0 to 4, the sum a+d is 1 to 5, in the case of d≥2, each $R^d$ may be the same or different, and two $R^d$ may bond together to form a ring with the atoms to which they are attached.

3. The sulfonium compound of claim 2, having the formula (A-2):

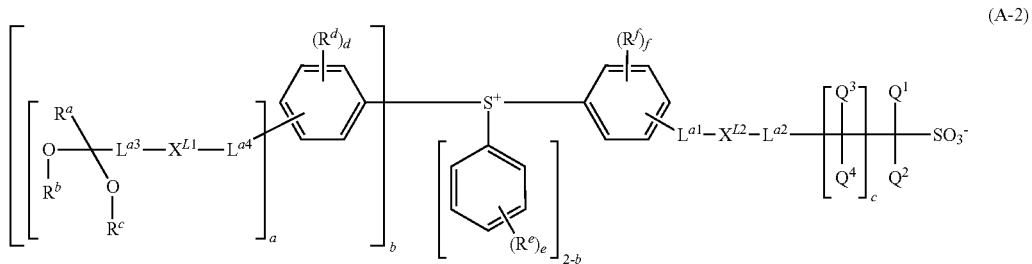

wherein $Q^1$ to $Q^4$, $L^{a1}$ to $L^{a4}$, $X^{L1}$, $X^{L2}$, $R^a$ to $R^d$, a, b, c and d are as defined above, $R^e$ and $R^f$ are each independently a $C_1$-$C_{20}$ monovalent hydrocarbon group which may contain a heteroatom, e is an integer of 0 to 5, f is an integer of 0 to 4, in the case of e≥2, each $R^e$ may be the same or different, and two $R^e$ may bond together to form a ring with the atoms to which they are attached, and in the case of f≥2, each $R^f$ may be the same or different, and two $R^f$ may bond together to form a ring with the atoms to which they are attached.

4. The sulfonium compound of claim 3, having the formula (A-3):

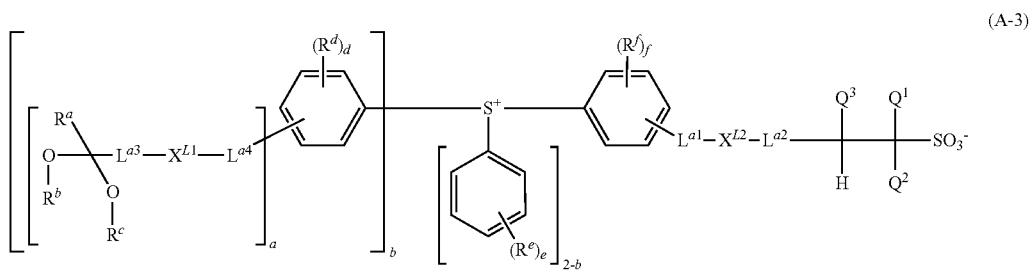

wherein $Q^1$ to $Q^3$, $L^{a1}$ to $L^{a4}$, $X^{L1}$, $X^{L2}$, $R^a$ to $R^f$, a, b, d, e and f are as defined above.

5. A photoacid generator comprising the sulfonium compound of claim 1.

6. A chemically amplified resist composition comprising the photoacid generator of claim 5 and a base resin comprising recurring units having the formula (a1) or (a2):

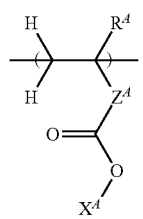

(a1)

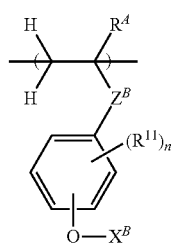

(a2)

wherein $R^A$ is each independently hydrogen, fluorine, methyl or trifluoromethyl, $Z^A$ is a single bond, phenylene, naphthylene or (backbone)-C(=O)—O—$Z^{A1}$—, $Z^{A1}$ is a $C_1$-$C_{10}$ alkanediyl group which may contain a hydroxyl moiety, ether bond, ester bond or lactone ring, or phenylene or naphthylene, $Z^B$ is a single bond or (backbone)-C(=O)—O—, $X^A$ and $X^B$ are each independently an acid labile group, $R^{11}$ is a $C_1$-$C_{20}$ monovalent hydrocarbon group which may contain a heteroatom, and n is an integer of 0 to 4.

7. The resist composition of claim 6 wherein the base resin further comprises recurring units having the formula (b1) or (b2):

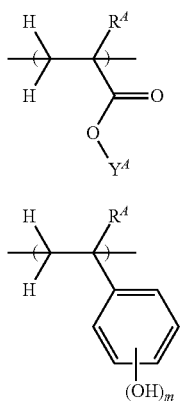

wherein $R^A$ is each independently hydrogen, fluorine, methyl or trifluoromethyl, $Y^A$ is hydrogen or a polar group containing at least one structure selected from the group consisting of hydroxyl, cyano, carbonyl, carboxyl, ether bond, ester bond, sulfonic acid ester bond, carbonate bond, lactone ring, sultone ring and carboxylic anhydride, and m is 1 or 2.

8. The resist composition of claim 6 wherein the base resin further comprises recurring units of at least one type selected from recurring units having the formulae (c1) to (c3):

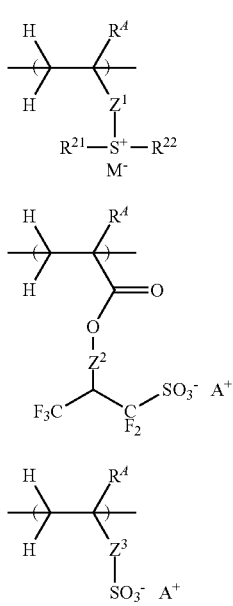

wherein $R^A$ is each independently hydrogen, fluorine, methyl or trifluoromethyl, $Z^1$ is a single bond, phenylene, —O—$Z^{11}$—, —C(=O)—O—$Z^{11}$— or —C(=O)—NH—$Z^{11}$—, $Z^{11}$ is a $C_1$-$C_{20}$ alkanediyl group, $C_2$-$C_{20}$ alkenediyl group or phenylene group, which may contain a carbonyl moiety, ester bond, ether bond or hydroxyl moiety, $Z^2$ is a single bond or —$Z^{21}$—C(=O)—O—, $Z^{21}$ is a $C_1$-$C_{20}$ divalent hydrocarbon group which may contain a heteroatom, $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group or phenylene group, which may contain a carbonyl moiety, ester bond, ether bond or hydroxyl moiety, $R^{21}$ and $R^{22}$ are each independently a $C_1$-$C_{20}$ monovalent hydrocarbon group which may contain a heteroatom, $R^{21}$ and $R^{22}$ may bond together to form a ring with the sulfur atom to which they are attached, $M^-$ is a non-nucleophilic counter ion, and $A^+$ is an ammonium, sulfonium or iodonium cation.

9. The resist composition of claim 6, further comprising an organic solvent.

10. The resist composition of claim 6, further comprising another photoacid generator other than the photoacid generator.

11. The resist composition of claim 10 wherein the other photoacid generator has the formula (1) or (2):

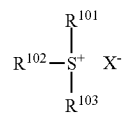

wherein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the following formulae (1A) to (1D):

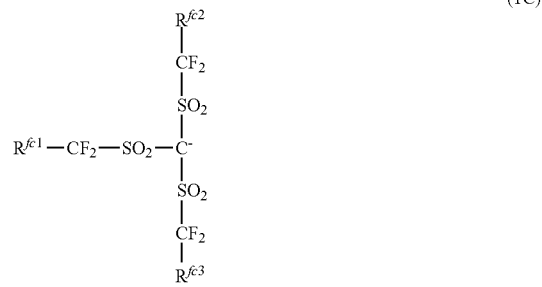

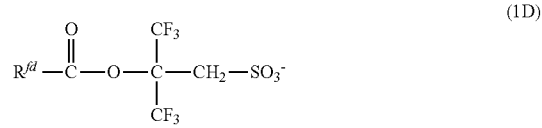

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom,

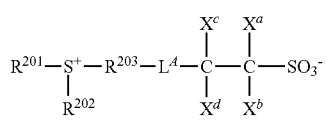

(2)

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^a$, $X^b$, $X^c$ and $X^d$ are each independently hydrogen, fluorine or trifluoromethyl, at least one of $X^a$, $X^b$, $X^c$ and $X^d$ being fluorine or trifluoromethyl.

12. The resist composition of claim 6, further comprising a compound having the formula (3) or (4):

(3)

(4)

wherein $R^{q1}$ is hydrogen or a $C_1$-$C_{40}$ monovalent hydrocarbon group which may contain a heteroatom, exclusive of the group wherein hydrogen bonded to the carbon atom at α-position relative to the sulfo group is substituted by fluorine or fluoroalkyl, $R^{q2}$ is hydrogen or a $C_1$-$C_{40}$ monovalent hydrocarbon group which may contain a heteroatom, and $Mq^+$ is an onium cation.

13. The resist composition of claim 6, further comprising an amine compound.

14. The resist composition of claim 6, further comprising a surfactant which is insoluble or substantially insoluble in water and soluble in alkaline developer, and/or a surfactant which is insoluble or substantially insoluble in water and alkaline developer.

15. A pattern forming process comprising the steps of applying the chemically amplified resist composition of claim 6 to form a resist film on a substrate, exposing a selected region of the resist film to KrF excimer laser, ArF excimer laser, EB or EUV, and developing the exposed resist film in a developer.

16. The pattern forming process of claim 15 wherein the developing step uses an alkaline aqueous solution as the developer, thereby forming a positive pattern in which an exposed region of the resist film is dissolved away and an unexposed region of the resist film is not dissolved.

17. The pattern forming process of claim 15 wherein the developing step uses an organic solvent as the developer, thereby forming a negative pattern in which an unexposed region of the resist film is dissolved away and an exposed region of the resist film is not dissolved.

18. The pattern forming process of claim 17 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

19. The process of claim 15 wherein the exposure step is carried out by immersion lithography while a liquid having a refractive index of at least 1.0 is held between the resist film and a projection lens.

20. The process of claim 19, further comprising the step of forming a protective film on the resist film prior to the exposure step, wherein immersion lithography is carried out while the liquid is held between the protective film and the projection lens.

* * * * *